United States Patent [19]

Christensen et al.

[11] Patent Number: 4,685,955
[45] Date of Patent: Aug. 11, 1987

[54] HERBICIDAL SULFONAMIDES

[75] Inventors: Joel R. Christensen; Paul H. Liang; Mark E. Thompson, all of Wilmington, Del.

[73] Assignee: E. I. Du Pont de Nemours and Company, Wilmington, Del.

[21] Appl. No.: 842,792

[22] Filed: Mar. 27, 1986

Related U.S. Application Data

[63] Continuation-in-part of Ser. No. 740,894, Jun. 3, 1985, abandoned.

[51] Int. Cl.$^4$ .................. C07D 407/12; C07D 409/12; C07D 403/12; A01N 47/36
[52] U.S. Cl. .......................................... 71/92; 71/90; 71/91; 71/93; 544/3; 544/60; 544/253; 544/278; 544/320; 544/321; 544/323; 544/324; 544/331; 544/332; 544/209; 544/212
[58] Field of Search ............... 544/320, 321, 331, 332, 544/323, 324, 3, 60, 253, 278; 71/90, 92, 91

[56] References Cited

U.S. PATENT DOCUMENTS 4,368,069 1/1983 Chen et al. ............................ 251/46
4,460,401 7/1984 Sauers ................................... 405/12

FOREIGN PATENT DOCUMENTS 106512 4/1984 European Pat. Off. .
836449 3/1984 South Africa .

Primary Examiner—Robert Gerstl

[57] ABSTRACT

This invention relates to certain sulfonylurea compounds having a ring structure, which is attached ortho to the sulfonyl bridge through a double bond, agricultural compositions thereof and a method of their use as general preemergence and/or postemergence herbicides or plant growth regulants.

58 Claims, No Drawings

HERBICIDAL SULFONAMIDES

RELATED APPLICATION

This application is a continuation-in-part of copending application U.S. Ser. No. 740,894, filed June 3, 1985 now abandoned.

BACKGROUND OF THE INVENTION

This invention relates to certain sulfonylurea compounds having a ring structure ortho to the sulfonyl bridge, agricultural compositions thereof and a method of use as general preemergence and/or postemergence herbicides or plant growth regulators.

New compounds effective for controlling the growth of undesired vegetation are in constant demand. In the most common situation, such compounds are sought to selectively control the growth of weeds in useful crops such as cotton, rice, corn, wheat, and soybeans, to name a few. Unchecked weed growth in such crops can cause significant losses, reducing profit to the farmer and increasing costs to the consumer. In other situations, herbicides which will control all plant growth are desired. Examples of areas in which complete control of all vegetation is desired are areas around fuel storage tanks, ammunition depots and industrial storage areas. There are many products commercially available for these purposes, but the search continues for products which are more effective, less costly and environmentally safe.

U.S. Pat. No. 4,368,069 discloses herbicidal sulfonylureas of the formula

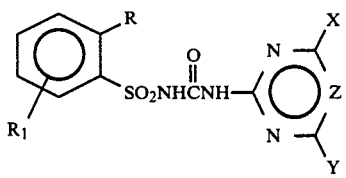

wherein
R is

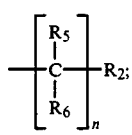

$R_2$ is $C_2$–$C_5$ alkenyl, $C_5$–$C_6$ cycloalkenyl or $C_2$–$C_3$ alkenyl substituted with 1–3 Cl; .
n is 0 or 1;
$R_1$ is, inter alia, H, F, Cl, Br;
$R_5$ and $R_6$ are independently H or $CH_3$; etc.

European Patent Application (EP-A) No. 106,512, published Apr. 25, 1984, discloses herbicidal sulfonylureas of the formula

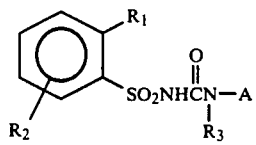

wherein
$R_1$ is, in part, $CH\!=\!CBr_2$, $CH\!=\!CHCO_2CH_3$, $CH\!=\!CF_2$ or $CH\!=\!CHR_9$;
$R_9$ is $OCH_3$ or $OC_2H_5$;
$R_2$ is H, F, Cl, $CH_3$, $OCH_3$ or $CF_3$;
$R_3$ is H or $CH_3$; etc.

U.S. Pat. No. 4,460,401 discloses herbicidal sulfonylureas of the formula

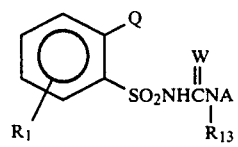

where, in part,
Q is an optionally substituted ring such as

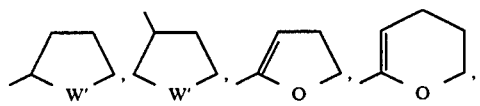

etc;
W' is O or S;
W is O or S;
$R_1$ is H, F, Cl, Br, $CH_3$, $CF_3$ or $OCH_3$;
$R_{13}$ is H or $CH_3$; etc.

U.S. Pat. No. 4,370,480 discloses herbicidal sulfonylureas of the formula

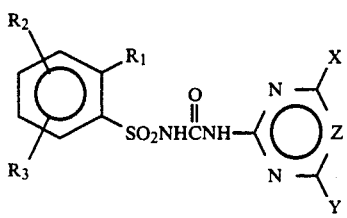

where, in part,
$R_1$ is

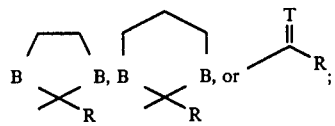

R is H, $C_1$–$C_{12}$ alkyl, $C_2$–$C_6$ alkenyl, etc.;
B is O or $S(O)_G$;
G is 0 or 2;
T is O or $=\!NOR_1{}^{III}$;
$R_2$ is, inter alia, H, F, Cl, Br or $C_1$–$C_3$ alkyl;
$R_3$ is H, F, Cl, Br or $CH_3$.

South African Patent Application No. 83/6449, published Mar. 1, 1984, discloses herbicidal sulfonylureas of the formula

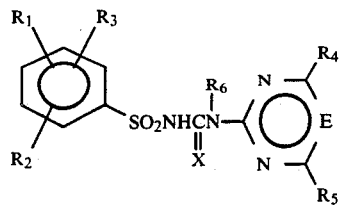

wherein
- $R_1$ is H, halogen, $NO_2$, $NH_2$, $C_1-C_5$ alkyl, $C_1-C_4$ haloalkyl or a $QR_7$, $CO_2R_8$ or $-(CO)_nNR_9R_{10}$ radical;
- $R_2$ is, inter alia, H, $C_1-C_4$ alkyl, $C_1-C_4$ alkoxy or $C_1-C_4$ alkylthio;
- $R_3$ is $C_2-C_{10}$ alkenyl which is substituted by one or more fluorine or bromine atoms or by one or more hydroxyl, cyano, nitro, $-(Y)_mCO(Z)_nR_8$, $-SO_2NR_{11}R_{12}$, $-S(O)_p-C_1-C_3$ haloalkyl or $-S(O)_n-C_1-C_3$ alkyl groups, and which may additionally be substituted by one or more chlorine atoms;
- X is O or S;
- $R_6$ is H, $C_1-C_3$ alkyl or $C_1-C_3$ alkoxy; etc.

SUMMARY OF THE INVENTION

Novel herbicidal compounds, agricultural compositions thereof and a method-of-use as general preemergence and/or postemergence herbicides or plant growth regulators have been found.

The novel compounds of the invention are compounds of the formula

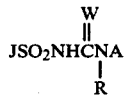
I wherein
J is

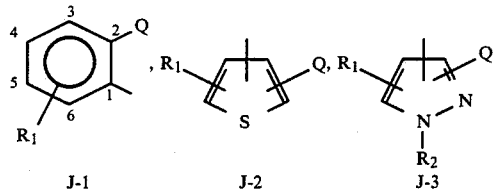

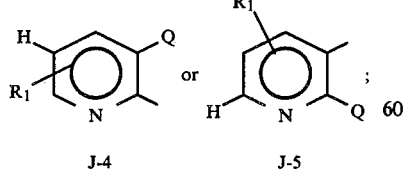

R is H or $CH_3$;
W is O or S;
$R_1$ is H, $C_1-C_3$ alkyl, $C_1-C_3$ haloalkyl, halogen, nitro, $C_1-C_3$ alkoxy, $SO_2NR_aR_b$, $C_1-C_3$ alkylthio, $C_1-C_3$ alkylsulfinyl, $C_1-C_3$ alkylsulfonyl, $CO_2R_c$, amino, $C_1-C_3$ alkylamino, di($C_1-C_3$)alkylamino, $CH_2OCH_3$, $CH_2SCH_3$ or $CH_2CN$;
$R_a$ is H, $C_1-C_4$ alkyl, $C_2-C_3$ cyanoalkyl, $OCH_3$ or $OC_2H_5$;
$R_b$ is H, $C_1-C_4$ alkyl or $C_3-C_4$ alkenyl; or
$R_a$ and $R_b$ may be taken together as $(CH_2)_3$, $(CH_2)_4$, $(CH_2)_5$ or $-CH_2CH_2OCH_2CH_2-$;
$R_c$ is $C_1-C_4$ alkyl, $C_3-C_4$ alkenyl, $C_3-C_4$ alkynyl, $C_2-C_4$ haloalkyl, $C_2-C_3$ cyanoalkyl, $C_5-C_6$ cycloalkyl, $C_4-C_7$ cycloalkylalkyl or $C_2-C_4$ alkoxyalkyl;
$R_2$ is H, $C_1-C_4$ alkyl, $C_3-C_4$ alkenyl, $C_3-C_4$ alkynyl, phenyl, phenyl substituted with Cl, $NO_2$, $CH_3$ or $OCH_3$, $C_1-C_3$ alkoxycarbonyl, $C_1-C_3$ alkylsulfonyl or di($C_1-C_2$)alkylamino sulfamoyl;
Q is

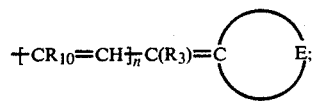

n is 0, 1 or 2;
$R_3$ is H, $C_1-C_4$ alkyl, Cl or Br;
$R_{10}$ is H or $C_1-C_4$ alkyl;
E is a bridge of 4 or 5 atoms, which may be substituted or unsubstituted, containing 0-2 heteroatoms selected from the group consisting of oxygen, sulfur and nitrogen, and also containing 2-5 carbon atoms, said bridge together with one carbon attachment site forming a partially saturated or a fully unsaturated, nonaromatic 5- or 6-membered carbocyclic or heterocyclic ring, with the proviso that when E contains two atoms of oxygen or sulfur, they must be separated by at least one atom of carbon, and that oxygen and sulfur are only linked to each other if the sulfur is in the form SO or $SO_2$; in the bridging group E, sulfur may take the form of S, SO or $SO_2$ and one or two of the carbon atoms may be a carbonyl, thiocarbonyl or the cyclic 5- and 6-membered ketals thereof; when one of the bridging atoms is a substituted carbon, the substituents on said carbon include H, $C_1-C_4$ alkyl, $C_1-C_4$ alkoxy, halogen, or $C_1-C_4$ haloalkoxy; when the bridging atom is a nitrogen, the substituent on said nitrogen includes H, $C_1-C_4$ alkyl, $C_1-C_4$ haloalkyl, $C_1-C_4$ alkoxyalkyl, $C_2-C_4$ cyanoalkyl, $C_3-C_4$ alkenyl or $C_3-C_4$ alkynyl;
A is

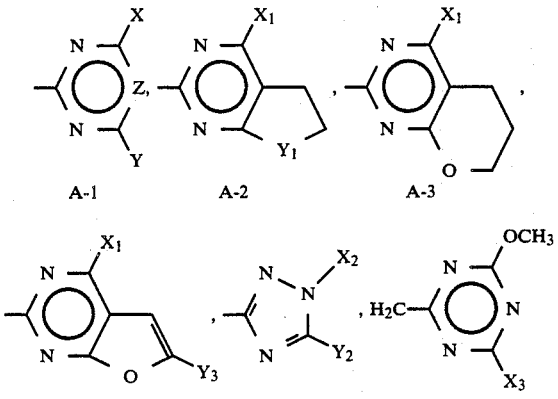

-continued or
$$\begin{array}{c} NC \quad X_4 \\ \diagdown \diagup \\ \text{---} \langle \bigcirc \rangle \text{---} Z_1; \\ \diagup \diagdown \\ N \quad Y_4 \end{array}$$

A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkoxy, amino, $C_1$-$C_3$ alkylamino or di($C_1$-$C_3$)alkylamino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$)alkylamino, $C_3$-$C_4$ alkenyloxy, $C_3$-$C_4$ alkynyloxy, $C_2$-$C_5$ alkylsulfinylalkyl, $C_1$-$C_4$ haloalkyl, $C_2$-$C_5$ alkylsulfonylalkyl, $C_3$-$C_5$ cycloalkyl, $C_2$-$C_4$ alkynyl, $C_2$-$C_5$ alkylthioalkyl, $$\underset{R_d}{\overset{O}{\underset{\parallel}{CR_d}}}, -\overset{W_1R_e}{\underset{R_d \phantom{xx} W_2R_f}{\overset{|}{\underset{|}{C}}}}, -\overset{W_1}{\underset{R_d \phantom{xx} W_2}{\overset{\diagup}{\underset{\diagdown}{C}}}}(CH_2)_m, CR_d, \overset{W_1}{\underset{W_2}{\overset{\diagup}{\underset{\diagdown}{C}}}}\overset{CH_3}{\underset{\phantom{x}}{\diagdown}}$$

$W_1$ and $W_2$ are independently O or S;
m is 2 or 3;
$R_d$ is H or $CH_3$;
$R_e$ is $C_1$-$C_2$ alkyl;
$R_f$ is $C_1$-$C_2$ alkyl;
Z is CH, N, $CCH_3$, $CC_2H_5$, CCl or CBr;
$Z_1$ is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $OCF_2H$, $SCF_2H$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that (a) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or $$\begin{array}{c} O \\ \diagup \\ CH \\ \diagdown \\ O \end{array};$$

(b) when X is Cl, Br, F or I, then Z is CH and Y is $OCH_3$, $OC_2H_5$, $NH_2$, $NHCH_3$, $N(CH_3)_2$, $OCF_2H$ or $N(OCH_3)CH_3$;
(c) when X or Y is $C_1$ haloalkoxy, then Z is CH;
(d) when the bridging group E contains a thiocarbonyl substituent, said thiocarbonyl carbon must be bonded to a nitrogen atom;
(e) when J is J-2 or J-3, the substituent Q and the sulfonylurea bridge are on adjacent carbon atoms;
(f) when the total number of carbon atoms in X and Y is greater than 4, then the total number of carbon atoms in $R_1$, $R_2$ and Q is less than or equal to 10; and
(g) $X_4$ and $Y_4$ are not simultaneously Cl.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g. vinyl, 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine and iodine.

Alkoxycarbonyl denotes methoxycarbonyl, ethoxycarbonyl, propoxycarbonyl and isopropoxycarbonyl.

Alkylsulfonyl denotes methylsulfonyl, ethylsulfonyl, propylsulfonyl and isopropylsulfonyl.

Alkylthio, alkylsulfinyl, alkylamino, etc. are defined in an analogous manner.

In terms such as $C_2$-$C_3$ alkylthioalkyl, the specified number of carbon atoms is meant to define the total number of carbon atoms in that substituent group. For example, $C_2$-$C_3$ alkylthioalkyl would designate $CH_2SCH_3$, $CH_2SC_2H_5$, $CH_2CH_2SCH_3$ or $CH(CH_3)SCH_3$, and $C_2$-$C_5$ alkoxyalkoxy would represent $OCH_2OCH_3$ through $O(CH_2)_4OCH_3$ or $OCH_2O(CH_2)_3CH_3$ and the various structural isomers embraced therein. The term $C_4$-$C_7$ cycloalkylalkyl is meant to represent a group which consists of a carbocyclic ring attached to an alkyl chain of at least one carbon atom wherein the total number of carbon atoms is between $C_4$ and $C_7$, inclusive.

The following compounds are preferred for reasons of increased ease of synthesis and/or greater herbicidal efficacy.

(1) Compounds of Formula I where W is O; R is H; Z is CH or N; and Q is $$-C(R_3)=\underset{\underset{O}{\parallel}}{\overset{R_4 \phantom{xx} R_5}{\diagup \diagdown}} W_3, \quad -C(R_3)=\underset{R_5}{\overset{R_4}{\diagup}}\underset{\diagdown}{\overset{W_3}{\diagdown}}_O,$$

Q-1         Q-2

$$-C(R_3)=\underset{\underset{O}{\parallel}}{\overset{R_4}{\diagup}}\underset{R_7}{\overset{R_5}{\diagdown}}, \quad -C(R_3)=\underset{R_7}{\overset{R_4}{\diagup}}\underset{\diagdown}{\overset{R_5}{\diagdown}}_O,$$

Q-3         Q-4

-continued

Q-5, Q-6, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-26, Q-27, Q-28, Q-29, Q-30, Q-31, Q-32, Q-33, Q-34, Q-35, Q-36

-continued
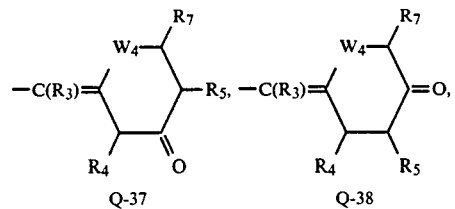
Q-37, Q-38
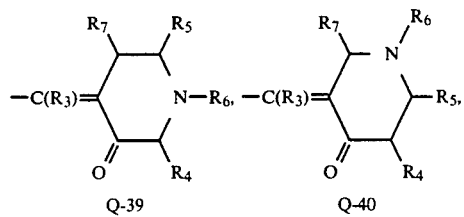
Q-39, Q-40
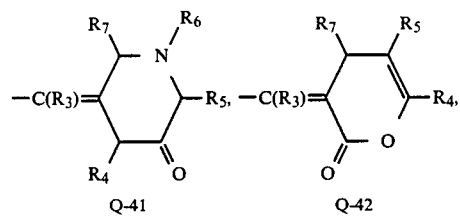
Q-41, Q-42
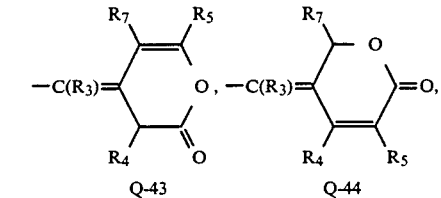
Q-43, Q-44
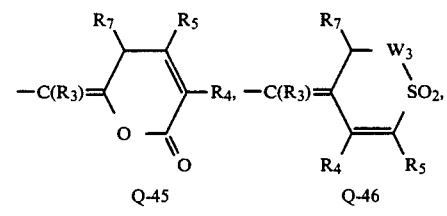
Q-45, Q-46
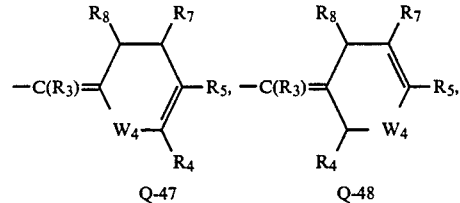
Q-47, Q-48
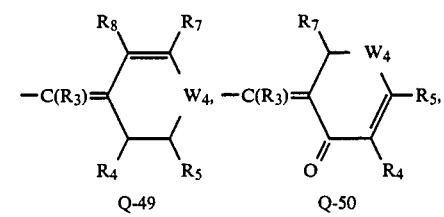
Q-49, Q-50
-continued
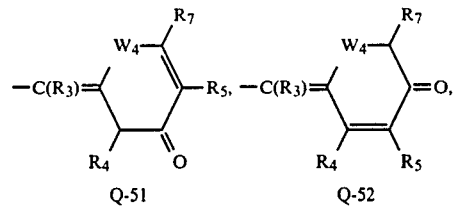
Q-51, Q-52
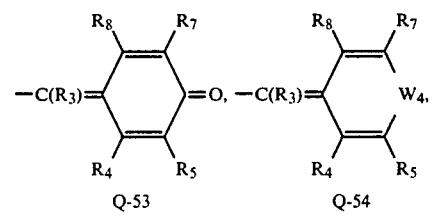
Q-53, Q-54
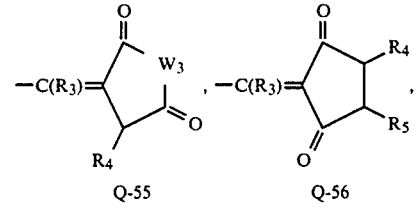
Q-55, Q-56
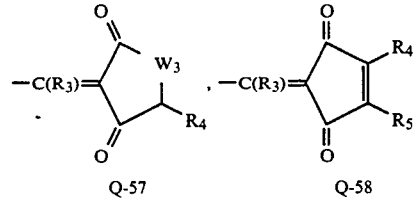
Q-57, Q-58
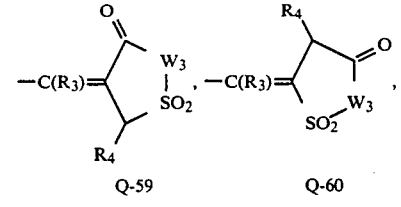
Q-59, Q-60
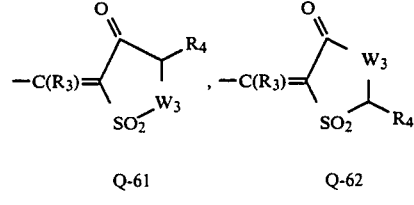
Q-61, Q-62
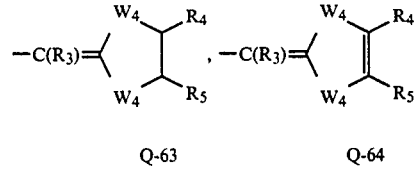
Q-63, Q-64
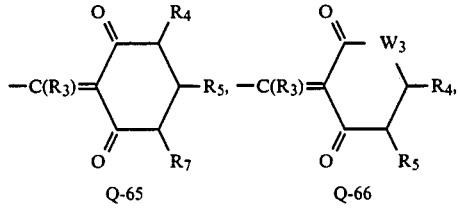
Q-65, Q-66

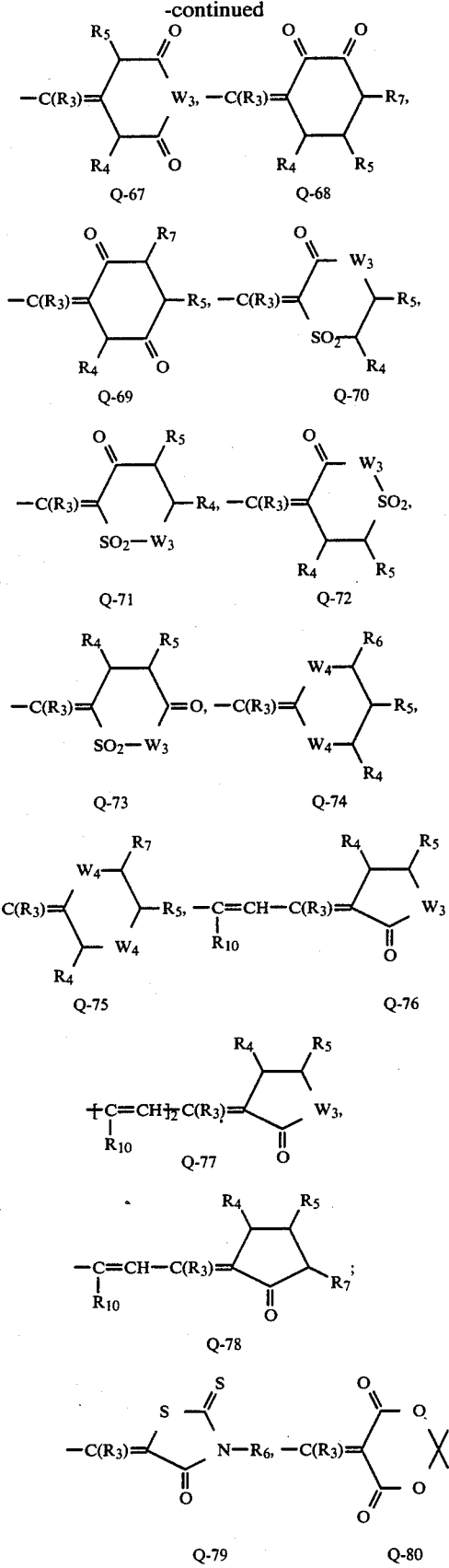

$W_3$ is O or $NR_6$;

$W_4$ is O, S, SO or $SO_2$;

$R_4$, $R_5$, $R_6$, $R_7$, $R_8$ and $R_9$ are independently H or $C_1$-$C_4$ alkyl and $R_{10}$ is H or $CH_3$;

provided that the total number of carbon atoms of $R_4$, $R_5$, $R_7$, $R_8$ and $R_9$ is less than or equal to 4.

(2) Compounds of Preferred 1 where X is $CH_3$, $OCH_3$, $OC_2H_5$, Cl, Br, F, I, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $CH_2SC_2H_5$, cyclopropyl, $$\overset{O}{\underset{}{\overset{\|}{CR_d}}}-\overset{W_1R_c}{\underset{R_d}{\overset{|}{C}}}-\overset{W_2R_f}{\underset{}{}}, \quad -\overset{W_1}{\underset{R_d}{\overset{}{C}}}\overset{}{\underset{W_2}{}}(CH_2)_m, \quad \overset{W_1}{\underset{W_2}{\overset{}{CR_d}}}\overset{CH_3}{\underset{}{}},$$

$OCF_2H$, $SCF_2H$, $C\equiv CH$ or $C\equiv CCH_3$.

(3) Compounds of Preferred 2 where $R_1$ is H, F, Cl, Br, $C_1$-$C_2$ alkyl, $C_1$-$C_2$ alkoxy or $C_1$-$C_2$ alkylthio.

(4) Compounds of Preferred 3 where $R_4$, $R_5$, $R_6$, $R_7$, $R_8$ and $R_9$ are independently H or $CH_3$; $R_3$ is H or $C_1$-$C_2$ alkyl; and $R_2$ is H, $C_1$-$C_2$ alkyl or $CH_2CH=CH_2$.

(5) Compounds of Preferred 4 where A is A-1; X is $CH_3$, $OCH_3$, $OC_2H_5$, Cl, $OCF_2H$ or $OCH_2CF_3$; Y is $CH_3$, $OCH_3$, $C_2H_5$, $CH_2OCH_3$, $NHCH_3$ or $CH(OCH_3)_2$; and Z is CH or N.

(6) Compounds of Preferred 5 where J is J-1 and $R_1$ is in the 5-position.

(7) Compounds of Preferred 5 where J is J-2 and $R_1$ is H.

(8) Compounds of Preferred 5 where J is J-3 and $R_1$ is H.

(9) Compounds of Preferred 5 where J is J-4 and $R_1$ is H.

(10) Compounds of Preferred 5 where J is J-5 and $R_1$ is H.

(11) Compounds of Preferred 6 where Q is Q-1.
(12) Compounds of Preferred 6 where Q is Q-2.
(13) Compounds of Preferred 6 where Q is Q-3.
(14) Compounds of Preferred 6 where Q is Q-4.
(15) Compounds of Preferred 6 where Q is Q-5.
(16) Compounds of Preferred 6 where Q is Q-6.
(17) Compounds of Preferred 6 where Q is Q-7.
(18) Compounds of Preferred 6 where Q is Q-8.
(19) Compounds of Preferred 6 where Q is Q-9.
(20) Compounds of Preferred 6 where Q is Q-10.
(21) Compounds of Preferred 6 where Q is Q-11.
(22) Compounds of Preferred 6 where Q is Q-12.
(23) Compounds of Preferred 6 where Q is Q-13.
(24) Compounds of Preferred 6 where Q is Q-14.
(25) Compounds of Preferred 6 where Q is Q-15.
(26) Compounds of Preferred 6 where Q is Q-16.
(27) Compounds of Preferred 6 where Q is Q-17.
(28) Compounds of Preferred 6 where Q is Q-18.
(29) Compounds of Preferred 6 where Q is Q-19.
(30) Compounds of Preferred 6 where Q is Q-20.
(31) Compounds of Preferred 6 where Q is Q-21.
(32) Compounds of preferred 6 where Q is Q-22.
(33) Compounds of Preferred 6 where Q is Q-23.
(34) Compounds of Preferred 6 where Q is Q-24.
(35) Compounds of Preferred 6 where Q is Q-25.
(36) Compounds of Preferred 6 where Q is Q-26.
(37) Compounds of Preferred 6 where Q is Q-27.

(38) Compounds of Preferred 6 where Q is Q-28.
(39) Compounds of Preferred 6 where Q is Q-29.
(40) Compounds of Preferred 6 where Q is Q-30.
(41) Compounds of Preferred 6 where Q is Q-31.
(42) Compounds of Preferred 6 where Q is Q-32.
(43) Compounds of Preferred 6 where Q is Q-33.
(44) Compounds of Preferred 6 where Q is Q-34.
(45) Compounds of Preferred 6 where Q is Q-35.
(46) Compounds of Preferred 6 where Q is Q-36.
(47) Compounds of Preferred 6 where Q is Q-37.
(48) Compounds of Preferred 6 where Q is Q-38.
(49) Compounds of Preferred 6 where Q is Q-39.
(50) Compounds of Preferred 6 where Q is Q-40.
(51) Compounds of Preferred 6 where Q is Q-41.
(52) Compounds of Preferred 6 where Q is Q-42.
(53) Compounds of Preferred 6 where Q is Q-43.
(54) Compounds of Preferred 6 where Q is Q-44.
(55) Compounds of Preferred 6 where Q is Q-45.
(56) Compounds of Preferred 6 where Q is Q-46.
(57) Compounds of Preferred 6 where Q is Q-47.
(58) Compounds of Preferred 6 where Q is Q-48.
(59) Compounds of Preferred 6 where Q is Q-49.
(60) Compounds of Preferred 6 where Q is Q-50.
(61) Compounds of Preferred 6 where Q is Q-51.
(62) Compounds of Preferred 6 where Q is Q-52.
(63) Compounds of Preferred 6 where Q is Q-53.
(64) Compounds of Preferred 6 where Q is Q-54.
(65) Compounds of Preferred 6 where Q is Q-55.
(66) Compounds of Preferred 6 where Q is Q-56.
(67) Compounds of Preferred 6 where Q is Q-57.
(68) Compounds of Preferred 6 where Q is Q-58.
(69) Compounds of Preferred 6 where Q is Q-59.
(70) Compounds of Preferred 6 where Q is Q-60.
(71) Compounds of Preferred 6 where Q is Q-61.
(72) Compounds of Preferred 6 where Q is Q-62.
(73) Compounds of Preferred 6 where Q is Q-63.
(74) Compounds of Preferred 6 where Q is Q-64.
(75) Compounds of Preferred 6 where Q is Q-65.
(76) Compounds of Preferred 6 where Q is Q-66.
(77) Compounds of Preferred 6 where Q is Q-67.
(78) Compounds of Preferred 6 where Q is Q-68.
(79) Compounds of Preferred 6 where Q is Q-69.
(80) Compounds of Preferred 6 where Q is Q-70.
(81) Compounds of Preferred 6 where Q is Q-71.
(82) Compounds of Preferred 6 where Q is Q-72.
(83) Compounds of Preferred 6 where Q is Q-73.
(84) Compounds of Preferred 6 where Q is Q-74.
(85) Compounds of Preferred 6 where Q is Q-75.
(86) Compounds of Preferred 6 where Q is Q-76.
(87) Compounds of Preferred 6 where Q is Q-77.
(88) Compounds of Preferred 6 where Q is Q-78.
(89) Compounds of Preferred 6 where Q is Q-79.
(90) Compounds of Preferred 6 where Q is Q-80.
(91) Compounds of Preferred 11 where $W_3$ is O.
(92) Compounds of Preferred 15 where $W_3$ is NH or $NCH_3$.
(93) Compounds of Preferred 17 where $W_4$ is S or $SO_2$.
(94) Compounds of Preferred 18 where $W_4$ is S or $SO_2$.
(95) Compounds of Preferred 26 where $W_3$ is O.
(96) Compounds of Preferred 32 where $W_3$ is NH or $NCH_3$.
(97) Compounds of Preferred 35 where $W_4$ is S or $SO_2$.
(98) Compounds of Preferred 36 where $W_4$ is S or $SO_2$.
(99) Compounds of Preferred 65 where $W_3$ is O.
(100) Compounds of Preferred 71 where $W_3$ is NH or $NCH_3$.
(101) Compounds of Preferred 72 where $W_3$ is NH or $NCH_3$.
(102) Compounds of Preferred 86 where $W_3$ is O.
(103) Compounds of Preferred 87 where $W_3$ is O.

Specifically Preferred for reasons of greatest ease of synthesis and/or greatest herbicidal efficacy are:

N-[(4,6-dimethoxypyrimidin-2-yl)aminocarbonyl]-2-2-[(2-oxotetrahydro-3-furanylidene)methyl]benzenesulfonamide, m.p. 185°–190° C.; and N-[(4-methoxy-6-methyltriazin-2-yl)aminocarbonyl]-2-[(2-oxotetrahydro-3-furanylidene)methyl]-3-chlorobenzenesulfonamide, m.p. 185°–190° C.(d).

DETAILED DESCRIPTION OF THE INVENTION

Synthesis

Compounds of Formula I can be synthesized by one or more of the methods shown below in Equations 1, 2, and 3.

Equation 1 illustrates the reaction of sulfonyl isocyanates II with the appropriate heterocyclic amines of Formula III to give the desired sulfonylureas I.

Equation 1

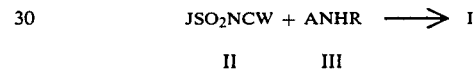

wherein J, R, W and A are as previously defined.

The reaction of Equation 1 is best carried out in an inert aprotic solvent such as methylene chloride, tetrahydrofuran or acetonitrile at a temperature between 0° and 82° C. A catalytic amount of 1,4-diazabicyclo[2,2,2]octane (DABCO) may be used to accelerate the reaction. In cases in which the products are insoluble in the reaction solvent, they may be isolated by simple filtration. When the products are soluble, they can be isolated by evaporation of the solvent and trituration of the residue with solvents such as 1-chlorobutane, diethyl ether or ethyl acetate, and filtration.

Compounds of Formula I can also be prepared as shown below in Equation 2 by treating sulfonamides of Formula IV with the methyl ester of a pyrimidine or triazine carbamic acid of Formula V in the presence of an equimolar quantity of trimethylaluminum.

Equation 2

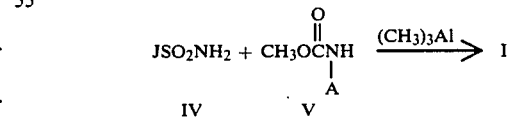

wherein J and A are as previously defined and W is O.

The reaction of Equation 2 is best carried out at temperatures between 25° and 83° C. in a solvent such as methylene chloride or 1,2-dichloroethane for 12 to 96 hours under an inert atmosphere, as taught in European Patent Application (EP-A) No. 83,975 (published July 20, 1983). The products of Formula I are conveniently isolated by acidifying the reaction solution with dilute aqueous hydrochloric acid, and extraction with a suitable solvent such as methylene chloride or ethyl acetate. If necessary, purification can be achieved by recrystallization or column chromatography. The methyl carbamates V can be synthesized by treatment of the corresponding heterocyclic amines of Formula III with dimethyl carbonate or methyl chloroformate in the presence of a base such as sodium hydride or pyridine.

Alternatively, compounds of Formula I can be prepared as shown below in Equation 3 by the reaction of sulfonamides IV with the phenyl ester of the appropriate carbamic acid, VI, in the presence of an equimolar quantity of a tertiary amine base such as 1,8-diazabicyclo[5.4.0]undec-7-ene (DBU).

Equation 3

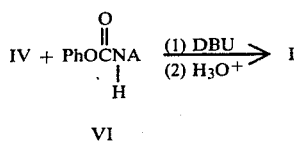

wherein J and A are as previously defined and W is O.

The reaction shown in Equation 3 is best carried out at 25° C. in a solvent such as dioxane or acetonitrile for 1-2 hours under an inert atmosphere as described in European Patent Application No. 70,804 (published Jan. 26, 1983). The desired products of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired products. The phenyl carbamates VI can be synthesized by treatment of the corresponding heterocyclic amines of Formula III with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12-36 hours.

Sulfonyl isocyanates of Formula II can be prepared as shown in Equation 4 by the reaction of sulfonamides of the general structure IV with phosgene in the presence of n-butyl isocyanate and a catalytic amount of 1,4-diazabicyclo[2.2.2]octane (DABCO).

Equation 4

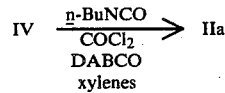

wherein J is as previously defined and W is O.

The reaction depicted in Equation 4 is best carried out according to the procedure described in U.S. Pat. No. 4,238,621.

Alternatively, sulfonyl isocyanates II can be prepared via phosgenation of the preformed n-butylureas of Formula VII as represented in Equation 5.

Equation 5

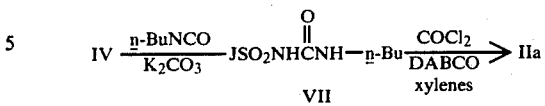

wherein J is as previously defined and W is O.

The compounds of Formula VII are conveniently prepared by stirring a mixture of the appropriate sulfonamide IV, anhydrous potassium carbonate, and n-butyl isocyanate in a suitable solvent such as acetone or methyl ethyl ketone at 25° to 80° C. until all of the isocyanate has reacted. The products are isolated by quenching in dilute aqueous acid and recrystallizing the insoluble solid. The n-butylureas VII are then treated with phosgene and a catalytic amount of DABCO in refluxing xylenes or chlorobenzene in a manner analogous to that described in the reference cited for Equation 4.

Another, somewhat milder, method for the preparation of sulfonyl isocyanates II is shown in Equation 6. Treatment of sulfonamides of Formula IV with thionyl chloride gives intermediate N-sulfinyl sulfonamides VIII, which afford sulfonyl isocyanates II upon exposure to phosgene in the presence of a catalytic amount of pyridine.

Equation 6

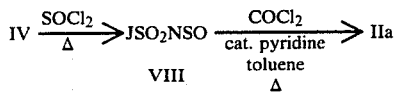

wherein J is as previously defined and W is O.

The reaction of Equation 6 can best be performed according to the procedure of H. Ulrich, B. Tucker, and A. Sayigh, *J. Org. Chem.*, 34, 3200 (1969).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

The required sulfonamides of Formula IV can be synthesized by one or both of the methods shown below in Equations 7 and 8.

Equation 7 depicts the reaction of sulfonyl chlorides of Formula IX with ammonia to give sulfonamides of Formula IV.

Equation 7

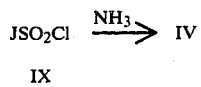

wherein J is as previously defined.

The amination of Equation 7 is conveniently effected by adding at least two molar equivalents of either anhydrous ammonia or concentrated ammonium hydroxide to a solution of the sulfonyl chloride IX in a suitable solvent such as diethyl ether, tetrahydrofuran, or methylene chloride at temperatures between −30° and 25° C. The desired sulfonamides of Formula IV are isolated either by filtration, in which case the by-product ammonium chloride is removed by washing with water, or extraction into a suitable organic solvent such as methylene chloride or ethyl acetate. Drying and evaporation of the solvent then affords the products IV, which are usually sufficiently pure to be carried directly on to the next step.

Sulfonamides of Formula IV can also be prepared as shown in Equation 8 by treatment of the corresponding N-t-butylsulfonamides X with an appropriate acid such as trifluoroacetic (TFA), polyphosphoric (PPA), or p-toluenesulfonic acid (p-TSA).

Equation 8

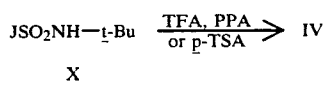

X wherein J is as previously defined.

The reaction of Equation 8 is conveniently carried out by stirring a solution of the compound of Formula X in excess trifluoroacetic acid (approximately 0.3M) at about 25° C. for 1–24 hours. The desired sulfonamides of Formula IV are then isolated by removal of the volatiles in vacuo and crystallization from a suitable solvent such as diethyl ether, 1-chlorobutane, or ethyl acetate. Alternatively, the N-t-butylsulfonamides of Formula X can be treated with a catalytic amount of p-toluenesulfonic acid monohydrate in a solvent such as toluene or xylenes at reflux temperature for 1–6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 39, 566 (1974).

Sulfonyl chlorides of Formula IX can be prepared by one or more of the methods shown below in Equations 9, 10, and 11.

Diazotization of appropriately substituted aniline derivatives of Formula XI as shown in Equation 9, and subsequent coupling with sulfur dioxide in the presence of either cupric or cuprous chloride give the desired products of Formula IX.

Equation 9

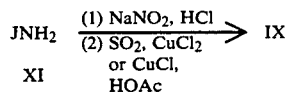

XI wherein J is as previously defined.

The reaction of Equation 9 can be effected by analogous methods described in EP-A Nos. 83,975 and 85,476 (published Aug. 10, 1983). In Equation 9, a substituted aniline XI in concentrated hydrochloric acid is treated with a solution of sodium nitrite in water at −5° to 5° C. After being stirred for 10–30 minutes at about 0° C., the solution is added to a mixture of excess sulfur dioxide and a catalytic amount of cupric or cuprous chloride in acetic acid at about 10° C. After stirring for 0.25 to 24 hours at temperatures between 10° to 25° C., the solution is poured into a large excess of ice water. The sulfonyl chlorides IX can be isolated by filtration, or by extraction into a solvent such as methylene chloride or diethyl ether, followed by drying and evaporation of the solvent.

Sulfonyl chlorides of Formula IX can also be prepared as shown below in Equation 10 by metal halogen exchange or directed lithiation of appropriately substituted aryl or heterocyclic substrates XII, and trapping with sulfuryl chloride.

Equation 10

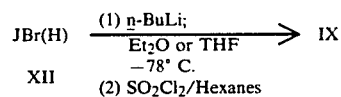

wherein J is as previously described.

The lithiation shown in Equation 10 can be performed according to the procedure of S. H. Bhattacharya, et al., *J. Chem. Soc.* (C), 1265 (1968) or by procedures reviewed by H. Gschwend and H. Rodriguez in *Organic Reactions*, Vol. 26, Wiley: New York, 1979.

Compounds of Formula IX can also be prepared via oxidative chlorination of the appropriate thioethers of Formula XIII as represented in Equation 11.

Equation 11

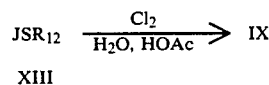

XIII wherein J is as previously defined; and $R_{12}$ is $C_2$–$C_4$ alkyl or benzyl.

The reaction of Equation 11 can be carried out by treating a solution of the thioether XIII in a solvent such as acetic acid in the presence of at least 2.5 equivalents of water and at least 3.0 equivalents of chlorine at 0°–30° C. for 0.25 to 5 hours. The reaction is poured into ice water and the product is isolated by extraction with a suitable solvent such as methylene chloride, dried, and the solvent evaporated to yield a product sufficiently pure to be carried directly on to the next step.

The requisite aniline derivatives of Formula XI can be prepared by reduction of the corresponding nitro compounds of Formula XV as depicted in Equation 12.

Equation 12

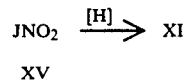

XV wherein J is as previously described.

The reduction reactions of Equation 12 can be accomplished by methods known in the literature by those skilled in the art. For details see, for example, EP-A No. 83,975.

The required thioethers of Formula XIII can be prepared by nucleophilic displacement of activated halo or nitro compounds of Formula XVI by the sodium or potassium salt of the appropriate mercaptan as depicted in Equation 13.

Equation 13

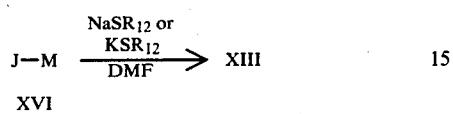

wherein J is as previously defined; $R_{12}$ is $C_2$–$C_4$ alkyl or benzyl; and M is Cl, Br or $NO_2$.

The reaction of Equation 13 can be accomplished by the addition of compounds of Formula XVI to a solution of the mercaptide salt, prepared by the action of a base such as sodium hydroxide or potassium t-butoxide on the corresponding mercaptan in dimethylformamide, at temperatures between 0° and 100° C. for 1 to 72 hours. The reaction mixture is poured into ice water and the product isolated by filtration or by extraction into a suitable solvent such as diethyl ether or methylene chloride followed by drying and evaporation of the solvent. If necessary, purification can be effected by recrystallization, vacuum distillation or chromatographic procedures.

The N-t-butylsulfonamides of Formula Xa can be synthesized by one or more of the methods shown below in Equations 14–21 which depict specific examples where J is $J_1$ but are also applicable to $J_2$–$J_5$.

Direct carbon-carbon double bond formation can be achieved for the synthesis of sulfonamides of Formula Xa where $R_3 \neq Cl$ or Br, as depicted in Equation 14, via the Wittig and related reactions such as the Horner. Wadsworth, Emmons olefination, and Peterson olefination reactions which are reviewed by H. O. House in *Modern Synthetic Reactions*, 2nd ed., W. A. Benjamin: Menlo Park, CA, 1972, pp. 682-709; W. Carruthers in *Some Modern Methods of Organic Synthesis*, 2nd ed., Cambridge: New York, 1978, pp. 106-127 and p. 318; and A. W. Johnson in *Ylid Chemistry*, Academic: London, 1966. In the Wittig reaction shown in Equation 14a, the phosphonium ylid XVIIIa can be reacted with sulfonamide XVII in a variety of organic solvents including benzene, methylene chloride, diethyl ether, tetrahydrofuran, acetonitrile, dimethylsulfoxide, and ethyl alcohol. The mixture is stirred at temperatures between 25° and 100° C. for 1-36 hours followed by aqueous workup and extraction with a solvent such as methylene chloride or diethyl ether. Drying and evaporation of the solvent affords the desired product.

Equation 14a

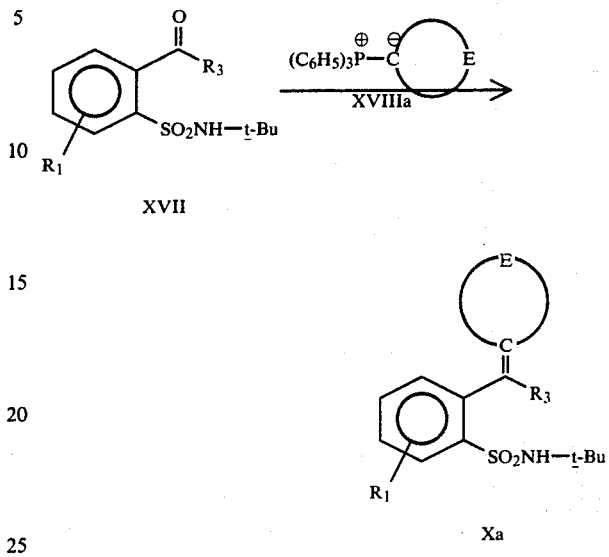

wherein $R_1$, $R_3$, and E are as previously defined except $R_3 \neq Br$, Cl.

Alternatively, sulfonamide XVII can be reacted with carbon nucleophiles of General Formula XVIIIb such as in the Aldol and related reactions, and with organometallic reagents such as alkyllithiums or Grignard reagents as depicted in Equation 14b. A general review of the additions of carbon nucleophiles to carbonyl compounds is available by C. D. Gutsche in *The Chemistry of Carbonyl Compounds*, Prentice Hall: Englewood Cliffs, NJ, 1967, pp. 71-99. For related examples, see also the previously mentioned H. O. House reference, pp. 629-682 and 817-818, and the W. Carruthers reference, pp. 52-71. Specific methods of formation and reactions of Grignard reagents can also be found in M. S. Kharasch and O. Reinmuth, *Grignard Reactions of Non-Metallic Substances*, Prentice Hall: Englewood Cliffs, NJ, 1954, pp. 5-91 and 138-528. The intermediate carbinol XIX can be dehydrated with a great variety of dehydrating agents to the unsaturated sulfonamide Xa. Acids such as sulfuric, oxalic, or phosphoric, bases such as potassium hydroxide, and other reagents such as phosphorous oxychloride or thionyl chloride can be used. For references to these procedures, see C. A. Buehler and D. E. Pearson in *Survey of Organic Syntheses*, Wiley: New York, 1970, p. 71.

Equation 14b

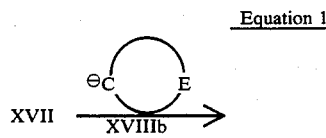

-continued
Equation 14b

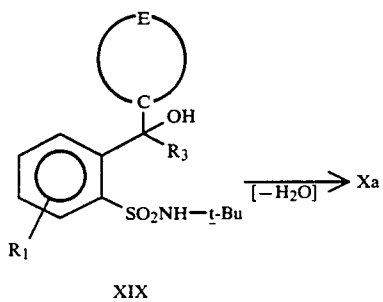

XIX wherein $R_1$, $R_3$, and E are as previously defined except $R_3 \neq Cl$, Br.

The usual starting materals for the preparation of the phosphonium ylids XVIIIa and the carbon nucleophiles of Formula XVIIIb are shown in Equation 15. Compounds of Formula XVIIIc and XVIIId are believed to be either known in the art or capable of being prepared by those skilled in the art. Methods for their conversion to the phosphonium ylids or carbon nucleophiles can be found in the references cited in Equations 14a and 14b.

Equation 15

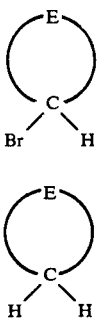

XVIIIc

XVIIId wherein
  E is as previously defined; and
  Br can be replaced by Cl or I.

Sulfonamides Xa can also be synthesized by the reaction of the dianions of either sulfonamide XX or XXI with an appropriately substituted carbonyl group such as XVIIIe or XVIIIf, respectively, as shown in Equation 16, followed by dehydration of the intermediate carbinols XIX or XXII as described in Equation 14b. The lithiations shown can be performed according to procedures reviewed by H. Rodriguez in *Organic Reactions*, Vol. 26, Wiley: New York, 1979, or according to the procedure of J. G. Lombardino, *J. Org. Chem.*, 36, 1843 (1971). See also D. E. Butler and H. A. Dewald, *J. Org. Chem.*, 36, 2542–2547 (1971) for a discussion of the metallation of substituted pyrazoles.

Equation 16

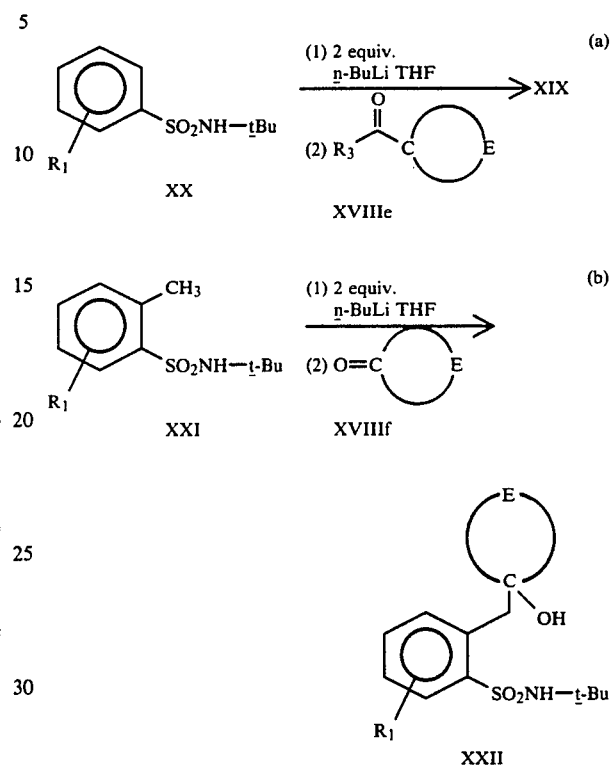

XIX or XXII $\xrightarrow[{[-H_2O]}]{}$ Xa wherein $R_1$, $R_3$, and E are as previously defined except $R_3 \neq Cl$, Br.

Carbonyl compounds of Formula XVIIIe and XVIIIf are either known in the art or are capable of being prepared by those skilled in the art.

The synthesis of sulfonamide XVIIb where $R_3 = C_1-C_4$ alkyl is depicted in Equation 17. Aldehyde XVIIa, which exists mostly as its cyclic tautomer but nonetheless also undergoes the reactions described previously in Equations 14a and 14b, can be treated with a $C_1-C_4$ alkyl organometallic reagent such as a Grignard or alkyllithium as described in Equation 14b, and the intermediate carbinol XXIII can be oxidized to the ketone XVIIb. A variety of oxidation procedures can be used, such as pyridinium chlorochromate as described by E. J. Corey and J. W. Suggs, *Tetrahedron Lett.*, 2647 (1975); Swern-type oxidations as reviewed by K. Omura and D. Swern, *Tetrahedron*, 34, 1651 (1978); and Jones oxidation as described by M. J. Ashton et al. in *J. Med. Chem.*, 27, 1245 (1984).

Equation 17

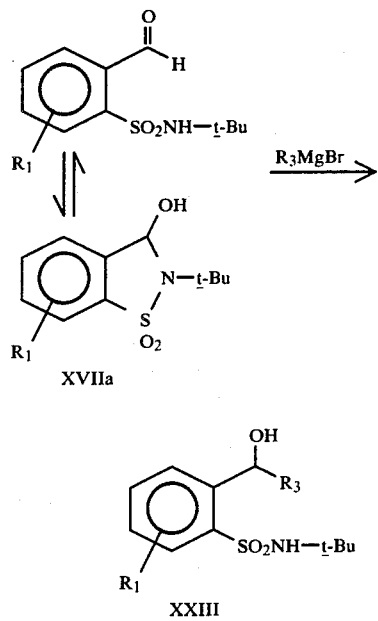

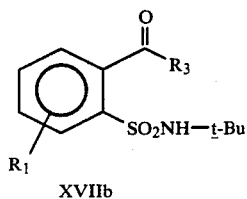

wherein
$R_1$ is as previously defined; and
$R_3$ is $C_1$–$C_4$ alkyl.

Alternatively, as depicted in Equation 18, the intermediate carbinol XIXa from Equation 14b can also be oxidized as described above (if $R_3=H$) to the corresponding ketone XXIV and then reacted with a $C_1$–$C_4$ alkyllithium or Grignard reagent followed by dehydration of the intermediate tertiary carbinol XIXb to sulfonamide Xb.

Equation 18

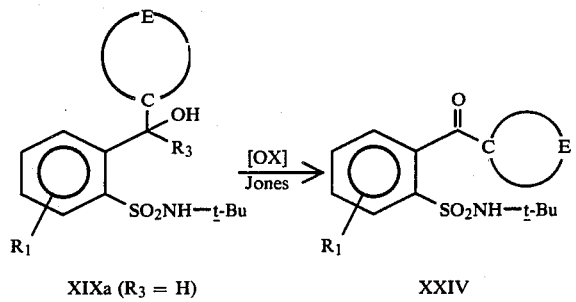

-continued
Equation 18

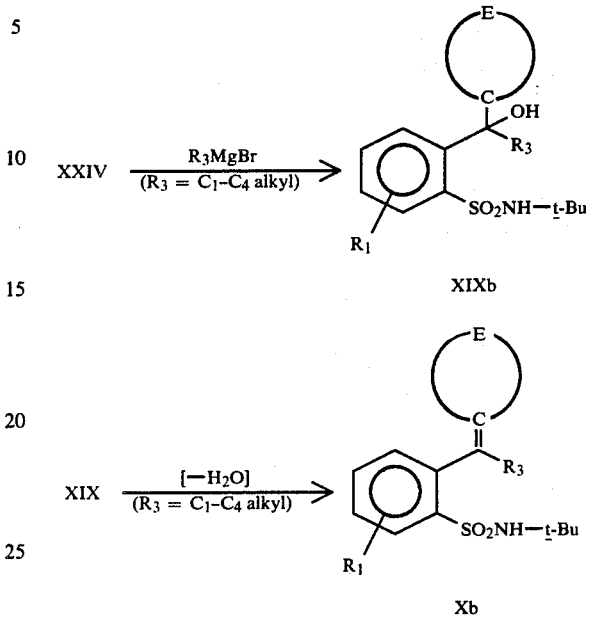

wherein
$R_1$ and E are as previously defined; and
$R_3$ is as defined above.

Aldehyde XVIIa from Equation 17 can be synthesized utilizing the procedure described in Equation 16a by the addition of N,N-dimethylformamide (DMF) to the dianion of sulfonamide XX which affords XVIIa directly as shown in Equation 19.

Equation 19a

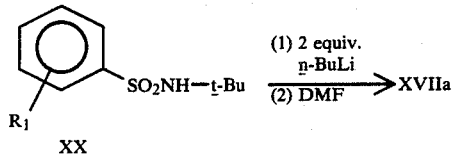

wherein $R_1$ is as previously defined.

The N-t-butylsulfonamides of Formula Xc, where $n=1$ or 2, can be prepared utilizing the intermediate aldehydes XVIIc and XVIId, respectively, as depicted in Equation 19b. The chemistry previously described in Equations 14a, 14b, 17 and 18 can also be applied to convert aldehydes XVIIc and XVIId to sulfonamides Xc. The aldehydes themselves can be prepared via the Wittig reaction (carried out either once or twice as shown) with sulfonamides XVIIa or XVIIb.

Equation 19b

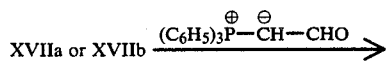

-continued
Equation 19b

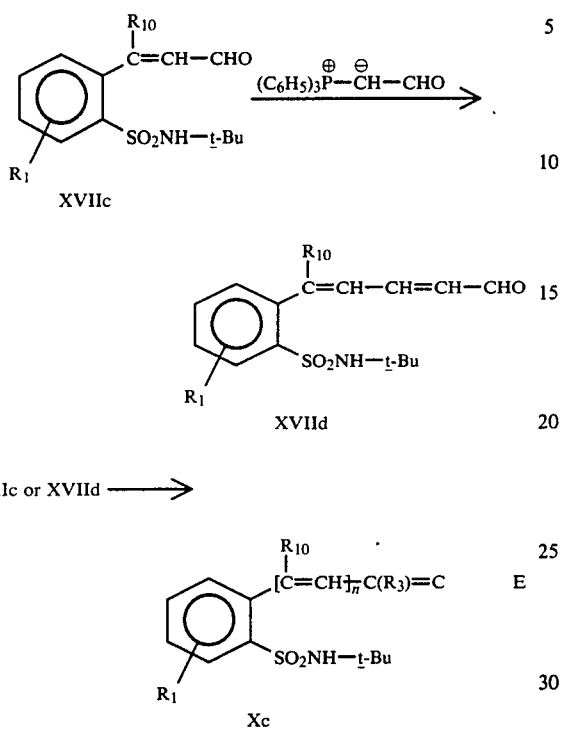

wherein
R$_1$, R$_{10}$ and E are as previously defined;
R$_3$ is H or C$_1$–C$_4$ alkyl; and
n is 1 or 2.

The sulfonamides of Formula Xa where R$_3$=Cl or Br can be synthesized as shown in Equation 20. For example, bromination of sulfonamide Xa where R$_3$=H in a suitable solvent such as carbon tetrachloride or acetic acid provides the dibromo intermediate XXV which can dehydrohalogenate when treated with sodium acetate in refluxing ethyl alcohol to produce the desired sulfonamide XXVI. The halogenation and dehydrohalogenation can be carried out according to the procedures of N. H. Cromwell et al., in *Organic Synthesis Collective Vol. III*, Wiley: New York, 1955, pp. 105–108 and 125–127.

Equation 20

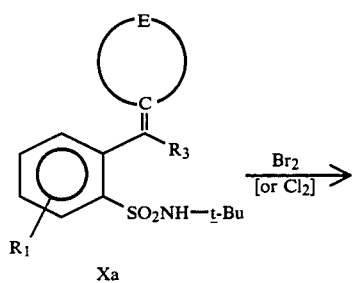

-continued
Equation 20

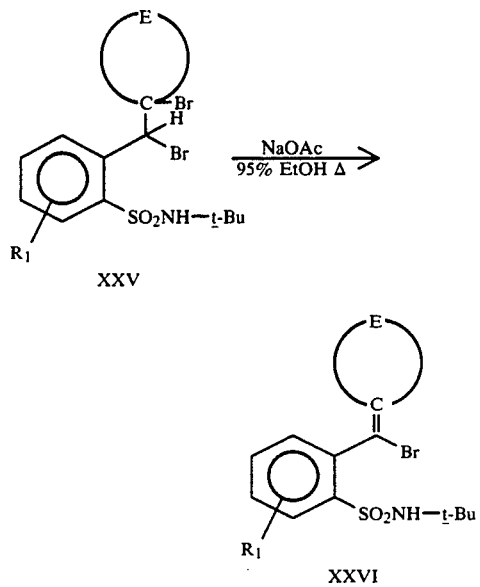

wherein
R$_1$ and E are as previously defined; and
R$_3$ is H.

The reactions described in Equation 20 may be applied to sulfonamide Xc (Equation 19b) when n is 1 or 2, provided that the olefinic bonds not containing R$_3$ (i.e. the —[CR$_{10}$=CH]$_n$ bonds) are suitably protected beforehand by methods known in the art.

One skilled in the art will recognize that many of the procedures described in Equations 14, 16, 18, 19b, and 20 may result in the formation of two possible geometrical isomers about each carbon-carbon double bond, E or Z. This invention is meant to encompass all isomers. In cases where a mixture is obtained, the isomers can be separated by standard methods, such as fractional recrystallization or chromatography. Alternatively, the compounds can be used as a mixture of double bond isomers.

The chemistry described in Equations 14, 17, 18, 19b, and 20 can also be applied to substituted aromatic carbonyl compounds of Formula XXVII as shown in Equation 21. Further elaboration to sulfonamide IV can be carried out by one or more of the methods described in Equations 7–13.

Equation 21

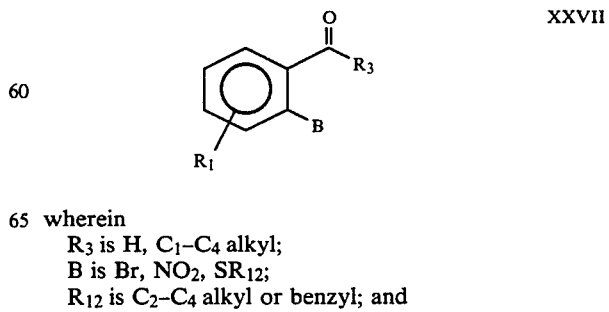

wherein
R$_3$ is H, C$_1$–C$_4$ alkyl;
B is Br, NO$_2$, SR$_{12}$;
R$_{12}$ is C$_2$–C$_4$ alkyl or benzyl; and $R_1$ is as previously defined.

A judicious choice of the appropriate methods for preparing compounds of Formulas I–XXVII can be made by those skilled in the art, taking into account the nature of the substituents contained within the J values ($J_1$–$J_5$), namely Q and $R_1$, and their chemical compatibility with the reaction conditions of Equations 1–21.

The heterocyclic amines of Formula III in Equation 1 above can be prepared by methods known in the literature, or simple modifications thereof, by those skilled in the art. Where A is A-1, EP-A No. 84,224 (published July 27, 1983) describes methods for preparing aminopyrimidines and triazines substituted by acetal groups such as dialkoxymethyl or 1,3-dioxolan-2-yl, among other groups. Also, for example, South African Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$, among other groups. South African Patent Application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

Compounds of Formula III, where A is A-2 or A-3, can be prepared by procedures disclosed in U.S. Pat. No. 4,339,267.

Compounds of Formula III, where A is A-4, can be prepared by methods taught in European Patent Application No. 46,677 (published Mar. 3, 1982).

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in European Patent Application No. 94,260 (published Nov. 16, 1983).

Compounds of Formula III, where A is A-7, can be prepared by methods taught in European Patent Application No. 125,864 (published Nov. 21, 1984).

In addition, general methods for preparing aminopyrimidines and triazines have been reviewed in the following publications;

"The Chemistry of Heterocyclic Compounds", a series published by Wiley-Interscience, Inc., New York and London;

"Pyrimidines", Vol. 16 of the same series by D. J. Brown, 1962;

"s-Triazines and Derivatives", Vol. 13 of the same series by E. M. Smolin and L. Rappoport, 1959; and F. C. Schaefer, U.S. Pat. No. 3,154,547 and K. R. Huffman and F. C. Schaefer, *J. Org. Chem.* 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Temperatures are reported in degrees Celsius; abbreviations for nuclear magnetic resonance (NMR) are: s=singlet, d=doublet, t=triplet, m=multiplet, and peak positions are reported as parts per million downfield from internal tetramethylsilane. Infrared (IR) peak positions are given in reciprocal centimeters ($cm^{-1}$).

EXAMPLE 1

2-(1,1-Dimethylethyl)-2,3-dihydro-1,2-benzisothiazole-3-ol, 1,1-dioxide

To a stirred solution of 45.0 g (0.211 mol) of N-(1,1-dimethylethyl)benzenesulfonamide in 300 mL dry tetrahydrofuran cooled to 0°–10° under nitrogen was added dropwise 277.5 mL (0.444 mol) of 1.6 molar n-butyllithium maintaining the temperature below 20°.

The solution was stirred at room temperature for 2.5 hours during which time a thick precipitate formed. The slurry was cooled to 10°–20° and a solution of 49.1 mL (46.4 g, 0.635 mol) of dimethylformamide in 100-mL dry tetrahydrofuran was added dropwise. The reaction mixture was stirred at room temperature overnight, and was then poured into ice water and acidified with 1N aqueous hydrochloric acid. The layers were separated and the water layer extracted with ether. The combined organic extracts were washed with brine, dried over magnesium sulfate, and evaporated to a yellow solid which was recrystallized (n-chlorobutane) to yield 41.7 g (82%) of the title compound: m.p. 114°–116°; IR (nujol) 3420, 1450, 1370, 1335, 1160, 1150, 1130 $cm^{-1}$; NMR (DMSO-$d_6$ 200 MHz) δ 1.51 (9H, s), 6.06 (1H, m), 6.8 (1H, m), 7.5–8.0 (4H, m).

EXAMPLE 2

N-(1,1-Dimethylethyl)-2-[(2-oxo-tetrahydro-3-furanylidene)methyl]benzenesulfonamide To a stirred suspension of 6.0 g (0.025 mol) of the product of Example 1 in 100 mL methylene chloride was added 9.05 g (0.026 mol) of butyrolactonylidene triphenylphosphorane. The resulting clear solution was stirred at room temperature overnight, and was then poured into water, the layers were separated, and the aqueous layer was extracted with methylene chloride. The combined organic extracts were washed with brine, dried over magnesium sulfate and evaporated to a solid which was washed with hot chlorobutane to yield 6.7 g (87%) of the title compound: m.p. 173°–176°; IR (nujol) 3300, 1760, 1660, 1355, 1330, 1320, 1185, 1155, 1125 cm$^{-1}$; NMR (CDCl$_3$, 200 MHz) δ 1.21, (9H, s), 3.1 (2H, m), 4.4 (2H, t, J=7 Hz), 4.76 (NH, s), 7.4–7.7 (3H, m), 8.1–8.2 (2H, m).

EXAMPLE 3

2-[(2-oxotetrahydro-3-furanylidene)methyl]benzenesulfonamide

A solution of 5.0 g (0.016 mol) of the product of Example 2 in 70 mL trifluoroacetic acid was stirred at room temperature overnight and was then evaporated to yield 3.6 g (88%) of the title compound: m.p. 178°–180°; IR (nujol) 3330, 3230, 3220, 1720, 1640, 1340, 1160 cm$^{-1}$; NMR (DMSO-d$_6$, 200 MHz) δ 3.12 (2H, m), 4.36 (2H, t, J=7 Hz), 7.5–7.7 (3H, m), 7.93 (1H, m), 8.07 (1H, m).

EXAMPLE 4

N-[(4,6-Dimethoxypyrimidin-2-yl)-aminocarbonyl]-2-[(2-oxotetrahydro-3-furanylidene)methyl]benzenesulfonamide To a stirred suspension of 0.09 g (0.0004 mol) of the product of Example 3 and 0.15 g (0.0005 mol) of (4,6-dimethoxy-2-pyrimidinyl)carbamic acid, phenyl ester in 1 mL dry acetonitrile under nitrogen was added dropwise 0.08 mL (0.08 g, 0.0005 mol) of 1,8-diazabicyclo[5.4.0]undec-7-ene. The mixture was stirred at room temperature for 30 min and was then diluted with water and acidified with 1N aqueous hydrochloric acid. The resulting precipitate was collected by filtration and washed well with water and ether to yield 0.1 g (64%) of the title compound: m.p. 185°–190° (gas evolution); IR (nujol) 3180 (br), 1755, 1740, 1710, 1700, 1610, 1560, 1355, 1165 cm$^{-1}$; NMR (CDCl$_3$, 200 MHz) δ 3.05 (2H, m), 4.29 (2H, t, J=7 Hz), 3.99 (6H, s), 5.83 (1H, s), 7.2 (NH, s), 7.4–7.8 (3H, m), 8.1 (1H, m), 8.12 (NH, s), 8.14 (1H, m).

EXAMPLE 5

4-Chloro-2-(1,1-dimethylethyl)-2,3-dihydro-1,2-benzisothiazole-3-ol, 1,1-dioxide To a stirred solution of 23.0 g (0.093 mol) of 3-chloro-N-(1,1-dimethylethyl)benzenesulfonamide in 140 mL dry tetrahydrofuran cooled to 0° under nitrogen was added dropwise 122.4 mL (0.196 mol) of 1.6 molar n-butyllithium maintaining the temperature below 10°. The solution was stirred at 0°–10° for 15 min and then at room temperature for 1 hour. The mixture was cooled back to 0° and a solution of 21.6 mL (20.4 g, 0.280 mol) of dimethylformamide in 45 mL dry tetrahydrofuran was added dropwise. The reaction mixture was stirred at room temperature overnight, and was then poured into ice water and acidified with 3N aqueous hydrochloric acid. The layers were separated and the water layer extracted with ether. The combined organic extracts were washed with brine, dried over magnesium sulfate, and evaporated to a yellow semi-solid which was washed with n-chlorobutane to yield 15.5 g (61%) of the title compound: m.p. 163° (dec); IR (nujol) 3280, 1370, 1140 cm$^{-1}$; NMR (CDCl$_3$, 200 MHz) δ 1.63 (9H, s), 3.1 (OH, d, J=10 Hz), 6.05 (1H, d, J=10 Hz), 7.4–7.7 (3H, m).

EXAMPLE 6

4-Chloro-N-(1,1-dimethylethyl)-2-[(2-oxotetrahydro-3-furanylidene)methyl]benzenesulfonamide To a stirred solution of 5.5 g (0.020 mol) of the product of Example 5 in 100 mL methylene chloride was added 13.8 g (0.040 mol) of butyrolactonylidene triphenylphosphorane and the mixture was refluxed 24 hours. The mixture was cooled to room temperature and then poured into water. The layers were separated and the aqueous layer was extracted with methylene chloride. The combined organic extracts were washed with brine, dried over magnesium sulfate and evaporated to a solid which was purified by flash chromatography (2:1, petroleum ether:ethyl acetate) to yield 2.2 g (32%) of the title compound: m.p. 198°–201°; IR (nujol) 3230, 1760, 1330, 1150 cm$^{-1}$; NMR (CDCl$_3$, 200 MHz) δ 1.24 (9H, s), 2.8 (2H, m), 4.4 (2H, m), 7.3–8.1 (4H, m).

EXAMPLE 7

3-Chloro-2-[(2-oxotetrahydro-3-furanylidene)methyl]-benzenesulfonamide

A solution of 2.1 g (0.0061 mol) of the product of Example 6 in 35 mL trifluoroacetic acid was stirred at room temperature overnight and was then evaporated to yield 1.4 g (80%) of the title compound: m.p. 172°–174°; IR (nujol) 3370, 3230, 1745, 1330, 1320, 1165, 1140 cm$^{-1}$; NMR (DMSO-d$_6$, 200 MHz) δ 2.64 (2H, m), 4.32 (2H, t, J=7 Hz), 7.4–7.9 (4H, m).

EXAMPLE 8

3-Chloro-N-[(4,6-dimethoxypyrimidin-2-yl)aminocarbonyl]-2-[(2-oxotetrahydro-3-furanylidene)methyl]benzenesulfonamide To a stirred suspension of 0.15 g (0.0005 mol) of the product of Example 7 and 0.21 g (0.0008 mol) of (4,6-dimethoxy-2-pyrimidinyl)carbamic acid, phenyl ester in 1 mL dry acetonitrile under nitrogen was added dropwise 0.12 mL (0.12 g, 0.0008 mol) of 1,8-diazabicyclo[5.4.0]undec-7-ene. The mixture was stirred at room temperature for 1 hour and was then diluted with water and acidified with 1N aqueous hydrochloric acid. The resulting precipitate was collected by filtration and washed well with water and ether to yield 0.2 g (83%) of the title compound: m.p. 212°–216° (dec); IR (nujol) 3410, 1765, 1730, 1605, 1365, 1340, 1155 cm$^{-1}$; NMR (CDCl$_3$, 200 MHz) δ 2.7–2.8 (2H, m), 3.94 (6H, s), 4.1–4.2 (2H, m), 5.84 (1H, s), 7.2–7.8 (3H, m), 8.25 (1H, m).

Using the techniques described in Equations 1–21 and Examples 1–8, or simple modifications thereof, one skilled in the art can prepare the following compounds in Tables 1–22.

In Tables 1–22: $R_3$, $R_4$, $R_5$, $R_6$, $R_7$, $R_8$, $R_9$, and $R_{10}$ are independently H unless otherwise noted under Q values.

General Formulas for Tables

General Formula 1
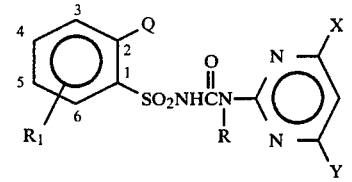

General Formula 2
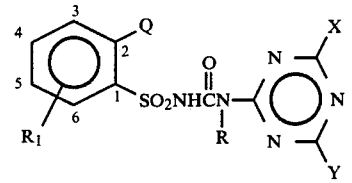

General Formula 3
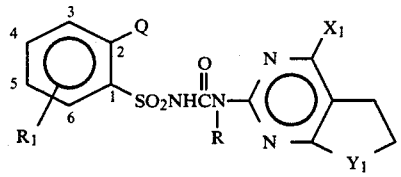

General Formula 4
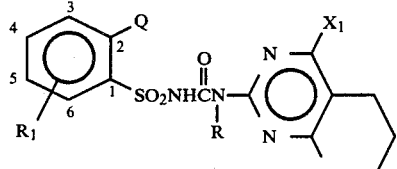

General Formula 5
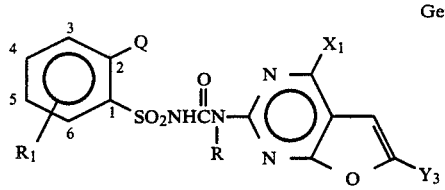

General Formula 6
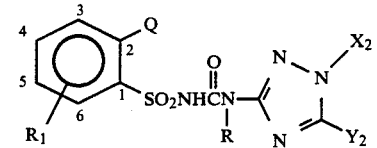

-continued
General Formulas for Tables

General Formula 7
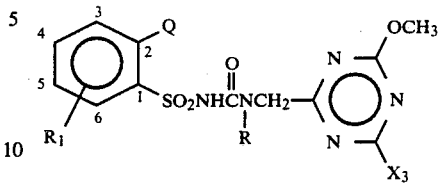

General Formula 8
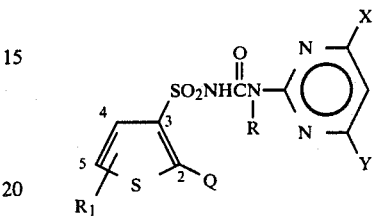

General Formula 9
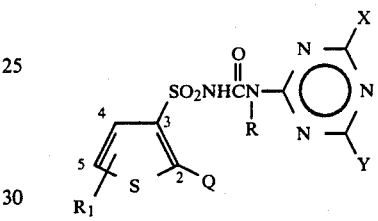

General Formula 10
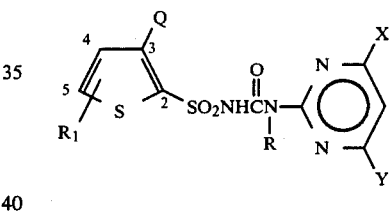

General Formula 11
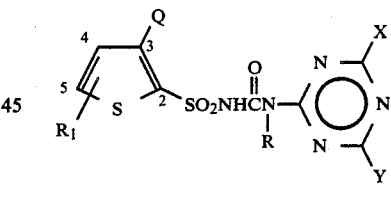

General Formula 12
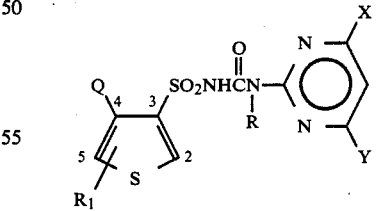

General Formula 13
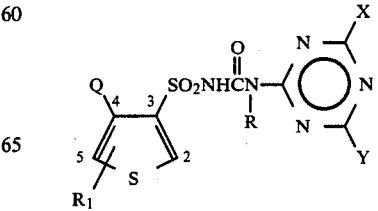

-continued
General Formulas for Tables

General Formula 14

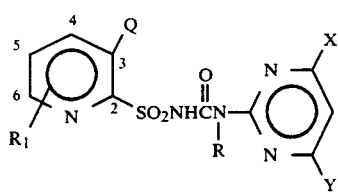

General Formula 15

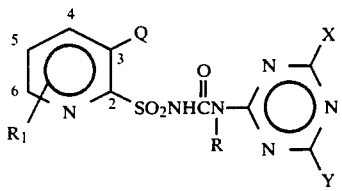

General Formula 16

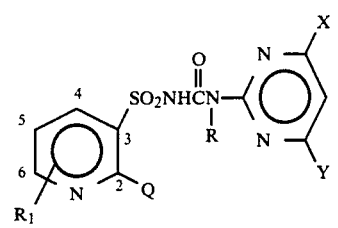

General Formula 17

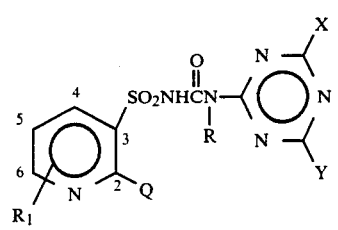

General Formula 18

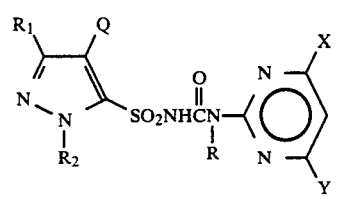

-continued
General Formulas for Tables

General Formula 19

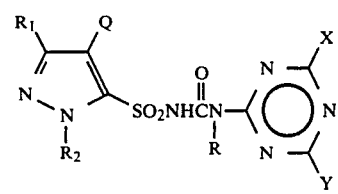

General Formula 20

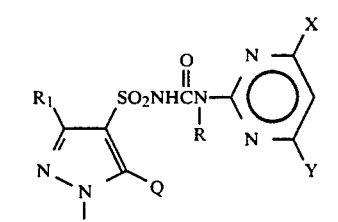

General Formula 21

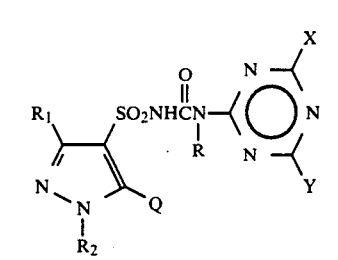

General Formula 22

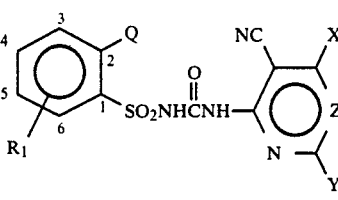

TABLE 1

| | | | | | | | | | |
|---|---|---|---|---|---|---|---|---|---|
| Q | R | $R_1$ | $R_2$ | $R_3$ | $W_3$ | $W_4$ | X | Y | m.p. (°C.) |
| 1 | H | H | | H | O | — | $CH_3$ | $CH_3$ | 198–201 |
| 1 | H | H | | H | O | — | $OCH_3$ | $CH_3$ | 193–203 |
| 1 | H | H | | H | O | — | $OCH_3$ | $OCH_3$ | 185–190 |
| 1 | $CH_3$ | H | | H | O | — | $OCH_3$ | $OCH_3$ | |
| 1 | $CH_3$ | H | | H | O | — | $OCH_3$ | $CH_3$ | |
| 1 | H | H | | $CH_3$ | O | — | $OCH_3$ | $OCH_3$ | |
| 1 | H | H | | $CH_3$ | O | — | $OCH_3$ | $CH_3$ | |
| 1 | H | H | | $CH_3$ | O | — | $CH_3$ | $CH_3$ | |
| 1 | H | 3-Cl | | H | O | — | $CH_3$ | $CH_3$ | 191–197 |
| 1 | H | 3-Cl | | H | O | — | $OCH_3$ | $CH_3$ | 197–199 |
| 1 | H | 3-Cl | | H | O | — | $OCH_3$ | $OCH_3$ | 212–216 |
| 1 | H | 3-Cl | | H | O | — | Cl | $OCH_3$ | 197–210 |
| 1 | $CH_3$ | 3-Cl | | H | O | — | $OCH_3$ | $OCH_3$ | |
| 1 | H | 5-$CH_3$ | | H | O | — | $OCH_3$ | $OCH_3$ | |
| 1 | H | 5-$OCH_3$ | | H | O | — | $OCH_3$ | $OCH_3$ | |
| 1 | H | 5-$OCH_2CH_3$ | | H | O | — | $OCH_3$ | $OCH_3$ | |
| 1 | H | 5-$OCF_2H$ | | H | O | — | $OCH_3$ | $OCH_3$ | |
| 1 | H | 5-$SCH_3$ | | H | O | — | $OCH_3$ | $OCH_3$ | |
| 1 | H | 5-$NHCH_3$ | | H | O | — | $OCH_3$ | $OCH_3$ | |
| 1 | H | 5-$N(CH_3)_2$ | | H | O | — | $OCH_3$ | $OCH_3$ | |

TABLE 1-continued

General Formula 1

| Q | R | $R_1$ | $R_2$ | $R_3$ | $W_3$ | $W_4$ | X | Y | m.p. (°C.) |
|---|---|---|---|---|---|---|---|---|---|
| 1 | H | 5-Cl | | H | O | — | $OCH_3$ | $OCH_3$ | |
| 1 | H | 5-$CF_3$ | | H | O | — | $OCH_3$ | $OCH_3$ | |
| 1 | H | 6-$SO_2N(CH_3)_2$ | | H | O | — | $OCH_3$ | $OCH_3$ | |
| 1 | H | 6-$CO_2CH_3$ | | H | O | — | $OCH_3$ | $OCH_3$ | |
| 1($R_5=CH_3$) | H | H | | H | O | — | $CH_3$ | $CH_3$ | 203–206 |
| 1($R_5=CH_3$) | H | H | | H | O | — | $OCH_3$ | $CH_3$ | 201–203 |
| 1($R_5=CH_3$) | H | H | | H | O | — | $OCH_3$ | $OCH_3$ | 160–163 |
| 1($R_5=CH_3$) | H | H | | H | O | — | Cl | $OCH_3$ | 180–183 |
| 1 | H | 6-$SO_2CH_3$ | | H | O | — | $OCH_3$ | $OCH_3$ | |
| 1 | H | H | | H | O | — | $OCF_2H$ | $OCH_3$ | |
| 1 | H | H | | H | O | — | $CH_2F$ | $OCH_3$ | |
| 1 | H | H | | H | O | — | $CH_2Cl$ | $OCH_3$ | |
| 1 | H | H | | H | O | — | $CF_3$ | $OCH_3$ | |
| 1 | H | H | | H | O | — | $SCH_3$ | $OCH_3$ | |
| 1 | H | H | | H | O | — | Cl | $OCH_3$ | 206–210 |
| 1 | H | H | | H | O | — | $NHCH_3$ | $OCH_2CH_3$ | |
| 1 | H | H | | H | O | — | $OCH_2CH=CH_2$ | $OCH_3$ | |
| 1 | H | H | | H | O | — | $OCH_2C\equiv CH$ | $OCH_3$ | |
| 1 | H | H | | H | O | — | cyclopropyl | $OCH_3$ | |
| 1 | H | H | | H | $NCH_3$ | — | $CH_3$ | $CH_3$ | |
| 1 | H | H | | H | $NCH_3$ | — | $OCH_3$ | $CH_3$ | |
| 1 | H | H | | H | $NCH_3$ | — | $OCH_3$ | $OCH_3$ | |
| 1 | H | H | | H | $NCH_3$ | — | $OCH_3$ | Cl | |
| 1 | H | 5-$OCH_3$ | | H | $NCH_3$ | — | $OCH_3$ | $OCH_3$ | |
| 1 | H | 5-$SCH_3$ | | H | $NCH_3$ | — | $OCH_3$ | $OCH_3$ | |
| 1 | H | H | | H | O | — | $C\equiv CH$ | $OCH_3$ | |
| 1 | H | H | | H | O | — | CHO | $OCH_3$ | |
| 1 | H | H | | H | O | — | 2-methyl-1,3-oxathiolan-2-yl- | $OCH_3$ | |
| 1 | H | H | | H | O | — | 2-methyl-1,3-dithian-2-yl | $OCH_3$ | |
| 1 | H | H | | H | O | — | 1,3-dioxan-2-yl | $OCH_3$ | |
| 2 | H | H | | H | O | — | $CH_3$ | $CH_3$ | |
| 2 | H | H | | H | O | — | $OCH_3$ | $CH_3$ | |
| 2 | H | H | | H | O | — | $OCH_3$ | $OCH_3$ | |
| 2 | H | H | | H | O | — | Cl | $OCH_3$ | |
| 2 | H | 5-$OCH_3$ | | H | O | — | $OCH_3$ | $OCH_3$ | |
| 2 | H | 5-$SCH_3$ | | H | O | — | $OCH_3$ | $OCH_3$ | |
| 2 | H | H | | H | $NCH_3$ | — | $CH_3$ | $CH_3$ | |
| 2 | H | H | | H | $NCH_3$ | — | $OCH_3$ | $CH_3$ | |
| 2 | H | H | | H | $NCH_3$ | — | $OCH_3$ | $OCH_3$ | |
| 2 | H | H | | H | $NCH_3$ | — | Cl | $OCH_3$ | |
| 2 | H | 5-$OCH_3$ | | H | $NCH_3$ | — | $OCH_3$ | $OCH_3$ | |
| 2 | H | 5-$SCH_3$ | | H | $NCH_3$ | — | $OCH_3$ | $OCH_3$ | |
| 3 | H | H | | H | — | — | $CH_3$ | $CH_3$ | 186–188 |
| 3 | H | H | | H | — | — | $OCH_3$ | $CH_3$ | 145–150 |
| 3 | H | H | | H | — | — | $OCH_3$ | $OCH_3$ | 146–155 |
| 3 | H | H | | H | — | — | Cl | $OCH_3$ | 192–194 |
| 3 | H | 5-$OCH_3$ | | H | — | — | $OCH_3$ | $OCH_3$ | |
| 3 | H | 5-$SCH_3$ | | H | — | — | $OCH_3$ | $OCH_3$ | |
| 4 | H | H | | H | — | — | $CH_3$ | $CH_3$ | |
| 4 | H | H | | H | — | — | $OCH_3$ | $CH_3$ | |
| 4 | H | H | | H | — | — | $OCH_3$ | $OCH_3$ | |
| 4 | H | H | | H | — | — | Cl | $OCH_3$ | |
| 4 | H | 5-$OCH_3$ | | H | — | — | $OCH_3$ | $OCH_3$ | |
| 4 | H | 5-$SCH_3$ | | H | — | — | $OCH_3$ | $OCH_3$ | |
| 5 | H | H | | H | $NCH_3$ | — | $CH_3$ | $CH_3$ | |
| 5 | H | H | | H | $NCH_3$ | — | $OCH_3$ | $CH_3$ | |
| 5 | H | H | | H | $NCH_3$ | — | $OCH_3$ | $OCH_3$ | |
| 5 | H | H | | H | $NCH_3$ | — | Cl | $OCH_3$ | |
| 5 | H | 5-$OCH_3$ | | H | $NCH_3$ | — | $OCH_3$ | $OCH_3$ | |
| 5 | H | 5-$SCH_3$ | | H | $NCH_3$ | — | $OCH_3$ | $OCH_3$ | |
| 5 | H | H | | H | O | — | $CH_3$ | $CH_3$ | |
| 5 | H | H | | H | O | — | $OCH_3$ | $CH_3$ | |
| 5 | H | H | | H | O | — | $OCH_3$ | $OCH_3$ | |
| 5 | H | H | | H | O | — | Cl | $OCH_3$ | |
| 5 | H | 5-$OCH_3$ | | H | O | — | $OCH_3$ | $OCH_3$ | |
| 5 | H | 5-$SCH_3$ | | H | O | — | $OCH_3$ | $OCH_3$ | |
| 6 | H | H | | H | O | — | $CH_3$ | $CH_3$ | |
| 6 | H | H | | H | O | — | $OCH_3$ | $CH_3$ | |
| 6 | H | H | | H | O | — | $OCH_3$ | $OCH_3$ | |
| 6 | H | H | | H | O | — | Cl | $OCH_3$ | |
| 6 | H | 5-$OCH_3$ | | H | O | — | $OCH_3$ | $OCH_3$ | |
| 6 | H | 5-$SCH_3$ | | H | O | — | $OCH_3$ | $OCH_3$ | |
| 6 | H | H | | H | $NCH_3$ | — | $CH_3$ | $CH_3$ | |
| 6 | H | H | | H | $NCH_3$ | — | $OCH_3$ | $CH_3$ | |
| 6 | H | H | | H | $NCH_3$ | — | $OCH_3$ | $OCH_3$ | |

TABLE 1-continued

General Formula 1

| Q | R | R$_1$ | R$_2$ | R$_3$ | W$_3$ | W$_4$ | X | Y | m.p. (°C.) |
|---|---|---|---|---|---|---|---|---|---|
| 6 | H | H | | H | NCH$_3$ | — | Cl | OCH$_3$ | |
| 6 | H | 5-OCH$_3$ | | H | NCH$_3$ | — | OCH$_3$ | OCH$_3$ | |
| 6 | H | 5-SCH$_3$ | | H | NCH$_3$ | — | OCH$_3$ | OCH$_3$ | |
| 7 | H | H | | H | — | S | CH$_3$ | CH$_3$ | |
| 7 | H | H | | H | — | S | OCH$_3$ | CH$_3$ | |
| 7 | H | H | | H | — | S | OCH$_3$ | OCH$_3$ | |
| 7 | H | H | | H | — | S | Cl | OCH$_3$ | |
| 7 | H | 5-OCH$_3$ | | H | — | S | OCH$_3$ | OCH$_3$ | |
| 7 | H | 5-SCH$_3$ | | H | — | S | OCH$_3$ | OCH$_3$ | |
| 7 | H | H | | H | — | SO$_2$ | CH$_3$ | CH$_3$ | |
| 7 | H | H | | H | — | SO$_2$ | OCH$_3$ | CH$_3$ | |
| 7 | H | H | | H | — | SO$_2$ | OCH$_3$ | OCH$_3$ | |
| 7 | H | H | | H | — | SO$_2$ | Cl | OCH$_3$ | |
| 7 | H | 5-OCH$_3$ | | H | — | SO$_2$ | OCH$_3$ | OCH$_3$ | |
| 7 | H | 5-SCH$_3$ | | H | — | SO$_2$ | OCH$_3$ | OCH$_3$ | |
| 8 | H | H | | H | — | S | CH$_3$ | CH$_3$ | |
| 8 | H | H | | H | — | S | OCH$_3$ | CH$_3$ | |
| 8 | H | H | | H | — | S | OCH$_3$ | OCH$_3$ | |
| 8 | H | H | | H | — | S | Cl | OCH$_3$ | |
| 8 | H | 5-OCH$_3$ | | H | — | S | OCH$_3$ | OCH$_3$ | |
| 8 | H | 5-SCH$_3$ | | H | — | S | OCH$_3$ | OCH$_3$ | |
| 8 | H | H | | H | — | SO$_2$ | CH$_3$ | CH$_3$ | |
| 8 | H | H | | H | — | SO$_2$ | OCH$_3$ | CH$_3$ | |
| 8 | H | H | | H | — | SO$_2$ | OCH$_3$ | OCH$_3$ | |
| 8 | H | H | | H | — | SO$_2$ | Cl | OCH$_3$ | |
| 8 | H | 5-OCH$_3$ | | H | — | SO$_2$ | OCH$_3$ | OCH$_3$ | |
| 8 | H | 5-SCH$_3$ | | H | — | SO$_2$ | OCH$_3$ | OCH$_3$ | |
| 9(R$_6$=CH$_3$) | H | H | | H | — | — | CH$_3$ | CH$_3$ | |
| 9(R$_6$=CH$_3$) | H | H | | H | — | — | OCH$_3$ | CH$_3$ | |
| 9(R$_6$=CH$_3$) | H | H | | H | — | — | OCH$_3$ | OCH$_3$ | |
| 9(R$_6$=CH$_3$) | H | H | | H | — | — | Cl | OCH$_3$ | |
| 9(R$_6$=CH$_3$) | H | 5-OCH$_3$ | | H | — | — | OCH$_3$ | OCH$_3$ | |
| 9(R$_6$=CH$_3$) | H | 5-SCH$_3$ | | H | — | — | OCH$_3$ | OCH$_3$ | |
| 10 | H | H | | H | — | — | CH$_3$ | CH$_3$ | |
| 10 | H | H | | H | — | — | OCH$_3$ | CH$_3$ | |
| 10 | H | H | | H | — | — | OCH$_3$ | OCH$_3$ | |
| 10 | H | H | | H | — | — | Cl | OCH$_3$ | |
| 10 | H | 5-OCH$_3$ | | H | — | — | OCH$_3$ | OCH$_3$ | |
| 10 | H | 5-SCH$_3$ | | H | — | — | OCH$_3$ | OCH$_3$ | |
| 11 | H | H | | H | — | O | CH$_3$ | CH$_3$ | |
| 11 | H | H | | H | — | O | OCH$_3$ | CH$_3$ | |
| 11 | H | H | | H | — | O | OCH$_3$ | OCH$_3$ | |
| 11 | H | H | | H | — | O | Cl | OCH$_3$ | |
| 11 | H | 5-OCH$_3$ | | H | — | O | OCH$_3$ | OCH$_3$ | |
| 11 | H | 5-SCH$_3$ | | H | — | O | OCH$_3$ | OCH$_3$ | |
| 11 | H | H | | H | — | S | CH$_3$ | CH$_3$ | |
| 11 | H | H | | H | — | S | OCH$_3$ | CH$_3$ | |
| 11 | H | H | | H | — | S | OCH$_3$ | OCH$_3$ | |
| 11 | H | H | | H | — | S | Cl | OCH$_3$ | |
| 11 | H | 5-OCH$_3$ | | H | — | S | OCH$_3$ | OCH$_3$ | |
| 11 | H | 5-SCH$_3$ | | H | — | S | OCH$_3$ | OCH$_3$ | |
| 12(R$_6$=CH$_3$) | H | H | | H | — | — | CH$_3$ | CH$_3$ | |
| 12(R$_6$=CH$_3$) | H | H | | H | — | — | OCH$_3$ | CH$_3$ | |
| 12(R$_6$=CH$_3$) | H | H | | H | — | — | OCH$_3$ | OCH$_3$ | |
| 12(R$_6$=CH$_3$) | H | H | | H | — | — | Cl | OCH$_3$ | |
| 12(R$_6$=CH$_3$) | H | 5-OCH$_3$ | | H | — | — | OCH$_3$ | OCH$_3$ | |
| 12(R$_6$=CH$_3$) | H | 5-SCH$_3$ | | H | — | — | OCH$_3$ | OCH$_3$ | |
| 13 | H | H | | H | — | S | CH$_3$ | CH$_3$ | |
| 13 | H | H | | H | — | S | OCH$_3$ | CH$_3$ | |
| 13 | H | H | | H | — | S | OCH$_3$ | OCH$_3$ | |
| 13 | H | H | | H | — | S | Cl | OCH$_3$ | |
| 13 | H | 5-OCH$_3$ | | H | — | S | OCH$_3$ | OCH$_3$ | |
| 13 | H | 5-SCH$_3$ | | H | — | S | OCH$_3$ | OCH$_3$ | |
| 13 | H | H | | H | — | SO$_2$ | CH$_3$ | CH$_3$ | |
| 13 | H | H | | H | — | SO$_2$ | OCH$_3$ | CH$_3$ | |
| 13 | H | H | | H | — | SO$_2$ | OCH$_3$ | OCH$_3$ | |
| 13 | H | H | | H | — | SO$_2$ | Cl | OCH$_3$ | |
| 13 | H | 5-OCH$_3$ | | H | — | SO$_2$ | OCH$_3$ | OCH$_3$ | |
| 13 | H | 5-SCH$_3$ | | H | — | SO$_2$ | OCH$_3$ | OCH$_3$ | |
| 14 | H | H | | H | — | O | CH$_3$ | CH$_3$ | |
| 14 | H | H | | H | — | O | OCH$_3$ | CH$_3$ | |
| 14 | H | H | | H | — | O | OCH$_3$ | OCH$_3$ | |
| 14 | H | H | | H | — | O | Cl | OCH$_3$ | |
| 14 | H | 5-OCH$_3$ | | H | — | O | OCH$_3$ | OCH$_3$ | |
| 14 | H | 5-SCH$_3$ | | H | — | O | OCH$_3$ | OCH$_3$ | |
| 15 | H | H | | H | — | — | CH$_3$ | CH$_3$ | |
| 15 | H | H | | H | — | — | OCH$_3$ | CH$_3$ | |
| 15 | H | H | | H | — | — | OCH$_3$ | OCH$_3$ | |
| 15 | H | H | | H | — | — | Cl | OCH$_3$ | |
| 15 | H | 5-OCH$_3$ | | H | — | — | OCH$_3$ | OCH$_3$ | |

TABLE 1-continued

General Formula 1

| Q | R | R₁ | R₂ | R₃ | W₃ | W₄ | X | Y | m.p. (°C.) |
|---|---|---|---|---|---|---|---|---|---|
| 15 | H | 5-SCH₃ | | H | — | — | OCH₃ | OCH₃ | |
| 16 | H | H | | H | O | — | CH₃ | CH₃ | |
| 16 | H | H | | H | O | — | OCH₃ | CH₃ | |
| 16 | H | H | | H | O | — | OCH₃ | OCH₃ | |
| 16 | CH₃ | H | | H | O | — | OCH₃ | OCH₃ | |
| 16 | CH₃ | H | | H | O | — | OCH₃ | CH₃ | |
| 16 | H | H | | CH₃ | O | — | OCH₃ | OCH₃ | |
| 16 | H | H | | CH₃ | O | — | OCH₃ | CH₃ | |
| 16 | H | H | | CH₃ | O | — | CH₃ | CH₃ | |
| 16 | H | 3-Cl | | H | O | — | CH₃ | CH₃ | |
| 16 | H | 3-Cl | | H | O | — | OCH₃ | CH₃ | |
| 16 | H | 3-Cl | | H | O | — | OCH₃ | OCH₃ | |
| 16 | H | 3-Cl | | H | O | — | OCH₃ | Cl | |
| 16 | CH₃ | 3-Cl | | H | O | — | OCH₃ | OCH₃ | |
| 16 | H | 5-CH₃ | | H | O | — | OCH₃ | OCH₃ | |
| 16 | H | 5-OCH₃ | | H | O | — | OCH₃ | OCH₃ | |
| 16 | H | 5-OCH₂CH₃ | | H | O | — | OCH₃ | OCH₃ | |
| 16 | H | 5-OCF₂H | | H | O | — | OCH₃ | OCH₃ | |
| 16 | H | 5-SCH₃ | | H | O | — | OCH₃ | OCH₃ | |
| 16 | H | 5-NHCH₃ | | H | O | — | OCH₃ | OCH₃ | |
| 16 | H | 5-N(CH₃)₂ | | H | O | — | OCH₃ | OCH₃ | |
| 16 | H | 5-Cl | | H | O | — | OCH₃ | OCH₃ | |
| 16 | H | 5-CF₃ | | H | O | — | OCH₃ | OCH₃ | |
| 16 | H | 6-SO₂N(CH₃)₂ | | H | O | — | OCH₃ | OCH₃ | |
| 16 | H | 6-CO₂CH₃ | | H | O | — | OCH₃ | OCH₃ | |
| 16 | H | 6-SO₂CH₃ | | H | O | — | OCH₃ | OCH₃ | |
| 16 | H | H | | H | O | — | OCF₂H | OCH₃ | |
| 16 | H | H | | H | O | — | CH₂F | OCH₃ | |
| 16 | H | H | | H | O | — | CH₂Cl | OCH₃ | |
| 16 | H | H | | H | O | — | CF3 | OCH₃ | |
| 16 | H | H | | H | O | — | SCH₃ | OCH₃ | |
| 16 | H | H | | H | O | — | Cl | OCH₃ | |
| 16 | H | H | | H | O | — | NHCH₃ | OCH₂CH₃ | |
| 16 | H | H | | H | O | — | OCH₂CH=CH₂ | OCH₃ | |
| 16 | H | H | | H | O | — | OCH₂C≡CH | OCH₃ | |
| 16 | H | H | | H | O | — | cyclopropyl | OCH₃ | |
| 16 | H | H | | H | NCH₃ | — | CH₃ | CH₃ | |
| 16 | H | H | | H | NCH₃ | — | OCH₃ | CH₃ | |
| 16 | H | H | | H | NCH₃ | — | OCH₃ | OCH₃ | |
| 16 | H | H | | H | NCH₃ | — | OCH₃ | Cl | |
| 16 | H | 5-OCH₃ | | H | NCH₃ | — | OCH₃ | OCH₃ | |
| 16 | H | 5-SCH₃ | | H | NCH₃ | — | OCH₃ | OCH₃ | |
| 16 | H | H | | H | O | — | C≡CH | OCH₃ | |
| 16 | H | H | | H | O | — | CHO | OCH₃ | |
| 16 | H | H | | H | O | — | 2-methyl-1,3-oxathiolan-2-yl | OCH₃ | |
| 16 | H | H | | H | O | — | 2-methyl-1,3-dithian-2-yl | OCH₃ | |
| 16 | H | H | | H | O | — | 1,3-dioxan-2-yl | OCH₃ | |
| 17 | H | H | | H | O | — | CH₃ | CH₃ | |
| 17 | H | H | | H | O | — | OCH₃ | CH₃ | |
| 17 | H | H | | H | O | — | OCH₃ | OCH₃ | |
| 17 | H | H | | H | O | — | Cl | OCH₃ | |
| 17 | H | 5-OCH₃ | | H | O | — | OCH₃ | OCH₃ | |
| 17 | H | 5-SCH₃ | | H | O | — | OCH₃ | OCH₃ | |
| 17 | H | H | | H | NCH₃ | — | CH₃ | CH₃ | |
| 17 | H | H | | H | NCH₃ | — | OCH₃ | CH₃ | |
| 17 | H | H | | H | NCH₃ | — | OCH₃ | OCH₃ | |
| 17 | H | H | | H | NCH₃ | — | Cl | OCH₃ | |
| 17 | H | 5-OCH₃ | | H | NCH₃ | — | OCH₃ | OCH₃ | |
| 17 | H | 5-SCH₃ | | H | NCH₃ | — | OCH₃ | OCH₃ | |
| 18 | H | H | | H | O | — | CH₃ | CH₃ | |
| 18 | H | H | | H | O | — | OCH₃ | CH₃ | |
| 18 | H | H | | H | O | — | OCH₃ | OCH₃ | |
| 18 | H | H | | H | O | — | Cl | OCH₃ | |
| 18 | H | 5-OCH₃ | | H | O | — | OCH₃ | OCH₃ | |
| 18 | H | 5-SCH₃ | | H | O | — | OCH₃ | OCH₃ | |
| 18 | H | H | | H | NCH₃ | — | CH₃ | CH₃ | |
| 18 | H | H | | H | NCH₃ | — | OCH₃ | CH₃ | |
| 18 | H | H | | H | NCH₃ | — | OCH₃ | OCH₃ | |
| 18 | H | H | | H | NCH₃ | — | Cl | OCH₃ | |
| 18 | H | 5-OCH₃ | | H | NCH₃ | — | OCH₃ | OCH₃ | |
| 18 | H | 5-SCH₃ | | H | NCH₃ | — | OCH₃ | OCH₃ | |
| 19 | H | H | | H | — | — | CH₃ | CH₃ | |
| 19 | H | H | | H | — | — | OCH₃ | CH₃ | |
| 19 | H | H | | H | — | — | OCH₃ | OCH₃ | |
| 19 | H | H | | H | — | — | Cl | OCH₃ | |

TABLE 1-continued

General Formula 1

| Q | R | R$_1$ | R$_2$ | R$_3$ | W$_3$ | W$_4$ | X | Y | m.p. (°C.) |
|---|---|---|---|---|---|---|---|---|---|
| 19 | H | 5-OCH$_3$ | | H | — | — | OCH$_3$ | OCH$_3$ | |
| 19 | H | 5-SCH$_3$ | | H | — | — | OCH$_3$ | OCH$_3$ | |
| 20 | H | H | | H | — | — | CH$_3$ | CH$_3$ | |
| 20 | H | H | | H | — | — | OCH$_3$ | CH$_3$ | |
| 20 | H | H | | H | — | — | OCH$_3$ | OCH$_3$ | |
| 20 | H | H | | H | — | — | Cl | OCH$_3$ | |
| 20 | H | 5-OCH$_3$ | | H | — | — | OCH$_3$ | OCH$_3$ | |
| 20 | H | 5-SCH$_3$ | | H | — | — | OCH$_3$ | OCH$_3$ | |
| 21 | H | H | | H | — | — | CH$_3$ | CH$_3$ | |
| 21 | H | H | | H | — | — | OCH$_3$ | CH$_3$ | |
| 21 | H | H | | H | — | — | OCH$_3$ | OCH$_3$ | |
| 21 | H | H | | H | — | — | Cl | OCH$_3$ | |
| 21 | H | 5-OCH$_3$ | | H | — | — | OCH$_3$ | OCH$_3$ | |
| 21 | H | 5-SCH$_3$ | | H | — | — | OCH$_3$ | OCH$_3$ | |
| 22 | H | H | | H | O | — | CH$_3$ | CH$_3$ | |
| 22 | H | H | | H | O | — | OCH$_3$ | CH$_3$ | |
| 22 | H | H | | H | O | — | OCH$_3$ | OCH$_3$ | |
| 22 | H | H | | H | O | — | Cl | OCH$_3$ | |
| 22 | H | 5-OCH$_3$ | | H | O | — | OCH$_3$ | OCH$_3$ | |
| 22 | H | 5-SCH$_3$ | | H | O | — | OCH$_3$ | OCH$_3$ | |
| 22 | H | H | | H | NCH$_3$ | — | CH$_3$ | CH$_3$ | |
| 22 | H | H | | H | NCH$_3$ | — | OCH$_3$ | CH$_3$ | |
| 22 | H | H | | H | NCH$_3$ | — | OCH$_3$ | OCH$_3$ | |
| 22 | H | H | | H | NCH$_3$ | — | Cl | OCH$_3$ | |
| 22 | H | 5-OCH$_3$ | | H | NCH$_3$ | — | OCH$_3$ | OCH$_3$ | |
| 22 | H | 5-SCH$_3$ | | H | NCH$_3$ | — | OCH$_3$ | OCH$_3$ | |
| 23 | H | H | | H | O | — | CH$_3$ | CH$_3$ | |
| 23 | H | H | | H | O | — | OCH$_3$ | CH$_3$ | |
| 23 | H | H | | H | O | — | OCH$_3$ | OCH$_3$ | |
| 23 | H | H | | H | O | — | Cl | OCH$_3$ | |
| 23 | H | 5-OCH$_3$ | | H | O | — | OCH$_3$ | OCH$_3$ | |
| 23 | H | 5-SCH$_3$ | | H | O | — | OCH$_3$ | OCH$_3$ | |
| 23 | H | H | | H | NCH$_3$ | — | CH$_3$ | CH$_3$ | |
| 23 | H | H | | H | NCH$_3$ | — | OCH$_3$ | CH$_3$ | |
| 23 | H | H | | H | NCH$_3$ | — | OCH$_3$ | OCH$_3$ | |
| 23 | H | H | | H | NCH$_3$ | — | Cl | OCH$_3$ | |
| 23 | H | 5-OCH$_3$ | | H | NCH$_3$ | — | OCH$_3$ | OCH$_3$ | |
| 23 | H | 5-SCH$_3$ | | H | NCH$_3$ | — | OCH$_3$ | OCH$_3$ | |
| 24 | H | H | | H | O | — | CH$_3$ | CH$_3$ | |
| 24 | H | H | | H | O | — | OCH$_3$ | CH$_3$ | |
| 24 | H | H | | H | O | — | OCH$_3$ | OCH$_3$ | |
| 24 | H | H | | H | O | — | Cl | OCH$_3$ | |
| 24 | H | 5-OCH$_3$ | | H | O | — | OCH$_3$ | OCH$_3$ | |
| 24 | H | 5-SCH$_3$ | | H | O | — | OCH$_3$ | OCH$_3$ | |
| 24 | H | H | | H | NCH$_3$ | — | CH$_3$ | CH$_3$ | |
| 24 | H | H | | H | NCH$_3$ | — | OCH$_3$ | CH$_3$ | |
| 24 | H | H | | H | NCH$_3$ | — | OCH$_3$ | OCH$_3$ | |
| 24 | H | H | | H | NCH$_3$ | — | Cl | OCH$_3$ | |
| 24 | H | 5-OCH$_3$ | | H | NCH$_3$ | — | OCH$_3$ | OCH$_3$ | |
| 24 | H | 5-SCH$_3$ | | H | NCH$_3$ | — | OCH$_3$ | OCH$_3$ | |
| 25 | H | H | | H | — | S | CH$_3$ | CH$_3$ | |
| 25 | H | H | | H | — | S | OCH$_3$ | CH$_3$ | |
| 25 | H | H | | H | — | S | OCH$_3$ | OCH$_3$ | |
| 25 | H | H | | H | — | S | Cl | OCH$_3$ | |
| 25 | H | 5-OCH$_3$ | | H | — | S | OCH$_3$ | OCH$_3$ | |
| 25 | H | 5-SCH$_3$ | | H | — | S | OCH$_3$ | OCH$_3$ | |
| 25 | H | H | | H | — | SO$_2$ | CH$_3$ | CH$_3$ | |
| 25 | H | H | | H | — | SO$_2$ | OCH$_3$ | CH$_3$ | |
| 25 | H | H | | H | — | SO$_2$ | OCH$_3$ | OCH$_3$ | |
| 25 | H | H | | H | — | SO$_2$ | Cl | OCH$_3$ | |
| 25 | H | 5-OCH$_3$ | | H | — | SO$_2$ | OCH$_3$ | OCH$_3$ | |
| 25 | H | 5-SCH$_3$ | | H | — | SO$_2$ | OCH$_3$ | OCH$_3$ | |
| 26 | H | H | | H | — | O | CH$_3$ | CH$_3$ | |
| 26 | H | H | | H | — | O | OCH$_3$ | CH$_3$ | |
| 26 | H | H | | H | — | O | OCH$_3$ | OCH$_3$ | |
| 26 | H | H | | H | — | O | Cl | OCH$_3$ | |
| 26 | H | 5-OCH$_3$ | | H | — | O | OCH$_3$ | OCH$_3$ | |
| 26 | H | 5-SCH$_3$ | | H | — | O | OCH$_3$ | OCH$_3$ | |
| 26 | H | H | | H | — | S | CH$_3$ | CH$_3$ | |
| 26 | H | H | | H | — | S | OCH$_3$ | CH$_3$ | |
| 26 | H | H | | H | — | S | OCH$_3$ | OCH$_3$ | |
| 26 | H | H | | H | — | S | Cl | OCH$_3$ | |
| 26 | H | 5-OCH$_3$ | | H | — | S | OCH$_3$ | OCH$_3$ | |
| 26 | H | 5-SCH$_3$ | | H | — | S | OCH$_3$ | OCH$_3$ | |
| 27 | H | H | | H | — | O | CH$_3$ | CH$_3$ | |
| 27 | H | H | | H | — | O | OCH$_3$ | CH$_3$ | |
| 27 | H | H | | H | — | O | OCH$_3$ | OCH$_3$ | |
| 27 | H | H | | H | — | O | Cl | OCH$_3$ | |
| 27 | H | 5-OCH$_3$ | | H | — | O | OCH$_3$ | OCH$_3$ | |
| 27 | H | 5-SCH$_3$ | | H | — | O | OCH$_3$ | OCH$_3$ | |

TABLE 1-continued

General Formula 1

| Q | R | R₁ | R₂ | R₃ | W₃ | W₄ | X | Y | m.p. (°C.) |
|---|---|---|---|---|---|---|---|---|---|
| 27 | H | H | | H | — | S | CH₃ | CH₃ | |
| 27 | H | H | | H | — | S | OCH₃ | CH₃ | |
| 27 | H | H | | H | — | S | OCH₃ | OCH₃ | |
| 27 | H | H | | H | — | S | Cl | OCH₃ | |
| 27 | H | 5-OCH₃ | | H | — | S | OCH₃ | OCH₃ | |
| 27 | H | 5-SCH₃ | | H | — | S | OCH₃ | OCH₃ | |
| 27 | H | H | | H | — | SO₂ | CH₃ | CH₃ | |
| 27 | H | H | | H | — | SO₂ | OCH₃ | CH₃ | |
| 27 | H | H | | H | — | SO₂ | OCH₃ | OCH₃ | |
| 27 | H | H | | H | — | SO₂ | Cl | OCH₃ | |
| 27 | H | 5-OCH₃ | | H | — | SO₂ | OCH₃ | OCH₃ | |
| 27 | H | 5-SCH₃ | | H | — | SO₂ | OCH₃ | OCH₃ | |
| 28(R₆=CH₃) | H | H | | H | — | — | CH₃ | CH₃ | |
| 28(R₆=CH₃) | H | H | | H | — | — | OCH₃ | CH₃ | |
| 28(R₆=CH₃) | H | H | | H | — | — | OCH₃ | OCH₃ | |
| 28(R₆=CH₃) | H | H | | H | — | — | Cl | OCH₃ | |
| 28(R₆=CH₃) | H | 5-OCH₃ | | H | — | — | OCH₃ | OCH₃ | |
| 28(R₆=CH₃) | H | 5-SCH₃ | | H | — | — | OCH₃ | OCH₃ | |
| 29(R₆=CH₃) | H | H | | H | — | — | CH₃ | CH₃ | |
| 29(R₆=CH₃) | H | H | | H | — | — | OCH₃ | CH₃ | |
| 29(R₆=CH₃) | H | H | | H | — | — | OCH₃ | OCH₃ | |
| 29(R₆=CH₃) | H | H | | H | — | — | Cl | OCH₃ | |
| 29(R₆=CH₃) | H | 5-OCH₃ | | H | — | — | OCH₃ | OCH₃ | |
| 29(R₆=CH₃) | H | 5-SCH₃ | | H | — | — | OCH₃ | OCH₃ | |
| 30 | H | H | | H | — | — | CH₃ | CH₃ | |
| 30 | H | H | | H | — | — | OCH₃ | CH₃ | |
| 30 | H | H | | H | — | — | OCH₃ | OCH₃ | |
| 30 | H | H | | H | — | — | Cl | OCH₃ | |
| 30 | H | 5-OCH₃ | | H | — | — | OCH₃ | OCH₃ | |
| 30 | H | 5-SCH₃ | | H | — | — | OCH₃ | OCH₃ | |
| 31 | H | H | | H | — | — | CH₃ | CH₃ | |
| 31 | H | H | | H | — | — | OCH₃ | CH₃ | |
| 31 | H | H | | H | — | — | OCH₃ | OCH₃ | |
| 31 | H | H | | H | — | — | Cl | OCH₃ | |
| 31 | H | 5-OCH₃ | | H | — | — | OCH₃ | OCH₃ | |
| 31 | H | 5-SCH₃ | | H | — | — | OCH₃ | OCH₃ | |
| 32 | H | H | | H | — | — | CH₃ | CH₃ | |
| 32 | H | H | | H | — | — | OCH₃ | CH₃ | |
| 32 | H | H | | H | — | — | OCH₃ | OCH₃ | |
| 32 | H | H | | H | — | — | Cl | OCH₃ | |
| 32 | H | 5-OCH₃ | | H | — | — | OCH₃ | OCH₃ | |
| 32 | H | 5-SCH₃ | | H | — | — | OCH₃ | OCH₃ | |
| 33 | H | H | | H | — | O | CH₃ | CH₃ | |
| 33 | H | H | | H | — | O | OCH₃ | CH₃ | |
| 33 | H | H | | H | — | O | OCH₃ | OCH₃ | |
| 33 | H | H | | H | — | O | Cl | OCH₃ | |
| 33 | H | 5-OCH₃ | | H | — | O | OCH₃ | OCH₃ | |
| 33 | H | 5-SCH₃ | | H | — | O | OCH₃ | OCH₃ | |
| 33 | H | H | | H | — | S | CH₃ | CH₃ | |
| 33 | H | H | | H | — | S | OCH₃ | CH₃ | |
| 33 | H | H | | H | — | S | OCH₃ | OCH₃ | |
| 33 | H | H | | H | — | S | Cl | OCH₃ | |
| 33 | H | 5-OCH₃ | | H | — | S | OCH₃ | OCH₃ | |
| 33 | H | 5-SCH₃ | | H | — | S | OCH₃ | OCH₃ | |
| 34 | H | H | | H | — | O | CH₃ | CH₃ | |
| 34 | H | H | | H | — | O | OCH₃ | CH₃ | |
| 34 | H | H | | H | — | O | OCH₃ | OCH₃ | |
| 34 | H | H | | H | — | O | Cl | OCH₃ | |
| 34 | H | 5-OCH₃ | | H | — | O | OCH₃ | OCH₃ | |
| 34 | H | 5-SCH₃ | | H | — | O | OCH₃ | OCH₃ | |
| 35 | H | H | | H | — | O | CH₃ | CH₃ | |
| 35 | H | H | | H | — | O | OCH₃ | CH₃ | |
| 35 | H | H | | H | — | O | OCH₃ | OCH₃ | |
| 35 | H | H | | H | — | O | Cl | OCH₃ | |
| 35 | H | 5-OCH₃ | | H | — | O | OCH₃ | OCH₃ | |
| 35 | H | 5-SCH₃ | | H | — | O | OCH₃ | OCH₃ | |
| 36 | H | H | | H | — | SO₂ | CH₃ | CH₃ | |
| 36 | H | H | | H | — | SO₂ | OCH₃ | CH₃ | |
| 36 | H | H | | H | — | SO₂ | OCH₃ | OCH₃ | |
| 36 | H | H | | H | — | SO₂ | Cl | OCH₃ | |
| 36 | H | 5-OCH₃ | | H | — | SO₂ | OCH₃ | OCH₃ | |
| 36 | H | 5-SCH₃ | | H | — | SO₂ | OCH₃ | OCH₃ | |
| 37 | H | H | | H | — | S | CH₃ | CH₃ | |
| 37 | H | H | | H | — | S | OCH₃ | CH₃ | |
| 37 | H | H | | H | — | S | OCH₃ | OCH₃ | |
| 37 | H | H | | H | — | S | Cl | OCH₃ | |
| 37 | H | 5-OCH₃ | | H | — | S | OCH₃ | OCH₃ | |
| 37 | H | 5-SCH₃ | | H | — | S | OCH₃ | OCH₃ | |
| 38 | H | H | | H | — | O | CH₃ | CH₃ | |
| 38 | H | H | | H | — | O | OCH₃ | CH₃ | |

TABLE 1-continued

General Formula 1

| Q | R | R₁ | R₂ | R₃ | W₃ | W₄ | X | Y | m.p. (°C.) |
|---|---|---|---|---|---|---|---|---|---|
| 38 | H | H | | H | — | O | OCH₃ | OCH₃ | |
| 38 | H | H | | H | — | O | Cl | OCH₃ | |
| 38 | H | 5-OCH₃ | | H | — | O | OCH₃ | OCH₃ | |
| 38 | H | 5-SCH₃ | | H | — | O | OCH₃ | OCH₃ | |
| 39(R₆=CH₃) | H | H | | H | — | — | CH₃ | CH₃ | |
| 39(R₆=CH₃) | H | H | | H | — | — | OCH₃ | CH₃ | |
| 39(R₆=CH₃) | H | H | | H | — | — | OCH₃ | OCH₃ | |
| 39(R₆=CH₃) | H | H | | H | — | — | Cl | OCH₃ | |
| 39(R₆=CH₃) | H | 5-OCH₃ | | H | — | — | OCH₃ | OCH₃ | |
| 39(R₆=CH₃) | H | 5-SCH₃ | | H | — | — | OCH₃ | OCH₃ | |
| 40(R₆=CH₃) | H | H | | H | — | — | CH₃ | CH₃ | |
| 40(R₆=CH₃) | H | H | | H | — | — | OCH₃ | CH₃ | |
| 40(R₆=CH₃) | H | H | | H | — | — | OCH₃ | OCH₃ | |
| 40(R₆=CH₃) | H | H | | H | — | — | Cl | OCH₃ | |
| 40(R₆=CH₃) | H | 5-OCH₃ | | H | — | — | OCH₃ | OCH₃ | |
| 40(R₆=CH₃) | H | 5-SCH₃ | | H | — | — | OCH₃ | OCH₃ | |
| 41(R₆=CH₃) | H | H | | H | — | — | CH₃ | CH₃ | |
| 41(R₆=CH₃) | H | H | | H | — | — | OCH₃ | CH₃ | |
| 41(R₆=CH₃) | H | H | | H | — | — | OCH₃ | OCH₃ | |
| 41(R₆=CH₃) | H | H | | H | — | — | Cl | OCH₃ | |
| 41(R₆=CH₃) | H | 5-OCH₃ | | H | — | — | OCH₃ | OCH₃ | |
| 41(R₆=CH₃) | H | 5-SCH₃ | | H | — | — | OCH₃ | OCH₃ | |
| 42 | H | H | | H | — | — | CH₃ | CH₃ | |
| 42 | H | H | | H | — | — | OCH₃ | CH₃ | |
| 42 | H | H | | H | — | — | OCH₃ | OCH₃ | |
| 42 | H | H | | H | — | — | Cl | OCH₃ | |
| 42 | H | 5-OCH₃ | | H | — | — | OCH₃ | OCH₃ | |
| 42 | H | 5-SCH₃ | | H | — | — | OCH₃ | OCH₃ | |
| 43 | H | H | | H | — | — | CH₃ | CH₃ | |
| 43 | H | H | | H | — | — | OCH₃ | CH₃ | |
| 43 | H | H | | H | — | — | OCH₃ | OCH₃ | |
| 43 | H | H | | H | — | — | Cl | OCH₃ | |
| 43 | H | 5-OCH₃ | | H | — | — | OCH₃ | OCH₃ | |
| 43 | H | 5-SCH₃ | | H | — | — | OCH₃ | OCH₃ | |
| 44 | H | H | | H | — | — | CH₃ | CH₃ | |
| 44 | H | H | | H | — | — | OCH₃ | CH₃ | |
| 44 | H | H | | H | — | — | OCH₃ | OCH₃ | |
| 44 | H | H | | H | — | — | Cl | OCH₃ | |
| 44 | H | 5-OCH₃ | | H | — | — | OCH₃ | OCH₃ | |
| 44 | H | 5-SCH₃ | | H | — | — | OCH₃ | OCH₃ | |
| 45 | H | H | | H | — | — | CH₃ | CH₃ | |
| 45 | H | H | | H | — | — | OCH₃ | CH₃ | |
| 45 | H | H | | H | — | — | OCH₃ | OCH₃ | |
| 45 | H | H | | H | — | — | Cl | OCH₃ | |
| 45 | H | 5-OCH₃ | | H | — | — | OCH₃ | OCH₃ | |
| 45 | H | 5-SCH₃ | | H | — | — | OCH₃ | OCH₃ | |
| 46 | H | H | | H | NCH₃ | — | CH₃ | CH₃ | |
| 46 | H | H | | H | NCH₃ | — | OCH₃ | CH₃ | |
| 46 | H | H | | H | NCH₃ | — | OCH₃ | OCH₃ | |
| 46 | H | H | | H | NCH₃ | — | Cl | OCH₃ | |
| 46 | H | 5-OCH₃ | | H | NCH₃ | — | OCH₃ | OCH₃ | |
| 46 | H | 5-SCH₃ | | H | NCH₃ | — | OCH₃ | OCH₃ | |
| 47 | H | H | | H | — | O | CH₃ | CH₃ | |
| 47 | H | H | | H | — | O | OCH₃ | CH₃ | |
| 47 | H | H | | H | — | O | OCH₃ | OCH₃ | |
| 47 | H | H | | H | — | O | Cl | OCH₃ | |
| 47 | H | 5-OCH₃ | | H | — | O | OCH₃ | OCH₃ | |
| 47 | H | 5-SCH₃ | | H | — | O | OCH₃ | OCH₃ | |
| 48 | H | H | | H | — | O | CH₃ | CH₃ | |
| 48 | H | H | | H | — | O | OCH₃ | CH₃ | |
| 48 | H | H | | H | — | O | OCH₃ | OCH₃ | |
| 48 | H | H | | H | — | O | Cl | OCH₃ | |
| 48 | H | 5-OCH₃ | | H | — | O | OCH₃ | OCH₃ | |
| 48 | H | 5-SCH₃ | | H | — | O | OCH₃ | OCH₃ | |
| 49 | H | H | | H | — | O | CH₃ | CH₃ | |
| 49 | H | H | | H | — | O | OCH₃ | CH₃ | |
| 49 | H | H | | H | — | O | OCH₃ | OCH₃ | |
| 49 | H | H | | H | — | O | Cl | OCH₃ | |
| 49 | H | 5-OCH₃ | | H | — | O | OCH₃ | OCH₃ | |
| 49 | H | 5-SCH₃ | | H | — | O | OCH₃ | OCH₃ | |
| 50 | H | H | | H | — | O | CH₃ | CH₃ | |
| 50 | H | H | | H | — | O | OCH₃ | CH₃ | |
| 50 | H | H | | H | — | O | OCH₃ | OCH₃ | |
| 50 | H | H | | H | — | O | Cl | OCH₃ | |
| 50 | H | 5-OCH₃ | | H | — | O | OCH₃ | OCH₃ | |
| 50 | H | 5-SCH₃ | | H | — | O | OCH₃ | OCH₃ | |
| 51 | H | H | | H | — | S | CH₃ | CH₃ | |
| 51 | H | H | | H | — | S | OCH₃ | CH₃ | |
| 51 | H | H | | H | — | S | OCH₃ | OCH₃ | |
| 51 | H | H | | H | — | S | Cl | OCH₃ | |

TABLE 1-continued

General Formula 1

| Q | R | R₁ | R₂ | R₃ | W₃ | W₄ | X | Y | m.p. (°C.) |
|---|---|---|---|---|---|---|---|---|---|
| 51 | H | 5-OCH₃ | | H | — | S | OCH₃ | OCH₃ | |
| 51 | H | 5-SCH₃ | | H | — | S | OCH₃ | OCH₃ | |
| 52 | H | H | | H | — | SO₂ | CH₃ | CH₃ | |
| 52 | H | H | | H | — | SO₂ | OCH₃ | CH₃ | |
| 52 | H | H | | H | — | SO₂ | OCH₃ | OCH₃ | |
| 52 | H | H | | H | — | SO₂ | Cl | OCH₃ | |
| 52 | H | 5-OCH₃ | | H | — | SO₂ | OCH₃ | OCH₃ | |
| 52 | H | 5-SCH₃ | | H | — | SO₂ | OCH₃ | OCH₃ | |
| 53 | H | H | | H | — | — | CH₃ | CH₃ | |
| 53 | H | H | | H | — | — | OCH₃ | CH₃ | |
| 53 | H | H | | H | — | — | OCH₃ | OCH₃ | |
| 53 | H | H | | H | — | — | Cl | OCH₃ | |
| 53 | H | 5-OCH₃ | | H | — | — | OCH₃ | OCH₃ | |
| 53 | H | 5-SCH₃ | | H | — | — | OCH₃ | OCH₃ | |
| 54 | H | H | | H | — | O | CH₃ | CH₃ | |
| 54 | H | H | | H | — | O | OCH₃ | CH₃ | |
| 54 | H | H | | H | — | O | OCH₃ | OCH₃ | |
| 54 | H | H | | H | — | O | Cl | OCH₃ | |
| 54 | H | 5-OCH₃ | | H | — | O | OCH₃ | OCH₃ | |
| 54 | H | 5-SCH₃ | | H | — | O | OCH₃ | OCH₃ | |
| 55 | H | H | | H | O | — | CH₃ | CH₃ | |
| 55 | H | H | | H | O | — | OCH₃ | CH₃ | |
| 55 | H | H | | H | O | — | OCH₃ | OCH₃ | |
| 55 | H | H | | H | O | — | Cl | OCH₃ | |
| 55 | H | 5-OCH₃ | | H | O | — | OCH₃ | OCH₃ | |
| 55 | H | 5-SCH₃ | | H | O | — | OCH₃ | OCH₃ | |
| 55 | H | H | | H | NCH₃ | — | CH₃ | CH₃ | |
| 55 | H | H | | H | NCH₃ | — | OCH₃ | CH₃ | |
| 55 | H | H | | H | NCH₃ | — | OCH₃ | OCH₃ | |
| 55 | H | H | | H | NCH₃ | — | Cl | OCH₃ | |
| 55 | H | 5-OCH₃ | | H | NCH₃ | — | OCH₃ | OCH₃ | |
| 55 | H | 5-SCH₃ | | H | NCH₃ | — | OCH₃ | OCH₃ | |
| 56 | H | H | | H | — | — | CH₃ | CH₃ | |
| 56 | H | H | | H | — | — | OCH₃ | CH₃ | |
| 56 | H | H | | H | — | — | OCH₃ | OCH₃ | |
| 56 | H | H | | H | — | — | Cl | OCH₃ | |
| 56 | H | 5-OCH₃ | | H | — | — | OCH₃ | OCH₃ | |
| 56 | H | 5-SCH₃ | | H | — | — | OCH₃ | OCH₃ | |
| 57 | H | H | | H | O | — | CH₃ | CH₃ | |
| 57 | H | H | | H | O | — | OCH₃ | CH₃ | |
| 57 | H | H | | H | O | — | OCH₃ | OCH₃ | |
| 57 | H | H | | H | O | — | Cl | OCH₃ | |
| 57 | H | 5-OCH₃ | | H | O | — | OCH₃ | OCH₃ | |
| 57 | H | 5-SCH₃ | | H | O | — | OCH₃ | OCH₃ | |
| 58 | H | H | | H | — | — | CH₃ | CH₃ | |
| 58 | H | H | | H | — | — | OCH₃ | CH₃ | |
| 58 | H | H | | H | — | — | OCH₃ | OCH₃ | |
| 58 | H | H | | H | — | — | Cl | OCH₃ | |
| 58 | H | 5-OCH₃ | | H | — | — | OCH₃ | OCH₃ | |
| 58 | H | 5-SCH₃ | | H | — | — | OCH₃ | OCH₃ | |
| 59 | H | H | | H | NCH₃ | — | CH₃ | CH₃ | |
| 59 | H | H | | H | NCH₃ | — | OCH₃ | CH₃ | |
| 59 | H | H | | H | NCH₃ | — | OCH₃ | OCH₃ | |
| 59 | H | H | | H | NCH₃ | — | Cl | OCH₃ | |
| 59 | H | 5-OCH₃ | | H | NCH₃ | — | OCH₃ | OCH₃ | |
| 59 | H | 5-SCH₃ | | H | NCH₃ | — | OCH₃ | OCH₃ | |
| 60 | H | H | | H | NCH₃ | — | CH₃ | CH₃ | |
| 60 | H | H | | H | NCH₃ | — | OCH₃ | CH₃ | |
| 60 | H | H | | H | NCH₃ | — | OCH₃ | OCH₃ | |
| 60 | H | H | | H | NCH₃ | — | Cl | OCH₃ | |
| 60 | H | 5-OCH₃ | | H | NCH₃ | — | OCH₃ | OCH₃ | |
| 60 | H | 5-SCH₃ | | H | NCH₃ | — | OCH₃ | OCH₃ | |
| 61 | H | H | | H | NCH₃ | — | CH₃ | CH₃ | |
| 61 | H | H | | H | NCH₃ | — | OCH₃ | CH₃ | |
| 61 | H | H | | H | NCH₃ | — | OCH₃ | OCH₃ | |
| 61 | H | H | | H | NCH₃ | — | Cl | OCH₃ | |
| 61 | H | 5-OCH₃ | | H | NCH₃ | — | OCH₃ | OCH₃ | |
| 61 | H | 5-SCH₃ | | H | NCH₃ | — | OCH₃ | OCH₃ | |
| 62 | H | H | | H | O | — | CH₃ | CH₃ | |
| 62 | H | H | | H | O | — | OCH₃ | CH₃ | |
| 62 | H | H | | H | O | — | OCH₃ | OCH₃ | |
| 62 | H | H | | H | O | — | Cl | OCH₃ | |
| 62 | H | 5-OCH₃ | | H | O | — | OCH₃ | OCH₃ | |
| 62 | H | 5-SCH₃ | | H | O | — | OCH₃ | OCH₃ | |
| 63 | H | H | H | H | — | O | CH₃ | CH₃ | |
| 63 | H | H | H | H | — | O | OCH₃ | CH₃ | |
| 63 | H | H | H | H | — | O | OCH₃ | OCH₃ | |
| 63 | H | H | H | H | — | O | Cl | OCH₃ | |
| 63 | H | 5-OCH₃ | H | H | — | O | OCH₃ | OCH₃ | |
| 63 | H | 5-SCH₃ | H | H | — | O | OCH₃ | OCH₃ | |

TABLE 1-continued

General Formula 1

| Q | R | $R_1$ | $R_2$ | $R_3$ | $W_3$ | $W_4$ | X | Y | m.p. (°C.) |
|---|---|---|---|---|---|---|---|---|---|
| 63 | H | H | H | | — | S | $CH_3$ | $CH_3$ | |
| 63 | H | H | H | | — | S | $OCH_3$ | $CH_3$ | |
| 63 | H | H | H | | — | S | $OCH_3$ | $OCH_3$ | |
| 63 | H | H | H | | — | S | Cl | $OCH_3$ | |
| 63 | H | 5-$OCH_3$ | H | | — | S | $OCH_3$ | $OCH_3$ | |
| 63 | H | 5-$SCH_3$ | H | | — | S | $OCH_3$ | $OCH_3$ | |
| 64 | H | H | H | | — | $SO_2$ | $CH_3$ | $CH_3$ | |
| 64 | H | H | H | | — | $SO_2$ | $OCH_3$ | $CH_3$ | |
| 64 | H | H | H | | — | $SO_2$ | $OCH_3$ | $OCH_3$ | |
| 64 | H | H | H | | — | $SO_2$ | Cl | $OCH_3$ | |
| 64 | H | 5-$OCH_3$ | H | | — | $SO_2$ | $OCH_3$ | $OCH_3$ | |
| 64 | H | 5-$SCH_3$ | H | | — | $SO_2$ | $OCH_3$ | $OCH_3$ | |
| 64 | H | H | H | | — | O | $CH_3$ | $CH_3$ | |
| 64 | H | H | H | | — | O | $OCH_3$ | $CH_3$ | |
| 64 | H | H | H | | — | O | $OCH_3$ | $OCH_3$ | |
| 64 | H | H | H | | — | O | Cl | $OCH_3$ | |
| 64 | H | 5-$OCH_3$ | H | | — | O | $OCH_3$ | $OCH_3$ | |
| 64 | H | 5-$SCH_3$ | H | | — | O | $OCH_3$ | $OCH_3$ | |
| 65 | H | H | H | | — | — | $CH_3$ | $CH_3$ | |
| 65 | H | H | H | | — | — | $OCH_3$ | $CH_3$ | |
| 65 | H | H | H | | — | — | $OCH_3$ | $OCH_3$ | |
| 65 | H | H | H | | — | — | Cl | $OCH_3$ | |
| 65 | H | 5-$OCH_3$ | H | | — | — | $OCH_3$ | $OCH_3$ | |
| 65 | H | 5-$SCH_3$ | H | | — | — | $OCH_3$ | $OCH_3$ | |
| 66 | H | H | H | | O | — | $CH_3$ | $CH_3$ | |
| 66 | H | H | H | | O | — | $OCH_3$ | $CH_3$ | |
| 66 | H | H | H | | O | — | $OCH_3$ | $OCH_3$ | |
| 66 | H | H | H | | O | — | Cl | $OCH_3$ | |
| 66 | H | 5-$OCH_3$ | H | | O | — | $OCH_3$ | $OCH_3$ | |
| 66 | H | 5-$SCH_3$ | H | | O | — | $OCH_3$ | $OCH_3$ | |
| 67 | H | H | H | | $NCH_3$ | — | $CH_3$ | $CH_3$ | |
| 67 | H | H | H | | $NCH_3$ | — | $OCH_3$ | $CH_3$ | |
| 67 | H | H | H | | $NCH_3$ | — | $OCH_3$ | $OCH_3$ | |
| 67 | H | H | H | | $NCH_3$ | — | Cl | $OCH_3$ | |
| 67 | H | 5-$OCH_3$ | H | | $NCH_3$ | — | $OCH_3$ | $OCH_3$ | |
| 67 | H | 5-$SCH_3$ | H | | $NCH_3$ | — | $OCH_3$ | $OCH_3$ | |
| 68 | H | H | H | | — | — | $CH_3$ | $CH_3$ | |
| 68 | H | H | H | | — | — | $OCH_3$ | $CH_3$ | |
| 68 | H | H | H | | — | — | $OCH_3$ | $OCH_3$ | |
| 68 | H | H | H | | — | — | Cl | $OCH_3$ | |
| 68 | H | 5-$OCH_3$ | H | | — | — | $OCH_3$ | $OCH_3$ | |
| 68 | H | 5-$SCH_3$ | H | | — | — | $OCH_3$ | $OCH_3$ | |
| 69 | H | H | H | | — | — | $CH_3$ | $CH_3$ | |
| 69 | H | H | H | | — | — | $OCH_3$ | $CH_3$ | |
| 69 | H | H | H | | — | — | $OCH_3$ | $OCH_3$ | |
| 69 | H | H | H | | — | — | Cl | $OCH_3$ | |
| 69 | H | 5-$OCH_3$ | H | | — | — | $OCH_3$ | $OCH_3$ | |
| 69 | H | 5-$SCH_3$ | H | | — | — | $OCH_3$ | $OCH_3$ | |
| 70 | H | H | H | | O | — | $CH_3$ | $CH_3$ | |
| 70 | H | H | H | | O | — | $OCH_3$ | $CH_3$ | |
| 70 | H | H | H | | O | — | $OCH_3$ | $OCH_3$ | |
| 70 | H | H | H | | O | — | Cl | $OCH_3$ | |
| 70 | H | 5-$OCH_3$ | H | | O | — | $OCH_3$ | $OCH_3$ | |
| 70 | H | 5-$SCH_3$ | H | | O | — | $OCH_3$ | $OCH_3$ | |
| 71 | H | H | H | | $NCH_3$ | — | $CH_3$ | $CH_3$ | |
| 71 | H | H | H | | $NCH_3$ | — | $OCH_3$ | $CH_3$ | |
| 71 | H | H | H | | $NCH_3$ | — | $OCH_3$ | $OCH_3$ | |
| 71 | H | H | H | | $NCH_3$ | — | Cl | $OCH_3$ | |
| 71 | H | 5-$OCH_3$ | H | | $NCH_3$ | — | $OCH_3$ | $OCH_3$ | |
| 71 | H | 5-$SCH_3$ | H | | $NCH_3$ | — | $OCH_3$ | $OCH_3$ | |
| 72 | H | H | H | | $NCH_3$ | — | $CH_3$ | $CH_3$ | |
| 72 | H | H | H | | $NCH_3$ | — | $OCH_3$ | $CH_3$ | |
| 72 | H | H | H | | $NCH_3$ | — | $OCH_3$ | $OCH_3$ | |
| 72 | H | H | H | | $NCH_3$ | — | Cl | $OCH_3$ | |
| 72 | H | 5-$OCH_3$ | H | | $NCH_3$ | — | $OCH_3$ | $OCH_3$ | |
| 72 | H | 5-$SCH_3$ | H | | $NCH_3$ | — | $OCH_3$ | $OCH_3$ | |
| 73 | H | H | H | | $NCH_3$ | — | $CH_3$ | $CH_3$ | |
| 73 | H | H | H | | $NCH_3$ | — | $OCH_3$ | $CH_3$ | |
| 73 | H | H | H | | $NCH_3$ | — | $OCH_3$ | $OCH_3$ | |
| 73 | H | H | H | | $NCH_3$ | — | Cl | $OCH_3$ | |
| 73 | H | 5-$OCH_3$ | H | | $NCH_3$ | — | $OCH_3$ | $OCH_3$ | |
| 73 | H | 5-$SCH_3$ | H | | $NCH_3$ | — | $OCH_3$ | $OCH_3$ | |
| 74 | H | H | H | | — | O | $CH_3$ | $CH_3$ | |
| 74 | H | H | H | | — | O | $OCH_3$ | $CH_3$ | |
| 74 | H | H | H | | — | O | $OCH_3$ | $OCH_3$ | |
| 74 | H | H | H | | — | O | Cl | $OCH_3$ | |
| 74 | H | 5-$OCH_3$ | H | | — | O | $OCH_3$ | $OCH_3$ | |
| 74 | H | 5-$SCH_3$ | H | | — | O | $OCH_3$ | $OCH_3$ | |
| 75 | H | H | H | | — | O | $CH_3$ | $CH_3$ | |
| 75 | H | H | H | | — | O | $OCH_3$ | $CH_3$ | |

TABLE 1-continued

General Formula 1

| Q | R | $R_1$ | $R_2$ | $R_3$ | $W_3$ | $W_4$ | X | Y | m.p. (°C.) |
|---|---|---|---|---|---|---|---|---|---|
| 75 | H | H | H | — | — | O | $OCH_3$ | $OCH_3$ | |
| 75 | H | H | H | — | — | O | Cl | $OCH_3$ | |
| 75 | H | 5-$OCH_3$ | H | — | — | O | $OCH_3$ | $OCH_3$ | |
| 75 | H | 5-$SCH_3$ | H | — | — | O | $OCH_3$ | $OCH_3$ | |
| 76 | H | H | H | — | O | — | $CH_3$ | $CH_3$ | 209–212 |
| 76 | H | H | H | — | O | — | $OCH_3$ | $CH_3$ | 199–201 |
| 76 | H | H | H | — | O | — | $OCH_3$ | $OCH_3$ | 199–212 |
| 76 | H | H | H | — | O | — | Cl | $OCH_3$ | 222–225 |
| 76 | H | 5-$OCH_3$ | H | — | O | — | $OCH_3$ | $OCH_3$ | |
| 76 | H | 5-$SCH_3$ | H | — | O | — | $OCH_3$ | $OCH_3$ | |
| 77 | H | H | H | — | O | — | $CH_3$ | $CH_3$ | |
| 77 | H | H | H | — | O | — | $OCH_3$ | $CH_3$ | 97–104 |
| 77 | H | H | H | — | O | — | $OCH_3$ | $OCH_3$ | 95–103 |
| 77 | H | H | H | — | O | — | Cl | $OCH_3$ | 95–103 |
| 77 | H | 5-$OCH_3$ | H | — | O | — | $OCH_3$ | $OCH_3$ | |
| 77 | H | 5-$SCH_3$ | H | — | O | — | $OCH_3$ | $OCH_3$ | |
| 78 | H | H | H | — | — | — | $CH_3$ | $CH_3$ | |
| 78 | H | H | H | — | — | — | $OCH_3$ | $CH_3$ | |
| 78 | H | H | H | — | — | — | $OCH_3$ | $OCH_3$ | |
| 78 | H | H | H | — | — | — | Cl | $OCH_3$ | |
| 78 | H | 5-$OCH_3$ | H | — | — | — | $OCH_3$ | $OCH_3$ | |
| 78 | H | 5-$SCH_3$ | H | — | — | — | $OCH_3$ | $OCH_3$ | |
| 79 | H | H | H | — | — | — | $CH_3$ | $CH_3$ | 190–192 |
| 79 | H | H | H | — | — | — | $OCH_3$ | $CH_3$ | 130–135 |
| 79 | H | H | H | — | — | — | $OCH_3$ | $OCH_3$ | 224–225 |
| 79 | H | H | H | — | — | — | Cl | $OCH_3$ | 208–210 |
| 79 | H | 5-$OCH_3$ | H | — | — | — | $OCH_3$ | $OCH_3$ | |
| 79 | H | 5-$SCH_3$ | H | — | — | — | $OCH_3$ | $OCH_3$ | |
| 79($R_6=CH_3$) | H | H | H | — | — | — | $CH_3$ | $CH_3$ | 196–197 |
| 79($R_6=CH_3$) | H | H | H | — | — | — | $OCH_3$ | $CH_3$ | 197–198 |
| 79($R_6=CH_3$) | H | H | H | — | — | — | $OCH_3$ | $OCH_3$ | 192–195 |
| 79($R_6=CH_3$) | H | H | H | — | — | — | Cl | $OCH_3$ | 159–165 |
| 79($R_6=CH_3$) | H | 5-$OCH_3$ | H | — | — | — | $OCH_3$ | $OCH_3$ | |
| 79($R_6=CH_3$) | H | 5-$SCH_3$ | H | — | — | — | $OCH_3$ | $OCH_3$ | |
| 80($R_4,R_5=CH_3$) | H | H | H | — | — | — | $CH_3$ | $CH_3$ | |
| 80($R_4,R_5=CH_3$) | H | H | H | — | — | — | $OCH_3$ | $CH_3$ | |
| 80($R_4,R_5=CH_3$) | H | H | H | — | — | — | $OCH_3$ | $OCH_3$ | |
| 80($R_4,R_5=CH_3$) | H | H | H | — | — | — | Cl | $OCH_3$ | |
| 80($R_4,R_5=CH_3$) | H | 5-$OCH_3$ | H | — | — | — | $OCH_3$ | $OCH_3$ | |
| 80($R_4,R_5=CH_3$) | H | 5-$SCH_3$ | H | — | — | — | $OCH_3$ | $OCH_3$ | |

TABLE 2

General Formula 2

| Q | R | $R_1$ | $R_3$ | $W_3$ | $W_4$ | X | Y | m.p. (°C.) |
|---|---|---|---|---|---|---|---|---|
| 1 | H | H | H | O | — | $CH_3$ | $CH_3$ | |
| 1 | H | H | H | O | — | $OCH_3$ | $CH_3$ | 188–193 |
| 1 | H | H | H | O | — | $OCH_3$ | $OCH_3$ | 188–191 |
| 1 | $CH_3$ | H | H | O | — | $OCH_3$ | $OCH_3$ | |
| 1 | $CH_3$ | H | H | O | — | $OCH_3$ | $CH_3$ | |
| 1 | H | H | $CH_3$ | O | — | $OCH_3$ | $OCH_3$ | |
| 1 | H | H | $CH_3$ | O | — | $OCH_3$ | $CH_3$ | |
| 1 | H | H | $CH_3$ | O | — | $CH_3$ | $CH_3$ | |
| 1 | H | 3-Cl | H | O | — | $CH_3$ | $CH_3$ | |
| 1 | H | 3-Cl | H | O | — | $OCH_3$ | $CH_3$ | 185–190 |
| 1 | H | 3-Cl | H | O | — | $OCH_3$ | $OCH_3$ | 194–198 |
| 1 | H | 3-Cl | H | O | — | $OCH_2CH_3$ | $NHCH_3$ | |
| 1 | $CH_3$ | 3-Cl | H | O | — | $OCH_3$ | $OCH_3$ | |
| 1 | H | 5-$CH_3$ | H | O | — | $OCH_3$ | $OCH_3$ | |
| 1 | H | 5-$OCH_3$ | H | O | — | $OCH_3$ | $OCH_3$ | |
| 1 | H | 5-$OCH_2CH_3$ | H | O | — | $OCH_3$ | $OCH_3$ | |
| 1 | H | 5-$OCF_2H$ | H | O | — | $OCH_3$ | $OCH_3$ | |
| 1 | H | 5-$SCH_3$ | H | O | — | $OCH_3$ | $OCH_3$ | |
| 1 | H | 5-$NHCH_3$ | H | O | — | $OCH_3$ | $OCH_3$ | |
| 1 | H | 5-$N(CH_3)_2$ | H | O | — | $OCH_3$ | $OCH_3$ | |
| 1 | H | 5-Cl | H | O | — | $OCH_3$ | $OCH_3$ | |
| 1 | H | 5-$CF_3$ | H | O | — | $OCH_3$ | $OCH_3$ | |
| 1 | H | 6-$SO_2N(CH_3)_2$ | H | O | — | $OCH_3$ | $OCH_3$ | |
| 1 | H | 6-$CO_2CH_3$ | H | O | — | $OCH_3$ | $OCH_3$ | |
| 1 ($R_5=CH_3$) | H | H | H | O | — | $CH_3$ | $CH_3$ | |
| 1 ($R_5=CH_3$) | H | H | H | O | — | $OCH_3$ | $CH_3$ | 188–190 |
| 1 ($R_5=CH_3$) | H | H | H | O | — | $OCH_3$ | $OCH_3$ | 183–186 |
| 1 ($R_5=CH_3$) | H | H | H | O | — | $OCH_2CH_3$ | $NHCH_3$ | 208–210 |
| 1 | H | 6-$SO_2CH_3$ | H | O | — | $OCH_3$ | $OCH_3$ | |
| 1 | H | H | H | O | — | $CH_2F$ | $OCH_3$ | |
| 1 | H | H | H | O | — | $CH_2Cl$ | $OCH_3$ | |
| 1 | H | H | H | O | — | $CF_3$ | $OCH_3$ | |
| 1 | H | H | H | O | — | $SCH_3$ | $OCH_3$ | |

TABLE 2-continued

General Formula 2

| Q | R | $R_1$ | $R_3$ | $W_3$ | $W_4$ | X | Y | m.p. (°C.) |
|---|---|---|---|---|---|---|---|---|
| 1 | H | H | H | O | — | $NHCH_3$ | $OCH_2CH_3$ | 238–240 |
| 1 | H | H | H | O | — | $OCH_2CH=CH_2$ | $OCH_3$ | |
| 1 | H | H | H | O | — | $OCH_2C\equiv CH$ | $OCH_3$ | |
| 1 | H | H | H | O | — | cyclopropyl | $OCH_3$ | |
| 1 | H | H | H | $NCH_3$ | — | $CH_3$ | $CH_3$ | |
| 1 | H | H | H | $NCH_3$ | — | $OCH_3$ | $CH_3$ | |
| 1 | H | H | H | $NCH_3$ | — | $OCH_3$ | $OCH_3$ | |
| 1 | H | 5-$OCH_3$ | H | $NCH_3$ | — | $OCH_3$ | $OCH_3$ | |
| 1 | H | 5-$SCH_3$ | H | $NCH_3$ | — | $OCH_3$ | $OCH_3$ | |
| 1 | H | H | H | O | — | $C\equiv CH$ | $OCH_3$ | |
| 1 | H | H | H | O | — | CHO | $OCH_3$ | |
| 1 | H | H | H | O | — | 2-methyl-1,3-oxathiolan-2-yl | $OCH_3$ | |
| 1 | H | H | H | O | — | 2-methyl-1,3-dithian-2-yl | $OCH_3$ | |
| 1 | H | H | H | O | — | 1,3-dioxan-2-yl | $OCH_3$ | |
| 2 | H | H | H | O | — | $OCH_3$ | $OCH_3$ | |
| 2 | H | H | H | O | — | $OCH_3$ | $CH_3$ | |
| 2 | $CH_3$ | H | H | O | — | $OCH_3$ | $CH_3$ | |
| 2 | H | H | H | O | — | $OCH_2CH_3$ | $NHCH_3$ | |
| 2 | H | 5-$OCH_3$ | H | O | — | $OCH_3$ | $OCH_3$ | |
| 2 | H | 5-$SCH_3$ | H | O | — | $OCH_3$ | $OCH_3$ | |
| 2 | H | H | H | $NCH_3$ | — | $OCH_3$ | $OCH_3$ | |
| 2 | H | H | H | $NCH_3$ | — | $OCH_3$ | $CH_3$ | |
| 2 | $CH_3$ | H | H | $NCH_3$ | — | $OCH_3$ | $CH_3$ | |
| 2 | H | H | H | $NCH_3$ | — | $OCH_2CH_3$ | $NHCH_3$ | |
| 2 | H | 5-$OCH_3$ | H | $NCH_3$ | — | $OCH_3$ | $OCH_3$ | |
| 2 | H | 5-$SCH_3$ | H | $NCH_3$ | — | $OCH_3$ | $OCH_3$ | |
| 3 | H | H | H | — | — | $OCH_3$ | $OCH_3$ | 160–166 |
| 3 | H | H | H | — | — | $OCH_3$ | $CH_3$ | 132–136 |
| 3 | $CH_3$ | H | H | — | — | $OCH_3$ | $CH_3$ | |
| 3 | H | H | H | — | — | $OCH_2CH_3$ | $NHCH_3$ | 181–184 |
| 3 | H | 5-$OCH_3$ | H | — | — | $OCH_3$ | $OCH_3$ | |
| 3 | H | 5-$SCH_3$ | H | — | — | $OCH_3$ | $OCH_3$ | |
| 4 | H | H | H | — | — | $OCH_3$ | $OCH_3$ | |
| 4 | H | H | H | — | — | $OCH_3$ | $CH_3$ | |
| 4 | $CH_3$ | H | H | — | — | $OCH_3$ | $CH_3$ | |
| 4 | H | H | H | — | — | $OCH_2CH_3$ | $NHCH_3$ | |
| 4 | H | 5-$OCH_3$ | H | — | — | $OCH_3$ | $OCH_3$ | |
| 4 | H | 5-$SCH_3$ | H | — | — | $OCH_3$ | $OCH_3$ | |
| 5 | H | H | H | $NCH_3$ | — | $OCH_3$ | $OCH_3$ | |
| 5 | H | H | H | $NCH_3$ | — | $OCH_3$ | $CH_3$ | |
| 5 | $CH_3$ | H | H | $NCH_3$ | — | $OCH_3$ | $CH_3$ | |
| 5 | H | H | H | $NCH_3$ | — | $OCH_2CH_3$ | $NHCH_3$ | |
| 5 | H | 5-$OCH_3$ | H | $NCH_3$ | — | $OCH_3$ | $OCH_3$ | |
| 5 | H | 5-$SCH_3$ | H | $NCH_3$ | — | $OCH_3$ | $OCH_3$ | |
| 5 | H | H | H | O | — | $OCH_3$ | $OCH_3$ | |
| 5 | H | H | H | O | — | $OCH_3$ | $CH_3$ | |
| 5 | $CH_3$ | H | H | O | — | $OCH_3$ | $CH_3$ | |
| 5 | H | H | H | O | — | $OCH_2CH_3$ | $NHCH_3$ | |
| 5 | H | 5-$OCH_3$ | H | O | — | $OCH_3$ | $OCH_3$ | |
| 5 | H | 5-$SCH_3$ | H | O | — | $OCH_3$ | $OCH_3$ | |
| 6 | H | H | H | O | — | $OCH_3$ | $OCH_3$ | |
| 6 | H | H | H | O | — | $OCH_3$ | $CH_3$ | |
| 6 | $CH_3$ | H | H | O | — | $OCH_3$ | $CH_3$ | |
| 6 | H | H | H | O | — | $OCH_2CH_3$ | $NHCH_3$ | |
| 6 | H | 5-$OCH_3$ | H | O | — | $OCH_3$ | $OCH_3$ | |
| 6 | H | 5-$SCH_3$ | H | O | — | $OCH_3$ | $OCH_3$ | |
| 6 | H | H | H | $NCH_3$ | — | $OCH_3$ | $OCH_3$ | |
| 6 | H | H | H | $NCH_3$ | — | $OCH_3$ | $CH_3$ | |
| 6 | $CH_3$ | H | H | $NCH_3$ | — | $OCH_3$ | $CH_3$ | |
| 6 | H | H | H | $NCH_3$ | — | $OCH_2CH_3$ | $NHCH_3$ | |
| 6 | H | 5-$OCH_3$ | H | $NCH_3$ | — | $OCH_3$ | $OCH_3$ | |
| 6 | H | 5-$SCH_3$ | H | $NCH_3$ | — | $OCH_3$ | $OCH_3$ | |
| 7 | H | H | H | — | S | $OCH_3$ | $OCH_3$ | |
| 7 | H | H | H | — | S | $OCH_3$ | $CH_3$ | |
| 7 | $CH_3$ | H | H | — | S | $OCH_3$ | $CH_3$ | |
| 7 | H | H | H | — | S | $OCH_2CH_3$ | $NHCH_3$ | |
| 7 | H | 5-$OCH_3$ | H | — | S | $OCH_3$ | $OCH_3$ | |
| 7 | H | 5-$SCH_3$ | H | — | S | $OCH_3$ | $OCH_3$ | |
| 7 | H | H | H | — | $SO_2$ | $OCH_3$ | $OCH_3$ | |
| 7 | H | H | H | — | $SO_2$ | $OCH_3$ | $CH_3$ | |
| 7 | $CH_3$ | H | H | — | $SO_2$ | $OCH_3$ | $CH_3$ | |
| 7 | H | H | H | — | $SO_2$ | $OCH_2CH_3$ | $NHCH_3$ | |
| 7 | H | 5-$OCH_3$ | H | — | $SO_2$ | $OCH_3$ | $OCH_3$ | |
| 7 | H | 5-$SCH_3$ | H | — | $SO_2$ | $OCH_3$ | $OCH_3$ | |
| 8 | H | H | H | — | S | $OCH_3$ | $OCH_3$ | |

TABLE 2-continued

General Formula 2

| Q | R | R₁ | R₃ | W₃ | W₄ | X | Y | m.p. (°C.) |
|---|---|---|---|---|---|---|---|---|
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | CH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 9 (R₆=CH₃) | H | H | H | — | — | OCH₃ | OCH₃ | |
| 9 (R₆=CH₃) | H | H | H | — | — | OCH₃ | CH₃ | |
| 9 (R₆=CH₃) | CH₃ | H | H | — | — | OCH₃ | CH₃ | |
| 9 (R₆=CH₃) | H | H | H | — | — | OCH₂CH₃ | NHCH₃ | |
| 9 (R₆=CH₃) | H | 5-OCH₃ | H | — | — | OCH₃ | OCH₃ | |
| 9 (R₆=CH₃) | H | 5-SCH₃ | H | — | — | OCH₃ | OCH₃ | |
| 10 | H | H | H | — | — | OCH₃ | OCH₃ | |
| 10 | H | H | H | — | — | OCH₃ | CH₃ | |
| 10 | CH₃ | H | H | — | — | OCH₃ | CH₃ | |
| 10 | H | H | H | — | — | OCH₂CH₃ | NHCH₃ | |
| 10 | H | 5-OCH₃ | H | — | — | OCH₃ | OCH₃ | |
| 10 | H | 5-SCH₃ | H | — | — | OCH₃ | OCH₃ | |
| 11 | H | H | H | — | O | OCH₃ | OCH₃ | |
| 11 | H | H | H | — | O | OCH₃ | CH₃ | |
| 11 | CH₃ | H | H | — | O | OCH₃ | CH₃ | |
| 11 | H | H | H | — | O | OCH₂CH₃ | NHCH₃ | |
| 11 | H | 5-OCH₃ | H | — | O | OCH₃ | OCH₃ | |
| 11 | H | 5-SCH₃ | H | — | O | OCH₃ | OCH₃ | |
| 11 | H | H | H | — | S | OCH₃ | OCH₃ | |
| 11 | H | H | H | — | S | OCH₃ | CH₃ | |
| 11 | CH₃ | H | H | — | S | OCH₃ | CH₃ | |
| 11 | H | H | H | — | S | OCH₂CH₃ | NHCH₃ | |
| 11 | H | 5-OCH₃ | H | — | S | OCH₃ | OCH₃ | |
| 11 | H | 5-SCH₃ | H | — | S | OCH₃ | OCH₃ | |
| 12 (R₆=CH₃) | H | H | H | — | — | OCH₃ | OCH₃ | |
| 12 (R₆=CH₃) | H | H | H | — | — | OCH₃ | CH₃ | |
| 12 (R₆=CH₃) | CH₃ | H | H | — | — | OCH₃ | CH₃ | |
| 12 (R₆=CH₃) | H | H | H | — | — | OCH₂CH₃ | NHCH₃ | |
| 12 (R₆=CH₃) | H | 5-OCH₃ | H | — | — | OCH₃ | OCH₃ | |
| 12 (R₆=CH₃) | H | 5-SCH₃ | H | — | — | OCH₃ | OCH₃ | |
| 13 | H | H | H | — | S | OCH₃ | OCH₃ | |
| 13 | H | H | H | — | S | OCH₃ | CH₃ | |
| 13 | CH₃ | H | H | — | S | OCH₃ | CH₃ | |
| 13 | H | H | H | — | S | OCH₂CH₃ | NHCH₃ | |
| 13 | H | 5-OCH₃ | H | — | S | OCH₃ | OCH₃ | |
| 13 | H | 5-SCH₃ | H | — | S | OCH₃ | OCH₃ | |
| 13 | H | H | H | — | SO₂ | OCH₃ | OCH₃ | |
| 13 | H | H | H | — | SO₂ | OCH₃ | CH₃ | |
| 13 | CH₃ | H | H | — | SO₂ | OCH₃ | CH₃ | |
| 13 | H | H | H | — | SO₂ | OCH₂CH₃ | NHCH₃ | |
| 13 | H | 5-OCH₃ | H | — | SO₂ | OCH₃ | OCH₃ | |
| 13 | H | 5-SCH₃ | H | — | SO₂ | OCH₃ | OCH₃ | |
| 14 | H | H | H | — | O | OCH₃ | OCH₃ | |
| 14 | H | H | H | — | O | OCH₃ | CH₃ | |
| 14 | CH₃ | H | H | — | O | OCH₃ | CH₃ | |
| 14 | H | H | H | — | O | OCH₂CH₃ | NHCH₃ | |
| 14 | H | 5-OCH₃ | H | — | O | OCH₃ | OCH₃ | |
| 14 | H | 5-SCH₃ | H | — | O | OCH₃ | OCH₃ | |
| 15 | H | H | H | — | — | OCH₃ | OCH₃ | |
| 15 | H | H | H | — | — | OCH₃ | CH₃ | |
| 15 | CH₃ | H | H | — | — | OCH₃ | CH₃ | |
| 15 | H | H | H | — | — | OCH₂CH₃ | NHCH₃ | |
| 15 | H | 5-OCH₃ | H | — | — | OCH₃ | OCH₃ | |
| 15 | H | 5-SCH₃ | H | — | — | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |

TABLE 2-continued

General Formula 2

| Q | R | $R_1$ | $R_3$ | $W_3$ | $W_4$ | X | Y | m.p. (°C.) |
|---|---|---|---|---|---|---|---|---|
| 16 | H | 5-OCF$_2$H | H | O | — | OCH$_3$ | OCH$_3$ | |
| 16 | H | 5-SCH$_3$ | H | O | — | OCH$_3$ | OCH$_3$ | |
| 16 | H | 5-NHCH$_3$ | H | O | — | OCH$_3$ | OCH$_3$ | |
| 16 | H | 5-N(CH$_3$)$_2$ | H | O | — | OCH$_3$ | OCH$_3$ | |
| 16 | H | 5-Cl | H | O | — | OCH$_3$ | OCH$_3$ | |
| 16 | H | 5-CF$_3$ | H | O | — | OCH$_3$ | OCH$_3$ | |
| 16 | H | 6-SO$_2$N(CH$_3$)$_2$ | H | O | — | OCH$_3$ | OCH$_3$ | |
| 16 | H | 6-CO$_2$CH$_3$ | H | O | — | OCH$_3$ | OCH$_3$ | |
| 16 | H | 6-SO$_2$CH$_3$ | H | O | — | OCH$_3$ | OCH$_3$ | |
| 16 | H | H | H | O | — | CH$_2$F | OCH$_3$ | |
| 16 | H | H | H | O | — | CH$_2$Cl | OCH$_3$ | |
| 16 | H | H | H | O | — | CF$_3$ | OCH$_3$ | |
| 16 | H | H | H | O | — | SCH$_3$ | OCH$_3$ | |
| 16 | H | H | H | O | — | NHCH$_3$ | OCH$_2$CH$_3$ | |
| 16 | H | H | H | O | — | OCH$_2$CH=CH$_2$ | OCH$_3$ | |
| 16 | H | H | H | O | — | OCH$_2$C≡CH$_3$ | OCH$_3$ | |
| 16 | H | H | H | O | — | cyclopropyl | OCH$_3$ | |
| 16 | H | H | H | NCH$_3$ | — | CH$_3$ | CH$_3$ | |
| 16 | H | H | H | NCH$_3$ | — | OCH$_3$ | CH$_3$ | |
| 16 | H | H | H | NCH$_3$ | — | OCH$_2$CH$_3$ | NHCH$_3$ | |
| 16 | H | H | H | NCH$_3$ | — | OCH$_3$ | OCH$_3$ | |
| 16 | H | 5-OCH$_3$ | H | NCH$_3$ | — | OCH$_3$ | OCH$_3$ | |
| 16 | H | 5-SCH$_3$ | H | NCH$_3$ | — | OCH$_3$ | OCH$_3$ | |
| 16 | H | H | H | O | — | C≡CH$_3$ | OCH$_3$ | |
| 16 | H | H | H | O | — | CHO | OCH$_3$ | |
| 16 | H | H | H | O | — | 2-methyl-1,3-oxathiolan-2-yl | OCH$_3$ | |
| 16 | H | H | H | O | — | 2-methyl-1,3-dithian-2-yl | OCH$_3$ | |
| 16 | H | H | H | O | — | 1,3-dioxan-2-yl | OCH$_3$ | |
| 17 | H | H | H | O | — | OCH$_3$ | OCH$_3$ | |
| 17 | H | H | H | O | — | OCH$_3$ | CH$_3$ | |
| 17 | CH$_3$ | H | H | O | — | OCH$_3$ | CH$_3$ | |
| 17 | H | H | H | O | — | OCH$_2$CH$_3$ | NHCH$_3$ | |
| 17 | H | 5-OCH$_3$ | H | O | — | OCH$_3$ | OCH$_3$ | |
| 17 | H | 5-SCH$_3$ | H | O | — | OCH$_3$ | OCH$_3$ | |
| 17 | H | H | H | NCH$_3$ | — | OCH$_3$ | OCH$_3$ | |
| 17 | H | H | H | NCH$_3$ | — | OCH$_3$ | CH$_3$ | |
| 17 | CH$_3$ | H | H | NCH$_3$ | — | OCH$_3$ | CH$_3$ | |
| 17 | H | H | H | NCH$_3$ | — | OCH$_2$CH$_3$ | NHCH$_3$ | |
| 17 | H | 5-OCH$_3$ | H | NCH$_3$ | — | OCH$_3$ | OCH$_3$ | |
| 17 | H | 5-SCH$_3$ | H | NCH$_3$ | — | OCH$_3$ | OCH$_3$ | |
| 18 | H | H | H | O | — | OCH$_3$ | OCH$_3$ | |
| 18 | H | H | H | O | — | OCH$_3$ | CH$_3$ | |
| 18 | CH$_3$ | H | H | O | — | OCH$_3$ | CH$_3$ | |
| 18 | H | H | H | O | — | OCH$_2$CH$_3$ | NHCH$_3$ | |
| 18 | H | 5-OCH$_3$ | H | O | — | OCH$_3$ | OCH$_3$ | |
| 18 | H | 5-SCH$_3$ | H | O | — | OCH$_3$ | OCH$_3$ | |
| 18 | H | H | H | NCH$_3$ | — | OCH$_3$ | OCH$_3$ | |
| 18 | H | H | H | NCH$_3$ | — | OCH$_3$ | CH$_3$ | |
| 18 | CH$_3$ | H | H | NCH$_3$ | — | OCH$_3$ | CH$_3$ | |
| 18 | H | H | H | NCH$_3$ | — | OCH$_2$CH$_3$ | NHCH$_3$ | |
| 18 | H | 5-OCH$_3$ | H | NCH$_3$ | — | OCH$_3$ | OCH$_3$ | |
| 18 | H | 5-SCH$_3$ | H | NCH$_3$ | — | OCH$_3$ | OCH$_3$ | |
| 19 | H | H | H | — | — | OCH$_3$ | OCH$_3$ | |
| 19 | H | H | H | — | — | OCH$_3$ | CH$_3$ | |
| 19 | CH$_3$ | H | H | — | — | OCH$_3$ | CH$_3$ | |
| 19 | H | H | H | — | — | OCH$_2$CH$_3$ | NHCH$_3$ | |
| 19 | H | 5-OCH$_3$ | H | — | — | OCH$_3$ | OCH$_3$ | |
| 19 | H | 5-SCH$_3$ | H | — | — | OCH$_3$ | OCH$_3$ | |
| 20 | H | H | H | — | — | CH$_3$ | OCH$_3$ | |
| 20 | H | H | H | — | — | OCH$_3$ | CH$_3$ | |
| 20 | CH$_3$ | H | H | — | — | OCH$_3$ | CH$_3$ | |
| 20 | H | H | H | — | — | OCH$_2$CH$_3$ | NHCH$_3$ | |
| 20 | H | 5-OCH$_3$ | H | — | — | OCH$_3$ | OCH$_3$ | |
| 20 | H | 5-SCH$_3$ | H | — | — | OCH$_3$ | OCH$_3$ | |
| 21 | H | H | H | — | — | OCH$_3$ | OCH$_3$ | |
| 21 | H | H | H | — | — | OCH$_3$ | CH$_3$ | |
| 21 | CH$_3$ | H | H | — | — | OCH$_3$ | CH$_3$ | |
| 21 | H | H | H | — | — | OCH$_2$CH$_3$ | NHCH$_3$ | |
| 21 | H | 5-OCH$_3$ | H | — | — | OCH$_3$ | OCH$_3$ | |
| 21 | H | 5-SCH$_3$ | H | — | — | OCH$_3$ | OCH$_3$ | |
| 22 | H | H | H | O | — | OCH$_3$ | OCH$_3$ | |
| 22 | H | H | H | O | — | OCH$_3$ | CH$_3$ | |
| 22 | CH$_3$ | H | H | O | — | OCH$_3$ | CH$_3$ | |
| 22 | H | H | H | O | — | OCH$_2$CH$_3$ | NHCH$_3$ | |
| 22 | H | 5-OCH$_3$ | H | O | — | OCH$_3$ | OCH$_3$ | |

TABLE 2-continued

General Formula 2

| Q | R | R₁ | R₃ | W₃ | W₄ | X | Y | m.p. (°C.) |
|---|---|---|---|---|---|---|---|---|
| 22 | H | 5-SCH₃ | H | O | — | OCH₃ | OCH₃ | |
| 23 | H | H | H | NCH₃ | — | OCH₃ | OCH₃ | |
| 23 | H | H | H | NCH₃ | — | OCH₃ | CH₃ | |
| 23 | CH₃ | H | H | NCH₃ | — | OCH₃ | CH₃ | |
| 23 | H | 5-OCH₃ | H | NCH₃ | — | OCH₃ | OCH₃ | |
| 23 | H | 5-SCH₃ | H | NCH₃ | — | OCH₃ | OCH₃ | |
| 23 | H | H | H | O | — | OCH₃ | OCH₃ | |
| 23 | H | H | H | O | — | OCH₃ | CH₃ | |
| 23 | CH₃ | H | H | O | — | OCH₃ | CH₃ | |
| 23 | H | H | H | O | — | OCH₂CH₃ | NHCH₃ | |
| 23 | H | 5-OCH₃ | H | O | — | OCH₃ | OCH₃ | |
| 23 | H | 5-SCH₃ | H | O | — | OCH₃ | OCH₃ | |
| 23 | H | H | H | NCH₃ | — | OCH₃ | OCH₃ | |
| 23 | H | H | H | NCH₃ | — | OCH₃ | CH₃ | |
| 23 | CH₃ | H | H | NCH₃ | — | OCH₃ | CH₃ | |
| 23 | H | H | H | NCH₃ | — | OCH₂CH₃ | NHCH₃ | |
| 23 | H | 5-OCH₃ | H | NCH₃ | — | OCH₃ | OCH₃ | |
| 23 | H | 5-SCH₃ | H | NCH₃ | — | OCH₃ | OCH₃ | |
| 24 | H | H | H | O | — | OCH₃ | OCH₃ | |
| 24 | H | H | H | O | — | OCH₃ | CH₃ | |
| 24 | CH₃ | H | H | O | — | OCH₃ | CH₃ | |
| 24 | H | H | H | O | — | OCH₂CH₃ | NHCH₃ | |
| 24 | H | 5-OCH₃ | H | O | — | OCH₃ | OCH₃ | |
| 24 | H | 5-SCH₃ | H | O | — | OCH₃ | OCH₃ | |
| 24 | H | H | H | NCH₃ | — | OCH₃ | OCH₃ | |
| 24 | H | H | H | NCH₃ | — | OCH₃ | CH₃ | |
| 24 | CH₃ | H | H | NCH₃ | — | OCH₃ | CH₃ | |
| 24 | H | H | H | NCH₃ | — | OCH₂CH₃ | NHCH₃ | |
| 24 | H | 5-OCH₃ | H | NCH₃ | — | OCH₃ | OCH₃ | |
| 24 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | OCH₃ | OCH₃ | |
| 25 | H | H | H | — | SO₂ | OCH₃ | CH₃ | |
| 25 | CH₃ | H | H | — | SO₂ | OCH₃ | CH₃ | |
| 25 | H | H | H | — | SO₂ | OCH₂CH₃ | NHCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | O | OCH₃ | OCH₃ | |
| 26 | H | H | H | — | O | OCH₃ | CH₃ | |
| 26 | CH₃ | H | H | — | O | OCH₃ | CH₃ | |
| 26 | H | H | H | — | O | OCH₂CH₃ | NHCH₃ | |
| 26 | H | 5-OCH₃ | H | — | O | OCH₃ | OCH₃ | |
| 26 | H | 5-SCH₃ | H | — | O | OCH₃ | OCH₃ | |
| 26 | H | H | H | — | S | OCH₃ | OCH₃ | |
| 26 | H | H | H | — | S | OCH₃ | CH₃ | |
| 26 | CH₃ | H | H | — | S | OCH₃ | CH₃ | |
| 26 | H | H | H | — | S | OCH₂CH₃ | NHCH₃ | |
| 26 | H | 5-OCH₃ | H | — | S | OCH₃ | OCH₃ | |
| 26 | H | 5-SCH₃ | H | — | S | OCH₃ | OCH₃ | |
| 27 | H | H | H | — | O | OCH₃ | OCH₃ | |
| 27 | H | H | H | — | O | OCH₃ | CH₃ | |
| 27 | CH₃ | H | H | — | O | OCH₃ | CH₃ | |
| 27 | H | H | H | — | O | OCH₂CH₃ | NHCH₃ | |
| 27 | H | 5-OCH₃ | H | — | O | OCH₃ | OCH₃ | |
| 27 | H | 5-SCH₃ | H | — | O | OCH₃ | OCH₃ | |
| 27 | H | H | H | — | S | OCH₃ | OCH₃ | |
| 27 | H | H | H | — | S | OCH₃ | CH₃ | |
| 27 | CH₃ | H | H | — | S | OCH₃ | CH₃ | |
| 27 | H | H | H | — | S | OCH₂CH₃ | NHCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | OCH₃ | OCH₃ | |
| 27 | H | H | H | — | SO₂ | OCH₃ | CH₃ | |
| 27 | CH₃ | H | H | — | SO₂ | OCH₃ | CH₃ | |
| 27 | H | H | H | — | SO₂ | OCH₂CH₃ | NHCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 28 ($R_6$=CH₃) | H | H | H | — | SO₂ | OCH₃ | OCH₃ | |
| 28 ($R_6$=CH₃) | H | H | H | — | SO₂ | OCH₃ | CH₃ | |
| 28 ($R_6$=CH₃) | CH₃ | H | H | — | SO₂ | OCH₃ | CH₃ | |
| 28 ($R_6$=CH₃) | H | H | H | — | SO₂ | OCH₂CH₃ | NHCH₃ | |
| 28 ($R_6$=CH₃) | H | 5-OCH₃ | H | — | SO₂ | OCH₃ | OCH₃ | |
| 28 ($R_6$=CH₃) | H | 5-SCH₃ | H | — | SO₂ | OCH₃ | OCH₃ | |
| 29 ($R_6$=CH₃) | H | H | H | — | — | OCH₃ | OCH₃ | |
| 29 ($R_6$=CH₃) | H | H | H | — | — | OCH₃ | CH₃ | |

TABLE 2-continued

| | | | General Formula 2 | | | | | |
|---|---|---|---|---|---|---|---|---|
| Q | R | $R_1$ | $R_3$ | $W_3$ | $W_4$ | X | Y | m.p. (°C.) |
| 29 ($R_6$=CH$_3$) | CH$_3$ | H | H | — | — | OCH$_3$ | CH$_3$ | |
| 29 ($R_6$=CH$_3$) | H | H | H | — | — | OCH$_2$CH$_3$ | NHCH$_3$ | |
| 29 ($R_6$=CH$_3$) | H | 5-OCH$_3$ | H | — | — | OCH$_3$ | OCH$_3$ | |
| 29 ($R_6$=CH$_3$) | H | 5-SCH$_3$ | H | — | — | OCH$_3$ | OCH$_3$ | |
| 30 | H | H | H | — | — | OCH$_3$ | OCH$_3$ | |
| 30 | H | H | H | — | — | OCH$_3$ | CH$_3$ | |
| 30 | CH$_3$ | H | H | — | — | OCH$_3$ | CH$_3$ | |
| 30 | H | H | H | — | — | OCH$_2$CH$_3$ | NHCH$_3$ | |
| 30 | H | 5-OCH$_3$ | H | — | — | OCH$_3$ | OCH$_3$ | |
| 30 | H | 5-SCH$_3$ | H | — | — | OCH$_3$ | OCH$_3$ | |
| 31 | H | H | H | — | — | OCH$_3$ | OCH$_3$ | |
| 31 | H | H | H | — | — | OCH$_3$ | CH$_3$ | |
| 31 | CH$_3$ | H | H | — | — | OCH$_3$ | CH$_3$ | |
| 31 | H | H | H | — | — | OCH$_2$CH$_3$ | NHCH$_3$ | |
| 31 | H | 5-OCH$_3$ | H | — | — | OCH$_3$ | OCH$_3$ | |
| 31 | H | 5-SCH$_3$ | H | — | — | OCH$_3$ | OCH$_3$ | |
| 32 | H | H | H | — | — | OCH$_3$ | OCH$_3$ | |
| 32 | H | H | H | — | — | OCH$_3$ | CH$_3$ | |
| 32 | CH$_3$ | H | H | — | — | OCH$_3$ | CH$_3$ | |
| 32 | H | H | H | — | — | OCH$_2$CH$_3$ | NHCH$_3$ | |
| 32 | H | 5-OCH$_3$ | H | — | — | OCH$_3$ | OCH$_3$ | |
| 32 | H | 5-SCH$_3$ | H | — | — | OCH$_3$ | OCH$_3$ | |
| 33 | H | H | H | — | O | OCH$_3$ | OCH$_3$ | |
| 33 | H | H | H | — | O | OCH$_3$ | CH$_3$ | |
| 33 | CH$_3$ | H | H | — | O | OCH$_3$ | CH$_3$ | |
| 33 | H | H | H | — | O | OCH$_2$CH$_3$ | NHCH$_3$ | |
| 33 | H | 5-OCH$_3$ | H | — | O | OCH$_3$ | OCH$_3$ | |
| 33 | H | 5-SCH$_3$ | H | — | O | OCH$_3$ | OCH$_3$ | |
| 33 | H | H | H | — | S | OCH$_3$ | OCH$_3$ | |
| 33 | H | H | H | — | S | OCH$_3$ | CH$_3$ | |
| 33 | CH$_3$ | H | H | — | S | OCH$_3$ | CH$_3$ | |
| 33 | H | H | H | — | S | OCH$_2$CH$_3$ | NHCH$_3$ | |
| 33 | H | 5-OCH$_3$ | H | — | S | OCH$_3$ | OCH$_3$ | |
| 33 | H | 5-SCH$_3$ | H | — | S | OCH$_3$ | OCH$_3$ | |
| 34 | H | H | H | — | O | OCH$_3$ | OCH$_3$ | |
| 34 | H | H | H | — | O | OCH$_3$ | CH$_3$ | |
| 34 | CH$_3$ | H | H | — | O | OCH$_3$ | CH$_3$ | |
| 34 | H | H | H | — | O | OCH$_2$CH$_3$ | NHCH$_3$ | |
| 34 | H | 5-OCH$_3$ | H | — | O | OCH$_3$ | OCH$_3$ | |
| 34 | H | 5-SCH$_3$ | H | — | O | OCH$_3$ | OCH$_3$ | |
| 35 | H | H | H | — | O | OCH$_3$ | OCH$_3$ | |
| 35 | H | H | H | — | O | OCH$_3$ | CH$_3$ | |
| 35 | CH$_3$ | H | H | — | O | OCH$_3$ | CH$_3$ | |
| 35 | H | H | H | — | O | OCH$_2$CH$_3$ | NHCH$_3$ | |
| 35 | H | 5-OCH$_3$ | H | — | O | OCH$_3$ | OCH$_3$ | |
| 35 | H | 5-SCH$_3$ | H | — | O | OCH$_3$ | OCH$_3$ | |
| 36 | H | H | H | — | SO$_2$ | OCH$_3$ | OCH$_3$ | |
| 36 | H | H | H | — | SO$_2$ | OCH$_3$ | CH$_3$ | |
| 36 | CH$_3$ | H | H | — | SO$_2$ | OCH$_3$ | CH$_3$ | |
| 36 | H | H | H | — | SO$_2$ | OCH$_2$CH$_3$ | NHCH$_3$ | |
| 36 | H | 5-OCH$_3$ | H | — | SO$_2$ | OCH$_3$ | OCH$_3$ | |
| 36 | H | 5-SCH$_3$ | H | — | SO$_2$ | OCH$_3$ | OCH$_3$ | |
| 37 | H | H | H | — | S | OCH$_3$ | OCH$_3$ | |
| 37 | H | H | H | — | S | OCH$_3$ | CH$_3$ | |
| 37 | CH$_3$ | H | H | — | S | OCH$_3$ | CH$_3$ | |
| 37 | H | H | H | — | S | OCH$_2$NH$_3$ | NHCH$_3$ | |
| 37 | H | 5-OCH$_3$ | H | — | S | OCH$_3$ | OCH$_3$ | |
| 37 | H | 5-SCH$_3$ | H | — | S | OCH$_3$ | OCH$_3$ | |
| 38 | H | H | H | — | O | OCH$_3$ | OCH$_3$ | |
| 38 | H | H | H | — | O | OCH$_3$ | CH$_3$ | |
| 38 | CH$_3$ | H | H | — | O | OCH$_3$ | CH$_3$ | |
| 38 | H | H | H | — | O | OCH$_2$CH$_3$ | NHCH$_3$ | |
| 38 | H | 5-OCH$_3$ | H | — | O | OCH$_3$ | OCH$_3$ | |
| 38 | H | 5-SCH$_3$ | H | — | O | OCH$_3$ | OCH$_3$ | |
| 39 ($R_6$=CH$_3$) | H | H | H | — | — | OCH$_3$ | OCH$_3$ | |
| 39 ($R_6$=CH$_3$) | H | H | H | — | — | OCH$_3$ | CH$_3$ | |
| 39 ($R_6$=CH$_3$) | CH$_3$ | H | H | — | — | OCH$_3$ | CH$_3$ | |
| 39 ($R_6$=CH$_3$) | H | H | H | — | — | OCH$_2$CH$_3$ | NHCH$_3$ | |
| 39 ($R_6$=CH$_3$) | H | 5-OCH$_3$ | H | — | — | OCH$_3$ | OCH$_3$ | |
| 39 ($R_6$=CH$_3$) | H | 5-SCH$_3$ | H | — | — | OCH$_3$ | OCH$_3$ | |
| 40 ($R_6$=CH$_3$) | H | H | H | — | — | OCH$_3$ | OCH$_3$ | |
| 40 ($R_6$=CH$_3$) | H | H | H | — | — | OCH$_3$ | CH$_3$ | |
| 40 ($R_6$=CH$_3$) | CH$_3$ | H | H | — | — | OCH$_3$ | CH$_3$ | |
| 40 ($R_6$=CH$_3$) | H | H | H | — | — | OCH$_2$CH$_3$ | NHCH$_3$ | |
| 40 ($R_6$=CH$_3$) | H | 5-OCH$_3$ | H | — | — | OCH$_3$ | OCH$_3$ | |
| 40 ($R_6$=CH$_3$) | H | 5-SCH$_3$ | H | — | — | OCH$_3$ | OCH$_3$ | |
| 41 ($R_6$=CH$_3$) | H | H | H | — | — | OCH$_3$ | OCH$_3$ | |
| 41 ($R_6$=CH$_3$) | H | H | H | — | — | OCH$_3$ | CH$_3$ | |
| 41 ($R_6$=CH$_3$) | CH$_3$ | H | H | — | — | OCH$_3$ | CH$_3$ | |
| 41 ($R_6$=CH$_3$) | H | H | H | — | — | OCH$_2$CH$_3$ | NHCH$_3$ | |

TABLE 2-continued

General Formula 2

| Q | R | R₁ | R₃ | W₃ | W₄ | X | Y | m.p. (°C.) |
|---|---|---|---|---|---|---|---|---|
| 41 (R₆=CH₃) | H | 5-OCH₃ | H | — | — | OCH₃ | OCH₃ | |
| 41 (R₆=CH₃) | H | 5-SCH₃ | H | — | — | OCH₃ | OCH₃ | |
| 42 | H | H | H | — | — | OCH₃ | OCH₃ | |
| 42 | H | H | H | — | — | OCH₃ | CH₃ | |
| 42 | CH₃ | H | H | — | — | OCH₃ | CH₃ | |
| 42 | H | H | H | — | — | OCH₂CH₃ | NHCH₃ | |
| 42 | H | 5-OCH₃ | H | — | — | OCH₃ | OCH₃ | |
| 42 | H | 5-SCH₃ | H | — | — | OCH₃ | OCH₃ | |
| 43 | H | H | H | — | — | OCH₃ | OCH₃ | |
| 43 | H | H | H | — | — | OCH₃ | CH₃ | |
| 43 | CH₃ | H | H | — | — | OCH₃ | CH₃ | |
| 43 | H | H | H | — | — | OCH₂CH₃ | NHCH₃ | |
| 43 | H | 5-OCH₃ | H | — | — | OCH₃ | OCH₃ | |
| 43 | H | 5-SCH₃ | H | — | — | OCH₃ | OCH₃ | |
| 44 | H | H | H | — | — | OCH₃ | OCH₃ | |
| 44 | H | H | H | — | — | OCH₃ | CH₃ | |
| 44 | CH₃ | H | H | — | — | OCH₃ | CH₃ | |
| 44 | H | H | H | — | — | OCH₂CH₃ | NHCH₃ | |
| 44 | H | 5-OCH₃ | H | — | — | OCH₃ | OCH₃ | |
| 44 | H | 5-SCH₃ | H | — | — | OCH₃ | OCH₃ | |
| 45 | H | H | H | — | — | OCH₃ | OCH₃ | |
| 45 | H | H | H | — | — | OCH₃ | CH₃ | |
| 45 | CH₃ | H | H | — | — | OCH₃ | CH₃ | |
| 45 | H | H | H | — | — | OCH₂CH₃ | NHCH₃ | |
| 45 | H | 5-OCH₃ | H | — | — | OCH₃ | OCH₃ | |
| 45 | H | 5-SCH₃ | H | — | — | OCH₃ | OCH₃ | |
| 46 | H | H | H | NCH₃ | — | OCH₃ | OCH₃ | |
| 46 | H | H | H | NCH₃ | — | OCH₃ | CH₃ | |
| 46 | CH₃ | H | H | NCH₃ | — | OCH₃ | CH₃ | |
| 46 | H | H | H | NCH₃ | — | OCH₂CH₃ | NHCH₃ | |
| 46 | H | 5-OCH₃ | H | NCH₃ | — | OCH₃ | OCH₃ | |
| 46 | H | 5-SCH₃ | H | NCH₃ | — | OCH₃ | OCH₃ | |
| 47 | H | H | H | — | O | OCH₃ | OCH₃ | |
| 47 | H | H | H | — | O | OCH₃ | CH₃ | |
| 47 | CH₃ | H | H | — | O | OCH₃ | CH₃ | |
| 47 | H | H | H | — | O | OCH₂CH₃ | NHCH₃ | |
| 47 | H | 5-OCH₃ | H | — | O | OCH₃ | OCH₃ | |
| 47 | H | 5-SCH₃ | H | — | O | OCH₃ | OCH₃ | |
| 48 | H | H | H | — | O | OCH₃ | OCH₃ | |
| 48 | H | H | H | — | O | OCH₃ | CH₃ | |
| 48 | CH₃ | H | H | — | O | OCH₃ | CH₃ | |
| 48 | H | H | H | — | O | OCH₂CH₃ | NHCH₃ | |
| 48 | H | 5-OCH₃ | H | — | O | OCH₃ | OCH₃ | |
| 48 | H | 5-SCH₃ | H | — | O | OCH₃ | OCH₃ | |
| 49 | H | H | H | — | O | OCH₃ | OCH₃ | |
| 49 | H | H | H | — | O | OCH₃ | CH₃ | |
| 49 | CH₃ | H | H | — | O | OCH₃ | CH₃ | |
| 49 | H | H | H | — | O | OCH₂CH₃ | NHCH₃ | |
| 49 | H | 5-OCH₃ | H | — | O | OCH₃ | OCH₃ | |
| 49 | H | 5-SCH₃ | H | — | O | OCH₃ | OCH₃ | |
| 50 | H | H | H | — | O | OCH₃ | OCH₃ | |
| 50 | H | H | H | — | O | OCH₃ | CH₃ | |
| 50 | CH₃ | H | H | — | O | OCH₃ | CH₃ | |
| 50 | H | H | H | — | O | OCH₂CH₃ | NHCH₃ | |
| 50 | H | 5-OCH₃ | H | — | O | OCH₃ | OCH₃ | |
| 50 | H | 5-SCH₃ | H | — | O | OCH₃ | OCH₃ | |
| 51 | H | H | H | — | S | OCH₃ | OCH₃ | |
| 51 | H | H | H | — | S | OCH₃ | CH₃ | |
| 51 | CH₃ | H | H | — | S | OCH₃ | CH₃ | |
| 51 | H | H | H | — | S | OCH₂CH₃ | NHCH₃ | |
| 51 | H | 5-OCH₃ | H | — | S | OCH₃ | OCH₃ | |
| 51 | H | 5-SCH₃ | H | — | S | OCH₃ | OCH₃ | |
| 52 | H | H | H | — | SO₂ | OCH₃ | OCH₃ | |
| 52 | H | H | H | — | SO₂ | OCH₃ | CH₃ | |
| 52 | CH₃ | H | H | — | SO₂ | OCH₃ | CH₃ | |
| 52 | H | H | H | — | SO₂ | OCH₂CH₃ | NHCH₃ | |
| 52 | H | 5-OCH₃ | H | — | SO₂ | OCH₃ | OCH₃ | |
| 52 | H | 5-SCH₃ | H | — | SO₂ | OCH₃ | OCH₃ | |
| 53 | H | H | H | — | — | OCH₃ | OCH₃ | |
| 53 | H | H | H | — | — | OCH₃ | CH₃ | |
| 53 | CH₃ | H | H | — | — | OCH₃ | CH₃ | |
| 53 | H | H | H | — | — | OCH₂CH₃ | NHCH₃ | |
| 53 | H | 5-OCH₃ | H | — | — | OCH₃ | OCH₃ | |
| 53 | H | 5-SCH₃ | H | — | — | OCH₃ | OCH₃ | |
| 54 | H | H | H | — | O | OCH₃ | OCH₃ | |
| 54 | H | H | H | — | O | OCH₃ | CH₃ | |
| 54 | CH₃ | H | H | — | O | OCH₃ | CH₃ | |
| 54 | H | H | H | — | O | OCH₂CH₃ | NHCH₃ | |
| 54 | H | 5-OCH₃ | H | — | O | OCH₃ | OCH₃ | |
| 54 | H | 5-SCH₃ | H | — | O | OCH₃ | OCH₃ | |

TABLE 2-continued

General Formula 2

| Q | R | $R_1$ | $R_3$ | $W_3$ | $W_4$ | X | Y | m.p. (°C.) |
|---|---|---|---|---|---|---|---|---|
| 55 | H | H | H | O | — | $OCH_3$ | $OCH_3$ | |
| 55 | H | H | H | O | — | $OCH_3$ | $CH_3$ | |
| 55 | $CH_3$ | H | H | O | — | $OCH_3$ | $CH_3$ | |
| 55 | H | H | H | O | — | $OCH_2CH_3$ | $NHCH_3$ | |
| 55 | H | 5-$OCH_3$ | H | O | — | $OCH_3$ | $OCH_3$ | |
| 55 | H | 5-$SCH_3$ | H | O | — | $OCH_3$ | $OCH_3$ | |
| 55 | H | H | H | $NCH_3$ | — | $OCH_3$ | $OCH_3$ | |
| 55 | H | H | H | $NCH_3$ | — | $OCH_3$ | $CH_3$ | |
| 55 | $CH_3$ | H | H | $NCH_3$ | — | $OCH_3$ | $CH_3$ | |
| 55 | H | H | H | $NCH_3$ | — | $OCH_2CH_3$ | $NHCH_3$ | |
| 55 | H | 5-$OCH_3$ | H | $NCH_3$ | — | $OCH_3$ | $OCH_3$ | |
| 55 | H | 5-$SCH_3$ | H | $NCH_3$ | — | $OCH_3$ | $OCH_3$ | |
| 56 | H | H | H | — | — | $OCH_3$ | $OCH_3$ | |
| 56 | H | H | H | — | — | $OCH_3$ | $CH_3$ | |
| 56 | $CH_3$ | H | H | — | — | $OCH_3$ | $CH_3$ | |
| 56 | H | H | H | — | — | $OCH_2CH_3$ | $NHCH_3$ | |
| 56 | H | 5-$OCH_3$ | H | — | — | $OCH_3$ | $OCH_3$ | |
| 56 | H | 5-$SCH_3$ | H | — | — | $OCH_3$ | $OCH_3$ | |
| 57 | H | H | H | O | — | $OCH_3$ | $OCH_3$ | |
| 57 | H | H | H | O | — | $OCH_3$ | $CH_3$ | |
| 57 | $CH_3$ | H | H | O | — | $OCH_3$ | $CH_3$ | |
| 57 | H | H | H | O | — | $OCH_2CH_3$ | $NHCH_3$ | |
| 57 | H | 5-$OCH_3$ | H | O | — | $OCH_3$ | $OCH_3$ | |
| 57 | H | 5-$SCH_3$ | H | O | — | $OCH_3$ | $OCH_3$ | |
| 58 | H | H | H | — | — | $OCH_3$ | $OCH_3$ | |
| 58 | H | H | H | — | — | $OCH_3$ | $OCH_3$ | |
| 58 | H | H | H | — | — | $OCH_3$ | $CH_3$ | |
| 58 | H | H | H | — | — | $OCH_2CH_3$ | $NHCH_3$ | |
| 58 | H | 5-$OCH_3$ | H | — | — | $OCH_3$ | $OCH_3$ | |
| 58 | H | 5-$SCH_3$ | H | — | — | $OCH_3$ | $OCH_3$ | |
| 59 | H | H | H | $NCH_3$ | — | $OCH_3$ | $OCH_3$ | |
| 59 | H | H | H | $NCH_3$ | — | $OCH_3$ | $CH_3$ | |
| 59 | $CH_3$ | H | H | $NCH_3$ | — | $OCH_3$ | $CH_3$ | |
| 59 | H | H | H | $NCH_3$ | — | $OCH_2CH_3$ | $NHCH_3$ | |
| 59 | H | 5-$OCH_3$ | H | $NCH_3$ | — | $OCH_3$ | $OCH_3$ | |
| 59 | H | 5-$SCH_3$ | H | $NCH_3$ | — | $OCH_3$ | $OCH_3$ | |
| 60 | H | H | H | $NCH_3$ | — | $OCH_3$ | $OCH_3$ | |
| 60 | H | H | H | $NCH_3$ | — | $OCH_3$ | $CH_3$ | |
| 60 | $CH_3$ | H | H | $NCH_3$ | — | $OCH_3$ | $CH_3$ | |
| 60 | H | H | H | $NCH_3$ | — | $OCH_2CH_3$ | $NHCH_3$ | |
| 60 | H | 5-$OCH_3$ | H | $NCH_3$ | — | $OCH_3$ | $OCH_3$ | |
| 60 | H | 5-$SCH_3$ | H | $NCH_3$ | — | $OCH_3$ | $OCH_3$ | |
| 61 | H | H | H | $NCH_3$ | — | $OCH_3$ | $OCH_3$ | |
| 61 | H | H | H | $NCH_3$ | — | $OCH_3$ | $CH_3$ | |
| 61 | $CH_3$ | H | H | $NCH_3$ | — | $OCH_3$ | $CH_3$ | |
| 61 | H | H | H | $NCH_3$ | — | $OCH_2CH_3$ | $NHCH_3$ | |
| 61 | H | 5-$OCH_3$ | H | $NCH_3$ | — | $OCH_3$ | $OCH_3$ | |
| 61 | H | 5-$SCH_3$ | H | $NCH_3$ | — | $OCH_3$ | $OCH_3$ | |
| 62 | H | H | H | O | — | $OCH_3$ | $OCH_3$ | |
| 62 | H | H | H | O | — | $OCH_3$ | $CH_3$ | |
| 62 | $CH_3$ | H | H | O | — | $OCH_3$ | $CH_3$ | |
| 62 | H | H | H | O | — | $OCH_2CH_3$ | $NHCH_3$ | |
| 62 | H | 5-$OCH_3$ | H | O | — | $OCH_3$ | $OCH_3$ | |
| 62 | H | 5-$SCH_3$ | H | O | — | $OCH_3$ | $OCH_3$ | |
| 63 | H | H | H | — | O | $OCH_3$ | $OCH_3$ | |
| 63 | H | H | H | — | O | $OCH_3$ | $CH_3$ | |
| 63 | $CH_3$ | H | H | — | O | $OCH_3$ | $CH_3$ | |
| 63 | H | H | H | — | O | $OCH_2CH_3$ | $NHCH_3$ | |
| 63 | H | 5-$OCH_3$ | H | — | O | $OCH_3$ | $OCH_3$ | |
| 63 | H | 5-$SCH_3$ | H | — | O | $OCH_3$ | $OCH_3$ | |
| 63 | H | H | H | — | S | $OCH_3$ | $OCH_3$ | |
| 63 | H | H | H | — | S | $OCH_3$ | $CH_3$ | |
| 63 | $CH_3$ | H | H | — | S | $OCH_3$ | $CH_3$ | |
| 63 | H | H | H | — | S | $OCH_2CH_3$ | $NHCH_3$ | |
| 63 | H | 5-$OCH_3$ | H | — | S | $OCH_3$ | $OCH_3$ | |
| 63 | H | 5-$SCH_3$ | H | — | S | $OCH_3$ | $OCH_3$ | |
| 64 | H | H | H | — | $SO_2$ | $OCH_3$ | $OCH_3$ | |
| 64 | H | H | H | — | $SO_2$ | $OCH_3$ | $CH_3$ | |
| 64 | $CH_3$ | H | H | — | $SO_2$ | $OCH_3$ | $CH_3$ | |
| 64 | H | H | H | — | $SO_2$ | $OCH_2CH_3$ | $NHCH_3$ | |
| 64 | H | 5-$OCH_3$ | H | — | $SO_2$ | $OCH_3$ | $OCH_3$ | |
| 64 | H | 5-$SCH_3$ | H | — | $SO_2$ | $OCH_3$ | $OCH_3$ | |
| 64 | H | H | H | — | O | $OCH_3$ | $OCH_3$ | |
| 64 | H | H | H | — | O | $OCH_3$ | $CH_3$ | |
| 64 | $CH_3$ | H | H | — | O | $OCH_3$ | $CH_3$ | |
| 64 | H | H | H | — | O | $OCH_2CH_3$ | $NHCH_3$ | |
| 64 | H | 5-$OCH_3$ | H | — | O | $OCH_3$ | $OCH_3$ | |
| 64 | H | 5-$SCH_3$ | H | — | O | $OCH_3$ | $OCH_3$ | |
| 65 | H | H | H | — | — | $OCH_3$ | $OCH_3$ | |
| 65 | H | H | H | — | — | $OCH_3$ | $CH_3$ | |

TABLE 2-continued

General Formula 2

| Q | R | $R_1$ | $R_3$ | $W_3$ | $W_4$ | X | Y | m.p. (°C.) |
|---|---|---|---|---|---|---|---|---|
| 65 | $CH_3$ | H | H | — | — | $OCH_3$ | $CH_3$ | |
| 65 | H | H | H | — | — | $OCH_2CH_3$ | $NHCH_3$ | |
| 65 | H | 5-$OCH_3$ | H | — | — | $OCH_3$ | $OCH_3$ | |
| 65 | H | 5-$SCH_3$ | H | — | — | $OCH_3$ | $OCH_3$ | |
| 66 | H | H | H | O | — | $OCH_3$ | $OCH_3$ | |
| 66 | H | H | H | O | — | $OCH_3$ | $CH_3$ | |
| 66 | $CH_3$ | H | H | O | — | $OCH_3$ | $CH_3$ | |
| 66 | H | H | H | O | — | $OCH_2CH_3$ | $NHCH_3$ | |
| 66 | H | 5-$OCH_3$ | H | O | — | $OCH_3$ | $OCH_3$ | |
| 66 | H | 5-$SCH_3$ | H | O | — | $OCH_3$ | $OCH_3$ | |
| 67 | H | H | H | $NCH_3$ | — | $OCH_3$ | $OCH_3$ | |
| 67 | H | H | H | $NCH_3$ | — | $OCH_3$ | $CH_3$ | |
| 67 | $CH_3$ | H | H | $NCH_3$ | — | $OCH_3$ | $CH_3$ | |
| 67 | H | H | H | $NCH_3$ | — | $OCH_2CH_3$ | $NHCH_3$ | |
| 67 | H | 5-$OCH_3$ | H | $NCH_3$ | — | $OCH_3$ | $OCH_3$ | |
| 67 | H | 5-$SCH_3$ | H | $NCH_3$ | — | $OCH_3$ | $OCH_3$ | |
| 68 | H | H | H | — | — | $OCH_3$ | $OCH_3$ | |
| 68 | H | H | H | — | — | $OCH_3$ | $CH_3$ | |
| 68 | $CH_3$ | H | H | — | — | $OCH_3$ | $CH_3$ | |
| 68 | H | H | H | — | — | $OCH_2CH_3$ | $NHCH_3$ | |
| 68 | H | 5-$OCH_3$ | H | — | — | $OCH_3$ | $OCH_3$ | |
| 68 | H | 5-$SCH_3$ | H | — | — | $OCH_3$ | $OCH_3$ | |
| 69 | H | H | H | — | — | $OCH_3$ | $OCH_3$ | |
| 69 | H | H | H | — | — | $OCH_3$ | $CH_3$ | |
| 69 | $CH_3$ | H | H | — | — | $OCH_3$ | $CH_3$ | |
| 69 | H | H | H | — | — | $OCH_2CH_3$ | $NHCH_3$ | |
| 69 | H | 5-$OCH_3$ | H | — | — | $OCH_3$ | $OCH_3$ | |
| 69 | H | 5-$SCH_3$ | H | — | — | $OCH_3$ | $OCH_3$ | |
| 70 | H | H | H | O | — | $OCH_3$ | $OCH_3$ | |
| 70 | H | H | H | O | — | $OCH_3$ | $CH_3$ | |
| 70 | $CH_3$ | H | H | O | — | $OCH_3$ | $CH_3$ | |
| 70 | H | H | H | O | — | $OCH_2CH_3$ | $NHCH_3$ | |
| 70 | H | 5-$OCH_3$ | H | O | — | $OCH_3$ | $OCH_3$ | |
| 70 | H | 5-$SCH_3$ | H | O | — | $OCH_3$ | $OCH_3$ | |
| 71 | H | H | H | $NCH_3$ | — | $OCH_3$ | $OCH_3$ | |
| 71 | H | H | H | $NCH_3$ | — | $OCH_3$ | $CH_3$ | |
| 71 | $CH_3$ | H | H | $NCH_3$ | — | $OCH_3$ | $CH_3$ | |
| 71 | H | H | H | $NCH_3$ | — | $OCH_2CH_3$ | $NHCH_3$ | |
| 71 | H | 5-$OCH_3$ | H | $NCH_3$ | — | $OCH_3$ | $OCH_3$ | |
| 71 | H | 5-$SCH_3$ | H | $NCH_3$ | — | $OCH_3$ | $OCH_3$ | |
| 72 | H | H | H | $NCH_3$ | — | $OCH_3$ | $OCH_3$ | |
| 72 | H | H | H | $NCH_3$ | — | $OCH_3$ | $CH_3$ | |
| 72 | $CH_3$ | H | H | $NCH_3$ | — | $OCH_3$ | $CH_3$ | |
| 72 | H | H | H | $NCH_3$ | — | $OCH_2CH_3$ | $NHCH_3$ | |
| 72 | H | 5-$OCH_3$ | H | $NCH_3$ | — | $OCH_3$ | $OCH_3$ | |
| 72 | H | 5-$SCH_3$ | H | $NCH_3$ | — | $OCH_3$ | $OCH_3$ | |
| 73 | H | H | H | $NCH_3$ | — | $OCH_3$ | $OCH_3$ | |
| 73 | H | H | H | $NCH_3$ | — | $OCH_3$ | $CH_3$ | |
| 73 | $CH_3$ | H | H | $NCH_3$ | — | $OCH_3$ | $CH_3$ | |
| 73 | H | H | H | $NCH_3$ | — | $OCH_2CH_3$ | $NHCH_3$ | |
| 73 | H | 5-$OCH_3$ | H | $NCH_3$ | — | $OCH_3$ | $OCH_3$ | |
| 73 | H | 5-$SCH_3$ | H | $NCH_3$ | — | $OCH_3$ | $OCH_3$ | |
| 74 | H | H | H | — | O | $OCH_3$ | $OCH_3$ | |
| 74 | H | H | H | — | O | $OCH_3$ | $CH_3$ | |
| 74 | $CH_3$ | H | H | — | O | $OCH_3$ | $CH_3$ | |
| 74 | H | H | H | — | O | $OCH_2CH_3$ | $NHCH_3$ | |
| 74 | H | 5-$OCH_3$ | H | — | O | $OCH_3$ | $OCH_3$ | |
| 74 | H | 5-$SCH_3$ | H | — | O | $OCH_3$ | $OCH_3$ | |
| 75 | H | H | H | — | O | $OCH_3$ | $OCH_3$ | |
| 75 | H | H | H | — | O | $OCH_3$ | $CH_3$ | |
| 75 | $CH_3$ | H | H | — | O | $OCH_3$ | $CH_3$ | |
| 75 | H | H | H | — | O | $OCH_2CH_3$ | $NHCH_3$ | |
| 75 | H | 5-$OCH_3$ | H | — | O | $OCH_3$ | $OCH_3$ | |
| 75 | H | 5-$SCH_3$ | H | — | O | $OCH_3$ | $OCH_3$ | |
| 76 | H | H | H | O | — | $OCH_3$ | $OCH_3$ | 216–217 |
| 76 | H | H | H | O | — | $OCH_3$ | $CH_3$ | 196–200 |
| 76 | $CH_3$ | H | H | O | — | $OCH_3$ | $CH_3$ | |
| 76 | H | H | H | O | — | $OCH_2CH_3$ | $NHCH_3$ | |
| 76 | H | 5-$OCH_3$ | H | O | — | $OCH_3$ | $OCH_3$ | |
| 76 | H | 5-$SCH_3$ | H | O | — | $OCH_3$ | $OCH_3$ | |
| 77 | H | H | H | O | — | $OCH_3$ | $OCH_3$ | |
| 77 | H | H | H | O | — | $OCH_3$ | $CH_3$ | |
| 77 | $CH_3$ | H | H | O | — | $OCH_3$ | $CH_3$ | |
| 77 | H | H | H | O | — | $OCH_2CH_3$ | $NHCH_3$ | |
| 77 | H | 5-$OCH_3$ | H | O | — | $OCH_3$ | $OCH_3$ | |
| 77 | H | 5-$SCH_3$ | H | O | — | $OCH_3$ | $OCH_3$ | |
| 78 | H | H | H | — | — | $OCH_3$ | $OCH_3$ | |
| 78 | H | H | H | — | — | $OCH_3$ | $CH_3$ | |
| 78 | $CH_3$ | H | H | — | — | $OCH_3$ | $CH_3$ | |
| 78 | H | H | H | — | — | $OCH_2CH_3$ | $NHCH_3$ | |

TABLE 2-continued

General Formula 2

| Q | R | $R_1$ | $R_3$ | $W_3$ | $W_4$ | X | Y | m.p. (°C.) |
|---|---|---|---|---|---|---|---|---|
| 78 | H | 5-$OCH_3$ | H | — | — | $OCH_3$ | $OCH_3$ | |
| 78 | H | 5-$SCH_3$ | H | — | — | $OCH_3$ | $OCH_3$ | |
| 79 | H | H | H | — | — | $OCH_3$ | $OCH_3$ | >260 |
| 79 | H | H | H | — | — | $OCH_3$ | $CH_3$ | 195–197 |
| 79 | $CH_3$ | H | H | — | — | $OCH_3$ | $CH_3$ | |
| 79 | H | H | H | — | — | $OCH_2CH_3$ | $NHCH_3$ | |
| 79 | H | 5-$OCH_3$ | H | — | — | $OCH_3$ | $OCH_3$ | |
| 79 | H | 5-$SCH_3$ | H | — | — | $OCH_3$ | $OCH_3$ | |
| 79 ($R_6=CH_3$) | H | H | H | — | — | $OCH_3$ | $OCH_3$ | 181–185 |
| 79 ($R_6=CH_3$) | H | H | H | — | — | $OCH_3$ | $CH_3$ | 168–172 |
| 79 ($R_6=CH_3$) | $CH_3$ | H | H | — | — | $OCH_3$ | $CH_3$ | |
| 79 ($R_6=CH_3$) | H | H | H | — | — | $OCH_2CH_3$ | $NHCH_3$ | 191–196 |
| 79 ($R_6=CH_3$) | H | 5-$OCH_3$ | H | — | — | $OCH_3$ | $OCH_3$ | |
| 79 ($R_6=CH_3$) | H | 5-$SCH_3$ | H | — | — | $OCH_3$ | $OCH_3$ | |
| 80 ($R_4, R_5=CH_3$) | H | H | H | — | — | $OCH_3$ | $OCH_3$ | |
| 80 ($R_4, R_5=CH_3$) | H | H | H | — | — | $OCH_3$ | $CH_3$ | |
| 80 ($R_4, R_5=CH_3$) | $CH_3$ | H | H | — | — | $OCH_3$ | $CH_3$ | |
| 80 ($R_4, R_5=CH_3$) | H | H | H | — | — | $OCH_2CH_3$ | $NHCH_3$ | |
| 80 ($R_4, R_5=CH_3$) | H | 5-$OCH_3$ | H | — | — | $OCH_3$ | $OCH_3$ | |
| 80 ($R_4, R_5=CH_3$) | H | 5-$SCH_3$ | H | — | — | $OCH_3$ | $OCH_3$ | |

TABLE 3

General Formula 3

| Q | R | $R_1$ | $R_3$ | $W_3$ | $W_4$ | $X_1$ | $Y_1$ | m.p.(°C.) |
|---|---|---|---|---|---|---|---|---|
| 1 | H | H | H | O | — | $CH_3$ | O | |
| 1 | H | H | H | O | — | $OCH_3$ | O | |
| 1 | H | H | H | O | — | $CH_3$ | $CH_2$ | |
| 1 | H | H | H | O | — | $OCH_3$ | $CH_2$ | |
| 1 | H | 5-$OCH_3$ | H | O | — | $CH_3$ | O | |
| 1 | H | 5-$SCH_3$ | H | O | — | $CH_3$ | O | |
| 1 | H | 5-Cl | H | O | — | $CH_3$ | O | |
| 1 | H | 5-$CF_3$ | H | O | — | $CH_3$ | O | |
| 1 | H | 6-$SO_2N(CH_3)_2$ | H | O | — | $CH_3$ | O | |
| 1 | H | 6-$CO_2CH_3$ | H | O | — | $CH_3$ | O | |
| 1 | H | 5-$OCF_2H$ | H | O | — | $CH_3$ | O | |
| 1 | H | H | H | O | — | $OCH_2CH_3$ | $CH_2$ | |
| 1 | H | H | H | O | — | $OCF_2H$ | $CH_2$ | |
| 1 | H | H | H | $NCH_3$ | — | $CH_3$ | O | |
| 1 | H | H | H | $NCH_3$ | — | $OCH_3$ | O | |
| 1 | H | H | H | $NCH_3$ | — | $CH_3$ | $CH_2$ | |
| 1 | H | H | H | $NCH_3$ | — | $OCH_3$ | $CH_2$ | |
| 1 | H | 5-$OCH_3$ | H | $NCH_3$ | — | $CH_3$ | O | |
| 1 | H | 5-$SCH_3$ | H | $NCH_3$ | — | $CH_3$ | O | |
| 3 | H | H | H | — | — | $CH_3$ | $CH_2$ | |
| 3 | H | H | H | — | — | $CH_3$ | O | |
| 3 | H | H | H | — | — | $OCH_3$ | $CH_2$ | |
| 3 | H | 5-$OCH_3$ | H | — | — | $OCH_3$ | $CH_2$ | |
| 3 | H | 5-$SCH_3$ | H | — | — | $OCH_3$ | $CH_2$ | |
| 5 | H | H | H | $NCH_3$ | — | $CH_3$ | $CH_2$ | |
| 5 | H | H | H | $NCH_3$ | — | $CH_3$ | O | |
| 5 | H | H | H | $NCH_3$ | — | $OCH_3$ | $CH_2$ | |
| 5 | H | 5-$OCH_3$ | H | $NCH_3$ | — | $OCH_3$ | $CH_2$ | |
| 5 | H | 5-$SCH_3$ | H | $NCH_3$ | — | $OCH_3$ | $CH_2$ | |
| 7 | H | H | H | — | S | $CH_3$ | $CH_2$ | |
| 7 | H | H | H | — | S | $CH_3$ | O | |
| 7 | H | H | H | — | S | $OCH_3$ | $CH_2$ | |
| 7 | H | 5-$OCH_3$ | H | — | S | $OCH_3$ | $CH_2$ | |
| 7 | H | 5-$SCH_3$ | H | — | S | $OCH_3$ | $CH_2$ | |
| 7 | H | H | H | — | $SO_2$ | $CH_3$ | $CH_2$ | |
| 7 | H | H | H | — | $SO_2$ | $CH_3$ | O | |
| 7 | H | H | H | — | $SO_2$ | $OCH_3$ | $CH_2$ | |
| 7 | H | 5-$OCH_3$ | H | — | $SO_2$ | $OCH_3$ | $CH_2$ | |
| 7 | H | 5-$SCH_3$ | H | — | $SO_2$ | $OCH_3$ | $CH_2$ | |
| 8 | H | H | H | — | S | $CH_3$ | $CH_2$ | |
| 8 | H | H | H | — | S | $CH_3$ | O | |
| 8 | H | H | H | — | S | $OCH_3$ | $CH_2$ | |
| 8 | H | 5-$OCH_3$ | H | — | S | $OCH_3$ | $CH_2$ | |
| 8 | H | 5-$SCH_3$ | H | — | S | $OCH_3$ | $CH_2$ | |
| 8 | H | H | H | — | $SO_2$ | $CH_3$ | $CH_2$ | |
| 8 | H | H | H | — | $SO_2$ | $CH_3$ | O | |
| 8 | H | H | H | — | $SO_2$ | $OCH_3$ | $CH_2$ | |
| 8 | H | 5-$OCH_3$ | H | — | $SO_2$ | $OCH_3$ | $CH_2$ | |
| 8 | H | 5-$SCH_3$ | H | — | $SO_2$ | $OCH_3$ | $CH_2$ | |
| 16 | H | H | H | O | — | $CH_3$ | O | |
| 16 | H | H | H | O | — | $OCH_3$ | O | |
| 16 | H | H | H | O | — | $CH_3$ | $CH_2$ | |
| 16 | H | H | H | O | — | $OCH_3$ | $CH_2$ | |

TABLE 3-continued

General Formula 3

| Q | R | R$_1$ | R$_3$ | W$_3$ | W$_4$ | X$_1$ | Y$_1$ | m.p.(°C.) |
|---|---|---|---|---|---|---|---|---|
| 16 | H | 5-OCH$_3$ | H | O | — | CH$_3$ | O | |
| 16 | H | 5-SCH$_3$ | H | O | — | CH$_3$ | O | |
| 16 | H | 5-Cl | H | O | — | CH$_3$ | O | |
| 16 | H | 5-CF$_3$ | H | O | — | CH$_3$ | O | |
| 16 | H | 6-SO$_2$N(CH$_3$)$_2$ | H | O | — | CH$_3$ | O | |
| 16 | H | 6-CO$_2$CH$_3$ | H | O | — | CH$_3$ | O | |
| 16 | H | 5-OCF$_2$H | H | O | — | CH$_3$ | O | |
| 16 | H | H | H | O | — | OCH$_2$CH$_3$ | CH$_2$ | |
| 16 | H | H | H | O | — | OCF$_2$H | CH$_2$ | |
| 19 | H | H | H | — | — | CH$_3$ | CH$_2$ | |
| 19 | H | H | H | — | — | CH$_3$ | O | |
| 19 | H | H | H | — | — | OCH$_3$ | CH$_2$ | |
| 19 | H | 5-OCH$_3$ | H | — | — | OCH$_3$ | CH$_2$ | |
| 19 | H | 5-SCH$_3$ | H | — | — | OCH$_3$ | CH$_2$ | |
| 20 | H | H | H | — | — | CH$_3$ | CH$_2$ | |
| 20 | H | H | H | — | — | CH$_3$ | O | |
| 20 | H | H | H | — | — | OCH$_3$ | CH$_2$ | |
| 20 | H | 5-OCH$_3$ | H | — | — | OCH$_3$ | CH$_2$ | |
| 20 | H | 5-SCH$_3$ | H | — | — | OCH$_3$ | CH$_2$ | |
| 21 | H | H | H | — | — | CH$_3$ | CH$_2$ | |
| 21 | H | H | H | — | — | CH$_3$ | O | |
| 21 | H | H | H | — | — | OCH$_3$ | CH$_2$ | |
| 21 | H | 5-OCH$_3$ | H | — | — | OCH$_3$ | CH$_2$ | |
| 21 | H | 5-SCH$_3$ | H | — | — | OCH$_3$ | CH$_2$ | |
| 22 | H | H | H | NCH$_3$ | — | CH$_3$ | CH$_2$ | |
| 22 | H | H | H | NCH$_3$ | — | CH$_3$ | O | |
| 22 | H | H | H | NCH$_3$ | — | OCH$_3$ | CH$_2$ | |
| 22 | H | 5-OCH$_3$ | H | NCH$_3$ | — | OCH$_3$ | CH$_2$ | |
| 22 | H | 5-SCH$_3$ | H | NCH$_3$ | — | OCH$_3$ | CH$_2$ | |
| 25 | H | H | H | — | S | CH$_3$ | CH$_2$ | |
| 25 | H | H | H | — | S | CH$_3$ | O | |
| 25 | H | H | H | — | S | OCH$_3$ | CH$_2$ | |
| 25 | H | 5-OCH$_3$ | H | — | S | OCH$_3$ | CH$_2$ | |
| 25 | H | 5-SCH$_3$ | H | — | S | OCH$_3$ | CH$_2$ | |
| 25 | H | H | H | — | SO$_2$ | CH$_3$ | CH$_2$ | |
| 25 | H | H | H | — | SO$_2$ | CH$_3$ | O | |
| 25 | H | H | H | — | SO$_2$ | OCH$_3$ | CH$_2$ | |
| 25 | H | 5-OCH$_3$ | H | — | SO$_2$ | OCH$_3$ | CH$_2$ | |
| 25 | H | 5-SCH$_3$ | H | — | SO$_2$ | OCH$_3$ | CH$_2$ | |
| 26 | H | H | H | — | S | CH$_3$ | CH$_2$ | |
| 26 | H | H | H | — | S | CH$_3$ | O | |
| 26 | H | H | H | — | S | OCH$_3$ | CH$_2$ | |
| 26 | H | 5-OCH$_3$ | H | — | S | OCH$_3$ | CH$_2$ | |
| 26 | H | 5-SCH$_3$ | H | — | S | OCH$_3$ | CH$_2$ | |
| 26 | H | H | H | — | SO$_2$ | CH$_3$ | CH$_2$ | |
| 26 | H | H | H | — | SO$_2$ | CH$_3$ | O | |
| 26 | H | H | H | — | SO$_2$ | OCH$_3$ | CH$_2$ | |
| 26 | H | 5-OCH$_3$ | H | — | SO$_2$ | OCH$_3$ | CH$_2$ | |
| 26 | H | 5-SCH$_3$ | H | — | SO$_2$ | OCH$_3$ | CH$_2$ | |
| 27 | H | H | H | — | S | CH$_3$ | CH$_2$ | |
| 27 | H | H | H | — | S | CH$_3$ | O | |
| 27 | H | H | H | — | S | OCH$_3$ | CH$_2$ | |
| 27 | H | 5-OCH$_3$ | H | — | S | OCH$_3$ | CH$_2$ | |
| 27 | H | 5-SCH$_3$ | H | — | S | OCH$_3$ | CH$_2$ | |
| 27 | H | H | H | — | SO$_2$ | CH$_3$ | CH$_2$ | |
| 27 | H | H | H | — | SO$_2$ | CH$_3$ | O | |
| 27 | H | H | H | — | SO$_2$ | OCH$_3$ | CH$_2$ | |
| 27 | H | 5-OCH$_3$ | H | — | SO$_2$ | OCH$_3$ | CH$_2$ | |
| 27 | H | 5-SCH$_3$ | H | — | SO$_2$ | OCH$_3$ | CH$_2$ | |
| 29(R$_6$=CH$_3$) | H | H | H | — | — | CH$_3$ | CH$_2$ | |
| 29(R$_6$=CH$_3$) | H | H | H | — | — | CH$_3$ | O | |
| 29(R$_6$=CH$_3$) | H | H | H | — | — | OCH$_3$ | CH$_2$ | |
| 29(R$_6$=CH$_3$) | H | 5-OCH$_3$ | H | — | — | OCH$_3$ | CH$_2$ | |
| 29(R$_6$=CH$_3$) | H | 5-SCH$_3$ | H | — | — | OCH$_3$ | CH$_2$ | |
| 55 | H | H | H | O | — | CH$_3$ | CH$_2$ | |
| 55 | H | H | H | O | — | CH$_3$ | O | |
| 55 | H | H | H | O | — | OCH$_3$ | CH$_2$ | |
| 55 | H | 5-OCH$_3$ | H | O | — | OCH$_3$ | CH$_2$ | |
| 55 | H | 5-SCH$_3$ | H | O | — | OCH$_3$ | CH$_2$ | |
| 55 | H | H | H | NCH$_3$ | — | CH$_3$ | CH$_2$ | |
| 55 | H | H | H | NCH$_3$ | — | CH$_3$ | O | |
| 55 | H | H | H | NCH$_3$ | — | OCH$_3$ | CH$_2$ | |
| 55 | H | 5-OCH$_3$ | H | NCH$_3$ | — | OCH$_3$ | CH$_2$ | |
| 55 | H | 5-SCH$_3$ | H | NCH$_3$ | — | OCH$_3$ | CH$_2$ | |
| 56 | H | H | H | — | — | CH$_3$ | CH$_2$ | |
| 56 | H | H | H | — | — | CH$_3$ | O | |
| 56 | H | H | H | — | — | OCH$_3$ | CH$_2$ | |
| 56 | H | 5-OCH$_3$ | H | — | — | OCH$_3$ | CH$_2$ | |
| 56 | H | 5-SCH$_3$ | H | — | — | OCH$_3$ | CH$_2$ | |
| 61 | H | H | H | NCH$_3$ | — | CH$_3$ | CH$_2$ | |

TABLE 3-continued

General Formula 3

| Q | R | R₁ | R₃ | W₃ | W₄ | X₁ | Y₁ | m.p.(°C.) |
|---|---|---|---|---|---|---|---|---|
| 61 | H | H | H | NCH₃ | — | CH₃ | O | |
| 61 | H | H | H | NCH₃ | — | OCH₃ | CH₂ | |
| 61 | H | 5-OCH₃ | H | NCH₃ | — | OCH₃ | CH₂ | |
| 61 | H | 5-SCH₃ | H | NCH₃ | — | OCH₃ | CH₂ | |
| 62 | H | H | H | NCH₃ | — | CH₃ | CH₂ | |
| 62 | H | H | H | NCH₃ | — | CH₃ | O | |
| 62 | H | H | H | NCH₃ | — | OCH₃ | CH₂ | |
| 62 | H | 5-OCH₃ | H | NCH₃ | — | OCH₃ | CH₂ | |
| 62 | H | 5-SCH₃ | H | NCH₃ | — | OCH₃ | CH₂ | |
| 65 | H | H | H | — | — | CH₃ | CH₂ | |
| 65 | H | H | H | — | — | CH₃ | O | |
| 65 | H | H | H | — | — | OCH₃ | CH₂ | |
| 65 | H | 5-OCH₃ | H | — | — | OCH₃ | CH₂ | |
| 65 | H | 5-SCH₃ | H | — | — | OCH₃ | CH₂ | |
| 68 | H | H | H | — | — | CH₃ | CH₂ | |
| 68 | H | H | H | — | — | CH₃ | O | |
| 68 | H | H | H | — | — | OCH₃ | CH₂ | |
| 68 | H | 5-OCH₃ | H | — | — | OCH₃ | CH₂ | |
| 68 | H | 5-SCH₃ | H | — | — | OCH₃ | CH₂ | |
| 76 | H | H | H | O | — | CH₃ | CH₂ | |
| 76 | H | H | H | O | — | CH₃ | O | |
| 76 | H | H | H | O | — | OCH₃ | CH₂ | |
| 76 | H | 5-OCH₃ | H | O | — | OCH₃ | CH₂ | |
| 76 | H | 5-SCH₃ | H | O | — | OCH₃ | CH₂ | |
| 78 | H | H | H | — | — | CH₃ | CH₂ | |
| 78 | H | H | H | — | — | CH₃ | O | |
| 78 | H | H | H | — | — | OCH₃ | CH₂ | |
| 78 | H | 5-OCH₃ | H | — | — | OCH₃ | CH₂ | |
| 78 | H | 5-SCH₃ | H | — | — | OCH₃ | CH₂ | |
| 79 | H | H | H | — | — | CH₃ | CH₂ | |
| 79 | H | H | H | — | — | CH₃ | O | |
| 79 | H | H | H | — | — | OCH₃ | CH₂ | |
| 79 | H | 5-OCH₃ | H | — | — | OCH₃ | CH₂ | |
| 79 | H | 5-SCH₃ | H | — | — | OCH₃ | CH₂ | |

TABLE 4

General Formula 4

| Q | R | R₁ | R₃ | W₃ | W₄ | X₁ | m.p. (°C.) |
|---|---|---|---|---|---|---|---|
| 1 | H | H | H | O | — | CH₃ | |
| 1 | H | H | H | O | — | OCH₃ | |
| 1 | H | 5-OCH₃ | H | O | — | CH₃ | |
| 1 | H | 5-SCH₃ | H | O | — | CH₃ | |
| 3 | H | H | H | — | — | CH₃ | |
| 3 | H | H | H | — | — | OCH₃ | |
| 3 | H | 5-OCH₃ | H | — | — | CH₃ | |
| 3 | H | 5-SCH₃ | H | — | — | CH₃ | |
| 5 | H | H | H | NCH₃ | — | CH₃ | |
| 5 | H | H | H | NCH₃ | — | OCH₃ | |
| 5 | H | 5-OCH₃ | H | NCH₃ | — | CH₃ | |
| 5 | H | 5-SCH₃ | H | NCH₃ | — | CH₃ | |
| 7 | H | H | H | — | S | CH₃ | |
| 7 | H | H | H | — | S | OCH₃ | |
| 7 | H | 5-OCH₃ | H | — | S | CH₃ | |
| 7 | H | 5-SCH₃ | H | — | S | CH₃ | |
| 7 | H | H | H | — | SO₂ | CH₃ | |
| 7 | H | H | H | — | SO₂ | OCH₃ | |
| 7 | H | 5-OCH₃ | H | — | SO₂ | CH₃ | |
| 7 | H | 5-SCH₃ | H | — | SO₂ | CH₃ | |
| 8 | H | H | H | — | S | CH₃ | |
| 8 | H | H | H | — | S | OCH₃ | |
| 8 | H | 5-OCH₃ | H | — | S | CH₃ | |
| 8 | H | 5-SCH₃ | H | — | S | CH₃ | |
| 8 | H | H | H | — | SO₂ | CH₃ | |
| 8 | H | H | H | — | SO₂ | OCH₃ | |
| 8 | H | 5-OCH₃ | H | — | SO₂ | CH₃ | |
| 8 | H | 5-SCH₃ | H | — | SO₂ | CH₃ | |
| 16 | H | H | H | — | — | CH₃ | |
| 16 | H | H | H | — | — | OCH₃ | |
| 16 | H | 5-OCH₃ | H | — | — | CH₃ | |
| 16 | H | 5-SCH₃ | H | — | — | CH₃ | |
| 19 | H | H | H | — | — | CH₃ | |
| 19 | H | H | H | — | — | OCH₃ | |
| 19 | H | 5-OCH₃ | H | — | — | CH₃ | |
| 19 | H | 5-SCH₃ | H | — | — | CH₃ | |
| 20 | H | H | H | — | — | CH₃ | |
| 20 | H | H | H | — | — | OCH₃ | |
| 20 | H | 5-OCH₃ | H | — | — | CH₃ | |
| 20 | H | 5-SCH₃ | H | — | — | CH₃ | |
| 21 | H | H | H | — | — | CH₃ | |
| 21 | H | H | H | — | — | OCH₃ | |
| 21 | H | 5-OCH₃ | H | — | — | CH₃ | |
| 21 | H | 5-SCH₃ | H | — | — | CH₃ | |
| 22 | H | H | H | NCH₃ | — | CH₃ | |
| 22 | H | H | H | NCH₃ | — | OCH₃ | |
| 22 | H | 5-OCH₃ | H | NCH₃ | — | CH₃ | |
| 22 | H | 5-SCH₃ | H | NCH₃ | — | CH₃ | |
| 25 | H | H | H | — | S | CH₃ | |
| 25 | H | H | H | — | S | OCH₃ | |
| 25 | H | 5-OCH₃ | H | — | S | CH₃ | |
| 25 | H | 5-SCH₃ | H | — | S | CH₃ | |
| 25 | H | H | H | — | SO₂ | CH₃ | |
| 25 | H | H | H | — | SO₂ | OCH₃ | |
| 25 | H | 5-OCH₃ | H | — | SO₂ | CH₃ | |
| 25 | H | 5-SCH₃ | H | — | SO₂ | CH₃ | |
| 26 | H | H | H | — | S | CH₃ | |
| 26 | H | H | H | — | S | OCH₃ | |
| 26 | H | 5-OCH₃ | H | — | S | CH₃ | |
| 26 | H | 5-SCH₃ | H | — | S | CH₃ | |
| 26 | H | H | H | — | SO₂ | CH₃ | |
| 26 | H | H | H | — | SO₂ | OCH₃ | |
| 26 | H | 5-OCH₃ | H | — | SO₂ | CH₃ | |
| 26 | H | 5-SCH₃ | H | — | SO₂ | CH₃ | |
| 27 | H | H | H | — | S | CH₃ | |
| 27 | H | H | H | — | S | OCH₃ | |
| 27 | H | 5-OCH₃ | H | — | S | CH₃ | |
| 27 | H | 5-SCH₃ | H | — | S | CH₃ | |
| 27 | H | H | H | — | SO₂ | CH₃ | |
| 27 | H | H | H | — | SO₂ | OCH₃ | |
| 27 | H | 5-OCH₃ | H | — | SO₂ | CH₃ | |
| 27 | H | 5-SCH₃ | H | — | SO₂ | CH₃ | |
| 29 (R₆=CH₃) | H | H | H | — | — | CH₃ | |
| 29 (R₆=CH₃) | H | H | H | — | — | OCH₃ | |
| 29 (R₆=CH₃) | H | 5-OCH₃ | H | — | — | CH₃ | |
| 29 (R₆=CH₃) | H | 5-SCH₃ | H | — | — | CH₃ | |

TABLE 4-continued

General Formula 4

| Q | R | R₁ | R₃ | W₃ | W₄ | X₁ | m.p. (°C.) |
|---|---|---|---|---|---|---|---|
| 55 | H | H | H | O | — | CH₃ | |
| 55 | H | H | H | O | — | OCH₃ | |
| 55 | H | 5-OCH₃ | H | O | — | CH₃ | |
| 55 | H | 5-SCH₃ | H | O | — | CH₃ | |
| 55 | H | H | H | NCH₃ | — | CH₃ | |
| 55 | H | H | H | NCH₃ | — | OCH₃ | |
| 55 | H | 5-OCH₃ | H | NCH₃ | — | CH₃ | |
| 55 | H | 5-SCH₃ | H | NCH₃ | — | CH₃ | |
| 56 | H | H | H | — | — | CH₃ | |
| 56 | H | H | H | — | — | OCH₃ | |
| 56 | H | 5-OCH₃ | H | — | — | CH₃ | |
| 56 | H | 5-SCH₃ | H | — | — | CH₃ | |
| 61 | H | H | H | NCH₃ | — | CH₃ | |
| 61 | H | H | H | NCH₃ | — | OCH₃ | |
| 61 | H | 5-OCH₃ | H | NCH₃ | — | CH₃ | |
| 61 | H | 5-SCH₃ | H | NCH₃ | — | CH₃ | |
| 62 | H | H | H | NCH₃ | — | CH₃ | |
| 62 | H | H | H | NCH₃ | — | OCH₃ | |
| 62 | H | 5-OCH₃ | H | NCH₃ | — | CH₃ | |
| 62 | H | 5-SCH₃ | H | NCH₃ | — | CH₃ | |
| 65 | H | H | H | — | — | CH₃ | |
| 65 | H | H | H | — | — | OCH₃ | |
| 65 | H | 5-OCH₃ | H | — | — | CH₃ | |
| 65 | H | 5-SCH₃ | H | — | — | CH₃ | |
| 68 | H | H | H | — | — | CH₃ | |
| 68 | H | H | H | — | — | OCH₃ | |
| 68 | H | 5-OCH₃ | H | — | — | CH₃ | |
| 68 | H | 5-SCH₃ | H | — | — | CH₃ | |
| 76 | H | H | H | O | — | CH₃ | |
| 76 | H | H | H | O | — | OCH₃ | |
| 76 | H | 5-OCH₃ | H | O | — | CH₃ | |
| 76 | H | 5-SCH₃ | H | O | — | CH₃ | |
| 78 | H | H | H | — | — | CH₃ | |
| 78 | H | H | H | — | — | OCH₃ | |
| 78 | H | 5-OCH₃ | H | — | — | CH₃ | |
| 78 | H | 5-SCH₃ | H | — | — | CH₃ | |
| 79 | H | H | H | — | — | CH₃ | |
| 79 | H | H | H | — | — | OCH₃ | |
| 79 | H | 5-OCH₃ | H | — | — | CH₃ | |
| 79 | H | 5-SCH₃ | H | — | — | CH₃ | |

TABLE 5

General Formula 5

| Q | R | R₁ | R₃ | W₃ | W₄ | X₁ | Y₃ | m.p. (°C.) |
|---|---|---|---|---|---|---|---|---|
| 1 | H | H | H | O | — | CH₃ | CH₃ | |
| 1 | H | H | H | O | — | CH₃ | H | |
| 1 | H | H | H | O | — | OCH₃ | CH₃ | |
| 1 | H | H | H | O | — | OCH₃ | H | |
| 1 | H | H | H | O | — | OCF₂H | CH₃ | |
| 1 | H | 5-OCH₃ | H | O | — | OCH₃ | H | |
| 1 | H | 5-SCH₃ | H | O | — | OCH₃ | H | |
| 1 | H | 5-Cl | H | O | — | OCH₃ | H | |
| 1 | H | 5-CF₃ | H | O | — | OCH₃ | H | |
| 1 | H | 5-OCF₂H | H | O | — | OCH₃ | H | |
| 1 | H | 6-SO₂N(CH₃)₂ | H | O | — | OCH₃ | H | |
| 1 | H | 6-CO₂CH₃ | H | O | — | OCH₃ | H | |
| 1 | H | 5-NHCH₃ | H | O | — | OCH₃ | H | |
| 1 | H | 5-N(CH₃)₂ | H | O | — | OCH₃ | H | |
| 1 | H | 5-SCH₃ | CH₃ | O | — | OCH₃ | H | |
| 3 | H | H | H | — | — | OCH₃ | H | |
| 3 | H | 5-OCH₃ | H | — | — | OCH₃ | H | |
| 3 | H | 5-SCH₃ | H | — | — | OCH₃ | H | |
| 5 | H | H | H | NCH₃ | — | OCH₃ | H | |
| 5 | H | 5-OCH₃ | H | NCH₃ | — | OCH₃ | H | |
| 5 | H | 5-SCH₃ | H | NCH₃ | — | OCH₃ | H | |
| 7 | H | H | H | — | S | OCH₃ | H | |
| 7 | H | 5-OCH₃ | H | — | S | OCH₃ | H | |
| 7 | H | 5-SCH₃ | H | — | S | OCH₃ | H | |
| 7 | H | H | H | — | SO₂ | OCH₃ | H | |
| 7 | H | 5-OCH₃ | H | — | SO₂ | OCH₃ | H | |
| 7 | H | 5-SCH₃ | H | — | SO₂ | OCH₃ | H | |
| 8 | H | H | H | — | S | OCH₃ | H | |
| 8 | H | 5-OCH₃ | H | — | S | OCH₃ | H | |
| 8 | H | 5-SCH₃ | H | — | S | OCH₃ | H | |
| 16 | H | H | H | — | — | OCH₃ | H | |
| 16 | H | 5-OCH₃ | H | — | — | OCH₃ | H | |
| 16 | H | 5-SCH₃ | H | — | — | OCH₃ | H | |
| 19 | H | H | H | — | — | OCH₃ | H | |
| 19 | H | 5-OCH₃ | H | — | — | OCH₃ | H | |
| 19 | H | 5-SCH₃ | H | — | — | OCH₃ | H | |
| 20 | H | H | H | — | — | OCH₃ | H | |
| 20 | H | 5-OCH₃ | H | — | — | OCH₃ | H | |
| 20 | H | 5-SCH₃ | H | — | — | OCH₃ | H | |
| 21 | H | H | H | — | — | OCH₃ | H | |
| 21 | H | 5-OCH₃ | H | — | — | OCH₃ | H | |
| 21 | H | 5-SCH₃ | H | — | — | OCH₃ | H | |
| 22 | H | H | H | NCH₃ | — | OCH₃ | H | |
| 22 | H | 5-OCH₃ | H | NCH₃ | — | OCH₃ | H | |
| 22 | H | 5-SCH₃ | H | NCH₃ | — | OCH₃ | H | |
| 25 | H | H | H | — | S | OCH₃ | H | |
| 25 | H | 5-OCH₃ | H | — | S | OCH₃ | H | |
| 25 | H | 5-SCH₃ | H | — | S | OCH₃ | H | |
| 25 | H | H | H | — | SO₂ | OCH₃ | H | |
| 25 | H | 5-OCH₃ | H | — | SO₂ | OCH₃ | H | |
| 25 | H | 5-SCH₃ | H | — | SO₂ | OCH₃ | H | |
| 26 | H | H | H | — | S | OCH₃ | H | |

TABLE 5-continued

General Formula 5

| Q | R | R₁ | R₃ | W₃ | W₄ | X₁ | Y₃ | m.p. (°C.) |
|---|---|---|---|---|---|---|---|---|
| 26 | H | 5-OCH₃ | H | — | S | OCH₃ | H | |
| 26 | H | 5-SCH₃ | H | — | S | OCH₃ | H | |
| 26 | H | H | H | — | SO₂ | OCH₃ | H | |
| 26 | H | 5-OCH₃ | H | — | SO₂ | OCH₃ | H | |
| 26 | H | 5-SCH₃ | H | — | SO₂ | OCH₃ | H | |
| 27 | H | H | H | — | S | OCH₃ | H | |
| 27 | H | 5-OCH₃ | H | — | S | OCH₃ | H | |
| 27 | H | 5-SCH₃ | H | — | S | OCH₃ | H | |
| 27 | H | H | H | — | SO₂ | OCH₃ | H | |
| 27 | H | 5-OCH₃ | H | — | SO₂ | OCH₃ | H | |
| 27 | H | 5-SCH₃ | H | — | SO₂ | OCH₃ | H | |
| 29 (R₆=CH₃) | H | H | H | — | — | OCH₃ | H | |
| 29 (R₆=CH₃) | H | 5-OCH₃ | H | — | — | OCH₃ | H | |
| 29 (R₆=CH₃) | H | 5-SCH₃ | H | — | — | OCH₃ | H | |
| 55 | H | H | H | O | — | OCH₃ | H | |
| 55 | H | 5-OCH₃ | H | O | — | OCH₃ | H | |
| 55 | H | 5-SCH₃ | H | O | — | OCH₃ | H | |
| 55 | H | H | H | NCH₃ | — | OCH₃ | H | |
| 55 | H | 5-OCH₃ | H | NCH₃ | — | OCH₃ | H | |
| 55 | H | 5-OCH₃ | H | NCH₃ | — | OCH₃ | H | |
| 56 | H | H | H | — | — | OCH₃ | H | |
| 56 | H | 5-OCH₃ | H | — | — | OCH₃ | H | |
| 56 | H | 5-SCH₃ | H | — | — | OCH₃ | H | |
| 61 | H | H | H | NCH₃ | — | OCH₃ | H | |
| 61 | H | 5-OCH₃ | H | NCH₃ | — | OCH₃ | H | |
| 61 | H | 5-SCH₃ | H | NCH₃ | — | OCH₃ | H | |
| 62 | H | H | H | NCH₃ | — | OCH₃ | H | |
| 62 | H | 5-OCH₃ | H | NCH₃ | — | OCH₃ | H | |
| 62 | H | 5-SCH₃ | H | NCH₃ | — | OCH₃ | H | |
| 65 | H | H | H | — | — | OCH₃ | H | |
| 65 | H | 5-OCH₃ | H | — | — | OCH₃ | H | |
| 65 | H | 5-SCH₃ | H | — | — | OCH₃ | H | |
| 68 | H | H | H | — | — | OCH₃ | H | |
| 68 | H | 5-OCH₃ | H | — | — | OCH₃ | H | |
| 68 | H | 5-SCH₃ | H | — | — | OCH₃ | H | |
| 76 | H | H | H | O | — | OCH₃ | H | |
| 76 | H | 5-OCH₃ | H | O | — | OCH₃ | H | |
| 76 | H | 5-SCH₃ | H | O | — | OCH₃ | H | |
| 78 | H | H | H | — | — | OCH₃ | H | |
| 78 | H | 5-OCH₃ | H | — | — | OCH₃ | H | |
| 78 | H | 5-SCH₃ | H | — | — | OCH₃ | H | |
| 79 | H | H | H | — | — | OCH₃ | H | |
| 79 | H | 5-OCH₃ | H | — | — | OCH₃ | H | |
| 79 | H | 5-SCH₃ | H | — | — | OCH₃ | H | |

TABLE 6

General Formula 6

| Q | R | R₁ | R₃ | W₃ | W₄ | X₂ | Y₂ | m.p. (°C.) |
|---|---|---|---|---|---|---|---|---|
| 1 | H | H | H | O | — | CH₃ | CH₃ | |
| 1 | H | H | H | O | — | CH₃ | OCH₃ | |
| 1 | H | H | H | O | — | CH₃ | SCH₃ | |
| 1 | H | H | H | O | — | CH₂CF₃ | CH₃ | |
| 1 | H | H | H | O | — | CH₂CF₃ | OCH₃ | |
| 1 | H | H | H | O | — | CH₂CF₃ | SCH₃ | |
| 1 | H | 5-OCH₃ | H | O | — | CH₃ | CH₃ | |
| 1 | H | 5-SCH₃ | H | O | — | CH₃ | CH₃ | |
| 1 | H | 5-Cl | H | O | — | CH₃ | CH₃ | |
| 1 | H | 5-OCF₂H | H | O | — | CH₃ | CH₃ | |
| 1 | H | 6-SO₂N(CH₃)₂ | H | O | — | CH₃ | CH₃ | |
| 1 | H | 6-CO₂CH₃ | H | O | — | CH₃ | CH₃ | |
| 1 | H | 5-NHCH₃ | H | O | — | CH₃ | CH₃ | |
| 1 | H | 5-N(CH₃)₂ | H | O | — | CH₃ | CH₃ | |
| 1 | H | 5-SCH₃ | CH₃ | O | — | CH₃ | CH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | CH₃ | SCH₃ | |
| 3 | H | H | H | — | — | CH₃ | CH₃ | |
| 3 | H | H | H | — | — | CH₃ | OCH₃ | |
| 3 | H | 5-OCH₃ | H | — | — | CH₃ | OCH₃ | |
| 3 | H | 5-SCH₃ | H | — | — | CH₃ | OCH₃ | |
| 5 | H | H | H | NCH₃ | — | CH₃ | CH₃ | |
| 5 | H | H | H | NCH₃ | — | CH₃ | OCH₃ | |
| 5 | H | 5-OCH₃ | H | NCH₃ | — | CH₃ | OCH₃ | |
| 5 | H | 5-SCH₃ | H | NCH₃ | — | CH₃ | OCH₃ | |
| 7 | H | H | H | — | S | CH₃ | CH₃ | |
| 7 | H | H | H | — | S | CH₃ | OCH₃ | |
| 7 | H | 5-OCH₃ | H | — | S | CH₃ | OCH₃ | |

TABLE 6-continued

General Formula 6

| Q | R | R₁ | R₃ | W₃ | W₄ | X₂ | Y₂ | m.p. (°C.) |
|---|---|---|---|---|---|---|---|---|
| 7 | H | 5-SCH₃ | H | — | S | CH₃ | OCH₃ | |
| 7 | H | H | H | — | SO₂ | CH₃ | CH₃ | |
| 7 | H | H | H | — | SO₂ | CH₃ | OCH₃ | |
| 7 | H | 5-OCH₃ | H | — | SO₂ | CH₃ | OCH₃ | |
| 7 | H | 5-SCH₃ | H | — | SO₂ | CH₃ | OCH₃ | |
| 8 | H | H | H | — | S | CH₃ | CH₃ | |
| 8 | H | H | H | — | S | CH₃ | OCH₃ | |
| 8 | H | 5-OCH₃ | H | — | S | CH₃ | OCH₃ | |
| 8 | H | 5-SCH₃ | H | — | S | CH₃ | OCH₃ | |
| 8 | H | H | H | — | SO₂ | CH₃ | CH₃ | |
| 8 | H | H | H | — | SO₂ | CH₃ | OCH₃ | |
| 8 | H | 5-OCH₃ | H | — | SO₂ | CH₃ | OCH₃ | |
| 8 | H | 5-SCH₃ | H | — | SO₂ | CH₃ | OCH₃ | |
| 16 | H | H | H | — | — | CH₃ | CH₃ | |
| 16 | H | H | H | — | — | CH₃ | OCH₃ | |
| 16 | H | 5-OCH₃ | H | — | — | CH₃ | OCH₃ | |
| 16 | H | 5-SCH₃ | H | — | — | CH₃ | OCH₃ | |
| 19 | H | H | H | — | — | CH₃ | CH₃ | |
| 19 | H | H | H | — | — | CH₃ | OCH₃ | |
| 19 | H | 5-OCH₃ | H | — | — | CH₃ | OCH₃ | |
| 19 | H | 5-SCH₃ | H | — | — | CH₃ | OCH₃ | |
| 20 | H | H | H | — | — | CH₃ | CH₃ | |
| 20 | H | H | H | — | — | CH₃ | OCH₃ | |
| 20 | H | 5-OCH₃ | H | — | — | CH₃ | OCH₃ | |
| 20 | H | 5-SCH₃ | H | — | — | CH₃ | OCH₃ | |
| 21 | H | H | H | — | — | CH₃ | CH₃ | |
| 21 | H | 5-OCH₃ | H | — | — | CH₃ | OCH₃ | |
| 21 | H | 5-SCH₃ | H | — | — | CH₃ | OCH₃ | |
| 22 | H | H | H | NCH₃ | — | CH₃ | CH₃ | |
| 22 | H | H | H | NCH₃ | — | CH₃ | OCH₃ | |
| 22 | H | 5-OCH₃ | H | NCH₃ | — | CH₃ | OCH₃ | |
| 22 | H | 5-SCH₃ | H | NCH₃ | — | CH₃ | OCH₃ | |
| 25 | H | H | H | — | S | CH₃ | CH₃ | |
| 25 | H | H | H | — | S | CH₃ | OCH₃ | |
| 25 | H | 5-OCH₃ | H | — | S | CH₃ | OCH₃ | |
| 25 | H | 5-SCH₃ | H | — | S | CH₃ | OCH₃ | |
| 25 | H | H | H | — | SO₂ | CH₃ | CH₃ | |
| 25 | H | H | H | — | SO₂ | CH₃ | OCH₃ | |
| 25 | H | 5-OCH₃ | H | — | SO₂ | CH₃ | OCH₃ | |
| 25 | H | 5-SCH₃ | H | — | SO₂ | CH₃ | OCH₃ | |
| 26 | H | H | H | — | S | CH₃ | CH₃ | |
| 26 | H | H | H | — | S | CH₃ | OCH₃ | |
| 26 | H | 5-OCH₃ | H | — | S | CH₃ | OCH₃ | |
| 26 | H | 5-SCH₃ | H | — | S | CH₃ | OCH₃ | |
| 26 | H | H | H | — | SO₂ | CH₃ | CH₃ | |
| 26 | H | H | H | — | SO₂ | CH₃ | OCH₃ | |
| 26 | H | 5-OCH₃ | H | — | SO₂ | CH₃ | OCH₃ | |
| 26 | H | 5-SCH₃ | H | — | SO₂ | CH₃ | OCH₃ | |
| 27 | H | H | H | — | S | CH₃ | CH₃ | |
| 27 | H | H | H | — | S | CH₃ | OCH₃ | |
| 27 | H | 5-OCH₃ | H | — | S | CH₃ | OCH₃ | |
| 27 | H | 5-SCH₃ | H | — | S | CH₃ | OCH₃ | |
| 27 | H | H | H | — | SO₂ | CH₃ | CH₃ | |
| 27 | H | H | H | — | SO₂ | CH₃ | OCH₃ | |
| 27 | H | 5-OCH₃ | H | — | SO₂ | CH₃ | OCH₃ | |
| 27 | H | 5-SCH₃ | H | — | SO₂ | CH₃ | OCH₃ | |
| 29 (R₆=CH₃) | H | H | H | — | — | CH₃ | CH₃ | |
| 29 (R₆=CH₃) | H | H | H | — | — | CH₃ | OCH₃ | |
| 29 (R₆=CH₃) | H | 5-OCH₃ | H | — | — | CH₃ | OCH₃ | |
| 29 (R₆=CH₃) | H | 5-SCH₃ | H | — | — | CH₃ | OCH₃ | |
| 55 | H | H | H | O | — | CH₃ | CH₃ | |
| 55 | H | H | H | O | — | CH₃ | OCH₃ | |
| 55 | H | 5-OCH₃ | H | O | — | CH₃ | OCH₃ | |
| 55 | H | 5-SCH₃ | H | O | — | CH₃ | OCH₃ | |
| 55 | H | H | H | NCH₃ | — | CH₃ | CH₃ | |
| 55 | H | H | H | NCH₃ | — | CH₃ | OCH₃ | |
| 55 | H | 5-OCH₃ | H | NCH₃ | — | CH₃ | OCH₃ | |
| 55 | H | 5-OCH₃ | H | NCH₃ | — | CH₃ | OCH₃ | |
| 56 | H | H | H | — | — | CH₃ | CH₃ | |
| 56 | H | H | H | — | — | CH₃ | OCH₃ | |
| 56 | H | 5-OCH₃ | H | — | — | CH₃ | OCH₃ | |
| 56 | H | 5-SCH₃ | H | — | — | CH₃ | OCH₃ | |
| 61 | H | H | H | NCH₃ | — | CH₃ | CH₃ | |
| 61 | H | H | H | NCH₃ | — | CH₃ | OCH₃ | |
| 61 | H | 5-OCH₃ | H | NCH₃ | — | CH₃ | OCH₃ | |
| 61 | H | 5-SCH₃ | H | NCH₃ | — | CH₃ | OCH₃ | |
| 62 | H | H | H | NCH₃ | — | CH₃ | CH₃ | |
| 62 | H | H | H | NCH₃ | — | CH₃ | OCH₃ | |
| 62 | H | 5-OCH₃ | H | NCH₃ | — | CH₃ | OCH₃ | |
| 62 | H | 5-SCH₃ | H | NCH₃ | — | CH₃ | OCH₃ | |

TABLE 6-continued

General Formula 6

| Q | R | R₁ | R₃ | W₃ | W₄ | X₂ | Y₂ | m.p. (°C.) |
|---|---|----|----|----|----|----|----|-----------|
| 65 | H | H | H | — | — | CH₃ | CH₃ | |
| 65 | H | H | H | — | — | CH₃ | OCH₃ | |
| 65 | H | 5-OCH₃ | H | — | — | CH₃ | OCH₃ | |
| 65 | H | 5-SCH₃ | H | — | — | CH₃ | OCH₃ | |
| 68 | H | H | H | — | — | CH₃ | CH₃ | |
| 68 | H | H | H | — | — | CH₃ | OCH₃ | |
| 68 | H | 5-OCH₃ | H | — | — | CH₃ | OCH₃ | |
| 68 | H | 5-SCH₃ | H | — | — | CH₃ | OCH₃ | |
| 76 | H | H | H | O | — | CH₃ | CH₃ | |
| 76 | H | H | H | O | — | CH₃ | OCH₃ | |
| 76 | H | 5-OCH₃ | H | O | — | CH₃ | OCH₃ | |
| 76 | H | 5-SCH₃ | H | O | — | CH₃ | OCH₃ | |
| 78 | H | H | H | — | — | CH₃ | CH₃ | |
| 78 | H | H | H | — | — | CH₃ | OCH₃ | |
| 78 | H | 5-OCH₃ | H | — | — | CH₃ | OCH₃ | |
| 78 | H | 5-SCH₃ | H | — | — | CH₃ | OCH₃ | |
| 79 | H | H | H | — | — | CH₃ | CH₃ | |
| 79 | H | H | H | — | — | CH₃ | OCH₃ | |
| 79 | H | 5-OCH₃ | H | — | — | CH₃ | OCH₃ | |
| 79 | H | 5-SCH₃ | H | — | — | CH₃ | OCH₃ | |

TABLE 7

General Formula 7

| Q | R | R₁ | R₃ | W₃ | W₄ | X₃ | m.p. (°C.) |
|---|---|----|----|----|----|----|-----------|
| 1 | H | H | H | O | — | OCH₃ | |
| 1 | H | 5-OCH₃ | H | O | — | OCH₃ | |
| 1 | H | 5-SCH₃ | H | O | — | OCH₃ | |
| 1 | H | H | H | NCH₃ | — | OCH₃ | |
| 1 | H | 5-OCH₃ | H | NCH₃ | — | OCH₃ | |
| 1 | H | 5-SCH₃ | H | NCH₃ | — | OCH₃ | |
| 3 | H | H | H | — | — | OCH₃ | |
| 3 | H | 5-OCH₃ | H | — | — | OCH₃ | |
| 3 | H | 5-SCH₃ | H | — | — | OCH₃ | |
| 5 | H | H | H | NCH₃ | — | OCH₃ | |
| 5 | H | 5-OCH₃ | H | NCH₃ | — | OCH₃ | |
| 5 | H | 5-SCH₃ | H | NCH₃ | — | OCH₃ | |
| 7 | H | H | H | — | S | OCH₃ | |
| 7 | H | 5-OCH₃ | H | — | S | OCH₃ | |
| 7 | H | 5-SCH₃ | H | — | S | OCH₃ | |
| 7 | H | H | H | — | SO₂ | OCH₃ | |
| 7 | H | 5-OCH₃ | H | — | SO₂ | OCH₃ | |
| 7 | H | 5-SCH₃ | H | — | SO₂ | OCH₃ | |
| 8 | H | H | H | — | S | OCH₃ | |
| 8 | H | 5-OCH₃ | H | — | S | OCH₃ | |
| 8 | H | 5-SCH₃ | H | — | S | OCH₃ | |
| 8 | H | H | H | — | SO₂ | OCH₃ | |
| 8 | H | 5-OCH₃ | H | — | SO₂ | OCH₃ | |
| 8 | H | 5-SCH₃ | H | — | SO₂ | OCH₃ | |
| 16 | H | H | H | — | — | OCH₃ | |
| 16 | H | 5-OCH₃ | H | — | — | OCH₃ | |
| 16 | H | 5-SCH₃ | H | — | — | OCH₃ | |
| 19 | H | H | H | — | — | OCH₃ | |
| 19 | H | 5-OCH₃ | H | — | — | OCH₃ | |
| 19 | H | 5-SCH₃ | H | — | — | OCH₃ | |
| 20 | H | H | H | — | — | OCH₃ | |
| 20 | H | 5-OCH₃ | H | — | — | OCH₃ | |
| 20 | H | 5-SCH₃ | H | — | — | OCH₃ | |
| 21 | H | H | H | — | — | OCH₃ | |
| 21 | H | 5-OCH₃ | H | — | — | OCH₃ | |
| 21 | H | 5-SCH₃ | H | — | — | OCH₃ | |
| 22 | H | H | H | NCH₃ | — | OCH₃ | |
| 22 | H | 5-OCH₃ | H | NCH₃ | — | OCH₃ | |
| 22 | H | 5-SCH₃ | H | NCH₃ | — | OCH₃ | |
| 25 | H | H | H | — | S | OCH₃ | |
| 25 | H | 5-OCH₃ | H | — | S | OCH₃ | |
| 25 | H | 5-SCH₃ | H | — | S | OCH₃ | |
| 25 | H | H | H | — | SO₂ | OCH₃ | |
| 25 | H | 5-OCH₃ | H | — | SO₂ | OCH₃ | |
| 25 | H | 5-SCH₃ | H | — | SO₂ | OCH₃ | |
| 26 | H | H | H | — | S | OCH₃ | |
| 26 | H | 5-OCH₃ | H | — | S | OCH₃ | |
| 26 | H | 5-SCH₃ | H | — | S | OCH₃ | |
| 26 | H | H | H | — | SO₂ | OCH₃ | |
| 26 | H | 5-OCH₃ | H | — | SO₂ | OCH₃ | |
| 26 | H | 5-SCH₃ | H | — | SO₂ | OCH₃ | |
| 27 | H | H | H | — | S | OCH₃ | |
| 27 | H | 5-OCH₃ | H | — | S | OCH₃ | |
| 27 | H | 5-SCH₃ | H | — | S | OCH₃ | |
| 27 | H | H | H | — | SO₂ | OCH₃ | |
| 27 | H | 5-OCH₃ | H | — | SO₂ | OCH₃ | |
| 27 | H | 5-SCH₃ | H | — | SO₂ | OCH₃ | |
| 29 (R₆=CH₃) | H | H | H | — | — | OCH₃ | |
| 29 (R₆=CH₃) | H | 5-OCH₃ | H | — | — | OCH₃ | |
| 29 (R₆=CH₃) | H | 5-SCH₃ | H | — | — | OCH₃ | |
| 55 | H | H | H | O | — | OCH₃ | |
| 55 | H | 5-OCH₃ | H | O | — | OCH₃ | |
| 55 | H | 5-SCH₃ | H | O | — | OCH₃ | |
| 55 | H | H | H | NCH₃ | — | OCH₃ | |
| 55 | H | 5-OCH₃ | H | NCH₃ | — | OCH₃ | |
| 55 | H | 5-SCH₃ | H | NCH₃ | — | OCH₃ | |
| 56 | H | H | H | — | — | OCH₃ | |
| 56 | H | 5-OCH₃ | H | — | — | OCH₃ | |
| 56 | H | 5-SCH₃ | H | — | — | OCH₃ | |
| 61 | H | H | H | NCH₃ | — | OCH₃ | |
| 61 | H | 5-OCH₃ | H | NCH₃ | — | OCH₃ | |
| 61 | H | 5-SCH₃ | H | NCH₃ | — | OCH₃ | |
| 62 | H | H | H | NCH₃ | — | OCH₃ | |
| 62 | H | 5-OCH₃ | H | NCH₃ | — | OCH₃ | |
| 62 | H | 5-SCH₃ | H | NCH₃ | — | OCH₃ | |
| 65 | H | H | H | — | — | OCH₃ | |
| 65 | H | 5-OCH₃ | H | — | — | OCH₃ | |
| 65 | H | 5-SCH₃ | H | — | — | OCH₃ | |
| 68 | H | H | H | — | — | OCH₃ | |
| 68 | H | 5-OCH₃ | H | — | — | OCH₃ | |
| 68 | H | 5-SCH₃ | H | — | — | OCH₃ | |
| 76 | H | H | H | O | — | OCH₃ | |
| 76 | H | 5-OCH₃ | H | O | — | OCH₃ | |
| 76 | H | 5-SCH₃ | H | O | — | OCH₃ | |
| 78 | H | H | H | — | — | OCH₃ | |
| 78 | H | 5-OCH₃ | H | — | — | OCH₃ | |
| 78 | H | 5-SCH₃ | H | — | — | OCH₃ | |
| 79 | H | H | H | — | — | OCH₃ | |
| 79 | H | 5-OCH₃ | H | — | — | OCH₃ | |
| 79 | H | 5-SCH₃ | H | — | — | OCH₃ | |

TABLE 8

General Formula 8

| Q | R | R₁ | R₃ | W₃ | W₄ | X | Y | m.p. (°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | H | 3-Cl | H | O | — | Cl | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1(R₅=CH₃) | H | H | H | O | — | Cl | OCH₃ | |
| 1 | H | 6-SO₂CH₃ | H | O | — | OCH₃ | OCH₃ | |
| 1 | H | H | H | O | — | OCF₂H | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | Cl | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | OCH₃ | Cl | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | Cl | OCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | CH₃ | CH₃ | |
| 3 | H | H | H | — | — | OCH₃ | CH₃ | |
| 3 | H | H | H | — | — | OCH₃ | OCH₃ | |
| 3 | H | H | H | — | — | Cl | OCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | CH₃ | CH₃ | |
| 5 | H | H | H | NCH₃ | — | OCH₃ | CH₃ | |
| 5 | H | H | H | NCH₃ | — | OCH₃ | OCH₃ | |
| 5 | H | H | H | NCH₃ | — | Cl | OCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | CH₃ | CH₃ | |
| 7 | H | H | H | — | S | OCH₃ | CH₃ | |
| 7 | H | H | H | — | S | OCH₃ | OCH₃ | |
| 7 | H | H | H | — | S | Cl | OCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | CH₃ | CH₃ | |
| 7 | H | H | H | — | SO₂ | OCH₃ | CH₃ | |
| 7 | H | H | H | — | SO₂ | OCH₃ | OCH₃ | |

TABLE 8-continued

General Formula 8

| Q | R | R₁ | R₃ | W₃ | W₄ | X | Y | m.p. (°C.) |
|---|---|---|---|---|---|---|---|---|
| 7 | H | H | H | — | SO₂ | Cl | OCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | CH₃ | CH₃ | |
| 8 | H | H | H | — | S | OCH₃ | CH₃ | |
| 8 | H | H | H | — | S | OCH₃ | OCH₃ | |
| 8 | H | H | H | — | S | Cl | OCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | CH₃ | CH₃ | |
| 8 | H | H | H | — | SO₂ | OCH₃ | CH₃ | |
| 8 | H | H | H | — | SO₂ | OCH₃ | OCH₃ | |
| 8 | H | H | H | — | SO₂ | Cl | OCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | H | 3-Cl | H | O | — | OCH₃ | Cl | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | OCF₂H | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | Cl | OCH₃ | |
| 16 | H | H | H | O | — | NHCH₃ | OCH₂CH₃ | |
| 16 | H | H | H | O | — | OCH₂CH=CH₃ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | NCH₃ | — | OCH₃ | Cl | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | | — | CH₃ | CH₃ | |
| 19 | H | H | H | | — | OCH₃ | CH₃ | |
| 19 | H | H | H | | — | OCH₃ | OCH₃ | |
| 19 | H | H | H | | — | Cl | OCH₃ | |
| 19 | H | 5-OCH₃ | H | | — | OCH₃ | OCH₃ | |
| 19 | H | 5-SCH₃ | H | | — | OCH₃ | OCH₃ | |
| 20 | H | H | H | | — | CH₃ | CH₃ | |
| 20 | H | H | H | | — | OCH₃ | CH₃ | |
| 20 | H | H | H | | — | OCH₃ | OCH₃ | |
| 20 | H | H | H | | — | Cl | OCH₃ | |
| 20 | H | 5-OCH₃ | H | | — | OCH₃ | OCH₃ | |
| 20 | H | 5-SCH₃ | H | | — | OCH₃ | OCH₃ | |
| 21 | H | H | H | | — | CH₃ | CH₃ | |
| 21 | H | H | H | | — | OCH₃ | CH₃ | |
| 21 | H | H | H | | — | OCH₃ | OCH₃ | |
| 21 | H | H | H | — | — | Cl | OCH₃ | |

TABLE 8-continued

General Formula 8

| Q | R | $R_1$ | $R_3$ | $W_3$ | $W_4$ | X | Y | m.p. (°C.) |
|---|---|---|---|---|---|---|---|---|
| 21 | H | 5-OCH$_3$ | H | — | — | OCH$_3$ | OCH$_3$ | |
| 21 | H | 5-SCH$_3$ | H | — | — | OCH$_3$ | OCH$_3$ | |
| 22 | H | H | H | NCH$_3$ | — | CH$_3$ | CH$_3$ | |
| 22 | H | H | H | NCH$_3$ | — | OCH$_3$ | CH$_3$ | |
| 22 | H | H | H | NCH$_3$ | — | OCH$_3$ | OCH$_3$ | |
| 22 | H | H | H | NCH$_3$ | — | Cl | OCH$_3$ | |
| 22 | H | 5-OCH$_3$ | H | NCH$_3$ | — | OCH$_3$ | OCH$_3$ | |
| 22 | H | 5-SCH$_3$ | H | NCH$_3$ | — | OCH$_3$ | OCH$_3$ | |
| 25 | H | H | H | — | S | CH$_3$ | CH$_3$ | |
| 25 | H | H | H | — | S | OCH$_3$ | CH$_3$ | |
| 25 | H | H | H | — | S | OCH$_3$ | OCH$_3$ | |
| 25 | H | H | H | — | S | Cl | OCH$_3$ | |
| 25 | H | 5-OCH$_3$ | H | — | S | OCH$_3$ | OCH$_3$ | |
| 25 | H | 5-SCH$_3$ | H | — | S | OCH$_3$ | OCH$_3$ | |
| 25 | H | H | H | — | SO$_2$ | CH$_3$ | CH$_3$ | |
| 25 | H | H | H | — | SO$_2$ | OCH$_3$ | CH$_3$ | |
| 25 | H | H | H | — | SO$_2$ | OCH$_3$ | OCH$_3$ | |
| 25 | H | H | H | — | SO$_2$ | Cl | OCH$_3$ | |
| 25 | H | 5-OCH$_3$ | H | — | SO$_2$ | OCH$_3$ | OCH$_3$ | |
| 25 | H | 5-SCH$_3$ | H | — | SO$_2$ | OCH$_3$ | OCH$_3$ | |
| 26 | H | H | H | — | S | CH$_3$ | CH$_3$ | |
| 26 | H | H | H | — | S | OCH$_3$ | CH$_3$ | |
| 26 | H | H | H | — | S | OCH$_3$ | OCH$_3$ | |
| 26 | H | H | H | — | S | Cl | OCH$_3$ | |
| 26 | H | 5-OCH$_3$ | H | — | S | OCH$_3$ | OCH$_3$ | |
| 26 | H | 5-SCH$_3$ | H | — | S | OCH$_3$ | OCH$_3$ | |
| 26 | H | H | H | — | SO$_2$ | CH$_3$ | CH$_3$ | |
| 26 | H | H | H | — | SO$_2$ | OCH$_3$ | CH$_3$ | |
| 26 | H | H | H | — | SO$_2$ | OCH$_3$ | OCH$_3$ | |
| 26 | H | H | H | — | SO$_2$ | Cl | OCH$_3$ | |
| 26 | H | 5-OCH$_3$ | H | — | SO$_2$ | OCH$_3$ | OCH$_3$ | |
| 26 | H | 5-SCH$_3$ | H | — | SO$_2$ | OCH$_3$ | OCH$_3$ | |
| 27 | H | H | H | — | S | CH$_3$ | CH$_3$ | |
| 27 | H | H | H | — | S | OCH$_3$ | CH$_3$ | |
| 27 | H | H | H | — | S | OCH$_3$ | OCH$_3$ | |
| 27 | H | H | H | — | S | Cl | OCH$_3$ | |
| 27 | H | 5-OCH$_3$ | H | — | S | OCH$_3$ | OCH$_3$ | |
| 27 | H | 5-SCH$_3$ | H | — | S | OCH$_3$ | OCH$_3$ | |
| 27 | H | H | H | — | SO$_2$ | CH$_3$ | CH$_3$ | |
| 27 | H | H | H | — | SO$_2$ | OCH$_3$ | CH$_3$ | |
| 27 | H | H | H | — | SO$_2$ | OCH$_3$ | OCH$_3$ | |
| 27 | H | H | H | — | SO$_2$ | Cl | OCH$_3$ | |
| 27 | H | 5-OCH$_3$ | H | — | SO$_2$ | OCH$_3$ | OCH$_3$ | |
| 27 | H | 5-SCH$_3$ | H | — | SO$_2$ | OCH$_3$ | OCH$_3$ | |
| 29($R_6$=CH$_3$) | H | H | H | — | — | CH$_3$ | CH$_3$ | |
| 29($R_6$=CH$_3$) | H | H | H | — | — | OCH$_3$ | CH$_3$ | |
| 29($R_6$=CH$_3$) | H | H | H | — | — | OCH$_3$ | OCH$_3$ | |
| 29($R_6$=CH$_3$) | H | H | H | — | — | Cl | OCH$_3$ | |
| 29($R_6$=CH$_3$) | H | 5-OCH$_3$ | H | — | — | OCH$_3$ | OCH$_3$ | |
| 29($R_6$=CH$_3$) | H | 5-SCH$_3$ | H | — | — | OCH$_3$ | OCH$_3$ | |
| 55 | H | H | H | O | — | CH$_3$ | CH$_3$ | |
| 55 | H | H | H | O | — | OCH$_3$ | CH$_3$ | |
| 55 | H | H | H | O | — | OCH$_3$ | OCH$_3$ | |
| 55 | H | H | H | O | — | Cl | OCH$_3$ | |
| 55 | H | 5-OCH$_3$ | H | O | — | OCH$_3$ | OCH$_3$ | |
| 55 | H | 5-SCH$_3$ | H | O | — | OCH$_3$ | OCH$_3$ | |
| 55 | H | H | H | NCH$_3$ | — | CH$_3$ | CH$_3$ | |
| 55 | H | H | H | NCH$_3$ | — | OCH$_3$ | CH$_3$ | |
| 55 | H | H | H | NCH$_3$ | — | OCH$_3$ | OCH$_3$ | |
| 55 | H | H | H | NCH$_3$ | — | Cl | OCH$_3$ | |
| 55 | H | 5-OCH$_3$ | H | NCH$_3$ | — | OCH$_3$ | OCH$_3$ | |
| 55 | H | 5-SCH$_3$ | H | NCH$_3$ | — | OCH$_3$ | OCH$_3$ | |
| 56 | H | H | H | — | — | CH$_3$ | CH$_3$ | |
| 56 | H | H | H | — | — | OCH$_3$ | CH$_3$ | |
| 56 | H | H | H | — | — | OCH$_3$ | OCH$_3$ | |
| 56 | H | H | H | — | — | Cl | OCH$_3$ | |
| 56 | H | 5-OCH$_3$ | H | — | — | OCH$_3$ | OCH$_3$ | |
| 56 | H | 5-SCH$_3$ | H | — | — | OCH$_3$ | OCH$_3$ | |
| 61 | H | H | H | NCH$_3$ | — | CH$_3$ | CH$_3$ | |
| 61 | H | H | H | NCH$_3$ | — | OCH$_3$ | CH$_3$ | |
| 61 | H | H | H | NCH$_3$ | — | OCH$_3$ | OCH$_3$ | |
| 61 | H | H | H | NCH$_3$ | — | Cl | OCH$_3$ | |
| 61 | H | 5-OCH$_3$ | H | NCH$_3$ | — | OCH$_3$ | OCH$_3$ | |
| 61 | H | 5-SCH$_3$ | H | NCH$_3$ | — | OCH$_3$ | OCH$_3$ | |
| 62 | H | H | H | NCH$_3$ | — | CH$_3$ | CH$_3$ | |
| 62 | H | H | H | NCH$_3$ | — | OCH$_3$ | CH$_3$ | |
| 62 | H | H | H | NCH$_3$ | — | OCH$_3$ | OCH$_3$ | |
| 62 | H | H | H | NCH$_3$ | — | Cl | OCH$_3$ | |
| 62 | H | 5-OCH$_3$ | H | NCH$_3$ | — | OCH$_3$ | OCH$_3$ | |
| 62 | H | 5-SCH$_3$ | H | NCH$_3$ | — | OCH$_3$ | OCH$_3$ | |

TABLE 8-continued

General Formula 8

| Q | R | R₁ | R₃ | W₃ | W₄ | X | Y | m.p. (°C.) |
|---|---|---|---|---|---|---|---|---|
| 65 | H | H | H | — | — | CH₃ | CH₃ | |
| 65 | H | H | H | — | — | OCH₃ | CH₃ | |
| 65 | H | H | H | — | — | OCH₃ | OCH₃ | |
| 65 | H | H | H | — | — | Cl | OCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | CH₃ | CH₃ | |
| 68 | H | H | H | — | — | OCH₃ | CH₃ | |
| 68 | H | H | H | — | — | OCH₃ | OCH₃ | |
| 68 | H | H | H | — | — | Cl | OCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | CH₃ | CH₃ | |
| 76 | H | H | H | O | — | OCH₃ | CH₃ | |
| 76 | H | H | H | O | — | OCH₃ | OCH₃ | |
| 76 | H | H | H | O | — | Cl | OCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | CH₃ | CH₃ | |
| 78 | H | H | H | — | — | OCH₃ | CH₃ | |
| 78 | H | H | H | — | — | OCH₃ | OCH₃ | |
| 78 | H | H | H | — | — | Cl | OCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | CH₃ | CH₃ | |
| 79 | H | H | H | — | — | OCH₃ | CH₃ | |
| 79 | H | H | H | — | — | OCH₃ | OCH₃ | |
| 79 | H | H | H | — | — | Cl | OCH₃ | |
| 79 | H | 5-OCH₃ | H | — | — | OCH₃ | OCH₃ | |
| 79 | H | 5-SCH₃ | H | — | — | OCH₃ | OCH₃ | |
| 80(R₃,R₄=CH₃) | H | H | H | — | — | CH₃ | CH₃ | 95–103 |
| 80(R₃,R₄=CH₃) | H | H | H | — | — | OCH₃ | CH₃ | 99–103 |
| 80(R₃,R₄=CH₃) | H | H | H | — | — | OCH₃ | OCH₃ | 104–112 |
| 80(R₃,R₄=CH₃) | H | H | H | — | — | Cl | OCH₃ | 103–112 |
| 80(R₃,R₄=CH₃) | H | 5-OCH₃ | H | — | — | OCH₃ | OCH₃ | |
| 80(R₃,R₄=CH₃) | H | 5-SCH₃ | H | — | — | OCH₃ | OCH₃ | |

TABLE 9

General Formula 9

| Q | R | R₁ | R₃ | W₃ | W₄ | X | Y | m.p. (°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1 | H | 6-SO₂CH₃ | H | O | — | OCH₃ | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | O | — | C≡CH | OCH₃ | |

TABLE 9-continued

General Formula 9

| Q | R | R₁ | R₃ | W₃ | W₄ | X | Y | m.p. (°C.) |
|---|---|---|---|---|---|---|---|---|
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | OCH₃ | OCH₃ | |
| 1 | H | H | H | NCH₃ | — | OCH₃ | CH₃ | |
| 1 | CH₃ | H | H | NCH₃ | — | OCH₃ | CH₃ | |
| 1 | H | H | H | NCH | — | OCH₂CH₃ | NHCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | OCH₃ | OCH₃ | |
| 3 | H | H | H | — | — | OCH₃ | CH₃ | |
| 3 | CH₃ | H | H | — | — | OCH₃ | CH₃ | |
| 3 | H | H | H | — | — | OCH₂CH₃ | NHCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | OCH₃ | OCH₃ | |
| 5 | H | H | H | NCH₃ | — | OCH₃ | CH₃ | |
| 5 | CH₃ | H | H | NCH₃ | — | OCH₃ | CH₃ | |
| 5 | H | H | H | NCH₃ | — | OCH₂CH₃ | NHCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | OCH₃ | OCH₃ | |
| 7 | H | H | H | — | S | OCH₃ | CH₃ | |
| 7 | CH₃ | H | H | — | S | OCH₃ | CH₃ | |
| 7 | H | H | H | — | S | OCH₂CH₃ | NHCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | OCH₃ | OCH₃ | |
| 7 | H | H | H | — | SO₂ | OCH₃ | CH₃ | |
| 7 | CH₃ | H | H | — | SO₂ | OCH₃ | CH₃ | |
| 7 | H | H | H | — | SO₂ | OCH₂CH₃ | NHCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | OCH₃ | OCH₃ | |
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | OCH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | NHCH₃ | OCH₂CH₃ | |

TABLE 9-continued

General Formula 9

| Q | R | R₁ | R₃ | W₃ | W₄ | X | Y | m.p. (°C.) |
|---|---|----|----|----|----|---|---|-----------|
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | OCH₃ | OCH₃ | |
| 19 | H | H | H | — | — | OCH₃ | CH₃ | |
| 19 | CH₃ | H | H | — | — | OCH₃ | CH₃ | |
| 19 | H | H | H | — | — | OCH₂CH₃ | NHCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | OCH₃ | OCH₃ | |
| 20 | H | H | H | — | — | OCH₃ | CH₃ | |
| 20 | CH₃ | H | H | — | — | OCH₃ | CH₃ | |
| 20 | H | H | H | — | — | OCH₂CH₃ | NHCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | OCH₃ | OCH₃ | |
| 21 | H | H | H | — | — | OCH₃ | CH₃ | |
| 21 | CH₃ | H | H | — | — | OCH₃ | CH₃ | |
| 21 | H | H | H | — | — | OCH₂CH₃ | NHCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | OCH₃ | OCH₃ | |
| 22 | H | H | H | NCH₃ | — | OCH₃ | CH₃ | |
| 22 | CH₃ | H | H | NCH₃ | — | OCH₃ | CH₃ | |
| 22 | H | H | H | NCH₃ | — | OCH₂CH₃ | NHCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | OCH₃ | OCH₃ | |
| 25 | H | H | H | — | SO₂ | OCH₃ | CH₃ | |
| 25 | CH₃ | H | H | — | SO₂ | OCH₃ | CH₃ | |
| 25 | H | H | H | — | SO₂ | OCH₂CH₃ | NHCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | OCH₃ | OCH₃ | |
| 26 | H | H | H | — | S | OCH₃ | CH₃ | |
| 26 | CH₃ | H | H | — | S | OCH₃ | CH₃ | |
| 26 | H | H | H | — | S | OCH₂CH₃ | NHCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | OCH₃ | OCH₃ | |
| 26 | H | H | H | — | SO₂ | OCH₃ | CH₃ | |
| 26 | CH₃ | H | H | — | SO₂ | OCH₃ | CH₃ | |
| 26 | H | H | H | — | SO₂ | OCH₂CH₃ | NHCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | OCH₃ | OCH₃ | |
| 27 | H | H | H | — | S | OCH₃ | CH₃ | |
| 27 | CH₃ | H | H | — | S | OCH₃ | CH₃ | |
| 27 | H | H | H | — | S | OCH₂CH₃ | NHCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | OCH₃ | OCH₃ | |
| 27 | H | H | H | — | SO₂ | OCH₃ | CH₃ | |
| 27 | CH₃ | H | H | — | SO₂ | OCH₃ | CH₃ | |
| 27 | H | H | H | — | SO₂ | OCH₂CH₃ | NHCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | OCH₃ | OCH₃ | |
| 29(R₆=CH₃) | H | H | H | — | — | OCH₃ | CH₃ | |
| 29(R₆=CH₃) | CH₃ | H | H | — | — | OCH₃ | CH₃ | |
| 29(R₆=CH₃) | H | H | H | — | — | OCH₂CH₃ | NHCH₃ | |

TABLE 9-continued

General Formula 9

| Q | R | $R_1$ | $R_3$ | $W_3$ | $W_4$ | X | Y | m.p. (°C.) |
|---|---|---|---|---|---|---|---|---|
| 29($R_6$=CH$_3$) | H | 5-OCH$_3$ | H | — | — | OCH$_3$ | OCH$_3$ | |
| 29($R_6$=CH$_3$) | H | 5-SCH$_3$ | H | — | — | OCH$_3$ | OCH$_3$ | |
| 55 | H | H | H | O | — | OCH$_3$ | OCH$_3$ | |
| 55 | H | H | H | O | — | OCH$_3$ | CH$_3$ | |
| 55 | CH$_3$ | H | H | O | — | OCH$_3$ | CH$_3$ | |
| 55 | H | H | H | O | — | OCH$_2$CH$_3$ | NHCH$_3$ | |
| 55 | H | 5-OCH$_3$ | H | O | — | OCH$_3$ | OCH$_3$ | |
| 55 | H | 5-SCH$_3$ | H | O | — | OCH$_3$ | OCH$_3$ | |
| 55 | H | H | H | NCH$_3$ | — | OCH$_3$ | OCH$_3$ | |
| 55 | H | H | H | NCH$_3$ | — | OCH$_3$ | CH$_3$ | |
| 55 | CH$_3$ | H | H | NCH$_3$ | — | OCH$_3$ | CH$_3$ | |
| 55 | H | H | H | NCH$_3$ | — | OCH$_2$CH$_3$ | NHCH$_3$ | |
| 55 | H | 5-OCH$_3$ | H | NCH$_3$ | — | OCH$_3$ | OCH$_3$ | |
| 55 | H | 5-SCH$_3$ | H | NCH$_3$ | — | OCH$_3$ | OCH$_3$ | |
| 56 | H | H | H | — | — | OCH$_3$ | OCH$_3$ | |
| 56 | H | H | H | — | — | OCH$_3$ | CH$_3$ | |
| 56 | CH$_3$ | H | H | — | — | OCH$_3$ | CH$_3$ | |
| 56 | H | H | H | — | — | OCH$_2$CH$_3$ | NHCH$_3$ | |
| 56 | H | 5-OCH$_3$ | H | — | — | OCH$_3$ | OCH$_3$ | |
| 56 | H | 5-SCH$_3$ | H | — | — | OCH$_3$ | OCH$_3$ | |
| 61 | H | H | H | NCH$_3$ | — | OCH$_3$ | OCH$_3$ | |
| 61 | H | H | H | NCH$_3$ | — | OCH$_3$ | CH$_3$ | |
| 61 | CH$_3$ | H | H | NCH$_3$ | — | OCH$_3$ | CH$_3$ | |
| 61 | H | H | H | NCH$_3$ | — | OCH$_2$CH$_3$ | NHCH$_3$ | |
| 61 | H | 5-OCH$_3$ | H | NCH$_3$ | — | OCH$_3$ | OCH$_3$ | |
| 61 | H | 5-SCH$_3$ | H | NCH$_3$ | — | OCH$_3$ | OCH$_3$ | |
| 62 | H | H | H | NCH$_3$ | — | OCH$_3$ | OCH$_3$ | |
| 62 | H | H | H | NCH$_3$ | — | OCH$_3$ | CH$_3$ | |
| 62 | CH$_3$ | H | H | NCH$_3$ | — | OCH$_3$ | CH$_3$ | |
| 62 | H | H | H | NCH$_3$ | — | OCH$_2$CH$_3$ | NHCH$_3$ | |
| 62 | H | 5-OCH$_3$ | H | NCH$_3$ | — | OCH$_3$ | OCH$_3$ | |
| 62 | H | 5-SCH$_3$ | H | NCH$_3$ | — | OCH$_3$ | OCH$_3$ | |
| 65 | H | H | H | — | — | OCH$_3$ | OCH$_3$ | |
| 65 | H | H | H | — | — | OCH$_3$ | CH$_3$ | |
| 65 | CH$_3$ | H | H | — | — | OCH$_3$ | CH$_3$ | |
| 65 | H | H | H | — | — | OCH$_2$CH$_3$ | NHCH$_3$ | |
| 65 | H | 5-OCH$_3$ | H | — | — | OCH$_3$ | OCH$_3$ | |
| 65 | H | 5-SCH$_3$ | H | — | — | OCH$_3$ | OCH$_3$ | |
| 68 | H | H | H | — | — | OCH$_3$ | OCH$_3$ | |
| 68 | H | H | H | — | — | OCH$_3$ | CH$_3$ | |
| 68 | CH$_3$ | H | H | — | — | OCH$_3$ | CH$_3$ | |
| 68 | H | H | H | — | — | OCH$_2$CH$_3$ | NHCH$_3$ | |
| 68 | H | 5-OCH$_3$ | H | — | — | OCH$_3$ | OCH$_3$ | |
| 68 | H | 5-SCH$_3$ | H | — | — | OCH$_3$ | OCH$_3$ | |
| 76 | H | H | H | O | — | OCH$_3$ | OCH$_3$ | |
| 76 | H | H | H | O | — | OCH$_3$ | CH$_3$ | |
| 76 | CH$_3$ | H | H | O | — | OCH$_3$ | CH$_3$ | |
| 76 | H | H | H | O | — | OCH$_2$CH$_3$ | NHCH$_3$ | |
| 76 | H | 5-OCH$_3$ | H | O | — | OCH$_3$ | OCH$_3$ | |
| 76 | H | 5-SCH$_3$ | H | O | — | OCH$_3$ | OCH$_3$ | |
| 78 | H | H | H | — | — | OCH$_3$ | OCH$_3$ | |
| 78 | H | H | H | — | — | OCH$_3$ | CH$_3$ | |
| 78 | CH$_3$ | H | H | — | — | OCH$_3$ | CH$_3$ | |
| 78 | H | H | H | — | — | OCH$_2$CH$_3$ | NHCH$_3$ | |
| 78 | H | 5-OCH$_3$ | H | — | — | OCH$_3$ | OCH$_3$ | |
| 78 | H | 5-SCH$_3$ | H | — | — | OCH$_3$ | OCH$_3$ | |
| 79 | H | H | H | — | — | OCH$_3$ | OCH$_3$ | |
| 79 | H | H | H | — | — | OCH$_3$ | CH$_3$ | |
| 79 | CH$_3$ | H | H | — | — | OCH$_3$ | CH$_3$ | |
| 79 | H | H | H | — | — | OCH$_2$CH$_3$ | NHCH$_3$ | |
| 79 | H | 5-OCH$_3$ | H | — | — | OCH$_3$ | OCH$_3$ | |
| 79 | H | 5-SCH$_3$ | H | — | — | OCH$_3$ | OCH$_3$ | |
| 80($R_4$,$R_5$=CH$_3$) | H | H | H | — | — | OCH$_3$ | OCH$_3$ | 110–116 |
| 80($R_4$,$R_5$=CH$_3$) | H | H | H | — | — | OCH$_3$ | CH$_3$ | 104–110 |
| 80($R_4$,$R_5$=CH$_3$) | CH$_3$ | H | H | — | — | OCH$_3$ | CH$_3$ | |
| 80($R_4$,$R_5$=CH$_3$) | H | H | H | — | — | OCH$_2$CH$_3$ | NHCH$_3$ | |
| 80($R_4$,$R_5$=CH$_3$) | H | 5-OCH$_3$ | H | — | — | OCH$_3$ | OCH$_3$ | |
| 80($R_4$,$R_5$=CH$_3$) | H | 5-SCH$_3$ | H | — | — | OCH$_3$ | OCH$_3$ | |

TABLE 10

General Structure 10

| Q | R | $R_1$ | $R_3$ | $W_3$ | $W_4$ | X | Y | m.p. (°C.) |
|---|---|---|---|---|---|---|---|---|
| 1 | H | H | H | O | — | CH$_3$ | CH$_3$ | |
| 1 | H | H | H | O | — | OCH$_3$ | CH$_3$ | |
| 1 | H | H | H | O | — | OCH$_3$ | OCH$_3$ | |
| 1 | CH$_3$ | H | H | O | — | OCH$_3$ | OCH$_3$ | |
| 1 | CH$_3$ | H | H | O | — | OCH$_3$ | CH$_3$ | |

TABLE 10-continued

General Structure 10

| Q | R | R₁ | R₃ | W₃ | W₄ | X | Y | m.p. (°C.) |
|---|---|---|---|---|---|---|---|---|
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | H | 3-Cl | H | O | — | Cl | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1(R₅=CH₃) | H | H | H | O | — | Cl | OCH₃ | |
| 1 | H | 6-SO₂CH₃ | H | O | — | OCH₃ | OCH₃ | |
| 1 | H | H | H | O | — | OCF₂H | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | Cl | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | OCH₃ | Cl | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | Cl | OCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | CH₃ | CH₃ | |
| 3 | H | H | H | — | — | OCH₃ | CH₃ | |
| 3 | H | H | H | — | — | OCH₃ | OCH₃ | |
| 3 | H | H | H | — | — | Cl | OCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | CH₃ | CH₃ | |
| 5 | H | H | H | NCH₃ | — | OCH₃ | CH₃ | |
| 5 | H | H | H | NCH₃ | — | OCH₃ | OCH₃ | |
| 5 | H | H | H | NCH₃ | — | Cl | OCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | CH₃ | CH₃ | |
| 7 | H | H | H | — | S | OCH₃ | CH₃ | |
| 7 | H | H | H | — | S | OCH₃ | OCH₃ | |
| 7 | H | H | H | — | S | Cl | OCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | CH₃ | CH₃ | |
| 7 | H | H | H | — | SO₂ | OCH₃ | CH₃ | |
| 7 | H | H | H | — | SO₂ | OCH₃ | OCH₃ | |
| 7 | H | H | H | — | SO₂ | Cl | OCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | CH₃ | CH₃ | |
| 8 | H | H | H | — | S | OCH₃ | CH₃ | |

TABLE 10-continued

General Structure 10

| Q | R | R₁ | R₃ | W₃ | W₄ | X | Y | m.p. (°C.) |
|---|---|---|---|---|---|---|---|---|
| 8 | H | H | H | — | S | OCH₃ | OCH₃ | |
| 8 | H | H | H | — | S | Cl | OCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | CH₃ | CH₃ | |
| 8 | H | H | H | — | SO₂ | OCH₃ | CH₃ | |
| 8 | H | H | H | — | SO₂ | OCH₃ | OCH₃ | |
| 8 | H | H | H | — | SO₂ | Cl | OCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | H | 3-Cl | H | O | — | OCH₃ | Cl | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | OCF₂H | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | Cl | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | NCH₃ | — | OCH₃ | Cl | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | CH₃ | CH₃ | |
| 19 | H | H | H | — | — | OCH₃ | CH₃ | |
| 19 | H | H | H | — | — | OCH₃ | OCH₃ | |
| 19 | H | H | H | — | — | Cl | OCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | CH₃ | CH₃ | |
| 20 | H | H | H | — | — | OCH₃ | CH₃ | |
| 20 | H | H | H | — | — | OCH₃ | OCH₃ | |
| 20 | H | H | H | — | — | Cl | OCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | CH₃ | CH₃ | |
| 21 | H | H | H | — | — | OCH₃ | CH₃ | |
| 21 | H | H | H | — | — | OCH₃ | OCH₃ | |
| 21 | H | H | H | — | — | Cl | OCH₃ | |
| 21 | H | 5-OCH₃ | H | — | OCH₃ | — | OCH₃ | |
| 21 | H | 5-SCH₃ | H | — | OCH₃ | — | OCH₃ | |
| 22 | H | H | H | NCH₃ | — | CH₃ | CH₃ | |
| 22 | H | H | H | NCH₃ | — | OCH₃ | CH₃ | |
| 22 | H | H | H | NCH₃ | — | OCH₃ | OCH₃ | |

TABLE 10-continued

General Structure 10

| Q | R | R₁ | R₃ | W₃ | W₄ | X | Y | m.p. (°C.) |
|---|---|---|---|---|---|---|---|---|
| 22 | H | H | H | NCH₃ | — | Cl | OCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | CH₃ | CH₃ | |
| 25 | H | H | H | — | S | OCH₃ | CH₃ | |
| 25 | H | H | H | — | S | OCH₃ | OCH₃ | |
| 25 | H | H | H | — | S | Cl | OCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | CH₃ | CH₃ | |
| 25 | H | H | H | — | SO₂ | OCH₃ | CH₃ | |
| 25 | H | H | H | — | SO₂ | OCH₃ | OCH₃ | |
| 25 | H | H | H | — | SO₂ | Cl | OCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | CH₃ | CH₃ | |
| 26 | H | H | H | — | S | OCH₃ | CH₃ | |
| 26 | H | H | H | — | S | OCH₃ | OCH₃ | |
| 26 | H | H | H | — | S | Cl | OCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | CH₃ | CH₃ | |
| 26 | H | H | H | — | SO₂ | OCH₃ | CH₃ | |
| 26 | H | H | H | — | SO₂ | OCH₃ | OCH₃ | |
| 26 | H | H | H | — | SO₂ | Cl | OCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | CH₃ | CH₃ | |
| 27 | H | H | H | — | S | OCH₃ | CH₃ | |
| 27 | H | H | H | — | S | OCH₃ | OCH₃ | |
| 27 | H | H | H | — | S | Cl | OCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | CH₃ | CH₃ | |
| 27 | H | H | H | — | SO₂ | OCH₃ | CH₃ | |
| 27 | H | H | H | — | SO₂ | OCH₃ | OCH₃ | |
| 27 | H | H | H | — | SO₂ | Cl | OCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | CH₃ | CH₃ | |
| 29(R₆=CH₃) | H | H | H | — | — | OCH₃ | CH₃ | |
| 29(R₆=CH₃) | H | H | H | — | — | OCH₃ | OCH₃ | |
| 29(R₆=CH₃) | H | H | H | — | — | Cl | OCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | CH₃ | CH₃ | |
| 55 | H | H | H | O | — | OCH₃ | CH₃ | |
| 55 | H | H | H | O | — | OCH₃ | OCH₃ | |
| 55 | H | H | H | O | — | Cl | OCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | CH₃ | CH₃ | |
| 55 | H | H | H | NCH₃ | — | OCH₃ | CH₃ | |
| 55 | H | H | H | NCH₃ | — | OCH₃ | OCH₃ | |
| 55 | H | H | H | NCH₃ | — | Cl | OCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | CH₃ | CH₃ | |
| 56 | H | H | H | — | — | OCH₃ | CH₃ | |
| 56 | H | H | H | — | — | OCH₃ | OCH₃ | |
| 56 | H | H | H | — | — | Cl | OCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | CH₃ | CH₃ | |
| 61 | H | H | H | NCH₃ | — | OCH₃ | CH₃ | |
| 61 | H | H | H | NCH₃ | — | OCH₃ | OCH₃ | |
| 61 | H | H | H | NCH₃ | — | Cl | OCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | CH₃ | CH₃ | |
| 62 | H | H | H | NCH₃ | — | OCH₃ | CH₃ | |
| 62 | H | H | H | NCH₃ | — | OCH₃ | OCH₃ | |
| 62 | H | H | H | NCH₃ | — | Cl | OCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | CH₃ | CH₃ | |
| 65 | H | H | H | — | — | OCH₃ | CH₃ | |
| 65 | H | H | H | — | — | OCH₃ | OCH₃ | |
| 65 | H | H | H | — | — | Cl | OCH₃ | |
| 65 | H | 5-OCH₃ | H | — | — | OCH₃ | OCH₃ | |

TABLE 10-continued

General Structure 10

| Q | R | R₁ | R₃ | W₃ | W₄ | X | Y | m.p. (°C.) |
|---|---|---|---|---|---|---|---|---|
| 65 | H | 5-SCH₃ | H | — | — | OCH₃ | OCH₃ | |
| 68 | H | H | H | — | — | CH₃ | CH₃ | |
| 68 | H | H | H | — | — | OCH₃ | CH₃ | |
| 68 | H | H | H | — | — | OCH₃ | OCH₃ | |
| 68 | H | H | H | — | — | Cl | OCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | CH₃ | CH₃ | |
| 76 | H | H | H | O | — | OCH₃ | CH₃ | |
| 76 | H | H | H | O | — | OCH₃ | OCH₃ | |
| 76 | H | H | H | O | — | Cl | OCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | CH₃ | CH₃ | |
| 78 | H | H | H | — | — | OCH₃ | CH₃ | |
| 78 | H | H | H | — | — | OCH₃ | OCH₃ | |
| 78 | H | H | H | — | — | Cl | OCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | CH₃ | CH₃ | |
| 79 | H | H | H | — | — | OCH₃ | CH₃ | |
| 79 | H | H | H | — | — | OCH₃ | OCH₃ | |
| 79 | H | H | H | — | — | Cl | OCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 11

General Formula 11

| Q | R | R₁ | R₃ | W₃ | W₄ | X | Y | m.p.(°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1 | H | 6-SO₂CH₃ | H | O | — | OCH₃ | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | OCH₃ | OCH₃ | |
| 1 | H | H | H | NCH₃ | — | OCH₃ | CH₃ | |

TABLE 11-continued

General Formula 11

| Q | R | R₁ | R₃ | W₃ | W₄ | X | Y | m.p.(°C.) |
|---|---|---|---|---|---|---|---|---|
| 1 | CH₃ | H | H | NCH₃ | — | OCH₃ | CH₃ | |
| 1 | H | H | H | NCH₃ | — | OCH₂CH₃ | NHCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | OCH₃ | OCH₃ | |
| 3 | H | H | H | — | — | OCH₃ | CH₃ | |
| 3 | CH₃ | H | H | — | — | OCH₃ | CH₃ | |
| 3 | H | H | H | — | — | OCH₂CH₃ | NHCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | OCH₃ | OCH₃ | |
| 5 | H | H | H | NCH₃ | — | OCH₃ | CH₃ | |
| 5 | CH₃ | H | H | NCH₃ | — | OCH₃ | CH₃ | |
| 5 | H | H | H | NCH₃ | — | OCH₂CH₃ | NHCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH | |
| 7 | H | H | H | — | S | OCH₃ | OCH₃ | |
| 7 | H | H | H | — | S | OCH₃ | CH₃ | |
| 7 | CH₃ | H | H | — | S | OCH₃ | CH₃ | |
| 7 | H | H | H | — | S | OCH₂CH₃ | NHCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | OCH₃ | OCH₃ | |
| 7 | H | H | H | — | SO₂ | OCH₃ | CH₃ | |
| 7 | CH₃ | H | H | — | SO₂ | OCH₃ | CH₃ | |
| 7 | H | H | H | — | SO₂ | OCH₂CH₃ | NHCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | OCH₃ | OCH₃ | |
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | OCH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |

TABLE 11-continued

General Formula 11

| Q | R | R₁ | R₃ | W₃ | W₄ | X | Y | m.p.(°C.) |
|---|---|---|---|---|---|---|---|---|
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | OCH₃ | OCH₃ | |
| 19 | H | H | H | — | — | OCH₃ | CH₃ | |
| 19 | CH₃ | H | H | — | — | OCH₃ | CH₃ | |
| 19 | H | H | H | — | — | OCH₂CH₃ | NHCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | OCH₃ | OCH₃ | |
| 20 | H | H | H | — | — | OCH₃ | CH₃ | |
| 20 | CH₃ | H | H | — | — | OCH₃ | CH₃ | |
| 20 | H | H | H | — | — | OCH₂CH₃ | NHCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | OCH₃ | OCH₃ | |
| 21 | H | H | H | — | — | OCH₃ | CH₃ | |
| 21 | CH₃ | H | H | — | — | OCH₃ | CH₃ | |
| 21 | H | H | H | — | — | OCH₂CH₃ | NHCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | OCH₃ | OCH₃ | |
| 22 | H | H | H | NCH₃ | — | OCH₃ | CH₃ | |
| 22 | CH₃ | H | H | NCH₃ | — | OCH₃ | CH₃ | |
| 22 | H | H | H | NCH₃ | — | OCH₂CH₃ | NHCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | OCH₃ | OCH₃ | |
| 25 | H | H | H | — | SO₂ | OCH₃ | CH₃ | |
| 25 | CH₃ | H | H | — | SO₂ | OCH₃ | CH₃ | |
| 25 | H | H | H | — | SO₂ | OCH₂CH₃ | NHCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | OCH₃ | OCH₃ | |
| 26 | H | H | H | — | S | OCH₃ | CH₃ | |
| 26 | CH₃ | H | H | — | S | OCH₃ | CH₃ | |
| 26 | H | H | H | — | S | OCH₂CH₃ | NHCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | OCH₃ | OCH₃ | |
| 26 | H | H | H | — | SO₂ | OCH₃ | CH₃ | |
| 26 | CH₃ | H | H | — | SO₂ | OCH₃ | CH₃ | |
| 26 | H | H | H | — | SO₂ | OCH₂CH₃ | NHCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | OCH₃ | OCH₃ | |
| 27 | H | H | H | — | S | OCH₃ | CH₃ | |
| 27 | CH₃ | H | H | — | S | OCH₃ | CH₃ | |
| 27 | H | H | H | — | S | OCH₂CH₃ | NHCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | OCH₃ | OCH₃ | |
| 27 | H | H | H | — | SO₂ | OCH₃ | CH₃ | |
| 27 | CH₃ | H | H | — | SO₂ | OCH₃ | CH₃ | |
| 27 | H | H | H | — | SO₂ | OCH₂CH₃ | NHCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | OCH₃ | OCH₃ | |
| 29(R₆=CH₃) | H | H | H | — | — | OCH₃ | CH₃ | |
| 29(R₆=CH₃) | CH₃ | H | H | — | — | OCH₃ | CH₃ | |
| 29(R₆=CH₃) | H | H | H | — | — | OCH₂CH₃ | NHCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | OCH₃ | OCH₃ | |
| 55 | H | H | H | O | — | OCH₃ | CH₃ | |
| 55 | CH₃ | H | H | O | — | OCH₃ | CH₃ | |
| 55 | H | H | H | O | — | OCH₂CH₃ | NHCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | OCH₃ | OCH₃ | |
| 55 | H | H | H | NCH₃ | — | OCH₃ | CH₃ | |
| 55 | CH₃ | H | H | NCH₃ | — | OCH₃ | CH₃ | |

TABLE 11-continued

General Formula 11

| Q | R | R₁ | R₃ | W₃ | W₄ | X | Y | m.p.(°C.) |
|---|---|---|---|---|---|---|---|---|
| 55 | H | H | H | NCH₃ | — | OCH₂CH₃ | NHCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | OCH₃ | OCH₃ | |
| 56 | H | H | H | — | — | OCH₃ | CH₃ | |
| 56 | CH₃ | H | H | — | — | OCH₃ | CH₃ | |
| 56 | H | H | H | — | — | OCH₂CH₃ | NHCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | OCH₃ | OCH₃ | |
| 61 | H | H | H | NCH₃ | — | OCH₃ | CH₃ | |
| 61 | CH₃ | H | H | NCH₃ | — | OCH₃ | CH₃ | |
| 61 | H | H | H | NCH₃ | — | CH₂CH₃ | NHCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | OCH₃ | OCH₃ | |
| 62 | H | H | H | NCH₃ | — | OCH₃ | CH₃ | |
| 62 | CH₃ | H | H | NCH₃ | — | OCH₃ | CH₃ | |
| 62 | H | H | H | NCH₃ | — | OCH₂CH₃ | NHCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | OCH₃ | OCH₃ | |
| 65 | H | H | H | — | — | OCH₃ | CH₃ | |
| 65 | CH₃ | H | H | — | — | OCH₃ | CH₃ | |
| 65 | H | H | H | — | — | OCH₂CH₃ | NHCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | OCH₃ | OCH₃ | |
| 68 | H | H | H | — | — | OCH₃ | CH₃ | |
| 68 | CH₃ | H | H | — | — | OCH₃ | CH₃ | |
| 68 | H | H | H | — | — | OCH₂CH₃ | NHCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | OCH₃ | OCH₃ | |
| 76 | H | H | H | O | — | OCH₃ | CH₃ | |
| 76 | CH₃ | H | H | O | — | OCH₃ | CH₃ | |
| 76 | H | H | H | O | — | OCH₂CH₃ | NHCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | OCH₃ | OCH₃ | |
| 78 | H | H | H | — | — | OCH₃ | CH₃ | |
| 78 | CH₃ | H | H | — | — | OCH₃ | CH₃ | |
| 78 | H | H | H | — | — | OCH₂CH₃ | NHCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | OCH₃ | OCH₃ | |
| 79 | H | H | H | — | — | OCH₃ | CH₃ | |
| 79 | CH₃ | H | H | — | — | OCH₃ | CH₃ | |
| 79 | H | H | H | — | — | OCH₂CH₃ | NHCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 12

General Formula 12

| Q | R | R₁ | R₃ | W₃ | W₄ | X | Y | m.p.(°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | H | 3-Cl | H | O | — | Cl | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |

TABLE 12-continued

General Formula 12

| Q | R | R$_1$ | R$_3$ | W$_3$ | W$_4$ | X | Y | m.p.(°C.) |
|---|---|---|---|---|---|---|---|---|
| 1 | H | 6-SO$_2$N(CH$_3$)$_2$ | H | O | — | OCH$_3$ | OCH$_3$ | |
| 1 | H | 6-CO$_2$CH$_3$ | H | O | — | OCH$_3$ | OCH$_3$ | |
| 1(R$_5$=CH$_3$) | H | H | H | O | — | CH$_3$ | CH$_3$ | |
| 1(R$_5$=CH$_3$) | H | H | H | O | — | OCH$_3$ | CH$_3$ | |
| 1(R$_5$=CH$_3$) | H | H | H | O | — | OCH$_3$ | OCH$_3$ | |
| 1(R$_5$=CH$_3$) | H | H | H | O | — | Cl | OCH$_3$ | |
| 1 | H | 6-SO$_2$CH$_3$ | H | O | — | OCH$_3$ | OCH$_3$ | |
| 1 | H | H | H | O | — | OCF$_2$H | OCH$_3$ | |
| 1 | H | H | H | O | — | CH$_2$F | OCH$_3$ | |
| 1 | H | H | H | O | — | CH$_2$Cl | OCH$_3$ | |
| 1 | H | H | H | O | — | CF$_3$ | OCH$_3$ | |
| 1 | H | H | H | O | — | SCH$_3$ | OCH$_3$ | |
| 1 | H | H | H | O | — | Cl | OCH$_3$ | |
| 1 | H | H | H | O | — | NHCH$_3$ | OCH$_2$CH$_3$ | |
| 1 | H | H | H | O | — | OCH$_2$CH=CH$_2$ | OCH$_3$ | |
| 1 | H | H | H | O | — | OCH$_2$C≡CH | OCH$_3$ | |
| 1 | H | H | H | O | — | cyclopropyl | OCH$_3$ | |
| 1 | H | H | H | NCH$_3$ | — | CH$_3$ | CH$_3$ | |
| 1 | H | H | H | NCH$_3$ | — | OCH$_3$ | CH$_3$ | |
| 1 | H | H | H | NCH$_3$ | — | OCH$_3$ | OCH$_3$ | |
| 1 | H | H | H | NCH$_3$ | — | OCH$_3$ | Cl | |
| 1 | H | H | H | O | — | C≡CH | OCH$_3$ | |
| 1 | H | H | H | O | — | CHO | OCH$_3$ | |
| 1 | H | H | H | O | — | 2-methyl-1,3-oxathiolan-2-yl | OCH$_3$ | |
| 1 | H | H | H | O | — | 2-methyl-1,3-dithian-2-yl | OCH$_3$ | |
| 1 | H | H | H | O | — | 1,3-dioxan-2-yl | OCH$_3$ | |
| 1 | H | H | H | NCH$_3$ | — | CH$_3$ | CH$_3$ | |
| 1 | H | H | H | NCH$_3$ | — | OCH$_3$ | CH$_3$ | |
| 1 | H | H | H | NCH$_3$ | — | OCH$_3$ | OCH$_3$ | |
| 1 | H | H | H | NCH$_3$ | — | Cl | OCH$_3$ | |
| 1 | H | 5-OCH$_3$ | H | NCH$_3$ | — | OCH$_3$ | OCH$_3$ | |
| 1 | H | 5-SCH$_3$ | H | NCH$_3$ | — | OCH$_3$ | OCH$_3$ | |
| 3 | H | H | H | — | — | CH$_3$ | CH$_3$ | |
| 3 | H | H | H | — | — | OCH$_3$ | CH$_3$ | |
| 3 | H | H | H | — | — | OCH$_3$ | OCH$_3$ | |
| 3 | H | H | H | — | — | Cl | OCH$_3$ | |
| 3 | H | 5-OCH$_3$ | H | — | — | OCH$_3$ | OCH$_3$ | |
| 3 | H | 5-SCH$_3$ | H | — | — | OCH$_3$ | OCH$_3$ | |
| 5 | H | H | H | NCH$_3$ | — | CH$_3$ | CH$_3$ | |
| 5 | H | H | H | NCH$_3$ | — | OCH$_3$ | CH$_3$ | |
| 5 | H | H | H | NCH$_3$ | — | OCH$_3$ | OCH$_3$ | |
| 5 | H | H | H | NCH$_3$ | — | Cl | OCH$_3$ | |
| 5 | H | 5-OCH$_3$ | H | NCH$_3$ | — | OCH$_3$ | OCH$_3$ | |
| 5 | H | 5-SCH$_3$ | H | NCH$_3$ | — | OCH$_3$ | OCH$_3$ | |
| 7 | H | H | H | — | S | CH$_3$ | CH$_3$ | |
| 7 | H | H | H | — | S | OCH$_3$ | CH$_3$ | |
| 7 | H | H | H | — | S | OCH$_3$ | OCH$_3$ | |
| 7 | H | H | H | — | S | Cl | OCH$_3$ | |
| 7 | H | 5-OCH$_3$ | H | — | S | OCH$_3$ | OCH$_3$ | |
| 7 | H | 5-SCH$_3$ | H | — | S | OCH$_3$ | OCH$_3$ | |
| 7 | H | H | H | — | SO$_2$ | CH$_3$ | CH$_3$ | |
| 7 | H | H | H | — | SO$_2$ | OCH$_3$ | CH$_3$ | |
| 7 | H | H | H | — | SO$_2$ | OCH$_3$ | OCH$_3$ | |
| 7 | H | H | H | — | SO$_2$ | Cl | OCH$_3$ | |
| 7 | H | 5-OCH$_3$ | H | — | SO$_2$ | OCH$_3$ | OCH$_3$ | |
| 7 | H | 5-SCH$_3$ | H | — | SO$_2$ | OCH$_3$ | OCH$_3$ | |
| 8 | H | H | H | — | S | CH$_3$ | CH$_3$ | |
| 8 | H | H | H | — | S | OCH$_3$ | CH$_3$ | |
| 8 | H | H | H | — | S | OCH$_3$ | OCH$_3$ | |
| 8 | H | H | H | — | S | Cl | OCH$_3$ | |
| 8 | H | 5-OCH$_3$ | H | — | S | OCH$_3$ | OCH$_3$ | |
| 8 | H | 5-SCH$_3$ | H | — | S | OCH$_3$ | OCH$_3$ | |
| 8 | H | H | H | — | SO$_2$ | CH$_3$ | CH$_3$ | |
| 8 | H | H | H | — | SO$_2$ | OCH$_3$ | CH$_3$ | |
| 8 | H | H | H | — | SO$_2$ | OCH$_3$ | OCH$_3$ | |
| 8 | H | H | H | — | SO$_2$ | Cl | OCH$_3$ | |
| 8 | H | 5-OCH$_3$ | H | — | SO$_2$ | OCH$_3$ | OCH$_3$ | |
| 8 | H | 5-SCH$_3$ | H | — | SO$_2$ | OCH$_3$ | OCH$_3$ | |
| 16 | H | H | H | — | O | CH$_3$ | CH$_3$ | |
| 16 | H | H | H | O | — | OCH$_3$ | CH$_3$ | |
| 16 | H | H | H | O | — | OCH$_3$ | OCH$_3$ | |
| 16 | CH$_3$ | H | H | O | — | OCH$_3$ | OCH$_3$ | |
| 16 | CH$_3$ | H | H | O | — | OCH$_3$ | CH$_3$ | |
| 16 | H | H | CH$_3$ | O | — | OCH$_3$ | OCH$_3$ | |
| 16 | H | H | CH$_3$ | O | — | OCH$_3$ | CH$_3$ | |

TABLE 12-continued

General Formula 12

| Q | R | R$_1$ | R$_3$ | W$_3$ | W$_4$ | X | Y | m.p.(°C.) |
|---|---|---|---|---|---|---|---|---|
| 16 | H | H | CH$_3$ | O | — | CH$_3$ | CH$_3$ | |
| 16 | H | 3-Cl | H | O | — | CH$_3$ | CH$_3$ | |
| 16 | H | 3-Cl | H | O | — | OCH$_3$ | CH$_3$ | |
| 16 | H | 3-Cl | H | O | — | OCH$_3$ | OCH$_3$ | |
| 16 | H | 3-Cl | H | O | — | OCH$_3$ | Cl | |
| 16 | CH$_3$ | 3-Cl | H | O | — | OCH$_3$ | OCH$_3$ | |
| 16 | H | 5-CH$_3$ | H | O | — | OCH$_3$ | OCH$_3$ | |
| 16 | H | 5-OCH$_3$ | H | O | — | OCH$_3$ | OCH$_3$ | |
| 16 | H | 5-OCH$_2$CH$_3$ | H | O | — | OCH$_3$ | OCH$_3$ | |
| 16 | H | 5-OCF$_2$H | H | O | — | OCH$_3$ | OCH$_3$ | |
| 16 | H | 5-SCH$_3$ | H | O | — | OCH$_3$ | OCH$_3$ | |
| 16 | H | 5-NHCH$_3$ | H | O | — | OCH$_3$ | OCH$_3$ | |
| 16 | H | 5-N(CH$_3$)$_2$ | H | O | — | OCH$_3$ | OCH$_3$ | |
| 16 | H | 5-Cl | H | O | — | OCH$_3$ | OCH$_3$ | |
| 16 | H | 5-CF$_3$ | H | O | — | OCH$_3$ | OCH$_3$ | |
| 16 | H | 6-SO$_2$N(CH$_3$)$_2$ | H | O | — | OCH$_3$ | OCH$_3$ | |
| 16 | H | 6-CO$_2$CH$_3$ | H | O | — | OCH$_3$ | OCH$_3$ | |
| 16 | H | 6-SO$_2$CH$_3$ | H | O | — | OCH$_3$ | OCH$_3$ | |
| 16 | H | H | H | O | — | OCF$_2$H | OCH$_3$ | |
| 16 | H | H | H | O | — | CH$_2$F | OCH$_3$ | |
| 16 | H | H | H | O | — | CH$_2$Cl | OCH$_3$ | |
| 16 | H | H | H | O | — | CF$_3$ | OCH$_3$ | |
| 16 | H | H | H | O | — | SCH$_3$ | OCH$_3$ | |
| 16 | H | H | H | O | — | Cl | OCH$_3$ | |
| 16 | H | H | H | O | — | NHCH$_3$ | OCH$_2$CH$_3$ | |
| 16 | H | H | H | O | — | OCH$_2$CH=CH$_2$ | OCH$_3$ | |
| 16 | H | H | H | O | — | OCH$_2$C≡CH | OCH$_3$ | |
| 16 | H | H | H | O | — | cyclopropyl | OCH$_3$ | |
| 16 | H | H | H | NCH$_3$ | — | CH$_3$ | CH$_3$ | |
| 16 | H | H | H | NCH$_3$ | — | OCH$_3$ | CH$_3$ | |
| 16 | H | H | H | NCH$_3$ | — | OCH$_3$ | OCH$_3$ | |
| 16 | H | H | H | NCH$_3$ | — | OCH$_3$ | Cl | |
| 16 | H | H | H | O | — | C≡CH | OCH$_3$ | |
| 16 | H | H | H | O | — | CHO | OCH$_3$ | |
| 16 | H | H | H | O | — | 2-methyl-1,3-oxathiolan-2-yl | OCH$_3$ | |
| 16 | H | H | H | O | — | 2-methyl-1,3-dithian-2-yl | OCH$_3$ | |
| 16 | H | H | H | O | — | 1,3-dioxan-2-yl | OCH$_3$ | |
| 19 | H | H | H | — | — | CH$_3$ | CH$_3$ | |
| 19 | H | H | H | — | — | OCH$_3$ | CH$_3$ | |
| 19 | H | H | H | — | — | OCH$_3$ | OCH$_3$ | |
| 19 | H | H | H | — | — | Cl | OCH$_3$ | |
| 19 | H | 5-OCH$_3$ | H | — | — | OCH$_3$ | OCH$_3$ | |
| 19 | H | 5-SCH$_3$ | H | — | — | OCH$_3$ | OCH$_3$ | |
| 20 | H | H | H | — | — | CH$_3$ | CH$_3$ | |
| 20 | H | H | H | — | — | OCH$_3$ | CH$_3$ | |
| 20 | H | H | H | — | — | OCH$_3$ | OCH$_3$ | |
| 20 | H | H | H | — | — | Cl | OCH$_3$ | |
| 20 | H | 5-OCH$_3$ | H | — | — | OCH$_3$ | OCH$_3$ | |
| 20 | H | 5-SCH$_3$ | H | — | — | OCH$_3$ | OCH$_3$ | |
| 21 | H | H | H | — | — | CH$_3$ | CH$_3$ | |
| 21 | H | H | H | — | — | OCH$_3$ | CH$_3$ | |
| 21 | H | H | H | — | — | OCH$_3$ | OCH$_3$ | |
| 21 | H | H | H | — | — | Cl | OCH$_3$ | |
| 21 | H | 5-OCH$_3$ | H | — | — | OCH$_3$ | OCH$_3$ | |
| 21 | H | 5-SCH$_3$ | H | — | — | OCH$_3$ | OCH$_3$ | |
| 22 | H | H | H | NCH$_3$ | — | CH$_3$ | CH$_3$ | |
| 22 | H | H | H | NCH$_3$ | — | OCH$_3$ | CH$_3$ | |
| 22 | H | H | H | NCH$_3$ | — | OCH$_3$ | OCH$_3$ | |
| 22 | H | H | H | NCH$_3$ | — | Cl | OCH$_3$ | |
| 22 | H | 5-OCH$_3$ | H | NCH$_3$ | — | OCH$_3$ | OCH$_3$ | |
| 22 | H | 5-SCH$_3$ | H | NCH$_3$ | — | OCH$_3$ | OCH$_3$ | |
| 25 | H | H | H | — | S | CH$_3$ | CH$_3$ | |
| 25 | H | H | H | — | S | OCH$_3$ | CH$_3$ | |
| 25 | H | H | H | — | S | OCH$_3$ | OCH$_3$ | |
| 25 | H | H | H | — | S | Cl | OCH$_3$ | |
| 25 | H | 5-OCH$_3$ | H | — | S | OCH$_3$ | OCH$_3$ | |
| 25 | H | 5-SCH$_3$ | H | — | S | OCH$_3$ | OCH$_3$ | |
| 25 | H | H | H | — | SO$_2$ | CH$_3$ | CH$_3$ | |
| 25 | H | H | H | — | SO$_2$ | OCH$_3$ | CH$_3$ | |
| 25 | H | H | H | — | SO$_2$ | OCH$_3$ | OCH$_3$ | |
| 25 | H | H | H | — | SO$_2$ | Cl | OCH$_3$ | |
| 25 | H | 5-OCH$_3$ | H | — | SO$_2$ | OCH$_3$ | OCH$_3$ | |
| 25 | H | 5-SCH$_3$ | H | — | SO$_2$ | OCH$_3$ | OCH$_3$ | |
| 26 | H | H | H | — | S | CH$_3$ | CH$_3$ | |
| 26 | H | H | H | — | S | OCH$_3$ | CH$_3$ | |

TABLE 12-continued

General Formula 12

| Q | R | R₁ | R₃ | W₃ | W₄ | X | Y | m.p.(°C.) |
|---|---|---|---|---|---|---|---|---|
| 26 | H | H | H | — | S | OCH₃ | OCH₃ | |
| 26 | H | H | H | — | S | Cl | OCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | CH₃ | CH₃ | |
| 26 | H | H | H | — | SO₂ | OCH₃ | CH₃ | |
| 26 | H | H | H | — | SO₂ | OCH₃ | OCH₃ | |
| 26 | H | H | H | — | SO₂ | Cl | OCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | CH₃ | CH₃ | |
| 27 | H | H | H | — | S | OCH₃ | CH₃ | |
| 27 | H | H | H | — | S | OCH₃ | OCH₃ | |
| 27 | H | H | H | — | S | Cl | OCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | CH₃ | CH₃ | |
| 27 | H | H | H | — | SO₂ | OCH₃ | CH₃ | |
| 27 | H | H | H | — | SO₂ | OCH₃ | OCH₃ | |
| 27 | H | H | H | — | SO₂ | Cl | OCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | CH₃ | CH₃ | |
| 29(R₆=CH₃) | H | H | H | — | — | OCH₃ | CH₃ | |
| 29(R₆=CH₃) | H | H | H | — | — | OCH₃ | OCH₃ | |
| 29(R₆=CH₃) | H | H | H | — | — | Cl | OCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | CH₃ | CH₃ | |
| 55 | H | H | H | O | — | OCH₃ | CH₃ | |
| 55 | H | H | H | O | — | OCH₃ | OCH₃ | |
| 55 | H | H | H | O | — | Cl | OCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | CH₃ | CH₃ | |
| 55 | H | H | H | NCH₃ | — | OCH₃ | CH₃ | |
| 55 | H | H | H | NCH₃ | — | OCH₃ | OCH₃ | |
| 55 | H | H | H | NCH₃ | — | Cl | OCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | CH₃ | CH₃ | |
| 56 | H | H | H | — | — | OCH₃ | CH₃ | |
| 56 | H | H | H | — | — | OCH₃ | OCH₃ | |
| 56 | H | H | H | — | — | Cl | OCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | CH₃ | CH₃ | |
| 61 | H | H | H | NCH₃ | — | OCH₃ | CH₃ | |
| 61 | H | H | H | NCH₃ | — | OCH₃ | OCH₃ | |
| 61 | H | H | H | NCH₃ | — | Cl | OCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | CH₃ | CH₃ | |
| 62 | H | H | H | NCH₃ | — | OCH₃ | CH₃ | |
| 62 | H | H | H | NCH₃ | — | OCH₃ | OCH₃ | |
| 62 | H | H | H | NCH₃ | — | Cl | OCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | CH₃ | CH₃ | |
| 65 | H | H | H | — | — | OCH₃ | CH₃ | |
| 65 | H | H | H | — | — | OCH₃ | OCH₃ | |
| 65 | H | H | H | — | — | Cl | OCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | CH₃ | CH₃ | |
| 68 | H | H | H | — | — | OCH₃ | CH₃ | |
| 68 | H | H | H | — | — | OCH₃ | OCH₃ | |
| 68 | H | H | H | — | — | Cl | OCH₃ | |
| 68 | H | 5-OCH₃ | H | — | — | OCH₃ | OCH₃ | |
| 68 | H | 5-SCH3 | H | — | — | OCH₃ | OCH₃ | |
| 76 | H | H | H | O | — | CH₃ | CH₃ | |
| 76 | H | H | H | O | — | OCH₃ | CH₃ | |
| 76 | H | H | H | O | — | OCH₃ | OCH₃ | |
| 76 | H | H | H | O | — | Cl | OCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | CH₃ | CH₃ | |
| 78 | H | H | H | — | — | OCH₃ | CH₃ | |
| 78 | H | H | H | — | — | OCH₃ | OCH₃ | |
| 78 | H | H | H | — | — | Cl | OCH₃ | |

TABLE 12-continued

General Formula 12

| Q  | R  | R₁      | R₃ | W₃ | W₄ | X    | Y    | m.p.(°C.) |
|----|----|---------|----|----|----|------|------|-----------|
| 78 | H  | 5-OCH₃  | H  | —  | —  | OCH₃ | OCH₃ |           |
| 78 | H  | 5-SCH₃  | H  | —  | —  | OCH₃ | OCH₃ |           |
| 79 | H  | H       | H  | —  | —  | CH₃  | CH₃  |           |
| 79 | H  | H       | H  | —  | —  | OCH₃ | CH₃  |           |
| 79 | H  | H       | H  | —  | —  | OCH₃ | OCH₃ |           |
| 79 | H  | H       | H  | —  | —  | Cl   | OCH₃ |           |
| 79 | H  | 5-OCH₃  | H  | —  | —  | OCH₃ | OCH₃ |           |
| 79 | H  | 5-SCH₃  | H  | —  | —  | OCH₃ | OCH₃ |           |

TABLE 13

General Structure 13

| Q           | R   | R₁                                    | R₃  | W₃   | W₄ | X                          | Y       | m.p. (°C.) |
|-------------|-----|---------------------------------------|-----|------|----|----------------------------|---------|------------|
| 1           | H   | H                                     | H   | O    | —  | CH₃                        | CH₃     |            |
| 1           | H   | H                                     | H   | O    | —  | OCH₃                       | CH₃     |            |
| 1           | H   | H                                     | H   | O    | —  | OCH₃                       | OCH₃    |            |
| 1           | CH₃ | H                                     | H   | O    | —  | OCH₃                       | OCH₃    |            |
| 1           | CH₃ | H                                     | H   | O    | —  | OCH₃                       | CH₃     |            |
| 1           | H   | H                                     | CH₃ | O    | —  | OCH₃                       | OCH₃    |            |
| 1           | H   | H                                     | CH₃ | O    | —  | OCH₃                       | CH₃     |            |
| 1           | H   | H                                     | CH₃ | O    | —  | CH₃                        | CH₃     |            |
| 1           | H   | 3-Cl                                  | H   | O    | —  | CH₃                        | CH₃     |            |
| 1           | H   | 3-Cl                                  | H   | O    | —  | OCH₃                       | CH₃     |            |
| 1           | H   | 3-Cl                                  | H   | O    | —  | OCH₃                       | OCH₃    |            |
| 1           | CH₃ | 3-Cl                                  | H   | O    | —  | OCH₃                       | OCH₃    |            |
| 1           | H   | 5-CH₃                                 | H   | O    | —  | OCH₃                       | OCH₃    |            |
| 1           | H   | 5-OCH₃                                | H   | O    | —  | OCH₃                       | OCH₃    |            |
| 1           | H   | 5-OCH₂CH₃                             | H   | O    | —  | OCH₃                       | OCH₃    |            |
| 1           | H   | 5-OCF₂H                               | H   | O    | —  | OCH₃                       | OCH₃    |            |
| 1           | H   | 5-SCH₃                                | H   | O    | —  | OCH₃                       | OCH₃    |            |
| 1           | H   | 5-NHCH₃                               | H   | O    | —  | OCH₃                       | OCH₃    |            |
| 1           | H   | 5-N(CH₃)₂                             | H   | O    | —  | OCH₃                       | OCH₃    |            |
| 1           | H   | 5-Cl                                  | H   | O    | —  | OCH₃                       | OCH₃    |            |
| 1           | H   | 5-CF₃                                 | H   | O    | —  | OCH₃                       | OCH₃    |            |
| 1           | H   | 6-SO₂N(CH₃)₂                          | H   | O    | —  | OCH₃                       | OCH₃    |            |
| 1           | H   | 6-CO₂CH₃                              | H   | O    | —  | OCH₃                       | OCH₃    |            |
| 1(R₅=CH₃)   | H   | H                                     | H   | O    | —  | CH₃                        | CH₃     |            |
| 1(R₅=CH₃)   | H   | H                                     | H   | O    | —  | OCH₃                       | CH₃     |            |
| 1(R₅=CH₃)   | H   | H                                     | H   | O    | —  | OCH₃                       | OCH₃    |            |
| 1           | H   | 6-SO₂CH₃                              | H   | O    | —  | OCH₃                       | OCH₃    |            |
| 1           | H   | H                                     | H   | O    | —  | CH₂F                       | OCH₃    |            |
| 1           | H   | H                                     | H   | O    | —  | CH₂Cl                      | OCH₃    |            |
| 1           | H   | H                                     | H   | O    | —  | CF₃                        | OCH₃    |            |
| 1           | H   | H                                     | H   | O    | —  | SCH₃                       | OCH₃    |            |
| 1           | H   | H                                     | H   | O    | —  | NHCH₃                      | OCH₂CH₃ |            |
| 1           | H   | H                                     | H   | O    | —  | OCH₂CH=CH₂                 | OCH₃    |            |
| 1           | H   | H                                     | H   | O    | —  | OCH₂C≡CH                   | OCH₃    |            |
| 1           | H   | H                                     | H   | O    | —  | cyclopropyl                | OCH₃    |            |
| 1           | H   | H                                     | H   | NCH₃ | —  | CH₃                        | CH₃     |            |
| 1           | H   | H                                     | H   | O    | —  | C≡CH                       | OCH₃    |            |
| 1           | H   | H                                     | H   | O    | —  | CHO                        | OCH₃    |            |
| 1           | H   | H                                     | H   | O    | —  | 2-methyl-1,3-oxathiolan-2-yl | OCH₃  |            |
| 1           | H   | H                                     | H   | O    | —  | 2-methyl-1,3-dithian-2-yl  | OCH₃    |            |
| 1           | H   | H                                     | H   | O    | —  | 1,3-dioxan-2-yl            | OCH₃    |            |
| 1           | H   | H                                     | H   | NCH₃ | —  | OCH₃                       | OCH₃    |            |
| 1           | H   | H                                     | H   | NCH₃ | —  | OCH₃                       | CH₃     |            |
| 1           | CH₃ | H                                     | H   | NCH₃ | —  | OCH₃                       | CH₃     |            |
| 1           | H   | H                                     | H   | NCH₃ | —  | OCH₂CH₃                    | NHCH₃   |            |
| 1           | H   | 5-OCH₃                                | H   | NCH₃ | —  | OCH₃                       | OCH₃    |            |
| 1           | H   | 5-SCH₃                                | H   | NCH₃ | —  | OCH₃                       | OCH₃    |            |
| 3           | H   | H                                     | H   | —    | —  | OCH₃                       | OCH₃    |            |
| 3           | H   | H                                     | H   | —    | —  | OCH₃                       | CH₃     |            |
| 3           | CH₃ | H                                     | H   | —    | —  | OCH₃                       | CH₃     |            |
| 3           | H   | H                                     | H   | —    | —  | OCH₂CH₃                    | NHCH₃   |            |
| 3           | H   | 5-OCH₃                                | H   | —    | —  | OCH₃                       | OCH₃    |            |
| 3           | H   | 5-SCH₃                                | H   | —    | —  | OCH₃                       | OCH₃    |            |
| 5           | H   | H                                     | H   | NCH₃ | —  | OCH₃                       | OCH₃    |            |
| 5           | H   | H                                     | H   | NCH₃ | —  | OCH₃                       | CH₃     |            |
| 5           | CH₃ | H                                     | H   | NCH₃ | —  | OCH₃                       | CH₃     |            |
| 5           | H   | H                                     | H   | NCH₃ | —  | OCH₂CH₃                    | NHCH₃   |            |
| 5           | H   | 5-OCH₃                                | H   | NCH₃ | —  | OCH₃                       | OCH₃    |            |
| 5           | H   | 5-SCH₃                                | H   | NCH₃ | —  | OCH₃                       | OCH₃    |            |
| 7           | H   | H                                     | H   | —    | S  | OCH₃                       | OCH₃    |            |

TABLE 13-continued

General Structure 13

| Q | R | R₁ | R₃ | W₃ | W₄ | X | Y | m.p. (°C.) |
|---|---|---|---|---|---|---|---|---|
| 7 | H | H | H | — | S | OCH₃ | CH₃ | |
| 7 | CH₃ | H | H | — | S | OCH₃ | CH₃ | |
| 7 | H | H | H | — | S | OCH₂CH₃ | NHCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | OCH₃ | OCH₃ | |
| 7 | H | H | H | — | SO₂ | OCH₃ | CH₃ | |
| 7 | CH₃ | H | H | — | SO₂ | OCH₃ | CH₃ | |
| 7 | H | H | H | — | SO₂ | OCH₂CH₃ | NHCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | OCH₃ | OCH₃ | |
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | OCH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | OCH₃ | OCH₃ | |
| 19 | H | H | H | — | — | OCH₃ | CH₃ | |
| 19 | CH₃ | H | H | — | — | OCH₃ | CH₃ | |
| 19 | H | H | H | — | — | OCH₂CH₃ | NHCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | OCH₃ | OCH₃ | |
| 20 | H | H | H | — | — | OCH₃ | CH₃ | |
| 20 | CH₃ | H | H | — | — | OCH₃ | CH₃ | |
| 20 | H | H | H | — | — | OCH₂CH₃ | NHCH₃ | |
| 20 | H | 5-OCH₃ | H | — | — | OCH₃ | OCH₃ | |
| 20 | H | 5-SCH₃ | H | — | — | OCH₃ | OCH₃ | |

TABLE 13-continued

General Structure 13

| Q | R | R₁ | R₃ | W₃ | W₄ | X | Y | m.p. (°C.) |
|---|---|---|---|---|---|---|---|---|
| 21 | H | H | H | — | — | OCH₃ | OCH₃ | |
| 21 | H | H | H | — | — | OCH₃ | CH₃ | |
| 21 | CH₃ | H | H | — | — | OCH₃ | CH₃ | |
| 21 | H | H | H | — | — | OCH₂CH₃ | NHCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | OCH₃ | OCH₃ | |
| 22 | H | H | H | NCH₃ | — | OCH₃ | CH₃ | |
| 22 | CH₃ | H | H | NCH₃ | — | OCH₃ | CH₃ | |
| 22 | H | H | H | NCH₃ | — | OCH₂CH₃ | NHCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | OCH₃ | OCH₃ | |
| 25 | H | H | H | — | SO₂ | OCH₃ | CH₃ | |
| 25 | CH₃ | H | H | — | SO₂ | OCH₃ | CH₃ | |
| 25 | H | H | H | — | SO₂ | OCH₂CH₃ | NHCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | OCH₃ | OCH₃ | |
| 26 | H | H | H | — | S | OCH₃ | CH₃ | |
| 26 | CH₃ | H | H | — | S | OCH₃ | CH₃ | |
| 26 | H | H | H | — | S | OCH₂CH₃ | NHCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | OCH₃ | OCH₃ | |
| 26 | H | H | H | — | SO₂ | OCH₃ | CH₃ | |
| 26 | CH₃ | H | H | — | SO₂ | OCH₃ | CH₃ | |
| 26 | H | H | H | — | SO₂ | OCH₂CH₃ | NHCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | OCH₃ | OCH₃ | |
| 27 | H | H | H | — | S | OCH₃ | CH₃ | |
| 27 | CH₃ | H | H | — | S | OCH₃ | CH₃ | |
| 27 | H | H | H | — | S | OCH₂CH₃ | NHCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | OCH₃ | OCH₃ | |
| 27 | H | H | H | — | SO₂ | OCH₃ | CH₃ | |
| 27 | CH₃ | H | H | — | SO₂ | OCH₃ | CH₃ | |
| 27 | H | H | H | — | SO₂ | OCH₂CH₃ | NHCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | OCH₃ | OCH₃ | |
| 29(R₆=CH₃) | H | H | H | — | — | OCH₃ | CH₃ | |
| 29(R₆=CH₃) | CH₃ | H | H | — | — | OCH₃ | CH₃ | |
| 29(R₆=CH₃) | H | H | H | — | — | OCH₂CH₃ | NHCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | OCH₃ | OCH₃ | |
| 55 | H | H | H | O | — | OCH₃ | CH₃ | |
| 55 | CH₃ | H | H | O | — | OCH₃ | CH₃ | |
| 55 | H | H | H | O | — | OCH₂CH₃ | NHCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | OCH₃ | OCH₃ | |
| 55 | H | H | H | NCH₃ | — | OCH₃ | CH₃ | |
| 55 | CH₃ | H | H | NCH₃ | — | OCH₃ | CH₃ | |
| 55 | H | H | H | NCH₃ | — | OCH₂CH₃ | NHCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | OCH₃ | OCH₃ | |
| 56 | H | H | H | — | — | OCH₃ | CH₃ | |
| 56 | CH₃ | H | H | — | — | OCH₃ | CH₃ | |
| 56 | H | H | H | — | — | OCH₂CH₃ | NHCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | OCH₃ | OCH₃ | |
| 61 | H | H | H | NCH₃ | — | OCH₃ | CH₃ | |
| 61 | CH₃ | H | H | NCH₃ | — | OCH₃ | CH₃ | |
| 61 | H | H | H | NCH₃ | — | OCH₂CH₃ | NHCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | OCH₃ | OCH₃ | |
| 62 | H | H | H | NCH₃ | — | OCH₃ | CH₃ | |

TABLE 13-continued

General Structure 13

| Q | R | R₁ | R₃ | W₃ | W₄ | X | Y | m.p. (°C.) |
|---|---|----|----|----|----|---|---|------------|
| 62 | CH₃ | H | H | NCH₃ | — | OCH₃ | CH₃ | |
| 62 | H | H | H | NCH₃ | — | OCH₂CH₃ | NHCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | OCH₃ | OCH₃ | |
| 65 | H | H | H | — | — | OCH₃ | CH₃ | |
| 65 | CH₃ | H | H | — | — | OCH₃ | CH₃ | |
| 65 | H | H | H | — | — | OCH₂CH₃ | NHCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | OCH₃ | OCH₃ | |
| 68 | H | H | H | — | — | OCH₃ | CH₃ | |
| 68 | CH₃ | H | H | — | — | OCH₃ | CH₃ | |
| 68 | H | H | H | — | — | OCH₂CH₃ | NHCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | OCH₃ | OCH₃ | |
| 76 | H | H | H | O | — | OCH₃ | CH₃ | |
| 76 | CH₃ | H | H | O | — | OCH₃ | CH₃ | |
| 76 | H | H | H | O | — | OCH₂CH₃ | NHCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | OCH₃ | OCH₃ | |
| 78 | H | H | H | — | — | OCH₃ | CH₃ | |
| 78 | CH₃ | H | H | — | — | OCH₃ | CH₃ | |
| 78 | H | H | H | — | — | OCH₂CH₃ | NHCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | OCH₃ | OCH₃ | |
| 79 | H | H | H | — | — | OCH₃ | CH₃ | |
| 79 | CH₃ | H | H | — | — | OCH₃ | CH₃ | |
| 79 | H | H | H | — | — | OCH₂CH₃ | NHCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 14

General Structure 14

| Q | R | R₁ | R₃ | W₃ | W₄ | X | Y | m.p. (°C.) |
|---|---|----|----|----|----|---|---|------------|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | H | 3-Cl | H | O | — | Cl | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1(R₅=CH₃) | H | H | H | O | — | Cl | OCH₃ | |
| 1 | H | 6-SO₂CH₃ | H | O | — | OCH₃ | OCH₃ | |
| 1 | H | H | H | O | — | OCF₂H | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | Cl | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |

TABLE 14-continued

General Structure 14

| Q | R | R₁ | R₃ | W₃ | W₄ | X | Y | m.p. (°C.) |
|---|---|---|---|---|---|---|---|---|
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | OCH₃ | Cl | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | Cl | OCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | CH₃ | CH₃ | |
| 3 | H | H | H | — | — | OCH₃ | CH₃ | |
| 3 | H | H | H | — | — | OCH₃ | OCH₃ | |
| 3 | H | H | H | — | — | Cl | OCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | CH₃ | CH₃ | |
| 5 | H | H | H | NCH₃ | — | OCH₃ | CH₃ | |
| 5 | H | H | H | NCH₃ | — | OCH₃ | OCH₃ | |
| 5 | H | H | H | NCH₃ | — | Cl | OCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | CH₃ | CH₃ | |
| 7 | H | H | H | — | S | OCH₃ | CH₃ | |
| 7 | H | H | H | — | S | OCH₃ | OCH₃ | |
| 7 | H | H | H | — | S | Cl | OCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | CH₃ | CH₃ | |
| 7 | H | H | H | — | SO₂ | OCH₃ | CH₃ | |
| 7 | H | H | H | — | SO₂ | OCH₃ | OCH₃ | |
| 7 | H | H | H | — | SO₂ | Cl | OCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | CH₃ | CH₃ | |
| 8 | H | H | H | — | S | OCH₃ | CH₃ | |
| 8 | H | H | H | — | S | OCH₃ | OCH₃ | |
| 8 | H | H | H | — | S | Cl | OCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | CH₃ | CH₃ | |
| 8 | H | H | H | — | SO₂ | OCH₃ | CH₃ | |
| 8 | H | H | H | — | SO₂ | OCH₃ | OCH₃ | |
| 8 | H | H | H | — | SO₂ | Cl | OCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | H | 3-Cl | H | O | — | OCH₃ | Cl | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |

TABLE 14-continued

General Structure 14

| Q | R | R₁ | R₃ | W₃ | W₄ | X | Y | m.p. (°C.) |
|---|---|---|---|---|---|---|---|---|
| 16 | H | 6-SO₂CH₃ | H | O | — | OCH₃ | OCH₃ | |
| 16 | H | H | H | O | — | OCF₂H | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | Cl | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | NCH₃ | — | OCH₃ | Cl | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | CH₃ | CH₃ | |
| 19 | H | H | H | — | — | OCH₃ | CH₃ | |
| 19 | H | H | H | — | — | OCH₃ | OCH₃ | |
| 19 | H | H | H | — | — | Cl | OCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | CH₃ | CH₃ | |
| 20 | H | H | H | — | — | OCH₃ | CH₃ | |
| 20 | H | H | H | — | — | OCH₃ | OCH₃ | |
| 20 | H | H | H | — | — | Cl | OCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | CH₃ | CH₃ | |
| 21 | H | H | H | — | — | OCH₃ | CH₃ | |
| 21 | H | H | H | — | — | OCH₃ | OCH₃ | |
| 21 | H | H | H | — | — | Cl | OCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | CH₃ | CH₃ | |
| 22 | H | H | H | NCH₃ | — | OCH₃ | CH₃ | |
| 22 | H | H | H | NCH₃ | — | OCH₃ | OCH₃ | |
| 22 | H | H | H | NCH₃ | — | Cl | OCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | CH₃ | CH₃ | |
| 25 | H | H | H | — | S | OCH₃ | CH₃ | |
| 25 | H | H | H | — | S | OCH₃ | OCH₃ | |
| 25 | H | H | H | — | S | Cl | OCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | CH₃ | CH₃ | |
| 25 | H | H | H | — | SO₂ | OCH₃ | CH₃ | |
| 25 | H | H | H | — | SO₂ | OCH₃ | OCH₃ | |
| 25 | H | H | H | — | SO₂ | Cl | OCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | CH₃ | CH₃ | |
| 26 | H | H | H | — | S | OCH₃ | CH₃ | |
| 26 | H | H | H | — | S | OCH₃ | OCH₃ | |
| 26 | H | H | H | — | S | Cl | OCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | CH₃ | CH₃ | |
| 26 | H | H | H | — | SO₂ | OCH₃ | CH₃ | |
| 26 | H | H | H | — | SO₂ | OCH₃ | OCH₃ | |
| 26 | H | H | H | — | SO₂ | Cl | OCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | CH₃ | CH₃ | |
| 27 | H | H | H | — | S | OCH₃ | CH₃ | |
| 27 | H | H | H | — | S | OCH₃ | OCH₃ | |
| 27 | H | H | H | — | S | Cl | OCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | CH₃ | CH₃ | |

TABLE 14-continued

General Structure 14

| Q | R | R₁ | R₃ | W₃ | W₄ | X | Y | m.p. (°C.) |
|---|---|----|----|----|----|---|---|------------|
| 27 | H | H | H | — | SO₂ | OCH₃ | CH₃ | |
| 27 | H | H | H | — | SO₂ | OCH₃ | OCH₃ | |
| 27 | H | H | H | — | SO₂ | Cl | OCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | CH₃ | CH₃ | |
| 29(R₆=CH₃) | H | H | H | — | — | OCH₃ | CH₃ | |
| 29(R₆=CH₃) | H | H | H | — | — | OCH₃ | OCH₃ | |
| 29(R₆=CH₃) | H | H | H | — | — | Cl | OCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | CH₃ | CH₃ | |
| 55 | H | H | H | O | — | OCH₃ | CH₃ | |
| 55 | H | H | H | O | — | OCH₃ | OCH₃ | |
| 55 | H | H | H | O | — | Cl | OCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | CH₃ | CH₃ | |
| 55 | H | H | H | NCH₃ | — | OCH₃ | CH₃ | |
| 55 | H | H | H | NCH₃ | — | OCH₃ | OCH₃ | |
| 55 | H | H | H | NCH₃ | — | Cl | OCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | CH₃ | CH₃ | |
| 56 | H | H | H | — | — | OCH₃ | CH₃ | |
| 56 | H | H | H | — | — | OCH₃ | OCH₃ | |
| 56 | H | H | H | — | — | Cl | OCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | CH₃ | CH₃ | |
| 61 | H | H | H | NCH₃ | — | OCH₃ | CH₃ | |
| 61 | H | H | H | NCH₃ | — | OCH₃ | OCH₃ | |
| 61 | H | H | H | NCH₃ | — | Cl | OCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | CH₃ | CH₃ | |
| 62 | H | H | H | NCH₃ | — | OCH₃ | CH₃ | |
| 62 | H | H | H | NCH₃ | — | OCH₃ | OCH₃ | |
| 62 | H | H | H | NCH₃ | — | Cl | OCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | CH₃ | CH₃ | |
| 65 | H | H | H | — | — | OCH₃ | CH₃ | |
| 65 | H | H | H | — | — | OCH₃ | OCH₃ | |
| 65 | H | H | H | — | — | Cl | OCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | CH₃ | CH₃ | |
| 68 | H | H | H | — | — | OCH₃ | CH₃ | |
| 68 | H | H | H | — | — | OCH₃ | OCH₃ | |
| 68 | H | H | H | — | — | Cl | OCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | CH₃ | CH₃ | |
| 76 | H | H | H | O | — | OCH₃ | CH₃ | |
| 76 | H | H | H | O | — | OCH₃ | OCH₃ | |
| 76 | H | H | H | O | — | Cl | OCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | CH₃ | CH₃ | |
| 78 | H | H | H | — | — | OCH₃ | CH₃ | |
| 78 | H | H | H | — | — | OCH₃ | OCH₃ | |
| 78 | H | H | H | — | — | Cl | OCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | CH₃ | CH₃ | |
| 79 | H | H | H | — | — | OCH₃ | CH₃ | |
| 79 | H | H | H | — | — | OCH₃ | OCH₃ | |
| 79 | H | H | H | — | — | Cl | OCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 15

General Structure 15

| Q | R | R₁ | R₃ | W₃ | W₄ | X | Y | m.p. (°C.) |
|---|---|----|----|----|----|---|---|------------|
| 1 | H | H | H | O | — | CH₃ | CH₃ | |
| 1 | H | H | H | O | — | OCH₃ | CH₃ | |

TABLE 15-continued

General Structure 15

| Q | R | R₁ | R₃ | W₃ | W₄ | X | Y | m.p. (°C.) |
|---|---|---|---|---|---|---|---|---|
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1 | H | 6-SO₂CH₃ | H | O | — | OCH₃ | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | OCH₃ | OCH₃ | |
| 1 | H | H | H | NCH₃ | — | OCH₃ | CH₃ | |
| 1 | CH₃ | H | H | NCH₃ | — | OCH₃ | CH₃ | |
| 1 | H | H | H | NCH₃ | — | OCH₂CH₃ | NHCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | OCH₃ | OCH₃ | |
| 3 | H | H | H | — | — | OCH₃ | CH₃ | |
| 3 | CH₃ | H | H | — | — | OCH₃ | CH₃ | |
| 3 | H | H | H | — | — | OCH₂CH₃ | NHCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | OCH₃ | OCH₃ | |
| 5 | H | H | H | NCH₃ | — | OCH₃ | CH₃ | |
| 5 | CH₃ | H | H | NCH₃ | — | OCH₃ | CH₃ | |
| 5 | H | H | H | NCH₃ | — | OCH₂CH₃ | NHCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | OCH₃ | OCH₃ | |
| 7 | H | H | H | — | S | OCH₃ | CH₃ | |
| 7 | CH₃ | H | H | — | S | OCH₃ | CH₃ | |
| 7 | H | H | H | — | S | OCH₂CH₃ | NHCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | OCH₃ | OCH₃ | |
| 7 | H | H | H | — | SO₂ | OCH₃ | CH₃ | |
| 7 | CH₃ | H | H | — | SO₂ | OCH₃ | CH₃ | |
| 7 | H | H | H | — | SO₂ | OCH₂CH₃ | NHCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | OCH₃ | OCH₃ | |
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |

TABLE 15-continued

General Structure 15

| Q | R | R₁ | R₃ | W₃ | W₄ | X | Y | m.p. (°C.) |
|---|---|---|---|---|---|---|---|---|
| 8 | H | H | H | — | SO₂ | OCH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | OCH₃ | OCH₃ | |
| 19 | H | H | H | — | — | OCH₃ | CH₃ | |
| 19 | CH₃ | H | H | — | — | OCH₃ | CH₃ | |
| 19 | H | H | H | — | — | OCH₂CH₃ | NHCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | OCH₃ | OCH₃ | |
| 20 | H | H | H | — | — | OCH₃ | CH₃ | |
| 20 | CH₃ | H | H | — | — | OCH₃ | CH₃ | |
| 20 | H | H | H | — | — | OCH₂CH₃ | NHCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | OCH₃ | OCH₃ | |
| 21 | H | H | H | — | — | OCH₃ | CH₃ | |
| 21 | CH₃ | H | H | — | — | OCH₃ | CH₃ | |
| 21 | H | H | H | — | — | OCH₂CH₃ | NHCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | OCH₃ | OCH₃ | |
| 22 | H | H | H | NCH₃ | — | OCH₃ | CH₃ | |
| 22 | CH₃ | H | H | NCH₃ | — | OCH₃ | CH₃ | |
| 22 | H | H | H | NCH₃ | — | OCH₂CH₃ | NHCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |

TABLE 15-continued

General Structure 15

| Q | R | $R_1$ | $R_3$ | $W_3$ | $W_4$ | X | Y | m.p. (°C.) |
|---|---|---|---|---|---|---|---|---|
| 25 | H | 5-SCH$_3$ | H | — | S | OCH$_3$ | OCH$_3$ | |
| 25 | H | H | H | — | SO$_2$ | OCH$_3$ | OCH$_3$ | |
| 25 | H | H | H | — | SO$_2$ | OCH$_3$ | CH$_3$ | |
| 25 | CH$_3$ | H | H | — | SO$_2$ | OCH$_3$ | CH$_3$ | |
| 25 | H | H | H | — | SO$_2$ | OCH$_2$CH$_3$ | NHCH$_3$ | |
| 25 | H | 5-OCH$_3$ | H | — | SO$_2$ | OCH$_3$ | OCH$_3$ | |
| 25 | H | 5-SCH$_3$ | H | — | SO$_2$ | OCH$_3$ | OCH$_3$ | |
| 26 | H | H | H | — | S | OCH$_3$ | OCH$_3$ | |
| 26 | H | H | H | — | S | OCH$_3$ | CH$_3$ | |
| 26 | CH$_3$ | H | H | — | S | OCH$_3$ | CH$_3$ | |
| 26 | H | H | H | — | S | OCH$_2$CH$_3$ | NHCH$_3$ | |
| 26 | H | 5-OCH$_3$ | H | — | S | OCH$_3$ | OCH$_3$ | |
| 26 | H | 5-SCH$_3$ | H | — | S | OCH$_3$ | OCH$_3$ | |
| 26 | H | H | H | — | SO$_2$ | OCH$_3$ | OCH$_3$ | |
| 26 | H | H | H | — | SO$_2$ | OCH$_3$ | CH$_3$ | |
| 26 | CH$_3$ | H | H | — | SO$_2$ | OCH$_3$ | CH$_3$ | |
| 26 | H | H | H | — | SO$_2$ | OCH$_2$CH$_3$ | NHCH$_3$ | |
| 26 | H | 5-OCH$_3$ | H | — | SO$_2$ | OCH$_3$ | OCH$_3$ | |
| 26 | H | 5-SCH$_3$ | H | — | SO$_2$ | OCH$_3$ | OCH$_3$ | |
| 27 | H | H | H | — | S | OCH$_3$ | OCH$_3$ | |
| 27 | H | H | H | — | S | OCH$_3$ | CH$_3$ | |
| 27 | CH$_3$ | H | H | — | S | OCH$_3$ | CH$_3$ | |
| 27 | H | H | H | — | S | OCH$_2$CH$_3$ | NHCH$_3$ | |
| 27 | H | 5-OCH$_3$ | H | — | S | OCH$_3$ | OCH$_3$ | |
| 27 | H | 5-SCH$_3$ | H | — | S | OCH$_3$ | OCH$_3$ | |
| 27 | H | H | H | — | SO$_2$ | OCH$_3$ | OCH$_3$ | |
| 27 | H | H | H | — | SO$_2$ | OCH$_3$ | CH$_3$ | |
| 27 | CH$_3$ | H | H | — | SO$_2$ | OCH$_3$ | CH$_3$ | |
| 27 | H | H | H | — | SO$_2$ | OCH$_2$CH$_3$ | NHCH$_3$ | |
| 27 | H | 5-OCH$_3$ | H | — | SO$_2$ | OCH$_3$ | OCH$_3$ | |
| 27 | H | 5-SCH$_3$ | H | — | SO$_2$ | OCH$_3$ | OCH$_3$ | |
| 29($R_6$=CH$_3$) | H | H | H | — | — | OCH$_3$ | OCH$_3$ | |
| 29($R_6$=CH$_3$) | H | H | H | — | — | OCH$_3$ | CH$_3$ | |
| 29($R_6$=CH$_3$) | CH$_3$ | H | H | — | — | OCH$_3$ | CH$_3$ | |
| 29($R_6$=CH$_3$) | H | H | H | — | — | OCH$_2$CH$_3$ | NHCH$_3$ | |
| 29($R_6$=CH$_3$) | H | 5-OCH$_3$ | H | — | — | OCH$_3$ | OCH$_3$ | |
| 29($R_6$=CH$_3$) | H | 5-SCH$_3$ | H | — | — | OCH$_3$ | OCH$_3$ | |
| 55 | H | H | H | O | — | OCH$_3$ | OCH$_3$ | |
| 55 | H | H | H | O | — | OCH$_3$ | CH$_3$ | |
| 55 | CH$_3$ | H | H | O | — | OCH$_3$ | CH$_3$ | |
| 55 | H | H | H | O | — | OCH$_2$CH$_3$ | NHCH$_3$ | |
| 55 | H | 5-OCH$_3$ | H | O | — | OCH$_3$ | OCH$_3$ | |
| 55 | H | 5-SCH$_3$ | H | O | — | OCH$_3$ | OCH$_3$ | |
| 55 | H | H | H | NCH$_3$ | — | OCH$_3$ | OCH$_3$ | |
| 55 | H | H | H | NCH$_3$ | — | OCH$_3$ | CH$_3$ | |
| 55 | CH$_3$ | H | H | NCH$_3$ | — | OCH$_3$ | CH$_3$ | |
| 55 | H | H | H | NCH$_3$ | — | OCH$_2$CH$_3$ | NHCH$_3$ | |
| 55 | H | 5-OCH$_3$ | H | NCH$_3$ | — | OCH$_3$ | OCH$_3$ | |
| 55 | H | 5-SCH$_3$ | H | NCH$_3$ | — | OCH$_3$ | OCH$_3$ | |
| 56 | H | H | H | — | — | OCH$_3$ | OCH$_3$ | |
| 56 | H | H | H | — | — | OCH$_3$ | CH$_3$ | |
| 56 | CH$_3$ | H | H | — | — | OCH$_3$ | CH$_3$ | |
| 56 | H | H | H | — | — | OCH$_2$CH$_3$ | NHCH$_3$ | |
| 56 | H | 5-OCH$_3$ | H | — | — | OCH$_3$ | OCH$_3$ | |
| 56 | H | 5-SCH$_3$ | H | — | — | OCH$_3$ | OCH$_3$ | |
| 61 | H | H | H | NCH$_3$ | — | OCH$_3$ | OCH$_3$ | |
| 61 | H | H | H | NCH$_3$ | — | OCH$_3$ | CH$_3$ | |
| 61 | CH$_3$ | H | H | NCH$_3$ | — | OCH$_3$ | CH$_3$ | |
| 61 | H | H | H | NCH$_3$ | — | OCH$_2$CH$_3$ | NHCH$_3$ | |
| 61 | H | 5-OCH$_3$ | H | NCH$_3$ | — | OCH$_3$ | OCH$_3$ | |
| 61 | H | 5-SCH$_3$ | H | NCH$_3$ | — | OCH$_3$ | OCH$_3$ | |
| 62 | H | H | H | NCH$_3$ | — | OCH$_3$ | OCH$_3$ | |
| 62 | H | H | H | NCH$_3$ | — | OCH$_3$ | CH$_3$ | |
| 62 | CH$_3$ | H | H | NCH$_3$ | — | OCH$_3$ | CH$_3$ | |
| 62 | H | H | H | NCH$_3$ | — | OCH$_2$CH$_3$ | NHCH$_3$ | |
| 62 | H | 5-OCH$_3$ | H | NCH$_3$ | — | OCH$_3$ | OCH$_3$ | |
| 62 | H | 5-SCH$_3$ | H | NCH$_3$ | — | OCH$_3$ | OCH$_3$ | |
| 65 | H | H | H | — | — | OCH$_3$ | OCH$_3$ | |
| 65 | H | H | H | — | — | OCH$_3$ | CH$_3$ | |
| 65 | CH$_3$ | H | H | — | — | OCH$_3$ | CH$_3$ | |
| 65 | H | H | H | — | — | OCH$_2$CH$_3$ | NHCH$_3$ | |
| 65 | H | 5-OCH$_3$ | H | — | — | OCH$_3$ | OCH$_3$ | |
| 65 | H | 5-SCH$_3$ | H | — | — | OCH$_3$ | OCH$_3$ | |
| 68 | H | H | H | — | — | OCH$_3$ | OCH$_3$ | |
| 68 | H | H | H | — | — | OCH$_3$ | CH$_3$ | |
| 68 | CH$_3$ | H | H | — | — | OCH$_3$ | CH$_3$ | |
| 68 | H | H | H | — | — | OCH$_2$CH$_3$ | NHCH$_3$ | |
| 68 | H | 5-OCH$_3$ | H | — | — | OCH$_3$ | OCH$_3$ | |
| 68 | H | 5-SCH$_3$ | H | — | — | OCH$_3$ | OCH$_3$ | |
| 76 | H | H | H | O | — | OCH$_3$ | OCH$_3$ | |

TABLE 15-continued

General Structure 15

| Q | R | R₁ | R₃ | W₃ | W₄ | X | Y | m.p. (°C.) |
|---|---|---|---|---|---|---|---|---|
| 76 | H | H | H | O | — | OCH₃ | CH₃ | |
| 76 | CH₃ | H | H | O | — | OCH₃ | CH₃ | |
| 76 | H | H | H | O | — | OCH₂CH₃ | NHCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | OCH₃ | OCH₃ | |
| 78 | H | H | H | — | — | OCH₃ | CH₃ | |
| 78 | CH₃ | H | H | — | — | OCH₃ | CH₃ | |
| 78 | H | H | H | — | — | OCH₂CH₃ | NHCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | OCH₃ | OCH₃ | |
| 79 | H | H | H | — | — | OCH₃ | CH₃ | |
| 79 | CH₃ | H | H | — | — | OCH₃ | CH₃ | |
| 79 | H | H | H | — | — | OCH₂CH₃ | NHCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 16

General Structure 16

| Q | R | R₁ | R₃ | W₃ | W₄ | X | Y | m.p. (°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | OCH₃ | CH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | H | 3-Cl | H | O | — | Cl | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1(R₅=CH₃) | H | H | H | O | — | Cl | OCH₃ | |
| 1 | H | 6-SO₂CH₃ | H | O | — | OCH₃ | OCH₃ | |
| 1 | H | H | H | O | — | OCF₂H | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | Cl | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | NCH₃ | — | OCH₃ | CH₃ | |
| 1 | H | H | H | NCH₃ | — | OCH₃ | OCH₃ | |
| 1 | H | H | H | NCH₃ | — | OCH₃ | Cl | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathio-lan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | — | CH₃ | CH₃ |
| 1 | H | H | H | NCH₃ | — | — | OCH₃ | CH₃ |
| 1 | H | H | H | NCH₃ | — | — | OCH₃ | OCH₃ |

TABLE 16-continued

General Structure 16

| Q | R | R₁ | R₃ | W₃ | W₄ | X | Y | m.p. (°C.) |
|---|---|---|---|---|---|---|---|---|
| 1 | H | H | H | NCH₃ | — | — | Cl | OCH₃ |
| 1 | H | 5-OCH₃ | H | NCH₃ | — | — | OCH₃ | OCH₃ |
| 1 | H | 5-SCH₃ | H | NCH₃ | — | — | OCH₃ | OCH₃ |
| 3 | H | H | H | — | — | — | CH₃ | CH₃ |
| 3 | H | H | H | — | — | — | OCH₃ | CH₃ |
| 3 | H | H | H | — | — | — | OCH₃ | OCH₃ |
| 3 | H | H | H | — | — | — | Cl | OCH₃ |
| 3 | H | 5-OCH₃ | H | — | — | — | OCH₃ | OCH₃ |
| 3 | H | 5-SCH₃ | H | — | — | OCH₃ | OCH₃ | |
| 5 | H | H | H | NCH₃ | — | CH₃ | CH₃ | |
| 5 | H | H | H | NCH₃ | — | OCH₃ | CH₃ | |
| 5 | H | H | H | NCH₃ | — | OCH₃ | OCH₃ | |
| 5 | H | H | H | NCH₃ | — | Cl | OCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | CH₃ | CH₃ | |
| 7 | H | H | H | — | S | OCH₃ | CH₃ | |
| 7 | H | H | H | — | S | OCH₃ | OCH₃ | |
| 7 | H | H | H | — | S | Cl | OCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | CH₃ | CH₃ | |
| 7 | H | H | H | — | SO₂ | OCH₃ | CH₃ | |
| 7 | H | H | H | — | SO₂ | OCH₃ | OCH₃ | |
| 7 | H | H | H | — | SO₂ | Cl | OCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | CH₃ | CH₃ | |
| 8 | H | H | H | — | S | OCH₃ | CH₃ | |
| 8 | H | H | H | — | S | OCH₃ | OCH₃ | |
| 8 | H | H | H | — | S | Cl | OCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | CH₃ | CH₃ | |
| 8 | H | H | H | — | SO₂ | OCH₃ | CH₃ | |
| 8 | H | H | H | — | SO₂ | OCH₃ | OCH₃ | |
| 8 | H | H | H | — | SO₂ | Cl | OCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |
| 16 | H | 3-Cl | H | O | — | OCH₃ | Cl | |
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | OCF₂H | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | Cl | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | NCH₃ | — | OCH₃ | Cl | |
| 16 | H | H | H | O | — | C≡CH | OCH₃ | |
| 16 | H | H | H | O | — | CHO | OCH₃ | |

TABLE 16-continued

General Structure 16

| Q | R | R₁ | R₃ | W₃ | W₄ | X | Y | m.p. (°C.) |
|---|---|---|---|---|---|---|---|---|
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | CH₃ | CH₃ | |
| 19 | H | H | H | — | — | OCH₃ | CH₃ | |
| 19 | H | H | H | — | — | OCH₃ | OCH₃ | |
| 19 | H | H | H | — | — | Cl | OCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | CH₃ | CH₃ | |
| 20 | H | H | H | — | — | OCH₃ | CH₃ | |
| 20 | H | H | H | — | — | OCH₃ | OCH₃ | |
| 20 | H | H | H | — | — | Cl | OCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | CH₃ | CH₃ | |
| 21 | H | H | H | — | — | OCH₃ | CH₃ | |
| 21 | H | H | H | — | — | OCH₃ | OCH₃ | |
| 21 | H | H | H | — | — | Cl | OCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | CH₃ | CH₃ | |
| 22 | H | H | H | NCH₃ | — | OCH₃ | CH₃ | |
| 22 | H | H | H | NCH₃ | — | OCH₃ | OCH₃ | |
| 22 | H | H | H | NCH₃ | — | Cl | OCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | CH₃ | CH₃ | |
| 25 | H | H | H | — | S | OCH₃ | CH₃ | |
| 25 | H | H | H | — | S | OCH₃ | OCH₃ | |
| 25 | H | H | H | — | S | Cl | OCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | CH₃ | CH₃ | |
| 25 | H | H | H | — | SO₂ | OCH₃ | CH₃ | |
| 25 | H | H | H | — | SO₂ | OCH₃ | OCH₃ | |
| 25 | H | H | H | — | SO₂ | Cl | OCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | CH₃ | CH₃ | |
| 26 | H | H | H | — | S | OCH₃ | CH₃ | |
| 26 | H | H | H | — | S | OCH₃ | OCH₃ | |
| 26 | H | H | H | — | S | Cl | OCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | CH₃ | CH₃ | |
| 26 | H | H | H | — | SO₂ | OCH₃ | CH₃ | |
| 26 | H | H | H | — | SO₂ | OCH₃ | OCH₃ | |
| 26 | H | H | H | — | SO₂ | Cl | OCH₃ | |
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | CH₃ | CH₃ | |
| 27 | H | H | H | — | S | OCH₃ | CH₃ | |
| 27 | H | H | H | — | S | OCH₃ | OCH₃ | |
| 27 | H | H | H | — | S | Cl | OCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | CH₃ | CH₃ | |
| 27 | H | H | H | — | SO₂ | OCH₃ | CH₃ | |
| 27 | H | H | H | — | SO₂ | OCH₃ | OCH₃ | |
| 27 | H | H | H | — | SO₂ | Cl | OCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | CH₃ | CH₃ | |
| 29(R₆=CH₃) | H | H | H | — | — | OCH₃ | CH₃ | |
| 29(R₆=CH₃) | H | H | H | — | — | OCH₃ | OCH₃ | |
| 29(R₆=CH₃) | H | H | H | — | — | Cl | OCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | CH₃ | CH₃ | |
| 55 | H | H | H | O | — | OCH₃ | CH₃ | |
| 55 | H | H | H | O | — | OCH₃ | OCH₃ | |
| 55 | H | H | H | O | — | Cl | OCH₃ | |
| 55 | H | 5-OCH₃ | H | O | — | OCH₃ | OCH₃ | |
| 55 | H | 5-SCH₃ | H | O | — | OCH₃ | OCH₃ | |

TABLE 16-continued

General Structure 16

| Q | R | R₁ | R₃ | W₃ | W₄ | X | Y | m.p. (°C.) |
|---|---|---|---|---|---|---|---|---|
| 55 | H | H | H | NCH₃ | — | CH₃ | CH₃ | |
| 55 | H | H | H | NCH₃ | — | OCH₃ | CH₃ | |
| 55 | H | H | H | NCH₃ | — | OCH₃ | OCH₃ | |
| 55 | H | H | H | NCH₃ | — | Cl | OCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | CH₃ | CH₃ | |
| 56 | H | H | H | — | — | OCH₃ | CH₃ | |
| 56 | H | H | H | — | — | OCH₃ | OCH₃ | |
| 56 | H | H | H | — | — | Cl | OCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | CH₃ | CH₃ | |
| 61 | H | H | H | NCH₃ | — | OCH₃ | CH₃ | |
| 61 | H | H | H | NCH₃ | — | OCH₃ | OCH₃ | |
| 61 | H | H | H | NCH₃ | — | Cl | OCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | CH₃ | CH₃ | |
| 62 | H | H | H | NCH₃ | — | OCH₃ | CH₃ | |
| 62 | H | H | H | NCH₃ | — | OCH₃ | OCH₃ | |
| 62 | H | H | H | NCH₃ | — | Cl | OCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | CH₃ | CH₃ | |
| 65 | H | H | H | — | — | OCH₃ | CH₃ | |
| 65 | H | H | H | — | — | OCH₃ | OCH₃ | |
| 65 | H | H | H | — | — | Cl | OCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | CH₃ | CH₃ | |
| 68 | H | H | H | — | — | OCH₃ | CH₃ | |
| 68 | H | H | H | — | — | OCH₃ | OCH₃ | |
| 68 | H | H | H | — | — | Cl | OCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | CH₃ | CH₃ | |
| 76 | H | H | H | O | — | OCH₃ | CH₃ | |
| 76 | H | H | H | O | — | OCH₃ | OCH₃ | |
| 76 | H | H | H | O | — | Cl | OCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | CH₃ | CH₃ | |
| 78 | H | H | H | — | — | OCH₃ | CH₃ | |
| 78 | H | H | H | — | — | OCH₃ | OCH₃ | |
| 78 | H | H | H | — | — | Cl | OCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | CH₃ | CH₃ | |
| 79 | H | H | H | — | — | OCH₃ | CH₃ | |
| 79 | H | H | H | — | — | OCH₃ | OCH₃ | |
| 79 | H | H | H | — | — | Cl | OCH₃ | |
| 79 | H | 5-OCH₃ | H | — | — | OCH₃ | OCH₃ | |
| 79 | H | 5-SCH₃ | H | — | — | OCH₃ | OCH₃ | |

TABLE 17

General Structure 17

| Q | R | R₁ | R₃ | W₃ | W₄ | X | Y | m.p. (°C.) |
|---|---|---|---|---|---|---|---|---|
| 1 | H | H | H | O | — | CH₃ | CH₃ | |
| 1 | H | H | H | O | — | OCH₃ | CH₃ | |
| 1 | H | H | H | O | — | OCH₃ | OCH₃ | |
| 1 | CH₃ | H | H | O | — | OCH₃ | OCH₃ | |
| 1 | CH₃ | H | H | O | — | OCH₃ | CH₃ | |
| 1 | H | H | CH₃ | O | — | OCH₃ | OCH₃ | |
| 1 | H | H | CH₃ | O | — | CH₃ | CH₃ | |
| 1 | H | 3-Cl | H | O | — | CH₃ | CH₃ | |
| 1 | H | 3-Cl | H | O | — | OCH₃ | CH₃ | |
| 1 | H | 3-Cl | H | O | — | OCH₃ | OCH₃ | |
| 1 | CH₃ | 3-Cl | H | O | — | OCH₃ | OCH₃ | |
| 1 | H | 5-CH₃ | H | O | — | OCH₃ | OCH₃ | |
| 1 | H | 5-OCH₃ | H | O | — | OCH₃ | OCH₃ | |
| 1 | H | 5-OCH₂CH₃ | H | O | — | OCH₃ | OCH₃ | |
| 1 | H | 5-OCF₂H | H | O | — | OCH₃ | OCH₃ | |
| 1 | H | 5-SCH₃ | H | O | — | OCH₃ | OCH₃ | |
| 1 | H | 5-NHCH₃ | H | O | — | OCH₃ | OCH₃ | |
| 1 | H | 5-N(CH₃)₂ | H | O | — | OCH₃ | OCH₃ | |

TABLE 17-continued

General Structure 17

| Q | R | R₁ | R₃ | W₃ | W₄ | X | Y | m.p. (°C.) |
|---|---|---|---|---|---|---|---|---|
| 1 | H | 5-Cl | H | O | — | OCH₃ | OCH₃ | |
| 1 | H | 5-CF₃ | H | O | — | OCH₃ | OCH₃ | |
| 1 | H | 6-SO₂N(CH₃)₂ | H | O | — | OCH₃ | OCH₃ | |
| 1 | H | 6-CO₂CH₃ | H | O | — | OCH₃ | OCH₃ | |
| 1(R₅=CH₃) | H | H | H | O | — | CH₃ | CH₃ | |
| 1(R₅=CH₃) | H | H | H | O | — | OCH₃ | CH₃ | |
| 1(R₅=CH₃) | H | H | H | O | — | OCH₃ | OCH₃ | |
| 1 | H | 6-SO₂CH₃ | H | O | — | OCH₃ | OCH₃ | |
| 1 | H | H | H | O | — | CH₂F | OCH₃ | |
| 1 | H | H | H | O | — | CH₂Cl | OCH₃ | |
| 1 | H | H | H | O | — | CF₃ | OCH₃ | |
| 1 | H | H | H | O | — | SCH₃ | OCH₃ | |
| 1 | H | H | H | O | — | NHCH₃ | OCH₂CH₃ | |
| 1 | H | H | H | O | — | OCH₂CH=CH₂ | OCH₃ | |
| 1 | H | H | H | O | — | OCH₂C≡CH | OCH₃ | |
| 1 | H | H | H | O | — | cyclopropyl | OCH₃ | |
| 1 | H | H | H | NCH₃ | — | CH₃ | CH₃ | |
| 1 | H | H | H | O | — | C≡CH | OCH₃ | |
| 1 | H | H | H | O | — | CHO | OCH₃ | |
| 1 | H | H | H | O | — | 2-methyl-1,3-oxathiolan-2-yl | OCH₃ | |
| 1 | H | H | H | O | — | 2-methyl-1,3-dithian-2-yl | OCH₃ | |
| 1 | H | H | H | O | — | 1,3-dioxan-2-yl | OCH₃ | |
| 1 | H | H | H | NCH₃ | — | OCH₃ | OCH₃ | |
| 1 | H | H | H | NCH₃ | — | OCH₃ | CH₃ | |
| 1 | CH₃ | H | H | NCH₃ | — | OCH₃ | CH₃ | |
| 1 | H | H | H | NCH | — | OCH₂CH₃ | NHCH₃ | |
| 1 | H | 5-OCH₃ | H | NCH₃ | — | OCH₃ | OCH₃ | |
| 1 | H | 5-SCH₃ | H | NCH₃ | — | OCH₃ | OCH₃ | |
| 3 | H | H | H | — | — | OCH₃ | OCH₃ | |
| 3 | H | H | H | — | — | OCH₃ | CH₃ | |
| 3 | CH₃ | H | H | — | — | OCH₃ | CH₃ | |
| 3 | H | H | H | — | — | OCH₂CH₃ | NHCH₃ | |
| 3 | H | 5-OCH₃ | H | — | — | OCH₃ | OCH₃ | |
| 3 | H | 5-SCH₃ | H | — | — | OCH₃ | OCH₃ | |
| 5 | H | H | H | NCH₃ | — | OCH₃ | OCH₃ | |
| 5 | H | H | H | NCH₃ | — | OCH₃ | CH₃ | |
| 5 | CH₃ | H | H | NCH₃ | — | OCH₃ | CH₃ | |
| 5 | H | H | H | NCH₃ | — | OCH₂CH₃ | NHCH₃ | |
| 5 | H | 5-OCH₃ | H | NCH₃ | — | OCH₃ | OCH₃ | |
| 5 | H | 5-SCH₃ | H | NCH₃ | — | OCH₃ | OCH₃ | |
| 7 | H | H | H | — | S | OCH₃ | OCH₃ | |
| 7 | H | H | H | — | S | OCH₃ | CH₃ | |
| 7 | CH₃ | H | H | — | S | OCH₃ | CH₃ | |
| 7 | H | H | H | — | S | OCH₂CH₃ | NHCH₃ | |
| 7 | H | 5-OCH₃ | H | — | S | OCH₃ | OCH₃ | |
| 7 | H | 5-SCH₃ | H | — | S | OCH₃ | OCH₃ | |
| 7 | H | H | H | — | SO₂ | OCH₃ | OCH₃ | |
| 7 | H | H | H | — | SO₂ | OCH₃ | CH₃ | |
| 7 | CH₃ | H | H | — | SO₂ | OCH₃ | CH₃ | |
| 7 | H | H | H | — | SO₂ | OCH₂CH₃ | NHCH₃ | |
| 7 | H | 5-OCH₃ | H | — | SO₂ | OCH₃ | OCH₃ | |
| 7 | H | 5-SCH₃ | H | — | SO₂ | OCH₃ | OCH₃ | |
| 8 | H | H | H | — | S | OCH₃ | OCH₃ | |
| 8 | H | H | H | — | S | OCH₃ | CH₃ | |
| 8 | CH₃ | H | H | — | S | OCH₃ | CH₃ | |
| 8 | H | H | H | — | S | OCH₂CH₃ | NHCH₃ | |
| 8 | H | 5-OCH₃ | H | — | S | OCH₃ | OCH₃ | |
| 8 | H | 5-SCH₃ | H | — | S | OCH₃ | OCH₃ | |
| 8 | H | H | H | — | SO₂ | OCH₃ | OCH₃ | |
| 8 | H | H | H | — | SO₂ | OCH₃ | CH₃ | |
| 8 | CH₃ | H | H | — | SO₂ | OCH₃ | CH₃ | |
| 8 | H | H | H | — | SO₂ | OCH₂CH₃ | NHCH₃ | |
| 8 | H | 5-OCH₃ | H | — | SO₂ | OCH₃ | OCH₃ | |
| 8 | H | 5-SCH₃ | H | — | SO₂ | OCH₃ | OCH₃ | |
| 16 | H | H | H | O | — | CH₃ | CH₃ | |
| 16 | H | H | H | O | — | OCH₃ | CH₃ | |
| 16 | H | H | H | O | — | OCH₃ | OCH₃ | |
| 16 | CH₃ | H | H | O | — | OCH₃ | OCH₃ | |
| 16 | CH₃ | H | H | O | — | OCH₃ | CH₃ | |
| 16 | H | H | CH₃ | O | — | OCH₃ | OCH₃ | |
| 16 | H | H | CH₃ | O | — | OCH₃ | CH₃ | |
| 16 | H | H | CH₃ | O | — | CH₃ | CH₃ | |
| 16 | H | 3-Cl | H | O | — | CH₃ | CH₃ | |
| 16 | H | 3-Cl | H | O | — | OCH₃ | CH₃ | |
| 16 | H | 3-Cl | H | O | — | OCH₃ | OCH₃ | |

TABLE 17-continued

General Structure 17

| Q | R | R₁ | R₃ | W₃ | W₄ | X | Y | m.p. (°C.) |
|---|---|---|---|---|---|---|---|---|
| 16 | CH₃ | 3-Cl | H | O | — | OCH₃ | OCH₃ | |
| 16 | H | 5-CH₃ | H | O | — | OCH₃ | OCH₃ | |
| 16 | H | 5-OCH₃ | H | O | — | OCH₃ | OCH₃ | |
| 16 | H | 5-OCH₂CH₃ | H | O | — | OCH₃ | OCH₃ | |
| 16 | H | 5-OCF₂H | H | O | — | OCH₃ | OCH₃ | |
| 16 | H | 5-SCH₃ | H | O | — | OCH₃ | OCH₃ | |
| 16 | H | 5-NHCH₃ | H | O | — | OCH₃ | OCH₃ | |
| 16 | H | 5-N(CH₃)₂ | H | O | — | OCH₃ | OCH₃ | |
| 16 | H | 5-Cl | H | O | — | OCH₃ | OCH₃ | |
| 16 | H | 5-CF₃ | H | O | — | OCH₃ | OCH₃ | |
| 16 | H | 6-SO₂N(CH₃)₂ | H | O | — | OCH₃ | OCH₃ | |
| 16 | H | 6-CO₂CH₃ | H | O | — | OCH₃ | OCH₃ | |
| 16 | H | 6-SO₂CH₃ | H | O | — | OCH₃ | OCH₃ | |
| 16 | H | H | H | O | — | CH₂F | OCH₃ | |
| 16 | H | H | H | O | — | CH₂Cl | OCH₃ | |
| 16 | H | H | H | O | — | CF₃ | OCH₃ | |
| 16 | H | H | H | O | — | SCH₃ | OCH₃ | |
| 16 | H | H | H | O | — | NHCH₃ | OCH₂CH₃ | |
| 16 | H | H | H | O | — | OCH₂CH=CH₂ | OCH₃ | |
| 16 | H | H | H | O | — | OCH₂C≡CH | OCH₃ | |
| 16 | H | H | H | O | — | cyclopropyl | OCH₃ | |
| 16 | H | H | H | NCH₃ | — | CH₃ | CH₃ | |
| 16 | H | H | H | NCH₃ | — | OCH₃ | CH₃ | |
| 16 | H | H | H | NCH₃ | — | OCH₃ | OCH₃ | |
| 16 | H | H | H | O | — | C≡CH | OCH₃ | |
| 16 | H | H | H | O | — | CHO | OCH₃ | |
| 16 | H | H | H | O | — | 2-methyl-1,3-oxathiolan-2-yl | OCH₃ | |
| 16 | H | H | H | O | — | 2-methyl-1,3-dithian-2-yl | OCH₃ | |
| 16 | H | H | H | O | — | 1,3-dioxan-2-yl | OCH₃ | |
| 19 | H | H | H | — | — | OCH₃ | OCH₃ | |
| 19 | H | H | H | — | — | OCH₃ | CH₃ | |
| 19 | CH₃ | H | H | — | — | OCH₃ | CH₃ | |
| 19 | H | H | H | — | — | OCH₂CH₃ | NHCH₃ | |
| 19 | H | 5-OCH₃ | H | — | — | OCH₃ | OCH₃ | |
| 19 | H | 5-SCH₃ | H | — | — | OCH₃ | OCH₃ | |
| 20 | H | H | H | — | — | OCH₃ | OCH₃ | |
| 20 | H | H | H | — | — | OCH₃ | CH₃ | |
| 20 | CH₃ | H | H | — | — | OCH₃ | CH₃ | |
| 20 | H | H | H | — | — | OCH₂CH₃ | NHCH₃ | |
| 20 | H | 5-OCH₃ | H | — | — | OCH₃ | OCH₃ | |
| 20 | H | 5-SCH₃ | H | — | — | OCH₃ | OCH₃ | |
| 21 | H | H | H | — | — | OCH₃ | OCH₃ | |
| 21 | H | H | H | — | — | OCH₃ | CH₃ | |
| 21 | CH₃ | H | H | — | — | OCH₃ | CH₃ | |
| 21 | H | H | H | — | — | OCH₂CH₃ | NHCH₃ | |
| 21 | H | 5-OCH₃ | H | — | — | OCH₃ | OCH₃ | |
| 21 | H | 5-SCH₃ | H | — | — | OCH₃ | OCH₃ | |
| 22 | H | H | H | NCH₃ | — | OCH₃ | OCH₃ | |
| 22 | H | H | H | NCH₃ | — | OCH₃ | CH₃ | |
| 22 | CH₃ | H | H | NCH₃ | — | OCH₃ | CH₃ | |
| 22 | H | H | H | NCH₃ | — | OCH₂CH₃ | NHCH₃ | |
| 22 | H | 5-OCH₃ | H | NCH₃ | — | OCH₃ | OCH₃ | |
| 22 | H | 5-SCH₃ | H | NCH₃ | — | OCH₃ | OCH₃ | |
| 25 | H | H | H | — | S | OCH₃ | OCH₃ | |
| 25 | H | H | H | — | S | OCH₃ | CH₃ | |
| 25 | CH₃ | H | H | — | S | OCH₃ | CH₃ | |
| 25 | H | H | H | — | S | OCH₂CH₃ | NHCH₃ | |
| 25 | H | 5-OCH₃ | H | — | S | OCH₃ | OCH₃ | |
| 25 | H | 5-SCH₃ | H | — | S | OCH₃ | OCH₃ | |
| 25 | H | H | H | — | SO₂ | OCH₃ | OCH₃ | |
| 25 | H | H | H | — | SO₂ | OCH₃ | CH₃ | |
| 25 | CH₃ | H | H | — | SO₂ | OCH₃ | CH₃ | |
| 25 | H | H | H | — | SO₂ | OCH₂CH₃ | NHCH₃ | |
| 25 | H | 5-OCH₃ | H | — | SO₂ | OCH₃ | OCH₃ | |
| 25 | H | 5-SCH₃ | H | — | SO₂ | OCH₃ | OCH₃ | |
| 26 | H | H | H | — | S | OCH₃ | OCH₃ | |
| 26 | H | H | H | — | S | OCH₃ | CH₃ | |
| 26 | CH₃ | H | H | — | S | OCH₃ | CH₃ | |
| 26 | H | H | H | — | S | OCH₂CH₃ | NHCH₃ | |
| 26 | H | 5-OCH₃ | H | — | S | OCH₃ | OCH₃ | |
| 26 | H | 5-SCH₃ | H | — | S | OCH₃ | OCH₃ | |
| 26 | H | H | H | — | SO₂ | OCH₃ | OCH₃ | |
| 26 | H | H | H | — | SO₂ | OCH₃ | CH₃ | |
| 26 | CH₃ | H | H | — | SO₂ | OCH₃ | CH₃ | |
| 26 | H | H | H | — | SO₂ | OCH₂CH₃ | NHCH₃ | |

TABLE 17-continued

General Structure 17

| Q | R | R₁ | R₃ | W₃ | W₄ | X | Y | m.p. (°C.) |
|---|---|----|----|----|----|----|----|---|
| 26 | H | 5-OCH₃ | H | — | SO₂ | OCH₃ | OCH₃ | |
| 26 | H | 5-SCH₃ | H | — | SO₂ | OCH₃ | OCH₃ | |
| 27 | H | H | H | — | S | OCH₃ | OCH₃ | |
| 27 | H | H | H | — | S | OCH₃ | CH₃ | |
| 27 | CH₃ | H | H | — | S | OCH₃ | CH₃ | |
| 27 | H | H | H | — | S | OCH₂CH₃ | NHCH₃ | |
| 27 | H | 5-OCH₃ | H | — | S | OCH₃ | OCH₃ | |
| 27 | H | 5-SCH₃ | H | — | S | OCH₃ | OCH₃ | |
| 27 | H | H | H | — | SO₂ | OCH₃ | OCH₃ | |
| 27 | H | H | H | — | SO₂ | OCH₃ | CH₃ | |
| 27 | CH₃ | H | H | — | SO₂ | OCH₃ | CH₃ | |
| 27 | H | H | H | — | SO₂ | OCH₂CH₃ | NHCH₃ | |
| 27 | H | 5-OCH₃ | H | — | SO₂ | OCH₃ | OCH₃ | |
| 27 | H | 5-SCH₃ | H | — | SO₂ | OCH₃ | OCH₃ | |
| 29(R₆=CH₃) | H | H | H | — | — | OCH₃ | OCH₃ | |
| 29(R₆=CH₃) | H | H | H | — | — | OCH₃ | CH₃ | |
| 29(R₆=CH₃) | CH₃ | H | H | — | — | OCH₃ | CH₃ | |
| 29(R₆=CH₃) | H | H | H | — | — | OCH₂CH₃ | NHCH₃ | |
| 29(R₆=CH₃) | H | 5-OCH₃ | H | — | — | OCH₃ | OCH₃ | |
| 29(R₆=CH₃) | H | 5-SCH₃ | H | — | — | OCH₃ | OCH₃ | |
| 55 | H | H | H | O | — | OCH₃ | OCH₃ | |
| 55 | H | H | H | O | — | OCH₃ | CH₃ | |
| 55 | CH₃ | H | H | O | — | OCH₃ | CH₃ | |
| 55 | H | H | H | O | — | OCH₂CH₃ | NHCH₃ | |
| 55 | H | 5-OCH₃ | H | O | — | OCH₃ | OCH₃ | |
| 55 | H | 5-SCH₃ | H | O | — | OCH₃ | OCH₃ | |
| 55 | H | H | H | NCH₃ | — | OCH₃ | OCH₃ | |
| 55 | H | H | H | NCH₃ | — | OCH₃ | CH₃ | |
| 55 | CH₃ | H | H | NCH₃ | — | OCH₃ | CH₃ | |
| 55 | H | H | H | NCH₃ | — | OCH₂CH₃ | NHCH₃ | |
| 55 | H | 5-OCH₃ | H | NCH₃ | — | OCH₃ | OCH₃ | |
| 55 | H | 5-SCH₃ | H | NCH₃ | — | OCH₃ | OCH₃ | |
| 56 | H | H | H | — | — | OCH₃ | OCH₃ | |
| 56 | H | H | H | — | — | OCH₃ | CH₃ | |
| 56 | CH₃ | H | H | — | — | OCH₃ | CH₃ | |
| 56 | H | H | H | — | — | OCH₂CH₃ | NHCH₃ | |
| 56 | H | 5-OCH₃ | H | — | — | OCH₃ | OCH₃ | |
| 56 | H | 5-SCH₃ | H | — | — | OCH₃ | OCH₃ | |
| 61 | H | H | H | NCH₃ | — | OCH₃ | OCH₃ | |
| 61 | H | H | H | NCH₃ | — | OCH₃ | CH₃ | |
| 61 | CH₃ | H | H | NCH₃ | — | OCH₃ | CH₃ | |
| 61 | H | H | H | NCH₃ | — | OCH₂CH₃ | NHCH₃ | |
| 61 | H | 5-OCH₃ | H | NCH₃ | — | OCH₃ | OCH₃ | |
| 61 | H | 5-SCH₃ | H | NCH₃ | — | OCH₃ | OCH₃ | |
| 62 | H | H | H | NCH₃ | — | OCH₃ | OCH₃ | |
| 62 | H | H | H | NCH₃ | — | OCH₃ | CH₃ | |
| 62 | CH₃ | H | H | NCH₃ | — | OCH₃ | CH₃ | |
| 62 | H | H | H | NCH₃ | — | OCH₂CH₃ | NHCH₃ | |
| 62 | H | 5-OCH₃ | H | NCH₃ | — | OCH₃ | OCH₃ | |
| 62 | H | 5-SCH₃ | H | NCH₃ | — | OCH₃ | OCH₃ | |
| 65 | H | H | H | — | — | OCH₃ | OCH₃ | |
| 65 | H | H | H | — | — | OCH₃ | CH₃ | |
| 65 | CH₃ | H | H | — | — | OCH₃ | CH₃ | |
| 65 | H | H | H | — | — | OCH₂CH₃ | NHCH₃ | |
| 65 | H | 5-OCH₃ | H | — | — | OCH₃ | OCH₃ | |
| 65 | H | 5-SCH₃ | H | — | — | OCH₃ | OCH₃ | |
| 68 | H | H | H | — | — | OCH₃ | OCH₃ | |
| 68 | H | H | H | — | — | OCH₃ | CH₃ | |
| 68 | CH₃ | H | H | — | — | OCH₃ | CH₃ | |
| 68 | H | H | H | — | — | OCH₂CH₃ | NHCH₃ | |
| 68 | H | 5-OCH₃ | H | — | — | OCH₃ | OCH₃ | |
| 68 | H | 5-SCH₃ | H | — | — | OCH₃ | OCH₃ | |
| 76 | H | H | H | O | — | OCH₃ | OCH₃ | |
| 76 | H | H | H | O | — | OCH₃ | CH₃ | |
| 76 | CH₃ | H | H | O | — | OCH₃ | CH₃ | |
| 76 | H | H | H | O | — | OCH₂CH₃ | NHCH₃ | |
| 76 | H | 5-OCH₃ | H | O | — | OCH₃ | OCH₃ | |
| 76 | H | 5-SCH₃ | H | O | — | OCH₃ | OCH₃ | |
| 78 | H | H | H | — | — | OCH₃ | OCH₃ | |
| 78 | H | H | H | — | — | OCH₃ | CH₃ | |
| 78 | CH₃ | H | H | — | — | OCH₃ | CH₃ | |
| 78 | H | H | H | — | — | OCH₂CH₃ | NHCH₃ | |
| 78 | H | 5-OCH₃ | H | — | — | OCH₃ | OCH₃ | |
| 78 | H | 5-SCH₃ | H | — | — | OCH₃ | OCH₃ | |
| 79 | H | H | H | — | — | OCH₃ | OCH₃ | |
| 79 | H | H | H | — | — | OCH₃ | CH₃ | |
| 79 | CH₃ | H | H | — | — | OCH₃ | CH₃ | |
| 79 | H | H | H | — | — | OCH₂CH₃ | NHCH₃ | |
| 79 | H | 5-OCH₃ | H | — | — | OCH₃ | OCH₃ | |

TABLE 17-continued

General Structure 17

| Q | R | R₁ | R₃ | W₃ | W₄ | X | Y | m.p. (°C.) |
|---|---|-----|----|----|----|----|---|-----------|
| 79 | H | 5-SCH₃ | H | — | — | OCH₃ | OCH₃ | |

TABLE 18

General Formula 18

| Q | R | R₁ | R₂ | R₃ | W₃ | W₄ | X | Y | m.p. (°C.) |
|---|---|----|----|----|----|----|---|---|-----------|
| 1 | H | H | CH₃ | H | O | — | CH₃ | CH₃ | |
| 1 | H | H | CH₃ | H | O | — | OCH₃ | CH₃ | |
| 1 | H | H | CH₃ | H | O | — | OCH₃ | OCH₃ | |
| 1 | CH₃ | H | CH₃ | H | O | — | OCH₃ | CH₃ | |
| 1 | H | H | CH₃ | H | O | — | OCF₂H | OCH₃ | |
| 1 | H | H | CH₃ | H | O | — | CH₂F | OCH₃ | |
| 1 | H | H | CH₃ | H | O | — | CH₂Cl | OCH₃ | |
| 1 | H | H | CH₃ | H | O | — | CF₃ | OCH₃ | |
| 1 | H | H | CH₃ | H | O | — | SCH₃ | OCH₃ | |
| 1 | H | H | CH₃ | H | O | — | Cl | OCH₃ | |
| 1 | H | H | CH₃ | H | O | — | NHCH₃ | OCH₂CH₃ | |
| 1 | H | H | CH₃ | H | O | — | OCH₂CH=CH | OCH₃ | |
| 1 | H | H | CH₃ | H | O | — | OCH₂C≡CH | OCH₃ | |
| 1 | H | H | CH₃ | H | O | — | cyclopropyl | OCH₃ | |
| 1 | H | H | CH₃ | H | O | — | C≡CH | OCH₃ | |
| 1 | H | H | CH₃ | H | O | — | CHO | OCH₃ | |
| 1 | H | H | CH₃ | H | O | — | 1,3-dioxan-2-yl | OCH₃ | |
| 1 | H | H | CH₃ | H | O | — | 2-methyl-1,3-oxathiolan-2-yl | OCH₃ | |
| 1 | H | H | CH₃ | H | NCH₃ | — | CH₃ | CH₃ | |
| 1 | H | H | CH₃ | H | NCH₃ | — | CH₃ | OCH₃ | |
| 1 | H | H | CH₃ | H | NCH₃ | — | OCH₃ | OCH₃ | |
| 1 | H | H | CH₃ | H | NCH₃ | — | Cl | OCH₃ | |
| 3 | H | H | CH₃ | H | — | — | CH₃ | CH₃ | |
| 3 | H | H | CH₃ | H | — | — | CH₃ | OCH₃ | |
| 3 | H | H | CH₃ | H | — | — | OCH₃ | OCH₃ | |
| 3 | H | H | CH₃ | H | — | — | Cl | OCH₃ | |
| 5 | H | H | CH₃ | H | NCH₃ | — | CH₃ | CH₃ | |
| 5 | H | H | CH₃ | H | NCH₃ | — | CH₃ | OCH₃ | |
| 5 | H | H | CH₃ | H | NCH₃ | — | OCH₃ | OCH₃ | |
| 5 | H | H | CH₃ | H | NCH₃ | — | Cl | OCH₃ | |
| 7 | H | H | CH₃ | H | — | S | CH₃ | CH₃ | |
| 7 | H | H | CH₃ | H | — | S | CH₃ | OCH₃ | |
| 7 | H | H | CH₃ | H | — | S | OCH₃ | OCH₃ | |
| 7 | H | H | CH₃ | H | — | S | Cl | OCH₃ | |
| 7 | H | H | CH₃ | H | — | SO₂ | CH₃ | CH₃ | |
| 7 | H | H | CH₃ | H | — | SO₂ | CH₃ | OCH₃ | |
| 7 | H | H | CH₃ | H | — | SO₂ | OCH₃ | OCH₃ | |
| 7 | H | H | CH₃ | H | — | SO₂ | Cl | OCH₃ | |
| 8 | H | H | CH₃ | H | — | S | CH₃ | CH₃ | |
| 8 | H | H | CH₃ | H | — | S | CH₃ | OCH₃ | |
| 8 | H | H | CH₃ | H | — | S | OCH₃ | OCH₃ | |
| 8 | H | H | CH₃ | H | — | S | Cl | OCH₃ | |
| 8 | H | H | CH₃ | H | — | SO₂ | CH₃ | CH₃ | |
| 8 | H | H | CH₃ | H | — | SO₂ | CH₃ | OCH₃ | |
| 8 | H | H | CH₃ | H | — | SO₂ | OCH₃ | OCH₃ | |
| 8 | H | H | CH₃ | H | — | SO₂ | Cl | OCH₃ | |
| 16 | H | H | CH₃ | H | O | — | CH₃ | CH₃ | |
| 16 | H | H | CH₃ | H | O | — | CH₃ | OCH₃ | |
| 16 | H | H | CH₃ | H | O | — | OCH₃ | OCH₃ | |
| 16 | H | H | CH₃ | H | O | — | Cl | OCH₃ | |
| 16 | H | H | CH₃ | H | NCH₃ | — | CH₃ | CH₃ | |
| 16 | H | H | CH₃ | H | NCH₃ | — | CH₃ | OCH₃ | |
| 16 | H | H | CH₃ | H | NCH₃ | — | OCH₃ | OCH₃ | |
| 16 | H | H | CH₃ | H | NCH₃ | — | Cl | OCH₃ | |
| 19 | H | H | CH₃ | H | — | — | CH₃ | CH₃ | |
| 19 | H | H | CH₃ | H | — | — | CH₃ | OCH₃ | |
| 19 | H | H | CH₃ | H | — | — | OCH₃ | OCH₃ | |
| 19 | H | H | CH₃ | H | — | — | Cl | OCH₃ | |
| 20 | H | H | CH₃ | H | — | — | CH₃ | CH₃ | |
| 20 | H | H | CH₃ | H | — | — | CH₃ | OCH₃ | |
| 20 | H | H | CH₃ | H | — | — | OCH₃ | OCH₃ | |
| 20 | H | H | CH₃ | H | — | — | Cl | OCH₃ | |
| 21 | H | H | CH₃ | H | — | — | CH₃ | CH₃ | |
| 21 | H | H | CH₃ | H | — | — | CH₃ | OCH₃ | |
| 21 | H | H | CH₃ | H | — | — | OCH₃ | OCH₃ | |
| 21 | H | H | CH₃ | H | — | — | Cl | OCH₃ | |
| 22 | H | H | CH₃ | H | NCH₃ | — | CH₃ | CH₃ | |
| 22 | H | H | CH₃ | H | NCH₃ | — | CH₃ | OCH₃ | |
| 22 | H | H | CH₃ | H | NCH₃ | — | OCH₃ | OCH₃ | |

TABLE 18-continued

General Formula 18

| Q | R | $R_1$ | $R_2$ | $R_3$ | $W_3$ | $W_4$ | X | Y | m.p. (°C.) |
|---|---|---|---|---|---|---|---|---|---|
| 22 | H | H | $CH_3$ | H | $NCH_3$ | — | Cl | $OCH_3$ | |
| 25 | H | H | $CH_3$ | H | — | S | $CH_3$ | $CH_3$ | |
| 25 | H | H | $CH_3$ | H | — | S | $CH_3$ | $OCH_3$ | |
| 25 | H | H | $CH_3$ | H | — | S | $OCH_3$ | $OCH_3$ | |
| 25 | H | H | $CH_3$ | H | — | S | Cl | $OCH_3$ | |
| 25 | H | H | $CH_3$ | H | — | $SO_2$ | $CH_3$ | $CH_3$ | |
| 25 | H | H | $CH_3$ | H | — | $SO_2$ | $CH_3$ | $OCH_3$ | |
| 25 | H | H | $CH_3$ | H | — | $SO_2$ | $OCH_3$ | $OCH_3$ | |
| 25 | H | H | $CH_3$ | H | — | $SO_2$ | Cl | $OCH_3$ | |
| 26 | H | H | $CH_3$ | H | — | S | $CH_3$ | $CH_3$ | |
| 26 | H | H | $CH_3$ | H | — | S | $CH_3$ | $OCH_3$ | |
| 26 | H | H | $CH_3$ | H | — | S | $OCH_3$ | $OCH_3$ | |
| 26 | H | H | $CH_3$ | H | — | S | Cl | $OCH_3$ | |
| 26 | H | H | $CH_3$ | H | — | $SO_2$ | $CH_3$ | $CH_3$ | |
| 26 | H | H | $CH_3$ | H | — | $SO_2$ | $CH_3$ | $OCH_3$ | |
| 26 | H | H | $CH_3$ | H | — | $SO_2$ | $OCH_3$ | $OCH_3$ | |
| 26 | H | H | $CH_3$ | H | — | $SO_2$ | Cl | $OCH_3$ | |
| 27 | H | H | $CH_3$ | H | — | S | $CH_3$ | $CH_3$ | |
| 27 | H | H | $CH_3$ | H | — | S | $CH_3$ | $OCH_3$ | |
| 27 | H | H | $CH_3$ | H | — | S | $OCH_3$ | $OCH_3$ | |
| 27 | H | H | $CH_3$ | H | — | S | Cl | $OCH_3$ | |
| 27 | H | H | $CH_3$ | H | — | $SO_2$ | $CH_3$ | $CH_3$ | |
| 27 | H | H | $CH_3$ | H | — | $SO_2$ | $CH_3$ | $OCH_3$ | |
| 27 | H | H | $CH_3$ | H | — | $SO_2$ | $OCH_3$ | $OCH_3$ | |
| 27 | H | H | $CH_3$ | H | — | $SO_2$ | Cl | $OCH_3$ | |
| 29($R_6=CH_3$) | H | H | $CH_3$ | H | — | — | $CH_3$ | $CH_3$ | |
| 29($R_6=CH_3$) | H | H | $CH_3$ | H | — | — | $CH_3$ | $OCH_3$ | |
| 29($R_6=CH_3$) | H | H | $CH_3$ | H | — | — | $OCH_3$ | $OCH_3$ | |
| 29($R_6=CH_3$) | H | H | $CH_3$ | H | — | — | Cl | $OCH_3$ | |
| 55 | H | H | $CH_3$ | H | O | — | $CH_3$ | $CH_3$ | |
| 55 | H | H | $CH_3$ | H | O | — | $CH_3$ | $OCH_3$ | |
| 55 | H | H | $CH_3$ | H | O | — | $OCH_3$ | $OCH_3$ | |
| 55 | H | H | $CH_3$ | H | O | — | Cl | $OCH_3$ | |
| 55 | H | H | $CH_3$ | H | $NCH_3$ | — | $CH_3$ | $CH_3$ | |
| 55 | H | H | $CH_3$ | H | $NCH_3$ | — | $CH_3$ | $OCH_3$ | |
| 55 | H | H | $CH_3$ | H | $NCH_3$ | — | $OCH_3$ | $OCH_3$ | |
| 55 | H | H | $CH_3$ | H | $NCH_3$ | — | Cl | $OCH_3$ | |
| 56 | H | H | $CH_3$ | H | — | — | $CH_3$ | $CH_3$ | |
| 56 | H | H | $CH_3$ | H | — | — | $CH_3$ | $OCH_3$ | |
| 56 | H | H | $CH_3$ | H | — | — | $OCH_3$ | $OCH_3$ | |
| 56 | H | H | $CH_3$ | H | — | — | Cl | $OCH_3$ | |
| 61 | H | H | $CH_3$ | H | $NCH_3$ | — | $CH_3$ | $CH_3$ | |
| 61 | H | H | $CH_3$ | H | $NCH_3$ | — | $CH_3$ | $OCH_3$ | |
| 61 | H | H | $CH_3$ | H | $NCH_3$ | — | $OCH_3$ | $OCH_3$ | |
| 61 | H | H | $CH_3$ | H | $NCH_3$ | — | Cl | $OCH_3$ | |
| 65 | H | H | $CH_3$ | H | — | — | $CH_3$ | $CH_3$ | |
| 65 | H | H | $CH_3$ | H | — | — | $CH_3$ | $OCH_3$ | |
| 65 | H | H | $CH_3$ | H | — | — | $OCH_3$ | $OCH_3$ | |
| 65 | H | H | $CH_3$ | H | — | — | Cl | $OCH_3$ | |
| 68 | H | H | $CH_3$ | H | — | — | $CH_3$ | $CH_3$ | |
| 68 | H | H | $CH_3$ | H | — | — | $CH_3$ | $OCH_3$ | |
| 68 | H | H | $CH_3$ | H | — | — | $OCH_3$ | $OCH_3$ | |
| 68 | H | H | $CH_3$ | H | — | — | Cl | $OCH_3$ | |
| 76 | H | H | $CH_3$ | H | O | — | $CH_3$ | $CH_3$ | |
| 76 | H | H | $CH_3$ | H | O | — | $CH_3$ | $OCH_3$ | |
| 76 | H | H | $CH_3$ | H | O | — | $OCH_3$ | $OCH_3$ | |
| 76 | H | H | $CH_3$ | H | O | — | Cl | $OCH_3$ | |
| 78 | H | H | $CH_3$ | H | — | — | $CH_3$ | $CH_3$ | |
| 78 | H | H | $CH_3$ | H | — | — | $CH_3$ | $OCH_3$ | |
| 78 | H | H | $CH_3$ | H | — | — | $OCH_3$ | $OCH_3$ | |
| 78 | H | H | $CH_3$ | H | — | — | Cl | $OCH_3$ | |
| 79 | H | H | $CH_3$ | H | — | — | $CH_3$ | $CH_3$ | |
| 79 | H | H | $CH_3$ | H | — | — | $CH_3$ | $OCH_3$ | |
| 79 | H | H | $CH_3$ | H | — | — | $OCH_3$ | $OCH_3$ | |
| 79 | H | H | $CH_3$ | H | — | — | Cl | $OCH_3$ | |

TABLE 19

General Formula 19

| Q | R | $R_1$ | $R_2$ | $R_3$ | $W_3$ | $W_4$ | X | Y | m.p.(°C.) |
|---|---|---|---|---|---|---|---|---|---|
| 1 | H | H | $CH_3$ | H | O | — | $CH_3$ | $CH_3$ | |
| 1 | H | H | $CH_3$ | H | O | — | $OCH_3$ | $CH_3$ | |
| 1 | H | H | $CH_3$ | H | O | — | $OCH_3$ | $OCH_3$ | |
| 1 | $CH_3$ | H | $CH_3$ | H | O | — | $OCH_3$ | $CH_3$ | |
| 1 | H | H | $CH_3$ | H | O | — | $CH_2F$ | $OCH_3$ | |
| 1 | H | H | $CH_3$ | H | O | — | $CH_2Cl$ | $OCH_3$ | |
| 1 | H | H | $CH_3$ | H | O | — | $CF_3$ | $OCH_3$ | |
| 1 | H | H | $CH_3$ | H | O | — | $SCH_3$ | $OCH_3$ | |

TABLE 19-continued

General Formula 19

| Q | R | $R_1$ | $R_2$ | $R_3$ | $W_3$ | $W_4$ | X | Y | m.p.(°C.) |
|---|---|---|---|---|---|---|---|---|---|
| 1 | H | H | $CH_3$ | H | O | — | $NHCH_3$ | $OCH_2CH_3$ | |
| 1 | H | H | $CH_3$ | H | O | — | $OCH_2CH=CH$ | $OCH_3$ | |
| 1 | H | H | $CH_3$ | H | O | — | $OCH_2C\equiv CH$ | $OCH_3$ | |
| 1 | H | H | $CH_3$ | H | O | — | cyclopropyl | $OCH_3$ | |
| 1 | H | H | $CH_3$ | H | O | — | $C\equiv CH$ | $OCH_3$ | |
| 1 | H | H | $CH_3$ | H | O | — | CHO | $OCH_3$ | |
| 1 | H | H | $CH_3$ | H | O | — | 1,3-dioxan-2-yl | $OCH_3$ | |
| 1 | H | H | $CH_3$ | H | O | — | 2-methyl-1,3-oxathiolan-2-yl | $OCH_3$ | |
| 1 | H | H | $CH_3$ | H | $NCH_3$ | — | $CH_3$ | $CH_3$ | |
| 1 | H | H | $CH_3$ | H | $NCH_3$ | — | $CH_3$ | $OCH_3$ | |
| 1 | H | H | $CH_3$ | H | $NCH_3$ | — | $OCH_3$ | $OCH_3$ | |
| 1 | H | H | $CH_3$ | H | $NCH_3$ | — | $OCH_2CH_3$ | $NHCH_3$ | |
| 3 | H | H | $CH_3$ | H | — | — | $CH_3$ | $CH_3$ | |
| 3 | H | H | $CH_3$ | H | — | — | $CH_3$ | $OCH_3$ | |
| 3 | H | H | $CH_3$ | H | — | — | $OCH_3$ | $OCH_3$ | |
| 5 | H | H | $CH_3$ | H | $NCH_3$ | — | $CH_3$ | $CH_3$ | |
| 5 | H | H | $CH_3$ | H | $NCH_3$ | — | $CH_3$ | $OCH_3$ | |
| 5 | H | H | $CH_3$ | H | $NCH_3$ | — | $OCH_3$ | $OCH_3$ | |
| 7 | H | H | $CH_3$ | H | — | S | $CH_3$ | $CH_3$ | |
| 7 | H | H | $CH_3$ | H | — | S | $CH_3$ | $OCH_3$ | |
| 7 | H | H | $CH_3$ | H | — | S | $OCH_3$ | $OCH_3$ | |
| 7 | H | H | $CH_3$ | H | — | $SO_2$ | $CH_3$ | $CH_3$ | |
| 7 | H | H | $CH_3$ | H | — | $SO_2$ | $CH_3$ | $OCH_3$ | |
| 7 | H | H | $CH_3$ | H | — | $SO_2$ | $OCH_3$ | $OCH_3$ | |
| 8 | H | H | $CH_3$ | H | — | S | $CH_3$ | $CH_3$ | |
| 8 | H | H | $CH_3$ | H | — | S | $CH_3$ | $OCH_3$ | |
| 8 | H | H | $CH_3$ | H | — | S | $OCH_3$ | $OCH_3$ | |
| 8 | H | H | $CH_3$ | H | — | $SO_2$ | $CH_3$ | $CH_3$ | |
| 8 | H | H | $CH_3$ | H | — | $SO_2$ | $CH_3$ | $OCH_3$ | |
| 8 | H | H | $CH_3$ | H | — | $SO_2$ | $OCH_3$ | $OCH_3$ | |
| 16 | H | H | $CH_3$ | H | O | — | $CH_3$ | $CH_3$ | |
| 16 | H | H | $CH_3$ | H | O | — | $CH_3$ | $OCH_3$ | |
| 16 | H | H | $CH_3$ | H | O | — | $OCH_3$ | $OCH_3$ | |
| 16 | H | H | $CH_3$ | H | O | — | $OCH_2CH_3$ | $NHCH_3$ | |
| 16 | H | H | $CH_3$ | H | $NCH_3$ | — | $CH_3$ | $CH_3$ | |
| 16 | H | H | $CH_3$ | H | $NCH_3$ | — | $CH_3$ | $OCH_3$ | |
| 16 | H | H | $CH_3$ | H | $NCH_3$ | — | $OCH_3$ | $OCH_3$ | |
| 16 | H | H | $CH_3$ | H | $NCH_3$ | — | $OCH_2CH_3$ | $NHCH_3$ | |
| 19 | H | H | $CH_3$ | H | — | — | $CH_3$ | $CH_3$ | |
| 19 | H | H | $CH_3$ | H | — | — | $CH_3$ | $OCH_3$ | |
| 19 | H | H | $CH_3$ | H | — | — | $OCH_3$ | $OCH_3$ | |
| 20 | H | H | $CH_3$ | H | — | — | $CH_3$ | $CH_3$ | |
| 20 | H | H | $CH_3$ | H | — | — | $CH_3$ | $CH_3$ | |
| 20 | H | H | $CH_3$ | H | — | — | $OCH_3$ | $OCH_3$ | |
| 21 | H | H | $CH_3$ | H | — | — | $CH_3$ | $CH_3$ | |
| 21 | H | H | $CH_3$ | H | — | — | $CH_3$ | $OCH_3$ | |
| 21 | H | H | $CH_3$ | H | — | — | $OCH_3$ | $OCH_3$ | |
| 22 | H | H | $CH_3$ | H | $NCH_3$ | — | $CH_3$ | $CH_3$ | |
| 22 | H | H | $CH_3$ | H | $NCH_3$ | — | $CH_3$ | $OCH_3$ | |
| 22 | H | H | $CH_3$ | H | $NCH_3$ | — | $OCH_3$ | $OCH_3$ | |
| 25 | H | H | $CH_3$ | H | — | S | $CH_3$ | $CH_3$ | |
| 25 | H | H | $CH_3$ | H | — | S | $CH_3$ | $OCH_3$ | |
| 25 | H | H | $CH_3$ | H | — | S | $OCH_3$ | $OCH_3$ | |
| 25 | H | H | $CH_3$ | H | — | $SO_2$ | $CH_3$ | $CH_3$ | |
| 25 | H | H | $CH_3$ | H | — | $SO_2$ | $CH_3$ | $OCH_3$ | |
| 25 | H | H | $CH_3$ | H | — | $SO_2$ | $OCH_3$ | $OCH_3$ | |
| 26 | H | H | $CH_3$ | H | — | S | $CH_3$ | $CH_3$ | |
| 26 | H | H | $CH_3$ | H | — | S | $CH_3$ | $OCH_3$ | |
| 26 | H | H | $CH_3$ | H | — | S | $OCH_3$ | $OCH_3$ | |
| 26 | H | H | $CH_3$ | H | — | $SO_2$ | $CH_3$ | $CH_3$ | |
| 26 | H | H | $CH_3$ | H | — | $SO_2$ | $CH_3$ | $OCH_3$ | |
| 26 | H | H | $CH_3$ | H | — | $SO_2$ | $OCH_3$ | $OCH_3$ | |
| 27 | H | H | $CH_3$ | H | — | S | $CH_3$ | $CH_3$ | |
| 27 | H | H | $CH_3$ | H | — | S | $CH_3$ | $OCH_3$ | |
| 27 | H | H | $CH_3$ | H | — | S | $OCH_3$ | $OCH_3$ | |
| 27 | H | H | $CH_3$ | H | — | $SO_2$ | $CH_3$ | $CH_3$ | |
| 27 | H | H | $CH_3$ | H | — | $SO_2$ | $CH_3$ | $OCH_3$ | |
| 27 | H | H | $CH_3$ | H | — | $SO_2$ | $OCH_3$ | $OCH_3$ | |
| 29($R_6=CH_3$) | H | H | $CH_3$ | H | — | — | $CH_3$ | $CH_3$ | |
| 29($R_6=CH_3$) | H | H | $CH_3$ | H | — | — | $CH_3$ | $OCH_3$ | |
| 29($R_6=CH_3$) | H | H | $CH_3$ | H | — | — | $OCH_3$ | $OCH_3$ | |
| 55 | H | H | $CH_3$ | H | O | — | $CH_3$ | $CH_3$ | |
| 55 | H | H | $CH_3$ | H | O | — | $CH_3$ | $OCH_3$ | |
| 55 | H | H | $CH_3$ | H | O | — | $OCH_3$ | $OCH_3$ | |
| 55 | H | H | $CH_3$ | H | $NCH_3$ | — | $CH_3$ | $CH_3$ | |
| 55 | H | H | $CH_3$ | H | $NCH_3$ | — | $CH_3$ | $OCH_3$ | |
| 55 | H | H | $CH_3$ | H | $NCH_3$ | — | $OCH_3$ | $OCH_3$ | |

TABLE 19-continued

General Formula 19

| Q | R | R$_1$ | R$_2$ | R$_3$ | W$_3$ | W$_4$ | X | Y | m.p.(°C.) |
|---|---|---|---|---|---|---|---|---|---|
| 56 | H | H | CH$_3$ | H | — | — | CH$_3$ | CH$_3$ | |
| 56 | H | H | CH$_3$ | H | — | — | CH$_3$ | OCH$_3$ | |
| 56 | H | H | CH$_3$ | H | — | — | OCH$_3$ | OCH$_3$ | |
| 61 | H | H | CH$_3$ | H | NCH$_3$ | — | CH$_3$ | CH$_3$ | |
| 61 | H | H | CH$_3$ | H | NCH$_3$ | — | CH$_3$ | OCH$_3$ | |
| 61 | H | H | CH$_3$ | H | NCH$_3$ | — | OCH$_3$ | OCH$_3$ | |
| 65 | H | H | CH$_3$ | H | — | — | CH$_3$ | CH$_3$ | |
| 65 | H | H | CH$_3$ | H | — | — | CH$_3$ | OCH$_3$ | |
| 65 | H | H | CH$_3$ | H | — | — | OCH$_3$ | OCH$_3$ | |
| 68 | H | H | CH$_3$ | H | — | — | CH$_3$ | CH$_3$ | |
| 68 | H | H | CH$_3$ | H | — | — | CH$_3$ | OCH$_3$ | |
| 68 | H | H | CH$_3$ | H | — | — | OCH$_3$ | OCH$_3$ | |
| 76 | H | H | CH$_3$ | H | O | — | CH$_3$ | CH$_3$ | |
| 76 | H | H | CH$_3$ | H | O | — | CH$_3$ | OCH$_3$ | |
| 76 | H | H | CH$_3$ | H | O | — | OCH$_3$ | OCH$_3$ | |
| 78 | H | H | CH$_3$ | H | — | — | CH$_3$ | CH$_3$ | |
| 78 | H | H | CH$_3$ | H | — | — | CH$_3$ | OCH$_3$ | |
| 78 | H | H | CH$_3$ | H | — | — | OCH$_3$ | OCH$_3$ | |
| 79 | H | H | CH$_3$ | H | — | — | CH$_3$ | CH$_3$ | |
| 79 | H | H | CH$_3$ | H | — | — | CH$_3$ | OCH$_3$ | |
| 79 | H | H | CH$_3$ | H | — | — | OCH$_3$ | OCH$_3$ | |

TABLE 20

General Formula 20

| Q | R | R$_1$ | R$_2$ | R$_3$ | W$_3$ | W$_4$ | X | Y | m.p.(°C.) |
|---|---|---|---|---|---|---|---|---|---|
| 1 | H | H | CH$_3$ | H | O | — | CH$_3$ | CH$_3$ | |
| 1 | H | H | CH$_3$ | H | O | — | OCH$_3$ | CH$_3$ | |
| 1 | H | H | CH$_3$ | H | O | — | OCH$_3$ | OCH$_3$ | |
| 1 | CH$_3$ | H | CH$_3$ | H | O | — | OCH$_3$ | CH$_3$ | |
| 1 | H | H | CH$_3$ | H | O | — | OCF$_2$H | OCH$_3$ | |
| 1 | H | H | CH$_3$ | H | O | — | CH$_2$F | OCH$_3$ | |
| 1 | H | H | CH$_3$ | H | O | — | CH$_2$Cl | OCH$_3$ | |
| 1 | H | H | CH$_3$ | H | O | — | CF$_3$ | OCH$_3$ | |
| 1 | H | H | CH$_3$ | H | O | — | SCH$_3$ | OCH$_3$ | |
| 1 | H | H | CH$_3$ | H | O | — | Cl | OCH$_3$ | |
| 1 | H | H | CH$_3$ | H | O | — | NHCH$_3$ | OCH$_2$CH$_3$ | |
| 1 | H | H | CH$_3$ | H | O | — | OCH$_2$CH=CH | OCH$_3$ | |
| 1 | H | H | CH$_3$ | H | O | — | OCH$_2$C≡CH | OCH$_3$ | |
| 1 | H | H | CH$_3$ | H | O | — | cyclopropyl | OCH$_3$ | |
| 1 | H | H | CH$_3$ | H | O | — | C≡CH3 | OCH$_3$ | |
| 1 | H | H | CH$_3$ | H | O | — | CHO | OCH$_3$ | |
| 1 | H | H | CH$_3$ | H | O | — | 1,3-dioxan-2-yl | OCH$_3$ | |
| 1 | H | H | CH$_3$ | H | O | — | 2-methyl-1,3-oxathiolan-2-yl | OCH$_3$ | |
| 1 | H | H | CH$_3$ | H | NCH$_3$ | — | CH$_3$ | CH$_3$ | |
| 1 | H | H | CH$_3$ | H | NCH$_3$ | — | CH$_3$ | OCH$_3$ | |
| 1 | H | H | CH$_3$ | H | NCH$_3$ | — | OCH$_3$ | OCH$_3$ | |
| 1 | H | H | CH$_3$ | H | NCH$_3$ | — | Cl | OCH$_3$ | |
| 3 | H | H | CH$_3$ | H | — | — | CH$_3$ | CH$_3$ | |
| 3 | H | H | CH$_3$ | H | — | — | CH$_3$ | OCH$_3$ | |
| 3 | H | H | CH$_3$ | H | — | — | OCH$_3$ | OCH$_3$ | |
| 3 | H | H | CH$_3$ | H | — | — | Cl | OCH$_3$ | |
| 5 | H | H | CH$_3$ | H | NCH$_3$ | — | CH$_3$ | CH$_3$ | |
| 5 | H | H | CH$_3$ | H | NCH$_3$ | — | CH$_3$ | OCH$_3$ | |
| 5 | H | H | CH$_3$ | H | NCH$_3$ | — | OCH$_3$ | OCH$_3$ | |
| 5 | H | H | CH$_3$ | H | NCH$_3$ | — | Cl | OCH$_3$ | |
| 7 | H | H | CH$_3$ | H | — | S | CH$_3$ | CH$_3$ | |
| 7 | H | H | CH$_3$ | H | — | S | CH$_3$ | OCH$_3$ | |
| 7 | H | H | CH$_3$ | H | — | S | OCH$_3$ | OCH$_3$ | |
| 7 | H | H | CH$_3$ | H | — | S | Cl | OCH$_3$ | |
| 7 | H | H | CH$_3$ | H | — | SO$_2$ | CH$_3$ | CH$_3$ | |
| 7 | H | H | CH$_3$ | H | — | SO$_2$ | CH$_3$ | OCH$_3$ | |
| 7 | H | H | CH$_3$ | H | — | SO$_2$ | OCH$_3$ | OCH$_3$ | |
| 7 | H | H | CH$_3$ | H | — | SO$_2$ | Cl | OCH$_3$ | |
| 8 | H | H | CH$_3$ | H | — | S | CH$_3$ | CH$_3$ | |
| 8 | H | H | CH$_3$ | H | — | S | CH$_3$ | OCH$_3$ | |
| 8 | H | H | CH$_3$ | H | — | S | OCH$_3$ | OCH$_3$ | |
| 8 | H | H | CH$_3$ | H | — | S | Cl | OCH$_3$ | |
| 8 | H | H | CH$_3$ | H | — | SO$_2$ | CH$_3$ | CH$_3$ | |
| 8 | H | H | CH$_3$ | H | — | SO$_2$ | CH$_3$ | OCH$_3$ | |
| 8 | H | H | CH$_3$ | H | — | SO$_2$ | OCH$_3$ | OCH$_3$ | |
| 8 | H | H | CH$_3$ | H | — | SO$_2$ | Cl | OCH$_3$ | |
| 16 | H | H | CH$_3$ | H | O | — | CH$_3$ | CH$_3$ | |
| 16 | H | H | CH$_3$ | H | O | — | CH$_3$ | OCH$_3$ | |
| 16 | H | H | CH$_3$ | H | O | — | OCH$_3$ | OCH$_3$ | |

TABLE 20-continued

General Formula 20

| Q | R | R₁ | R₂ | R₃ | W₃ | W₄ | X | Y | m.p.(°C.) |
|---|---|----|----|----|----|----|---|---|-----------|
| 16 | H | H | CH₃ | H | O | — | Cl | OCH₃ | |
| 16 | H | H | CH₃ | H | NCH₃ | — | CH₃ | CH₃ | |
| 16 | H | H | CH₃ | H | NCH₃ | — | CH₃ | OCH₃ | |
| 16 | H | H | CH₃ | H | NCH₃ | — | OCH₃ | OCH₃ | |
| 16 | H | H | CH₃ | H | NCH₃ | — | Cl | OCH₃ | |
| 19 | H | H | CH₃ | H | — | — | CH₃ | CH₃ | |
| 19 | H | H | CH₃ | H | — | — | CH₃ | OCH₃ | |
| 19 | H | H | CH₃ | H | — | — | OCH₃ | OCH₃ | |
| 19 | H | H | CH₃ | H | — | — | Cl | OCH₃ | |
| 20 | H | H | CH₃ | H | — | — | CH₃ | CH₃ | |
| 20 | H | H | CH₃ | H | — | — | CH₃ | OCH₃ | |
| 20 | H | H | CH₃ | H | — | — | OCH₃ | OCH₃ | |
| 20 | H | H | CH₃ | H | — | — | Cl | OCH₃ | |
| 21 | H | H | CH₃ | H | — | — | CH₃ | CH₃ | |
| 21 | H | H | CH₃ | H | — | — | CH₃ | OCH₃ | |
| 21 | H | H | CH₃ | H | — | — | OCH₃ | OCH₃ | |
| 21 | H | H | CH₃ | H | — | — | Cl | OCH₃ | |
| 22 | H | H | CH₃ | H | NCH₃ | — | CH₃ | CH₃ | |
| 22 | H | H | CH₃ | H | NCH₃ | — | CH₃ | OCH₃ | |
| 22 | H | H | CH₃ | H | NCH₃ | — | OCH₃ | OCH₃ | |
| 22 | H | H | CH₃ | H | NCH₃ | — | Cl | OCH₃ | |
| 25 | H | H | CH₃ | H | — | S | CH₃ | CH₃ | |
| 25 | H | H | CH₃ | H | — | S | CH₃ | OCH₃ | |
| 25 | H | H | CH₃ | H | — | S | OCH₃ | OCH₃ | |
| 25 | H | H | CH₃ | H | — | S | Cl | OCH₃ | |
| 25 | H | H | CH₃ | H | — | SO₂ | CH₃ | CH₃ | |
| 25 | H | H | CH₃ | H | — | SO₂ | CH₃ | OCH₃ | |
| 25 | H | H | CH₃ | H | — | SO₂ | OCH₃ | OCH₃ | |
| 25 | H | H | CH₃ | H | — | SO₂ | Cl | OCH₃ | |
| 26 | H | H | CH₃ | H | — | S | CH₃ | CH₃ | |
| 26 | H | H | CH₃ | H | — | S | CH₃ | OCH₃ | |
| 26 | H | H | CH₃ | H | — | S | OCH₃ | OCH₃ | |
| 26 | H | H | CH₃ | H | — | S | Cl | OCH₃ | |
| 26 | H | H | CH₃ | H | — | SO₂ | CH₃ | CH₃ | |
| 26 | H | H | CH₃ | H | — | SO₂ | CH₃ | OCH₃ | |
| 26 | H | H | CH₃ | H | — | SO₂ | OCH₃ | OCH₃ | |
| 26 | H | H | CH₃ | H | — | SO₂ | Cl | OCH₃ | |
| 27 | H | H | CH₃ | H | — | S | CH₃ | CH₃ | |
| 27 | H | H | CH₃ | H | — | S | CH₃ | OCH₃ | |
| 27 | H | H | CH₃ | H | — | S | OCH₃ | OCH₃ | |
| 27 | H | H | CH₃ | H | — | S | Cl | OCH₃ | |
| 27 | H | H | CH₃ | H | — | SO₂ | CH₃ | CH₃ | |
| 27 | H | H | CH₃ | H | — | SO₂ | CH₃ | OCH₃ | |
| 27 | H | H | CH₃ | H | — | SO₂ | OCH₃ | OCH₃ | |
| 27 | H | H | CH₃ | H | — | SO₂ | Cl | OCH₃ | |
| 29(R₆=CH₃) | H | H | CH₃ | H | — | — | CH₃ | CH₃ | |
| 29(R₆=CH₃) | H | H | CH₃ | H | — | — | CH₃ | OCH₃ | |
| 29(R₆=CH₃) | H | H | CH₃ | H | — | — | OCH₃ | OCH₃ | |
| 29(R₆=CH₃) | H | H | CH₃ | H | — | — | Cl | OCH₃ | |
| 55 | H | H | CH₃ | H | O | — | CH₃ | CH₃ | |
| 55 | H | H | CH₃ | H | O | — | CH₃ | OCH₃ | |
| 55 | H | H | CH₃ | H | O | — | OCH₃ | OCH₃ | |
| 55 | H | H | CH₃ | H | O | — | Cl | OCH₃ | |
| 55 | H | H | CH₃ | H | NCH₃ | — | CH₃ | CH₃ | |
| 55 | H | H | CH₃ | H | NCH₃ | — | CH₃ | OCH₃ | |
| 55 | H | H | CH₃ | H | NCH₃ | — | OCH₃ | OCH₃ | |
| 55 | H | H | CH₃ | H | NCH₃ | — | Cl | OCH₃ | |
| 56 | H | H | CH₃ | H | — | — | CH₃ | CH₃ | |
| 56 | H | H | CH₃ | H | — | — | CH₃ | OCH₃ | |
| 56 | H | H | CH₃ | H | — | — | OCH₃ | OCH₃ | |
| 56 | H | H | CH₃ | H | — | — | Cl | OCH₃ | |
| 61 | H | H | CH₃ | H | NCH₃ | — | CH₃ | CH₃ | |
| 61 | H | H | CH₃ | H | NCH₃ | — | CH₃ | OCH₃ | |
| 61 | H | H | CH₃ | H | NCH₃ | — | OCH₃ | OCH₃ | |
| 61 | H | H | CH₃ | H | NCH₃ | — | Cl | OCH₃ | |
| 65 | H | H | CH₃ | H | — | — | CH₃ | CH₃ | |
| 65 | H | H | CH₃ | H | — | — | CH₃ | OCH₃ | |
| 65 | H | H | CH₃ | H | — | — | OCH₃ | OCH₃ | |
| 65 | H | H | CH₃ | H | — | — | Cl | OCH₃ | |
| 68 | H | H | CH₃ | H | — | — | CH₃ | CH₃ | |
| 68 | H | H | CH₃ | H | — | — | CH₃ | OCH₃ | |
| 68 | H | H | CH₃ | H | — | — | OCH₃ | OCH₃ | |
| 68 | H | H | CH₃ | H | — | — | Cl | OCH₃ | |
| 76 | H | H | CH₃ | H | O | — | CH₃ | CH₃ | |
| 76 | H | H | CH₃ | H | O | — | CH₃ | OCH₃ | |
| 76 | H | H | CH₃ | H | O | — | OCH₃ | OCH₃ | |
| 76 | H | H | CH₃ | H | O | — | Cl | OCH₃ | |
| 78 | H | H | CH₃ | H | — | — | CH₃ | CH₃ | |
| 78 | H | H | CH₃ | H | — | — | CH₃ | OCH₃ | |
| 78 | H | H | CH₃ | H | — | — | OCH₃ | OCH₃ | |

TABLE 20-continued

General Formula 20

| Q | R | R₁ | R₂ | R₃ | W₃ | W₄ | X | Y | m.p.(°C.) |
|---|---|----|----|----|----|----|---|---|-----------|
| 78 | H | H | CH₃ | H | — | — | Cl | OCH₃ | |
| 79 | H | H | CH₃ | H | — | — | CH₃ | CH₃ | |
| 79 | H | H | CH₃ | H | — | — | CH₃ | OCH₃ | |
| 79 | H | H | CH₃ | H | — | — | OCH₃ | OCH₃ | |
| 79 | H | H | CH₃ | H | — | — | Cl | OCH₃ | |

TABLE 21

General Formula 21

| Q | R | R₁ | R₂ | R₃ | W₃ | W₄ | X | Y | m.p.(°C.) |
|---|---|----|----|----|----|----|---|---|-----------|
| 1 | H | H | CH₃ | H | O | — | CH₃ | CH₃ | |
| 1 | H | H | CH₃ | H | O | — | OCH₃ | CH₃ | |
| 1 | H | H | CH₃ | H | O | — | OCH₃ | OCH₃ | |
| 1 | CH₃ | H | CH₃ | H | O | — | OCH₃ | CH₃ | |
| 1 | H | H | CH₃ | H | O | — | CH₂F | OCH₃ | |
| 1 | H | H | CH₃ | H | O | — | CH₂Cl | OCH₃ | |
| 1 | H | H | CH₃ | H | O | — | CF₃ | OCH₃ | |
| 1 | H | H | CH₃ | H | O | — | SCH₃ | OCH₃ | |
| 1 | H | H | CH₃ | H | O | — | NHCH₃ | OCH₂CH₃ | |
| 1 | H | H | CH₃ | H | O | — | OCH₂CH=CH | OCH₃ | |
| 1 | H | H | CH₃ | H | O | — | OCH₂C≡CH | OCH₃ | |
| 1 | H | H | CH₃ | H | O | — | cyclopropyl | OCH₃ | |
| 1 | H | H | CH₃ | H | O | — | C≡CH | OCH₃ | |
| 1 | H | H | CH₃ | H | O | — | CHO | OCH₃ | |
| 1 | H | H | CH₃ | H | O | — | 1,3-dioxan-2-yl | OCH₃ | |
| 1 | H | H | CH₃ | H | O | — | 2-methyl-1,3-oxathiolan-2-yl | OCH₃ | |
| 1 | H | H | CH₃ | H | NCH₃ | — | CH₃ | CH₃ | |
| 1 | H | H | CH₃ | H | NCH₃ | — | CH₃ | OCH₃ | |
| 1 | H | H | CH₃ | H | NCH₃ | — | OCH₃ | OCH₃ | |
| 1 | H | H | CH₃ | H | NCH₃ | — | OCH₂CH₃ | NHCH₃ | |
| 3 | H | H | CH₃ | H | — | — | CH₃ | CH₃ | |
| 3 | H | H | CH₃ | H | — | — | CH₃ | OCH₃ | |
| 3 | H | H | CH₃ | H | — | — | OCH₃ | OCH₃ | |
| 5 | H | H | CH₃ | H | NCH₃ | — | CH₃ | CH₃ | |
| 5 | H | H | CH₃ | H | NCH₃ | — | CH₃ | OCH₃ | |
| 5 | H | H | CH₃ | H | NCH₃ | — | OCH₃ | OCH₃ | |
| 7 | H | H | CH₃ | H | — | S | CH₃ | CH₃ | |
| 7 | H | H | CH₃ | H | — | S | CH₃ | OCH₃ | |
| 7 | H | H | CH₃ | H | — | S | OCH₃ | OCH₃ | |
| 7 | H | H | CH₃ | H | — | SO₂ | CH₃ | CH₃ | |
| 7 | H | H | CH₃ | H | — | SO₂ | CH₃ | OCH₃ | |
| 7 | H | H | CH₃ | H | — | SO₂ | OCH₃ | OCH₃ | |
| 8 | H | H | CH₃ | H | — | S | CH₃ | CH₃ | |
| 8 | H | H | CH₃ | H | — | S | CH₃ | OCH₃ | |
| 8 | H | H | CH₃ | H | — | S | OCH₃ | OCH₃ | |
| 8 | H | H | CH₃ | H | — | SO₂ | CH₃ | CH₃ | |
| 8 | H | H | CH₃ | H | — | SO₂ | CH₃ | OCH₃ | |
| 8 | H | H | CH₃ | H | — | SO₂ | OCH₃ | OCH₃ | |
| 16 | H | H | CH₃ | H | O | — | CH₃ | CH₃ | |
| 16 | H | H | CH₃ | H | O | — | CH₃ | OCH₃ | |
| 16 | H | H | CH₃ | H | O | — | OCH₃ | OCH₃ | |
| 16 | H | H | CH₃ | H | O | — | OCH₂CH₃ | NHCH₃ | |
| 16 | H | H | CH₃ | H | NCH₃ | — | CH₃ | CH₃ | |
| 16 | H | H | CH₃ | H | NCH₃ | — | CH₃ | OCH₃ | |
| 16 | H | H | CH₃ | H | NCH₃ | — | OCH₃ | OCH₃ | |
| 16 | H | H | CH₃ | H | NCH₃ | — | OCH₂CH₃ | NHCH₃ | |
| 19 | H | H | CH₃ | H | — | — | CH₃ | CH₃ | |
| 19 | H | H | CH₃ | H | — | — | CH₃ | OCH₃ | |
| 19 | H | H | CH₃ | H | — | — | OCH₃ | OCH₃ | |
| 20 | H | H | CH₃ | H | — | — | CH₃ | CH₃ | |
| 20 | H | H | CH₃ | H | — | — | CH₃ | OCH₃ | |
| 20 | H | H | CH₃ | H | — | — | OCH₃ | OCH₃ | |
| 21 | H | H | CH₃ | H | — | — | CH₃ | CH₃ | |
| 21 | H | H | CH₃ | H | — | — | CH₃ | OCH₃ | |
| 21 | H | H | CH₃ | H | — | — | OCH₃ | OCH₃ | |
| 22 | H | H | CH₃ | H | NCH₃ | — | CH₃ | CH₃ | |
| 22 | H | H | CH₃ | H | NCH₃ | — | CH₃ | OCH₃ | |
| 22 | H | H | CH₃ | H | NCH₃ | — | OCH₃ | OCH₃ | |
| 25 | H | H | CH₃ | H | — | S | CH₃ | CH₃ | |
| 25 | H | H | CH₃ | H | — | S | CH₃ | OCH₃ | |
| 25 | H | H | CH₃ | H | — | S | OCH₃ | OCH₃ | |
| 25 | H | H | CH₃ | H | — | SO₂ | CH₃ | CH₃ | |
| 25 | H | H | CH₃ | H | — | SO₂ | CH₃ | OCH₃ | |
| 25 | H | H | CH₃ | H | — | SO₂ | OCH₃ | OCH₃ | |
| 26 | H | H | CH₃ | H | — | S | CH₃ | CH₃ | |

TABLE 21-continued

General Formula 21

| Q | R | R$_1$ | R$_2$ | R$_3$ | W$_3$ | W$_4$ | X | Y | m.p.(°C.) |
|---|---|---|---|---|---|---|---|---|---|
| 26 | H | H | CH$_3$ | H | — | S | CH$_3$ | OCH$_3$ | |
| 26 | H | H | CH$_3$ | H | — | S | OCH$_3$ | OCH$_3$ | |
| 26 | H | H | CH$_3$ | H | — | SO$_2$ | CH$_3$ | CH$_3$ | |
| 26 | H | H | CH$_3$ | H | — | SO$_2$ | CH$_3$ | OCH$_3$ | |
| 26 | H | H | CH$_3$ | H | — | SO$_2$ | OCH$_3$ | OCH$_3$ | |
| 27 | H | H | CH$_3$ | H | — | S | CH$_3$ | CH$_3$ | |
| 27 | H | H | CH$_3$ | H | — | S | CH$_3$ | OCH$_3$ | |
| 27 | H | H | CH$_3$ | H | — | S | OCH$_3$ | OCH$_3$ | |
| 27 | H | H | CH$_3$ | H | — | SO$_2$ | CH$_3$ | CH$_3$ | |
| 27 | H | H | CH$_3$ | H | — | SO$_2$ | CH$_3$ | OCH$_3$ | |
| 27 | H | H | CH$_3$ | H | — | SO$_2$ | OCH$_3$ | OCH$_3$ | |
| 29(R$_6$=CH$_3$) | H | H | CH$_3$ | H | — | — | CH$_3$ | CH$_3$ | |
| 29(R$_6$=CH$_3$) | H | H | CH$_3$ | H | — | — | CH$_3$ | OCH$_3$ | |
| 29(R$_6$=CH$_3$) | H | H | CH$_3$ | H | — | — | OCH$_3$ | OCH$_3$ | |
| 55 | H | H | CH$_3$ | H | O | — | CH$_3$ | CH$_3$ | |
| 55 | H | H | CH$_3$ | H | O | — | CH$_3$ | OCH$_3$ | |
| 55 | H | H | CH$_3$ | H | O | — | OCH$_3$ | OCH$_3$ | |
| 55 | H | H | CH$_3$ | H | NCH$_3$ | — | CH$_3$ | CH$_3$ | |
| 55 | H | H | CH$_3$ | H | NCH$_3$ | — | CH$_3$ | OCH$_3$ | |
| 55 | H | H | CH$_3$ | H | NCH$_3$ | — | OCH$_3$ | OCH$_3$ | |
| 56 | H | H | CH$_3$ | H | — | — | CH$_3$ | CH$_3$ | |
| 56 | H | H | CH$_3$ | H | — | — | CH$_3$ | OCH$_3$ | |
| 56 | H | H | CH$_3$ | H | — | — | OCH$_3$ | OCH$_3$ | |
| 61 | H | H | CH$_3$ | H | NCH$_3$ | — | CH$_3$ | CH$_3$ | |
| 61 | H | H | CH$_3$ | H | NCH$_3$ | — | CH$_3$ | OCH$_3$ | |
| 61 | H | H | CH$_3$ | H | NCH$_3$ | — | OCH$_3$ | OCH$_3$ | |
| 65 | H | H | CH$_3$ | H | — | — | CH$_3$ | CH$_3$ | |
| 65 | H | H | CH$_3$ | H | — | — | CH$_3$ | OCH$_3$ | |
| 65 | H | H | CH$_3$ | H | — | — | OCH$_3$ | OCH$_3$ | |
| 68 | H | H | CH$_3$ | H | — | — | CH$_3$ | CH$_3$ | |
| 68 | H | H | CH$_3$ | H | — | — | CH$_3$ | OCH$_3$ | |
| 68 | H | H | CH$_3$ | H | — | — | OCH$_3$ | OCH$_3$ | |
| 76 | H | H | CH$_3$ | H | O | — | CH$_3$ | CH$_3$ | |
| 76 | H | H | CH$_3$ | H | O | — | CH$_3$ | OCH$_3$ | |
| 76 | H | H | CH$_3$ | H | O | — | OCH$_3$ | OCH$_3$ | |
| 78 | H | H | CH$_3$ | H | — | — | CH$_3$ | CH$_3$ | |
| 78 | H | H | CH$_3$ | H | — | — | CH$_3$ | OCH$_3$ | |
| 78 | H | H | CH$_3$ | H | — | — | OCH$_3$ | OCH$_3$ | |
| 79 | H | H | CH$_3$ | H | — | — | CH$_3$ | CH$_3$ | |
| 79 | H | H | CH$_3$ | H | — | — | CH$_3$ | OCH$_3$ | |
| 79 | H | H | CH$_3$ | H | — | — | OCH$_3$ | OCH$_3$ | |

TABLE 22

General Formula 22

| Q | R | R$_1$ | R$_3$ | W$_3$ | W$_4$ | X$_4$ | Y$_4$ | Z$_1$ | m.p. (°C.) |
|---|---|---|---|---|---|---|---|---|---|
| 1 | H | H | H | O | — | CH$_3$ | CH$_3$ | CH | |
| 1 | H | H | H | O | — | CH$_3$ | CH$_3$ | N | |
| 1 | CH$_3$ | H | H | O | — | CH$_3$ | CH$_3$ | CH | |
| 1 | H | H | H | O | — | CH$_3$ | OCH$_3$ | CH | |
| 1 | H | H | H | NCH$_3$ | — | CH$_3$ | CH$_3$ | CH | |
| 1 | H | H | H | NCH$_3$ | — | CH$_3$ | CH$_3$ | N | |
| 1 | CH$_3$ | H | H | NCH$_3$ | — | CH$_3$ | CH$_3$ | CH | |
| 1 | H | H | H | NCH$_3$ | — | CH$_3$ | OCH$_3$ | CH | |
| 3 | H | H | H | — | — | CH$_3$ | CH$_3$ | CH | |
| 3 | H | H | H | — | — | CH$_3$ | CH$_3$ | N | |
| 3 | CH$_3$ | H | H | — | — | CH$_3$ | CH$_3$ | CH | |
| 3 | H | H | H | — | — | CH$_3$ | OCH$_3$ | CH | |
| 5 | H | H | H | NCH$_3$ | — | CH$_3$ | CH$_3$ | CH | |
| 5 | H | H | H | NCH$_3$ | — | CH$_3$ | CH$_3$ | N | |
| 5 | CH$_3$ | H | H | NCH$_3$ | — | CH$_3$ | CH$_3$ | CH | |
| 5 | H | H | H | NCH$_3$ | — | CH$_3$ | OCH$_3$ | CH | |
| 7 | H | H | H | — | S | CH$_3$ | CH$_3$ | CH | |
| 7 | H | H | H | — | S | CH$_3$ | CH$_3$ | N | |
| 7 | CH$_3$ | H | H | — | S | CH$_3$ | CH$_3$ | CH | |
| 7 | H | H | H | — | S | CH$_3$ | OCH$_3$ | CH | |
| 7 | H | H | H | — | SO$_2$ | CH$_3$ | CH$_3$ | CH | |
| 7 | H | H | H | — | SO$_2$ | CH$_3$ | CH$_3$ | N | |
| 7 | CH$_3$ | H | H | — | SO$_2$ | CH$_3$ | CH$_3$ | CH | |
| 7 | H | H | H | — | SO$_2$ | CH$_3$ | OCH$_3$ | CH | |
| 8 | H | H | H | — | S | CH$_3$ | CH$_3$ | CH | |
| 8 | H | H | H | — | S | CH$_3$ | CH$_3$ | N | |
| 8 | CH$_3$ | H | H | — | S | CH$_3$ | CH$_3$ | CH | |
| 8 | H | H | H | — | S | CH$_3$ | OCH$_3$ | CH | |
| 8 | H | H | H | — | SO$_2$ | CH$_3$ | CH$_3$ | CH | |
| 8 | H | H | H | — | SO$_2$ | CH$_3$ | CH$_3$ | N | |
| 8 | CH$_3$ | H | H | — | SO$_2$ | CH$_3$ | CH$_3$ | CH | |
| 8 | H | H | H | — | SO$_2$ | CH$_3$ | OCH$_3$ | CH | |

TABLE 22-continued

General Formula 22

| Q | R | $R_1$ | $R_3$ | $W_3$ | $W_4$ | $X_4$ | $Y_4$ | $Z_1$ | m.p. (°C.) |
|---|---|---|---|---|---|---|---|---|---|
| 16 | H | H | H | O | — | $CH_3$ | $CH_3$ | CH | |
| 16 | H | H | H | O | — | $CH_3$ | $CH_3$ | N | |
| 16 | $CH_3$ | H | H | O | — | $CH_3$ | $CH_3$ | CH | |
| 16 | H | H | H | O | — | $CH_3$ | $OCH_3$ | CH | |
| 16 | H | H | H | $NCH_3$ | — | $CH_3$ | $CH_3$ | CH | |
| 16 | H | H | H | $NCH_3$ | — | $CH_3$ | $CH_3$ | N | |
| 16 | $CH_3$ | H | H | $NCH_3$ | — | $CH_3$ | $CH_3$ | CH | |
| 16 | H | H | H | $NCH_3$ | — | $CH_3$ | $OCH_3$ | CH | |
| 19 | H | H | H | — | — | $CH_3$ | $CH_3$ | CH | |
| 19 | H | H | H | — | — | $CH_3$ | $CH_3$ | N | |
| 19 | $CH_3$ | H | H | — | — | $CH_3$ | $CH_3$ | CH | |
| 19 | H | H | H | — | — | $CH_3$ | $OCH_3$ | CH | |
| 20 | H | H | H | — | — | $CH_3$ | $CH_3$ | CH | |
| 20 | H | H | H | — | — | $CH_3$ | $CH_3$ | N | |
| 20 | $CH_3$ | H | H | — | — | $CH_3$ | $CH_3$ | CH | |
| 20 | H | H | H | — | — | $CH_3$ | $OCH_3$ | CH | |
| 21 | H | H | H | — | — | $CH_3$ | $CH_3$ | CH | |
| 21 | H | H | H | — | — | $CH_3$ | $CH_3$ | N | |
| 21 | $CH_3$ | H | H | — | — | $CH_3$ | $CH_3$ | CH | |
| 21 | H | H | H | — | — | $CH_3$ | $OCH_3$ | CH | |
| 22 | H | H | H | $NCH_3$ | — | $CH_3$ | $CH_3$ | CH | |
| 22 | H | H | H | $NCH_3$ | — | $CH_3$ | $CH_3$ | N | |
| 22 | $CH_3$ | H | H | $NCH_3$ | — | $CH_3$ | $CH_3$ | CH | |
| 22 | H | H | H | $NCH_3$ | — | $CH_3$ | $OCH_3$ | CH | |
| 25 | H | H | H | — | S | $CH_3$ | $CH_3$ | CH | |
| 25 | H | H | H | — | S | $CH_3$ | $CH_3$ | N | |
| 25 | $CH_3$ | H | H | — | S | $CH_3$ | $CH_3$ | CH | |
| 25 | H | H | H | — | S | $CH_3$ | $OCH_3$ | CH | |
| 25 | H | H | H | — | $SO_2$ | $CH_3$ | $CH_3$ | CH | |
| 25 | H | H | H | — | $SO_2$ | $CH_3$ | $CH_3$ | N | |
| 25 | $CH_3$ | H | H | — | $SO_2$ | $CH_3$ | $CH_3$ | CH | |
| 25 | H | H | H | — | $SO_2$ | $CH_3$ | $OCH_3$ | CH | |
| 26 | H | H | H | — | S | $CH_3$ | $CH_3$ | CH | |
| 26 | H | H | H | — | S | $CH_3$ | $CH_3$ | N | |
| 26 | $CH_3$ | H | H | — | S | $CH_3$ | $CH_3$ | CH | |
| 26 | H | H | H | — | S | $CH_3$ | $OCH_3$ | CH | |
| 26 | H | H | H | — | $SO_2$ | $CH_3$ | $CH_3$ | CH | |
| 26 | H | H | H | — | $SO_2$ | $CH_3$ | $CH_3$ | N | |
| 26 | $CH_3$ | H | H | — | $SO_2$ | $CH_3$ | $CH_3$ | CH | |
| 26 | H | H | H | — | $SO_2$ | $CH_3$ | $OCH_3$ | CH | |
| 27 | H | H | H | — | S | $CH_3$ | $CH_3$ | CH | |
| 27 | H | H | H | — | S | $CH_3$ | $CH_3$ | N | |
| 27 | $CH_3$ | H | H | — | S | $CH_3$ | $CH_3$ | CH | |
| 27 | H | H | H | — | S | $CH_3$ | $OCH_3$ | CH | |
| 27 | H | H | H | — | $SO_2$ | $CH_3$ | $CH_3$ | CH | |
| 27 | H | H | H | — | $SO_2$ | $CH_3$ | $CH_3$ | N | |
| 27 | $CH_3$ | H | H | — | $SO_2$ | $CH_3$ | $CH_3$ | CH | |
| 27 | H | H | H | — | $SO_2$ | $CH_3$ | $OCH_3$ | CH | |
| 29 ($R_6=CH_3$) | H | H | H | — | — | $CH_3$ | $CH_3$ | CH | |
| 29 ($R_6=CH_3$) | H | H | H | — | — | $CH_3$ | $CH_3$ | N | |
| 29 ($R_6=CH_3$) | $CH_3$ | H | H | — | — | $CH_3$ | $CH_3$ | CH | |
| 29 ($R_6=CH_3$) | H | H | H | — | — | $CH_3$ | $OCH_3$ | CH | |
| 55 | H | H | H | O | — | $CH_3$ | $CH_3$ | CH | |
| 55 | H | H | H | O | — | $CH_3$ | $CH_3$ | N | |
| 55 | $CH_3$ | H | H | O | — | $CH_3$ | $CH_3$ | CH | |
| 55 | H | H | H | O | — | $CH_3$ | $OCH_3$ | CH | |
| 55 | H | H | H | $NCH_3$ | — | $CH_3$ | $CH_3$ | CH | |
| 55 | H | H | H | $NCH_3$ | — | $CH_3$ | $CH_3$ | N | |
| 55 | $CH_3$ | H | H | $NCH_3$ | — | $CH_3$ | $CH_3$ | CH | |
| 55 | H | H | H | $NCH_3$ | — | $CH_3$ | $OCH_3$ | CH | |
| 56 | H | H | H | — | — | $CH_3$ | $CH_3$ | CH | |
| 56 | H | H | H | — | — | $CH_3$ | $CH_3$ | N | |
| 56 | $CH_3$ | H | H | — | — | $CH_3$ | $CH_3$ | CH | |
| 56 | H | H | H | — | — | $CH_3$ | $OCH_3$ | CH | |
| 61 | H | H | H | $NCH_3$ | — | $CH_3$ | $CH_3$ | CH | |
| 61 | H | H | H | $NCH_3$ | — | $CH_3$ | $CH_3$ | N | |
| 61 | $CH_3$ | H | H | $NCH_3$ | — | $CH_3$ | $CH_3$ | CH | |
| 61 | H | H | H | $NCH_3$ | — | $CH_3$ | $OCH_3$ | CH | |
| 62 | H | H | H | $NCH_3$ | — | $CH_3$ | $CH_3$ | CH | |
| 62 | H | H | H | $NCH_3$ | — | $CH_3$ | $CH_3$ | N | |
| 62 | $CH_3$ | H | H | $NCH_3$ | — | $CH_3$ | $CH_3$ | CH | |
| 62 | H | H | H | $NCH_3$ | — | $CH_3$ | $OCH_3$ | CH | |
| 65 | H | H | H | — | — | $CH_3$ | $CH_3$ | CH | |
| 65 | H | H | H | — | — | $CH_3$ | $CH_3$ | N | |
| 65 | $CH_3$ | H | H | — | — | $CH_3$ | $CH_3$ | CH | |
| 65 | H | H | H | — | — | $CH_3$ | $OCH_3$ | CH | |
| 68 | H | H | H | — | — | $CH_3$ | $CH_3$ | CH | |
| 68 | H | H | H | — | — | $CH_3$ | $CH_3$ | N | |
| 68 | $CH_3$ | H | H | — | — | $CH_3$ | $CH_3$ | CH | |
| 68 | H | H | H | — | — | $CH_3$ | $OCH_3$ | CH | |

TABLE 22-continued

| | | | General Formula 22 | | | | | |
|---|---|---|---|---|---|---|---|---|
| Q | R | $R_1$ | $R_3$ | $W_3$ | $W_4$ | $X_4$ | $Y_4$ | $Z_1$ | m.p. (°C.) |
| 76 | H | H | H | O | — | $CH_3$ | $CH_3$ | CH | |
| 76 | H | H | H | O | — | $CH_3$ | $CH_3$ | N | |
| 76 | $CH_3$ | H | H | O | — | $CH_3$ | $CH_3$ | CH | |
| 76 | H | H | H | O | — | $CH_3$ | $OCH_3$ | CH | |
| 78 | H | H | H | — | — | $CH_3$ | $CH_3$ | CH | |
| 78 | H | H | H | — | — | $CH_3$ | $CH_3$ | N | |
| 78 | $CH_3$ | H | H | — | — | $CH_3$ | $CH_3$ | CH | |
| 78 | H | H | H | — | — | $CH_3$ | $OCH_3$ | CH | |
| 79 | H | H | H | — | — | $CH_3$ | $CH_3$ | CH | |
| 79 | H | H | H | — | — | $CH_3$ | $CH_3$ | N | |
| 79 | $CH_3$ | H | H | — | — | $CH_3$ | $CH_3$ | CH | |
| 79 | H | H | H | — | — | $CH_3$ | $OCH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are somtimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

| Wettable Powder | |
|---|---|
| N—[(4-methoxy-6-methyltriazin-2-yl)aminocarbonyl]-2-[(2-oxotetrahydro-3-furanylidene)methyl]-3-chlorobenzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| Wettable Powder | |
|---|---|
| N—[(4,6-dimethoxypyrimidin-2-yl)aminocarbonyl]-2-[(2-oxotetrahydro-3-furanylidene)methyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
|---|---|
| Wettable Powder of Example 10 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 12

| Extruded Pellet | |
|---|---|
| N—[(4,6-dimethoxypyrimidin-2-yl)aminocarbonyl]-2-[(2-oxotetrahydro-3-furanylidene)methyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| Oil Suspension | |
|---|---|
| N—[(4-methoxy-6-methyltriazin-2-yl)aminocarbonyl]-2-[(2-oxotetrahydro-3-furanylidene)methyl]-3-chlorobenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

| Wettable Powder | |
|---|---|
| N—[(4,6-dimethoxypyrimidin-2-yl)aminocarbonyl]-2-[(2-oxotetrahydro-3-furanylidene)methyl]benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 15

| Low Strength Granule | |
|---|---|
| N—[(4-methoxy-6-methyltriazin-2-yl)aminocarbonyl]-2-[(2-oxotetrahydro-3-furanylidene)methyl]-3-chlorobenzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
|---|---|
| N—[(4,6-dimethoxypyrimidin-2-yl)aminocarbonyl]-2-[(2-oxotetrahydro-3-furanylidene)methyl]benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| N—[(4-methoxy-6-methyltriazin-2-yl)aminocarbonyl]-2-[(2-oxotetrahydro-3-furanylidene)methyl]-3-chlorobenzenesulfonamide, ammonium salt | 5% |
| water | 95% |

The salt is added directly to the water with stirring to produce the solution, which may then be packaged for use.

EXAMPLE 18

| Low Strength Granule | |
|---|---|
| N—[(4,6-dimethoxypyrimidin-2-yl)aminocarbonyl]-2- | 0.1% |

-continued

| Low Strength Granule | |
|---|---|
| [(2-oxotetrahydro-3-furanylidene)methyl]benzene-sulfonamide attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

| Granule | |
|---|---|
| N—[(4-methoxy-6-methyltriazin-2-yl)aminocarbonyl]-2-[(2-oxotetrahydro-3-furanylidene)methyl]-3-chloro-benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 20

| High Strength Concentrate | |
|---|---|
| N—[(4-methoxy-6-methyltriazin-2-yl)aminocarbonyl]-2-[(2-oxotetrahydro-3-furanylidene)methyl]-3-chloro-benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 21

| Wettable Powder | |
|---|---|
| N—[(4,6-dimethoxypyrimidin-2-yl)aminocarbonyl]-2-[(2-oxotetrahydro-3-furanylidene)methyl]benzene-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S No. 50 screen and then packaged.

EXAMPLE 22

| Wettable Powder | |
|---|---|
| N—[(4-methoxy-6-methyltriazin-2-yl)aminocarbonyl]-2-[(2-oxotetrahydro-3-furanylidene)methyl]-3-chloro-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

| Oil Suspension | |
|---|---|
| N—[(4,6-dimethoxypyrimidin-2-yl)aminocarbonyl]-2-[(2-oxotetrahydro-3-furanylidene)methyl]benzene-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 24

| Dust | |
|---|---|
| N—[(4,6-dimethoxypyrimidin-2-yl)aminocarbonyl]-2-[(2-oxotetrahydro-3-furanylidene)methyl]benzene-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 25

| Emulsifiable Concentrate | |
|---|---|
| N—[(4-methoxy-6-methyltriazin-2-yl)aminocarbonyl]-2-[(2-oxotetrahydro-3-furanylidene)methyl]-3-chloro-benzenesulfonamide | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as corn, wheat and soybeans. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate, and bipyridylium types. The herbicidal properties of the subject compounds were discovered in a number of greenhouse tests. The test procedures and results follow.

Test A

Seeds of crabgrass (Digitaria spp.), barnyardgrass (*Echinochloa crusgalli*), wild oats (*Avena fatua*), cheatgrass (*Bromus secalinus*), velvetleaf (*Abutilon theophrasti*), morningglory (Ipomoea sp.), cocklebur (*Xanthium pennsylvanicum*), sorghum, corn, soybean, sugarbeet, cotton, rice, wheat, and purple nutsedge (*Cyperus rotundus*) tubers were planted treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis
B=burn
D=defoliation
E=emergence inhibition
G=growth retardation
H=formative effects
U=unusual pigmentation
X=axillary stimulation
S=albinism
6Y=abscised buds or flowers.

Compounds

| Compound | $R_1$ | Z | X | Y |
|---|---|---|---|---|
| 1 | H | CH | $OCH_3$ | $OCH_3$ |
| 2 | H | CH | $OCH_3$ | $CH_3$ |
| 3 | H | CH | Cl | $OCH_3$ |
| 4 | H | CH | $CH_3$ | $CH_3$ |
| 5 | H | N | $OCH_3$ | $OCH_3$ |
| 6 | H | N | $OCH_3$ | $CH_3$ |
| 7 | 3-Cl | CH | $OCH_3$ | $OCH_3$ |
| 8 | 3-Cl | CH | $OCH_3$ | $CH_3$ |
| 9 | 3-Cl | CH | $CH_3$ | $CH_3$ |
| 10 | 3-Cl | N | $OCH_3$ | $OCH_3$ |
| 11 | 3-Cl | N | $OCH_3$ | $CH_3$ |
| 12 | H | N | $OC_2H_5$ | $NHCH_3$ |

| Compound | $R_6$ | Z | X | Y |
|---|---|---|---|---|
| 13 | $CH_3$ | CH | $OCH_3$ | $OCH_3$ |
| 14 | $CH_3$ | CH | $CH_3$ | $OCH_3$ |
| 15 | H | CH | $OCH_3$ | $OCH_3$ |
| 16 | H | CH | $CH_3$ | $OCH_3$ |

| Compound | Z | X | Y |
|---|---|---|---|
| 17 | CH | $OCH_3$ | $OCH_3$ |
| 18 | CH | $CH_3$ | $OCH_3$ |

-continued

Compounds

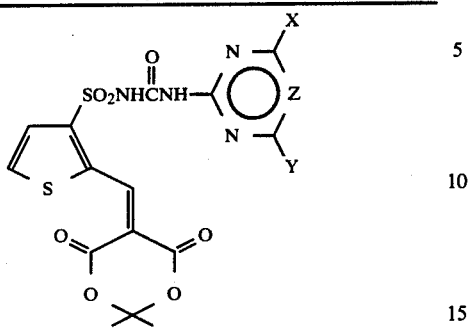

| Compound | Z | X | Y |
|---|---|---|---|
| 19 | CH | CH₃ | OCH₃ |
| 20 | CH | OCH₃ | OCH₃ |

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.05 |
|---|---|---|---|---|---|---|---|---|---|---|---|
| | | | | | POSTEMERGENCE | | | | | | |
| Morningglory | 10C | 10C | 3C,7G | 2C,5G | 5C,9G | 9C | 5C,9G | 4C,9G | 9C | 0 | 3C,8G |
| Cocklebur | 10C | 9C | 8C | 4C,9H | 5C,9G | 5C,9G | 5C,9G | 3C,8H | 8G | 0 | 5C,9G |
| Velvetleaf | 10C | 10C | 3C,8G | 4C,9G | 3C,7H | 4C,7H | 9C | 4C,8G | 3C,8G | 0 | 2C,5G |
| Nutsedge | 9C | 9C | 5C,9G | 2C,8G | 2C,6G | 3C,6G | 2C,8G | 2C,7G | 3G | 0 | 2C,4G |
| Crabgrass | 2C,7G | 2C,7G | 3G | 7G | 1H | 0 | 0 | 4G | 2C,4G | 0 | 2G |
| Barnyardgrass | 9C | 9C | 10C | 9H | 2H | 2H | 4C,8H | 8H | 3C,8H | 0 | 3H |
| Cheatgrass | 6C,9G | 9C | 4C,9G | 5C,9G | 0 | 0 | 9G | 2C,9G | 2C,9G | 0 | 0 |
| Wild Oats | 3C,7G | 4C,9G | 2C,6G | 6C,9G | 0 | 0 | 0 | 0 | 8G | 0 | 0 |
| Wheat | 8G | 2C,9G | 6G | 9G | 0 | 0 | 0 | 5G | 0 | 0 | 0 |
| Corn | 3U,9H | 9C | 7H | 10C | 8H | 8H | 0 | 2C,5H | 3C,6H | 0 | 3C,7H |
| Soybean | 5C,9G | 9C | 4C,9G | 5C,9G | 9C | 5C,9G | 5C,9G | 5C,9G | 5C,9G | 0 | 5C,9G |
| Rice | 6C,9G | 6C,9G | 4C,9G | 6C,9G | 6G | 7G | 0 | 3G | 2C,8G | 0 | 3G |
| Sorghum | 4C,9H | 4C,9H | 3C,8H | 3C,9H | 2C,3H | 3C,8H | 2C,8H | 3C,8H | 3C,9H | 0 | 3C,8H |
| Sugarbeets | 9C | 9C | 4C,9H | 3C,7G | 9C | 9C | 3C,5G | 1H | 0 | 0 | 3C,8G |
| Cotton | 10C | 9C | 2C,7G | 2C,8G | 2C,5G | 2C,5G | 3G | 3C,7G | 2G | 0 | 3C,5G |
| Giant Foxtail | | | | | | | | | | | |
| Barley | | | | | | | | | | | |
| | | | | | PREEMERGENCE | | | | | | |
| Morningglory | 8G | 9H | 3C,7H | 6G | 8G | 2C,7H | 4G | 8G | 0 | 0 | 0 |
| Cocklebur | 8H | 9H | 9H | 2H | 8H | 8H | 4G | 2H | 0 | 0 | 5G |
| Velvetleaf | 9G | 9C | 5C,9G | 4C,8G | 0 | 6G | 8G | 2H | 0 | 0 | 6G |
| Nutsedge | 10E | 10E | 10E | 4G | 0 | 0 | 4G | 0 | 0 | 0 | 0 |
| Crabgrass | 3G | 3C,7G | 2C | 4G | 0 | 0 | 0 | 2G | 0 | 0 | 0 |
| Barnyardgrass | 2C,9H | 9H | 2C,5H | 3C,7H | 3G | 3G | 0 | 0 | 0 | 0 | 0 |
| Cheatgrass | 9H | 10E | 3C,8G | 2C,7G | 4G | 5G | 0 | 0 | 0 | 0 | 0 |
| Wild Oats | 2C,8G | 6C,9G | 2C,6G | 3C,7H | 0 | 3G | 0 | 0 | 0 | 0 | 0 |
| Wheat | 3C,9G | 9C | 2C,5G | 2C,7G | 0 | 0 | 0 | 0 | 0 | 0 | 0 |
| Corn | 3C,9G | 3C,9H | 4G | 2C,5G | 6G | 2C,7H | 0 | 0 | 0 | 0 | 5G |
| Soybean | 9H | 3C,7H | 0 | 2C,3G | 2C,2H | 2C,2H | 1H | 2H | 0 | 0 | 0 |
| Rice | 3C,9H | 4C,9H | 7H | 7H | 8H | 7H | 0 | 0 | 0 | 0 | 0 |
| Sorghum | 2C,7H | 4C,9H | 3C,5H | 3G | 2C,2H | 3C,5G | 0 | 3C,8H | 0 | 0 | 0 |
| Sugarbeets | 10E | 10E | 10C | 9G | 4C,9G | 5C,9G | 0 | 2G | 0 | 0 | 5G |
| Cotton | 9G | 8G | 7G | 8G | 2C,8G | 2C,8G | 0 | 0 | 0 | 0 | 0 |
| Giant Foxtail | | | | | | | | | | | |
| Barley | | | | | | | | | | | |

| Rate kg/ha | Cmpd. 12 0.05 | Compound 13 0.05 | | Compound 14 0.05 | | Cmpd. 15 0.05 | Cmpd. 16 0.05 | Cmpd. 17 0.05 | Cmpd. 18 0.05 | Cmpd. 19 0.05 | Cmpd. 20 0.05 |
|---|---|---|---|---|---|---|---|---|---|---|---|
| | | | 0.01 | | 0.01 | | | | | | |
| | | | | | POSTEMERGENCE | | | | | | |
| Morningglory | 5C,9G | 2C,5G | 0 | 2H | 0 | 2C,6G | 2C,3H | 2C,6G | 2C,5G | 1C | 1H |
| Cocklebur | 4C,9H | 0 | 0 | 0 | 0 | 3C,9G | 3C,8H | 2C,8G | 2C,7G | 1H | 0 |
| Velvetleaf | 4C,9G | 7G | 0 | 0 | 0 | 3C,8G | 3C,6G | 2C,7G | 5G | 7G | 2H |
| Nutsedge | 0 | 4G | 0 | 2G | 0 | 9G | 3C,7G | 3C,8G | 5G | 0 | 4G |
| Crabgrass | 0 | 0 | 0 | 0 | 0 | 2G | 0 | 0 | 0 | 3G | 0 |
| Barnyardgrass | 5C,9H | 3C,8H | 1H | 2C,8H | 2H | 3C,9H | 2C,8H | 3C,9H | 3C,9H | 7H | 3H |
| Cheatgrass | 2C,6G | 5G | 0 | 2G | 0 | 0 | 0 | 0 | 0 | 0 | 0 |
| Wild Oats | 2C,8G | 0 | 0 | 2C,5G | 0 | 0 | 0 | 0 | 2C* | 0 | 0 |
| Wheat | 0 | 0 | 0 | 2C | 0 | 0 | 0 | 0 | 0 | 0 | 0 |
| Corn | 3C,8H | 1C,5G | 1H | 2C,9H | 0 | 2C,9G | 3C,9H | 3C,8H | 3C,9H | 2C,7H | 5G |
| Soybean | 5C,9G | 2H,8G | 3H | 3C,7G | 1H | 3C,9G | 3C,8H | 4C,9G | 4C,9G | 4G | 3H |
| Rice | 9C | 8G | 3G | 7G | 0 | 8G | 5G | 9G | 8G | 8G | 5G |
| Sorghum | 3C,8H | 2C,7H | 2G | 3C,9G | 4G | 3C,9G | 2C,8H | 3C,9H | 3C,7H | 3C,6G | 4G |
| Sugarbeets | 4C,8G | 3C,8G | 2G | 4G | 0 | 3C,5G | 3C,6H | 9C | 3C,8G | 4C,9G | 3C,5G |

TABLE A-continued

| | | | | | | | | | | | |
|---|---|---|---|---|---|---|---|---|---|---|---|
| Cotton | 2G | 4G | 0 | 0 | 0 | 3C,8H | 3C,6G | 3C,9G | 2C,5G | 2C,5G | 3C,6H |
| Giant Foxtail | | 2G | 0 | 3G | 0 | 3C,8G | 3G | 6G | 4G | 4G | 3G |
| Barley | | 2G | 0 | 0 | 0 | 2C,4G | 1C | 0 | 0 | 0 | 0 |
| PREEMERGENCE | | | | | | | | | | | |
| Morningglory | 9G | 0 | 0 | 0 | 0 | 2H | 5G | 5G | 5G | 5G | 4G |
| Cocklebur | 5H | — | 0 | 0 | 0 | 2H | 4G | 7G | 9H | 9H | 8H |
| Velvetleaf | 5C,9G | 2G | 0 | 2H | 0 | 3G | 3G | 7G | 5G | 3G | 8G |
| Nutsedge | 5G | 0 | 0 | 0 | 0 | 0 | 0 | 0 | 0 | 0 | 0 |
| Crabgrass | 0 | 0 | 0 | 0 | 0 | 0 | 0 | 0 | 0 | 5G | 0 |
| Barnyardgrass | 8G | 0 | 0 | 3G | 0 | 5G | 2C | 7H | 3G | 6G | 3C,3G |
| Cheatgrass | 3C,6G | 0 | 0 | 5G | 0 | 0 | 0 | 0 | 3G | 4G | 2G |
| Wild Oats | 2C,8G | 0 | 0 | 5G | 0 | 0 | 2C | 0 | 0 | 2C | 0 |
| Wheat | 5G | 0 | 0 | 3G | 0 | 0 | 2G | 0 | 0 | 0 | 0 |
| Corn | 2C,8G | 2C,7G | 0 | 3C,9H | 0 | 3C,5G | 3C,7G | 3C,7H | 3C,8H | 5G | 3G |
| Soybean | 3C,7H | 3G | 0 | 2C,5G | 0 | 3C,5H | 3C,6G | 3C,5G | 2C,6G | 4G | 3G |
| Rice | 9H | 7G | 0 | 8H | 0 | 3G | 2C,5G | 5G | 7G | 5G | 3G |
| Sorghum | 2C,5G | 0 | 0 | 3C,8H | 0 | 3C,5G | 3C,7G | 2C,4G | 2C,7G | 2C,5G | 4G |
| Sugarbeets | 5C,9G | 0 | 0 | 2H | 0 | 8G | 1H | 8G | 8G | 8G | 7G |
| Cotton | 8G | 0 | 0 | 5G | 0 | 0 | 6G | 7G | 6G | 7G | 7G |
| Giant Foxtail | | 0 | 0 | 2G | 0 | 0 | 0 | 3G | 5G | 6G | 3C,3G |
| Barley | | 3G | 0 | 5G | 0 | 3G | 3C,7G | 2G | 2G | 4G | 0 |

What is claimed is:

1. A compound of the formula $$JSO_2NHCNA \atop \substack{\| \\ W} \substack{\\ | \\ R}$$   I wherein J is J-1, J-2, J-3, J-4 or J-5

R is H or CH$_3$;
W is O or S;
R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CO$_2$R$_c$, amino, C$_1$-C$_3$ alkylamino, di(C$_1$-C$_3$)alkylamino, CH$_2$OCH$_3$, CH$_2$SCH$_3$ or CH$_2$CN;
R$_a$ is H, C$_1$-C$_4$ alkyl, C$_2$-C$_3$ cyanoalkyl, OCH$_3$ or OC$_2$H$_5$;
R$_b$ is H, C$_1$-C$_4$ alkyl or C$_3$-C$_4$ alkenyl; or
R$_a$ and R$_b$ may be taken together as (CH$_2$)$_3$, (CH$_2$)$_4$, (CH$_2$)$_5$ or —CH$_2$CH$_2$OCH$_2$CH$_2$—;
R$_c$ is C$_1$-C$_4$ alkyl, C$_3$-C$_4$ alkenyl, C$_3$-C$_4$ alkynyl, C$_2$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;
R$_2$ is H, C$_1$-C$_4$ alkyl, C$_3$-C$_4$ alkenyl, C$_3$-C$_4$ alkynyl, phenyl, phenyl substituted with Cl, NO$_2$, CH$_3$ or OCH$_3$, C$_1$-C$_3$ alkoxycarbonyl, C$_1$-C$_3$ alkylsulfonyl or di(C$_1$-C$_2$)alkylamino sulfamoyl;

Q is $+CR_{10}=CH\frac{}{n}C(R_3)=C$ E;

n is 0, 1 or 2;
R$_3$ is H, C$_1$-C$_4$ alkyl, Cl or Br;
R$_{10}$ is H or C$_1$-C$_4$ alkyl;
E is a bridge of 4 or 5 atoms, which may be substituted or unsubstituted, containing 0-2 heteroatoms selected from the group consisting of oxygen, sulfur and nitrogen, and also containing 2-5 carbon atoms, said bridge together with one carbon attachment site forming a partially saturated or a fully unsaturated, nonaromatic 5- or 6-membered carbocyclic or heterocyclic ring, with the proviso that when E contains two atoms of oxygen or sulfur, they must be separated by at least one atom of carbon, and that oxygen and sulfur are only linked to each other if the sulfur is in the form SO or SO$_2$; in the bridging group E, sulfur may take the form of S, SO or SO$_2$ and one or two of the carbon atoms may be a carbonyl, thiocarbonyl or the cyclic 5- and 6-membered ketals thereof; when one of the bridging atoms is a substituted carbon, the substituents on said carbon include H, C$_1$-C$_4$ alkyl, C$_1$-C$_4$ alkoxy, halogen or C$_1$-C$_4$ haloalkoxy; when the bridging atom is a nitrogen, the substituent on said nitrogen is H, C$_1$-C$_4$ alkyl, C$_1$-C$_4$ haloalkyl, C$_1$-C$_4$ alkoxyalkyl, C$_2$-C$_4$ cyanoalkyl, C$_3$-C$_4$ alkenyl or C$_3$-C$_4$ alkynyl;

A is

A-1, A-2 or A-3

-continued

A-4  A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkoxy, amino, $C_1$–$C_3$ alkylamino or di($C_1$–$C_3$)alkylamino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, Di($C_1$–$C_3$)alkylamino, $C_3$–$C_4$ alkenyloxy, $C_3$–$C_4$ alkynyloxy, $C_2$–$C_5$ alkylsulfinylalkyl, $C_1$–$C_4$ haloalkyl, $C_2$–$C_5$ alkylsulfonylalkyl, $C_3$–$C_5$ cycloalkyl, $C_2$–$C_4$ alkynyl, $C_2$–$C_5$ alkylthioalkyl, $W_1$ and $W_2$ are independently O or S;
m is 2 or 3;
$R_d$ is H or $CH_3$;
$R_e$ is $C_1$–$C_2$ alkyl;
$R_f$ is $C_1$–$C_2$ alkyl;
Z is CH, $CCH_3$, $CC_2H_5$, CCl or CBr;
$Z_1$ is N;
$Y_1$ is O or $CH_2$;
$X_1$ is $CH_3$, $OCH_3$, $OC_2H_5$ or $OCF_2H$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(a) when W is S, then R is H, A is A-1, Z is CH and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or (b) when X is Cl, Br, F or I, then Z is CH and Y is $OCH_3$, $OC_2H_5$, $NH_2$, $NHCH_3$, $N(CH_3)_2$, $OCF_2H$ or $N(OCH_3)CH_3$;
(c) when X or Y is $C_1$ haloalkoxy, then Z is CH;
(d) when the bridging group E contains a thiocarbonyl substituent, said thiocarbonyl carbon must be bonded to a nitrogen atom;
(e) when J is J-2 or J-3, the substituent Q and the sulfonylurea bridge are on adjacent carbon atoms;
(f) when the total number of carbon atoms in X and Y is greater than 4, then the total number of carbon atoms in $R_1$, $R_2$ and Q is less than or equal to 10; and
(g) $X_4$ and $Y_4$ are not simultaneously Cl.

2. The compounds of claim 1 where W is O; R is H; Z is CH; and Q is

Q-1  Q-2
Q-3  Q-4
Q-5  Q-6
Q-7  Q-8
Q-9  Q-10
Q-11  Q-12
Q-13  Q-14
Q-15  Q-16

-continued
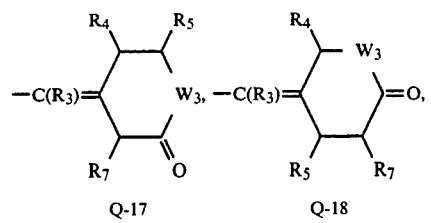
Q-17   Q-18
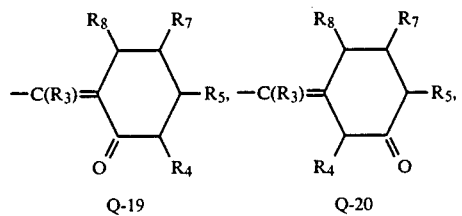
Q-19   Q-20
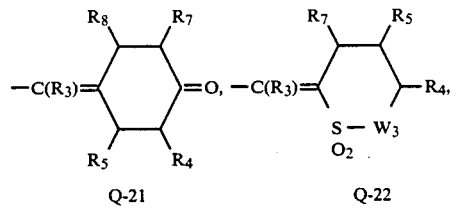
Q-21   Q-22
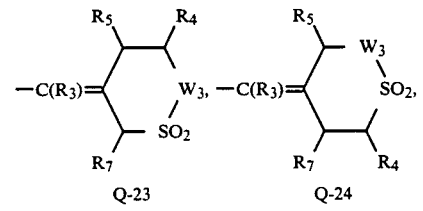
Q-23   Q-24
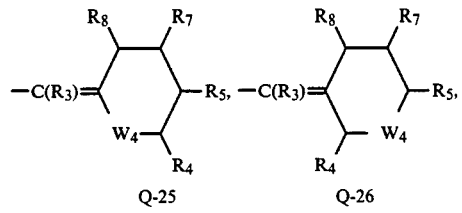
Q-25   Q-26
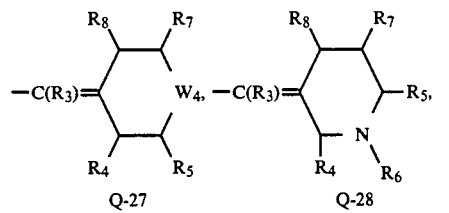
Q-27   Q-28
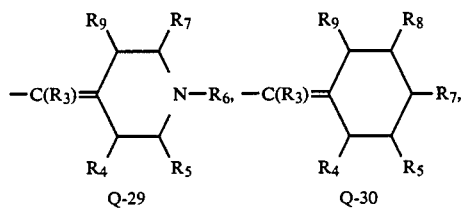
Q-29   Q-30
-continued
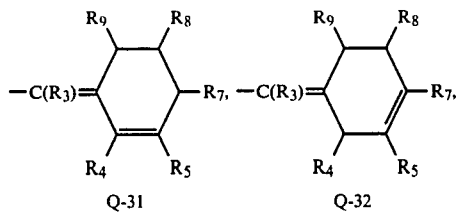
Q-31   Q-32
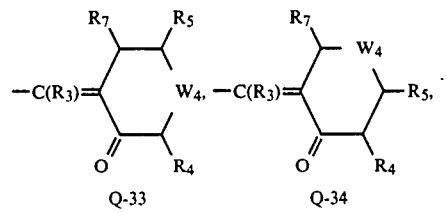
Q-33   Q-34
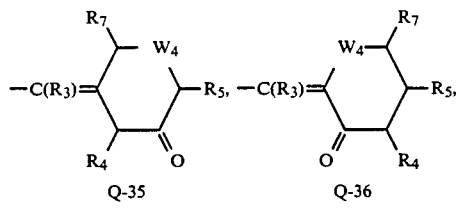
Q-35   Q-36
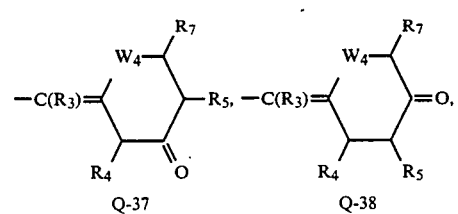
Q-37   Q-38
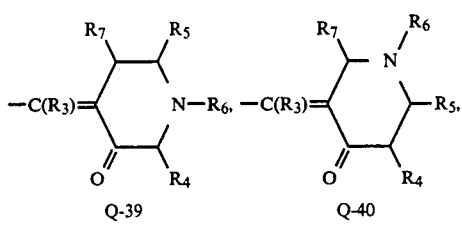
Q-39   Q-40
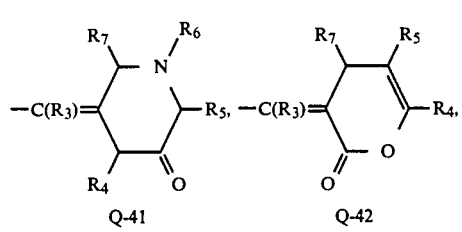
Q-41   Q-42
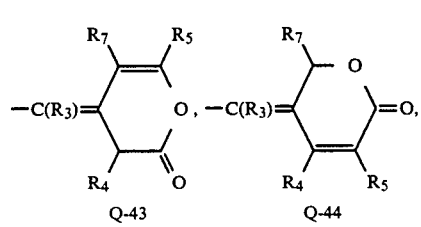
Q-43   Q-44

-continued
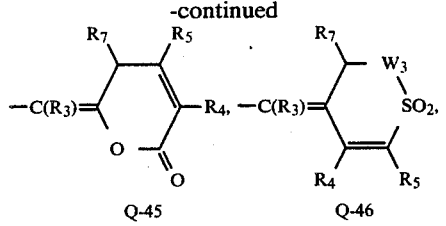
Q-45, Q-46
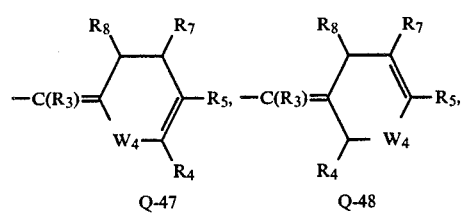
Q-47, Q-48
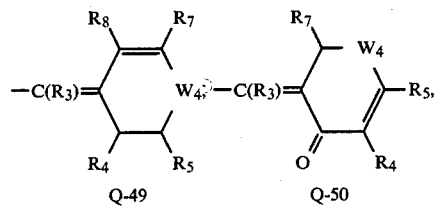
Q-49, Q-50
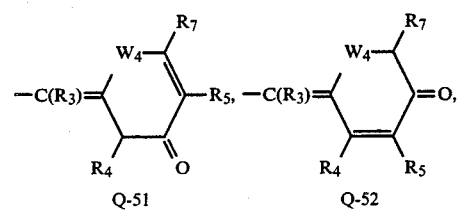
Q-51, Q-52
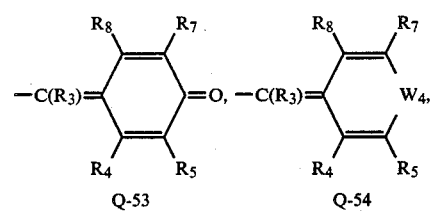
Q-53, Q-54
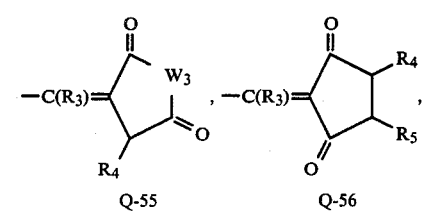
Q-55, Q-56
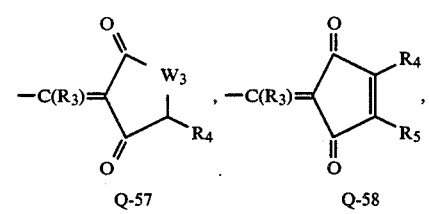
Q-57, Q-58
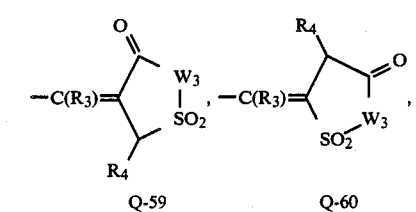
Q-59, Q-60
-continued
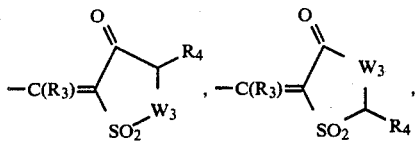
Q-61, Q-62
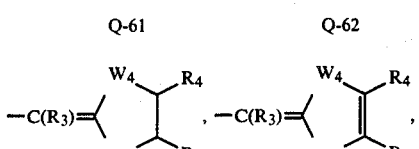
Q-63, Q-64
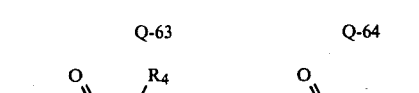
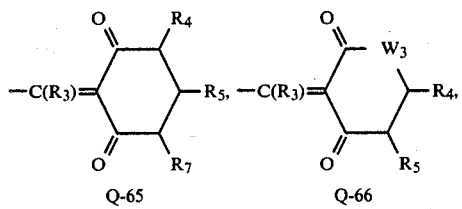
Q-65, Q-66
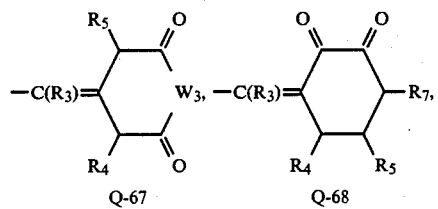
Q-67, Q-68
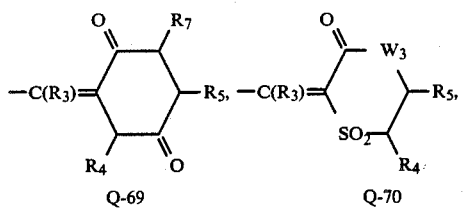
Q-69, Q-70
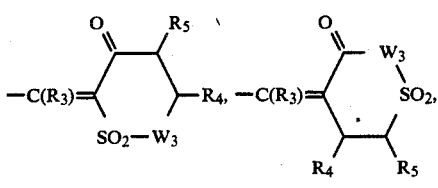
Q-71, Q-72
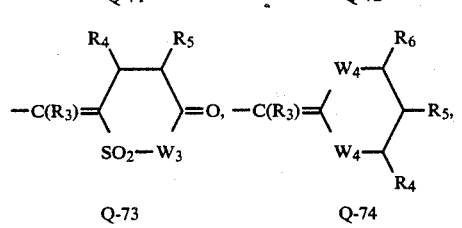
Q-73, Q-74
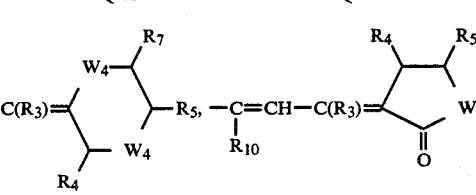
Q-75, Q-76

185
-continued

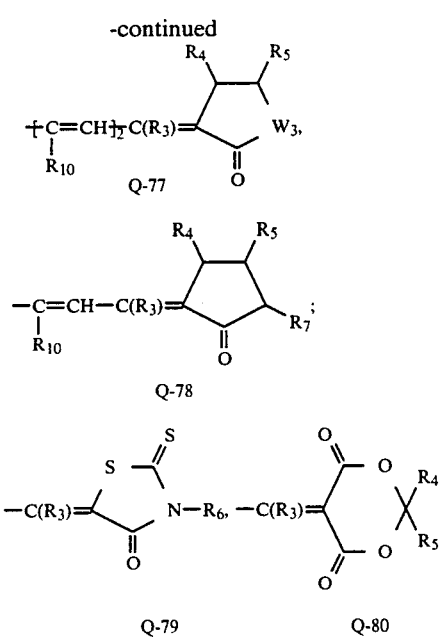

$W_3$ is O or $NR_6$;
$W_4$ is O, S, SO or $SO_2$;
$R_4$, $R_5$, $R_6$, $R_7$, $R_8$ and $R_9$ are independently H or $C_1$–$C_4$ alkyl and $R_{10}$ is H or $CH_3$;
provided that the total number of carbon atoms of $R_4$, $R_5$, $R_7$, $R_8$ and $R_9$ is less than or equal to 4.

3. Compounds of claim 2 where X is $CH_3$, $OCH_3$, $OC_2H_5$, Cl, Br, F, I, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $CH_3$, $OCH_3$, $OC_2H_5$, $CH_2OCH_3$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $CH_2SC_2H_5$, cyclopropyl,

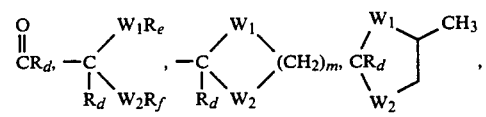

$OCF_2H$, $SCF_2H$, $C\equiv CH$ or $C\equiv CCH_3$.

4. The compounds of claim 3 where $R_1$ is H, F, Cl, Br, $C_1$–$C_2$ alkyl, $C_1$–$C_2$ alkoxy or $C_1$–$C_2$ alkylthio.

5. The compounds of claim 4 where $R_4$, $R_5$, $R_6$, $R_7$, $R_8$ and $R_9$ are independently H or $CH_3$; $R_3$ is H or $C_1$–$C_2$ alkyl; and $R_2$ is H, $C_1$–$C_2$ alkyl or $CH_2CH=CH_2$.

6. The compounds of claim 5 where A is A-1; X is $CH_3$, $OCH_3$, $OC_2H_5$, Cl, $OCF_2H$ or $OCH_2CF_3$; Y is $CH_3$, $OCH_3$, $C_2H_5$, $CH_2OCH_3$, $NHCH_3$ or $CH(OCH_3)_2$; and Z is CH or N.

7. The compounds of claim 6 where J is J-1 and $R_1$ is in the 5-position.

8. The compounds of claim 6 where J is J-2 and $R_1$ is H.

9. The compounds of claim 6 where J is J-3 and $R_1$ is H.

10. The compounds of claim 6 where J is J-4 and $R_1$ is H.

11. The compounds of claim 6 where J is J-5 and $R_1$ is H.

12. The compounds of claim 7 where Q is Q-1.

13. The compounds of claim 7 where Q is Q-3.
14. The compounds of claim 7 where Q is Q-5.
15. The compounds of claim 7 where Q is Q-7.
16. The compounds of claim 7 where Q is Q-8.
17. The compounds of claim 7 where Q is Q-16.
18. The compounds of claim 7 where Q is Q-19.
19. The compounds of claim 7 where Q is Q-22.
20. The compounds of claim 7 where Q is Q-25.
21. The compounds of claim 7 where Q is Q-26.
22. The compounds of claim 7 where Q is Q-27.
23. The compounds of claim 7 where Q is Q-55.
24. The compounds of claim 7 where Q is Q-56.
25. The compounds of claim 7 where Q is Q-61.
26. The compounds of claim 7 where Q is Q-62.
27. The compounds of claim 7 where Q is Q-68.
28. The compounds of claim 7 where Q is Q-76.
29. The compounds of claim 7 where Q is Q-77.
30. The compounds of claim 7 where Q is Q-78.
31. The compounds of claim 7 where Q is Q-79.
32. The compounds of claim 7 where Q is Q-80.
33. The compounds of claim 12 where $W_3$ is O.
34. The compounds of claim 14 where $W_3$ is NH or $NCH_3$.
35. The compounds of claim 15 where $W_4$ is S or $SO_2$.
36. The compounds of claim 16 where $W_4$ is S or $SO_2$.
37. The compounds of claim 17 where $W_3$ is O.
38. The compounds of claim 19 where $W_3$ is NH or $NCH_3$.
39. The compounds of claim 20 where $W_4$ is S or $SO_2$.
40. The compounds of claim 21 where $W_4$ is S or $SO_2$.
41. The compounds of claim 23 where $W_3$ is O.
42. The compounds of claim 25 where $W_3$ is NH or $NCH_3$.
43. The compounds of claim 26 where $W_3$ is NH or $NCH_3$.
44. The compound of claim 1 which is N-[(4,6-dimethoxypyrimidin-2-yl)aminocarbonyl]-2-[(2-oxotetrahydro-3-furanylidene)methyl]benzenesulfonamide.
45. An agriculturally suitable composition for controlling the growth of undesired vegetation comprising an effective amount of a compound of claim 1 and at least one of the following surfactant, solid or liquid diluent.
46. An agriculturally suitable composition for controlling the growth of undesired vegetation comprising an effective amount of a compound of claim 2 and at least one of the following surfactant, solid or liquid diluent.
47. An agriculturally suitable composition for controlling the growth of undesired vegetation comprising an effective amount of a compound of claim 3 and at least one of the following surfactant, solid or liquid diluent.
48. An agriculturally suitable composition for controlling the growth of undesired vegetation comprising an effective amount of a compound of claim 4 and at least one of the following surfactant, solid or liquid diluent.
49. An agriculturally suitable composition for controlling the growth of undesired vegetation comprising an effective amount of a compound of claim 5 and at least one of the following surfactant, solid or liquid diluent.

50. An agriculturally suitable composition for controlling the growth of undesired vegetation comprising an effective amount of a compound of claim 6 and at least one of the following surfactant, solid or liquid diluent.

51. An agriculturally suitable composition for controlling the growth of undesired vegetation comprising an effective amount of a compound of claim 7 and at least one of the following surfactant, solid or liquid diluent.

52. A method for controlling the growth of undesired vegetation which comprises applying to the locus to be protected an effective amount of a compound of claim 1.

53. A method for controlling the growth of undesired vegetation which comprises applying to the locus to be protected an effective amount of a compound of claim 2.

54. A method for controlling the growth of undesired vegetation which comprises applying to the locus to be protected an effective amount of a compound of claim 3.

55. A method for controlling the growth of undesired vegetation which comprises applying to the locus to be protected an effective amount of a compound of claim 4.

56. A method for controlling the growth of undesired vegetation which comprises applying to the locus to be protected an effective amount of a compound of claim 5.

57. A method for controlling the growth of undesired vegetation which comprises applying to the locus to be protected an effective amount of a compound of claim 6.

58. A method for controlling the growth of undesired vegetation which comprises applying to the locus to be protected an effective amount of a compound of claim 7.

* * * * *

UNITED STATES PATENT AND TRADEMARK OFFICE
CERTIFICATE OF CORRECTION

PATENT NO. : 4,685,955
DATED : August 11, 1987
INVENTOR(S) : Joel R. Christensen, Paul H. Liang and Mark E. Thompson It is certified that error appears in the above—identified patent and that said Letters Patent is hereby corrected as shown below:

Column 5, line 28, before the definition of $W_1$ add
-- or $N(OCH_3)CH_3$; --

Column 5, line 27, change double bond between C and Rd to a single bond.

Column 179, line 18 substitute case letter "d" for capital letter -- D --.

Column 179, line 27, change double bond between C and Rd to a single bond.

Column 179, line 28, before the definition of $W_1$ add
-- or $N(OCH_3)CH_3$; --

Column 179, line 40 in the definition of $Y_4$ after $OCH_3$ substitute a comma for the period.

Signed and Sealed this

Seventeenth Day of May, 1988

*Attest:*

DONALD J. QUIGG

*Attesting Officer*     *Commissioner of Patents and Trademarks*